US012331330B2

(12) United States Patent
Hummel et al.

(10) Patent No.: US 12,331,330 B2
(45) Date of Patent: Jun. 17, 2025

(54) COMPOSITIONS AND METHODS FOR RNA-TEMPLATED EDITING IN PLANTS

(71) Applicant: Pairwise Plants Services, Inc., Durham, NC (US)

(72) Inventors: Aaron Hummel, Hillsborough, NC (US); Joseph Matthew Watts, Cary, NC (US); Shai Joshua Lawit, Durham, NC (US); Nathaniel Graham, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 132 days.

(21) Appl. No.: 17/078,919

(22) Filed: Oct. 23, 2020

(65) Prior Publication Data

US 2021/0147862 A1 May 20, 2021

Related U.S. Application Data

(60) Provisional application No. 62/925,097, filed on Oct. 23, 2019.

(51) Int. Cl.
*C12N 9/22* (2006.01)

(52) U.S. Cl.
CPC ............ *C12N 9/22* (2013.01); *C07K 2319/80* (2013.01); *C12N 2310/20* (2017.05)

(58) Field of Classification Search
CPC .................... C12N 2310/20; C12Y 207/07049
See application file for complete search history.

(56) References Cited

U.S. PATENT DOCUMENTS

| | | | |
|---|---|---|---|
| 5,459,252 | A | 10/1995 | Conkling et al. |
| 5,604,121 | A | 2/1997 | Hilder et al. |
| 5,625,136 | A | 4/1997 | Koziel et al. |
| 5,641,876 | A | 6/1997 | McElroy et al. |
| 6,040,504 | A | 3/2000 | Rice et al. |
| 7,141,424 | B2 | 11/2006 | Shin et al. |
| 7,166,770 | B2 | 1/2007 | Hohn et al. |
| 7,579,516 | B2 | 8/2009 | Boudreau |
| 9,790,490 | B2 | 10/2017 | Zhang et al. |
| 9,982,053 | B2 | 5/2018 | Pantaleo et al. |
| 10,421,972 | B2 | 9/2019 | Lira et al. |
| 11,293,019 | B2 | 4/2022 | Park et al. |
| 11,447,770 | B1 | 9/2022 | Liu et al. |
| 2014/0123341 | A1 | 5/2014 | Azhakanandam |
| 2016/0362667 | A1 | 12/2016 | Donohoue et al. |
| 2017/0219596 | A1 | 8/2017 | Tanenbaum et al. |
| 2017/0247671 | A1 | 8/2017 | Yung et al. |
| 2018/0155716 | A1 | 6/2018 | Zhang et al. |
| 2018/0170985 | A1 | 6/2018 | Tremblay et al. |
| 2018/0298392 | A1 | 10/2018 | Cotta-Ramusino |
| 2018/0327785 | A1 | 11/2018 | Cigan et al. |
| 2019/0010441 | A1 | 1/2019 | Kindaichi |
| 2019/0010481 | A1 | 1/2019 | Joung et al. |
| 2019/0100775 | A1 | 4/2019 | Donohoue et al. |
| 2019/0136249 | A1 | 5/2019 | Sakai et al. |
| 2019/0161760 | A1 | 5/2019 | Hummel |
| 2019/0203216 | A1 * | 7/2019 | Jacobsen ............ C12N 15/8216 |
| 2019/0218547 | A1 | 7/2019 | Lee et al. |
| 2019/0256900 | A1 | 8/2019 | Zhang et al. |
| 2021/0130835 | A1 | 5/2021 | Watts et al. |
| 2022/0145334 | A1 | 5/2022 | Kim et al. |

FOREIGN PATENT DOCUMENTS

| | | | | |
|---|---|---|---|---|
| CN | 104968784 | A | 10/2015 | |
| CN | 107406875 | A | 11/2017 | |
| CN | 107787367 | A | 3/2018 | |
| CN | 108025188 | A | 5/2018 | |
| EP | 0255378 | A2 | 2/1988 | |
| EP | 0342926 | A2 | 11/1989 | |
| EP | 0452269 | A2 | 10/1991 | |
| KR | 20190071623 | A | 6/2019 | |
| WO | 9307278 | A1 | 4/1993 | |
| WO | 9942587 | A1 | 8/1999 | |
| WO | 0173087 | A1 | 10/2001 | |
| WO | 2014186686 | A2 | 11/2014 | |
| WO | 2015026886 | A1 | 2/2015 | |
| WO | WO 2017/189308 | A1 | 11/2017 | |
| WO | WO 2018/022634 | A1 | 2/2018 | |
| WO | 2018049168 | A1 | 3/2018 | |
| WO | 2018083128 | A2 | 5/2018 | |
| WO | 2018136783 | A1 | 7/2018 | |
| WO | 2018202199 | A1 | 11/2018 | |
| WO | 2020191153 | A2 | 9/2020 | |
| WO | 2020191241 | A1 | 9/2020 | |
| WO | 2020191249 | A1 | 9/2020 | |
| WO | WO 2020/191243 | A1 | 9/2020 | |
| WO | WO-2020191234 | A1 * | 9/2020 | ............ A61K 38/45 |
| WO | WO 2020/191171 | A9 | 10/2020 | |
| WO | WO 2021/092130 | A1 | 5/2021 | |

OTHER PUBLICATIONS

Anzalone_2019.10.21_online_publication_date (Year: 2019).*
Orlova et al (Reverse Transcriptase of Moloney Murine Leukemia Virus Binds to Eukaryotic Release Factor 1 to Modulate Suppression of Translational Termination. Cell, vol. 115, 319-331, 2003). (Year: 2003).*
Anzalone_2019.10.21_supplement (Year: 2019).*
Anzalone et al (Search-and-replace genome editing without double-strand breaks or donor DNA. Nature 1-19, published online Oct. 21, 2019) (Year: 2019).*
International Search Report and the Written Opinion of the International Searching Authority corresponding to International Patent Application No. PCT/US2020/057121 (21 pages) (mailed Feb. 8, 2021).

(Continued)

*Primary Examiner* — Charles Logsdon
*Assistant Examiner* — Wayne Zhong
(74) *Attorney, Agent, or Firm* — Myers Bigel, P.A.

(57) ABSTRACT

This invention relates to recombinant nucleic constructs comprising a DNA binding domain, an endonuclease and a reverse transcriptase and methods of use thereof for modifying nucleic acids in plants.

29 Claims, 14 Drawing Sheets

Specification includes a Sequence Listing.

(56) References Cited

OTHER PUBLICATIONS

Mohr et al. "A Reverse Transcriptase-Cas1 Fusion Protein Contains a Cas6 Domain Required for Both CRISPR RNA Biogenesis and RNA Spacer Acquisition" Molecular Cell, 72(4):700-714 (2018).
Anzalone et al. "Search-and-replace genome editing without double-strand breaks or donor DNA" Nature, 576:149-157 (2019).
Balakrishnan et al. "Flap Endonuclease 1" Annual Review of Biochemistry, 82:119-138 (2013).
Barrangou, Rodolphe "Diversity of CRISPR-Cas immune systems and molecular machines" Genome Biology, 16(247):1-11 (2015).
Briner et al. "Lactobacillus buchneri Genotyping on the Basis of Clustered Regularly Interspaced Short Palindromic Repeat (CRISPR) Locus Diversity" Applied and Environmental Microbiology, 80(3):994-1001 (2014).
Gilbreth et al. "Structural Insights for Engineering Binding Proteins Based on Non-Antibody Scaffolds" Current Opinion in Structural Biology, 22(4):413-420 (2012).
Grissa et al. "CRISPRFinder: a web tool to identify clustered regularly interspaced short palindromic repeats" Nucleic Acids Research, 35:W52-W57 (2007).
Jankowsky et al. "Specificity and non-specificity in RNA-protein interactions" Nature Reviews Molecular Cell Biology, 16(9):533-544 (2015).
Jiang et al. "CRISPR-assisted editing of bacterial genomes" Nature Biotechnology, 31(3):233-239 (2013).
Levin et al. "Dynamic interactions between transposable elements and their hosts" Nat. Rev Genet, 12:1-31 2011.
Mali et al. "Cas9 as a versatile tool for engineering biology" Nature Methods, 10(10):957-963 (2013).
Mali et al. "RNA-Guided Human Genome Engineering via Cas9" Science, 339(6121):823-826 (2013).
Ran et al. "Genome engineering using the CRISPR-Cas9 system" Nature Protocols, 8(11):2281-2308 (2013).
Sha et al. "Monobodies and other synthetic binding proteins for expanding protein science" Protein Science, 26:910-924 (2017).
Sundararaman et al. "Resources for the Comprehensive Discovery of Functional RNA Elements" Mol Cell, 61:903-913 2016.
Tak et al. "Inducible and multiplex gene regulation using CRISPR-Cpf1-based transcription factors" Nature Methods, 14(12):1163-1166 (2017).
Tanenbaum et al. "A protein tagging system for signal amplification in gene expression and fluorescence imaging" Cell 159, 635-646 (2014).
Vob et al. "Chemically induced dimerization: reversible and spatiotemporal control of protein function in cells" Current Opinion in Chemical Biology, 28:194-201 (2015).
U.S. Appl. No. 17/300,668, filed Mar. 19, 2020.
U.S. Appl. No. 17/219,590, filed Mar. 31, 2021.
U.S. Appl. No. 17/219,635, filed Mar. 31, 2021.
U.S. Appl. No. 17/751,599, filed May 23, 2022.
Baba et al. "Further increase in thermostability of Moloney murine leukemia virus reverse transcriptase by mutational combination" *Protein Engineering, Design & Selection* 30(8):551-557 (2017).
Bandyopadhyay et al. "CRISPR-Cas12a (Cpf1): A Versatile Tool in the Plant Genome Editing Tool Box for Agricultural Advancement" *Frontiers in Plant Science* 11(584151) (17 pages) (2020).
Epstein et al. "Engineering a Self-Inactivating CRISPR System for AAV Vectors" *Molecular Therapy* 24(Supplement 1):S50 (2016).
Gaudelli et al. "Programmable base editing of A•T to G•C in genomic DNA without DNA cleavage" *Nature* 551(7681):464-471 (2017).
Jiang et al. "Prime editing efficiently generates W542L and S621I double mutations in two ALS genes in maize" *Genome Biology* 21:257 (10 pages) (2020).
Lin et al. "Prime genome editing in rice and wheat" *Nature Biotechnology* 38:582-585 (2020).
Ming et al. "CRISPR-Cas12b enables efficient plant genome engineering" *Nature Plants* 6(3):202-208 (2020).
Rocha et al. "Design of Specie-Specific Primers for Virus Diagnosis in Plants with PCR" *Proceedings of the Fourth IEEE Symposium on Bioinformatics and Bioengineering* (pp. 149-155) (2004).
Xu et al. "Development of Plant Prime-Editing Systems for Precise Genome Editing" *Plant Communications* 1:100043 (8 pages) (2020).
Yamano et al. "Structural Basis for the Canonical and Non-canonical PAM Recognition by CRISPR-Cpf1" Molecular Cell 67(4):633-645 (2017).
Extended European Search Report corresponding to European Patent Application No. 20879965.0 (7 pages) (dated Nov. 8, 2023).
Swarts , et al., "Cas9 versus Cas12a/Cpf1: Structure-function comparisons and implications for genome editing", WIREs RNA, 9(5):e1481 (2018).
"New Kid on the Block: Prime Editing as a Precision Gene Editing Tool", A Comprehensive Guide on CRISPR Methods, Chapter 4. Retrieved from: https://www.synthego.com/guide/crispr-methods/prime-editing on Sep. 14, 2023, 7 pages.
"Science", Prime Medicine. Retrieved from: https://primemedicine.com/science/ on Dec. 17, 2022, 16 pages.
Adikusuma, Fatwa , et al., "Optimized nickase- and nuclease-based prime editing in human and mouse cells", Nucleic Acids Research, 49(18), 2021, 10785-10795.
Anzalone, Andrew V., et al., "Programmable large DNA deletion, replacement, integration, and inversion with twin prime editing and site-specific recombinases", bioRxiv. doi: https://doi.org/10.1101/2021.11.01.466790, 2021.
Cofsky, Joshua C., et al., "CRISPR-Cas12a exploits R-loop asymmetry to form double-strand breaks", eLife. 9:e55143, 2020.
Jiang, Fuguo , et al., "Structures of a CRISPR-Cas9 R-loop complex primed for DNA cleavage", Science. 351 (6275): 867-871, 2016.
Kim, Y. Bill , et al., "A novel mechanistic framework for precise sequence replacement using reverse transcriptase and diverse CRISPR-Cas systems", bioRxiv, doi: https://doi.org/10.1101/2022.12.13.520319, 2022.
Kim, Hui Kwon , et al., "Predicting the efficiency of prime editing guide RNAs in human cells", Nature Biotechnology. 39: 198-206 (2021).
Li , et al., "CRISPR-Cas12a has both cis-and trans-cleavage activities on single-stranded DNA", Cell research, 28(4), 2018, 491-493.
Li , et al., "Supplementary Information—CRISPR-Cas 12a has both cis-and trans-cleavage activities on single-stranded DNA", Cell research, 28(4), 2018, 491-493.
Nelson, James W., et al., "Engineered pegRNAs improve prime editing efficiency", Nat Biotechnol. 40(3): 402-410, 2022.
Yan, Winston X., et al., "Functionally diverse type V CRISPR-Cas systems", Science 363, 2019, 88-91.
Zhong , et al., "Cpf1 proteins excise CRIS PR RNAs from mRNA transcripts in mammalian cells", Nature chemical biology, 13(8), 2017, 839-841.
Zhong , et al., "Supplementary Information—Cpf1 proteins excise CRIS PR RNAs from mRNA transcripts in mammalian cells", Nature chemical biology, 13(8), 2017, 839-841.

* cited by examiner

| | No PEG | 5GtoT | 7AtoC | 4GATins | 6Gdel |
|---|---|---|---|---|---|
| nCas9 RT in trans | | 0.0% | 0.5% | 0.27% | 2.4% |
| nCas9-RT Suntag | | 0.0% | 0.7% | 0.84% | 2.4% |
| Cas9 PE2 | | 0.0% | 0.9% | 0.88% | 2.6% |

nCas9 RT in trans nCas9-RT Suntag Cas9 PE2

| | No PEG | 5GtoT | 6GtoC | 1TCAins | 3-5AGGdel |
|---|---|---|---|---|---|
| nCas9 RT in trans | | 2.1% | 9.6% | 1.00% | 2.10% |
| nCas9-RT Suntag | | 1.6% | 4.0% | 0.77% | 0.67% |
| Cas9 PE2 | | 0.8% | 3.5% | 0.79% | 0.26% |

nCas9 RT in trans nCas9-RT Suntag Cas9 PE2

| | No PEG | 5GtoT | 6GtoC | 1ATGins | 2Gdel |
|---|---|---|---|---|---|
| nCas9 RT in trans | 0 | 6.0% | 7.5% | 1.96% | 0.4% |
| nCas9-RT Suntag | 0 | 5.0% | 5.9% | 1.73% | 0.6% |
| Cas9 PE2 | 0 | 4.4% | 5.9% | 1.89% | 0.3% |

nCas9 RT in trans nCas9-RT Suntag Cas9 PE2

| | No PEG | 4AtoC | 4AtoG | 5GtoT | 6GtoA |
|---|---|---|---|---|---|
| nCas9 RT in trans | 0 | 0.5% | 0.7% | 4.5% | 3.8% |
| nCas9-RT Suntag | 0 | 0.3% | 0.3% | 3.2% | 3.6% |
| Cas9 PE2 | 0 | 0.4% | 0.9% | 2.7% | 3.3% |

nCas9 RT in trans nCas9-RT Suntag Cas9 PE2

Site O2:

WT:   ggaatcccttctgcagcacc[TGG]atcgcttttccgagct[TCT]ggcggtctc[AAG]cactactacgtcagcacctgggacccc Edit: ggaatcccttctgcagcacc[GCA]atcgcttttccgagct[CAC]ggcggtctc[GGA]cactactacgtcagcacctgggacccc Site O3:

WT:   ccaaggtgaaagcggaagta[CGG]cctttcgcgcacctcatgaatcccttctgcagcacc[TGG]atcgcttttccgagct[TCT]ggccggtccaagcactactacgtcagcacctgggaccc Edit: ccaaggtgaaagcggaagta[ATT]ctttcgcgcacctcatgaatcccttctgcagcacc[GCA]atcgcttttccgagct[CAG]ggccggtccaagcactactacgtcagcacctgggaccc

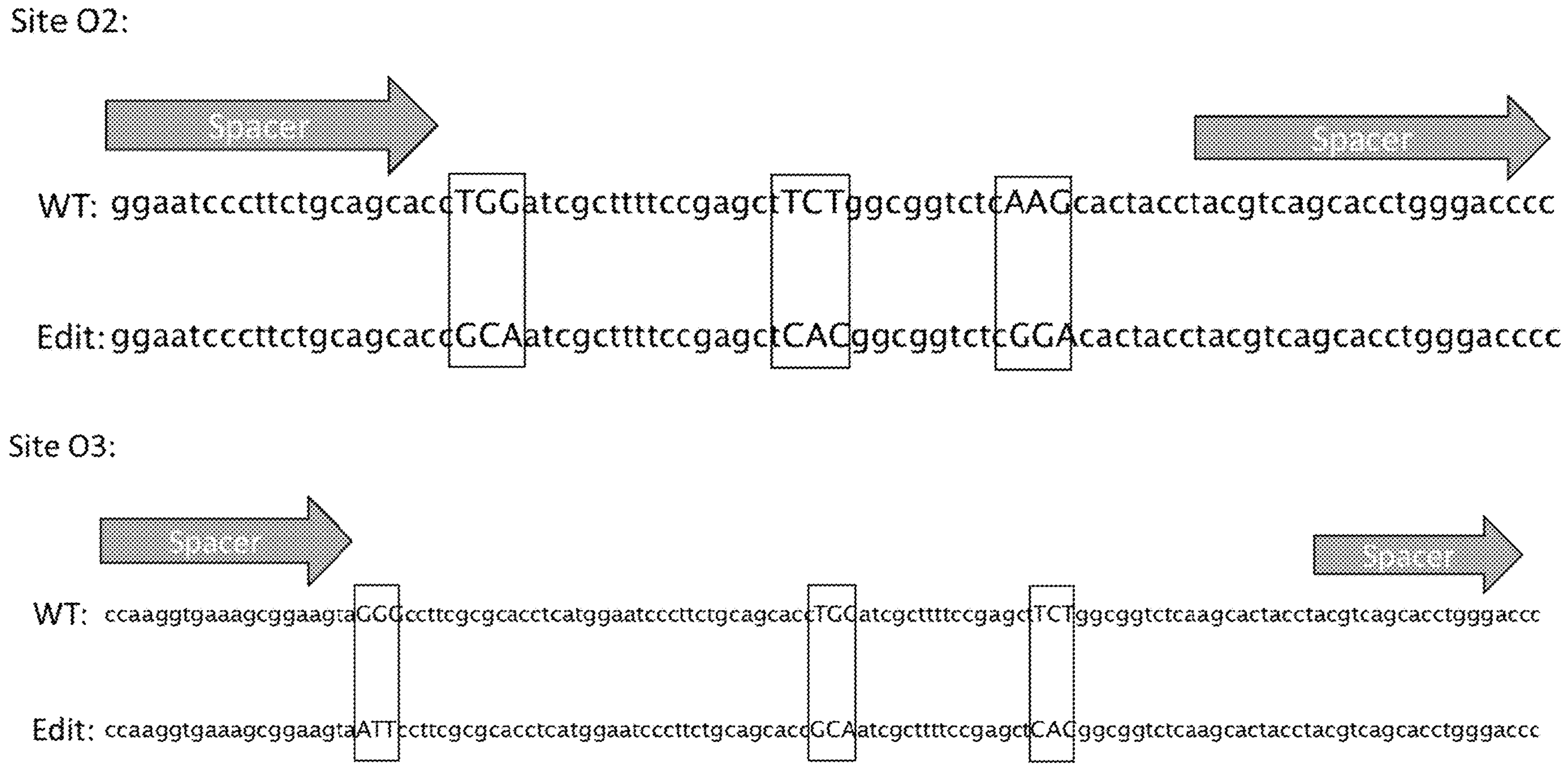

FIG. 12

COMPOSITIONS AND METHODS FOR RNA-TEMPLATED EDITING IN PLANTS

STATEMENT REGARDING ELECTRONIC FILING OF A SEQUENCE LISTING

A Sequence Listing in ASCII text format, submitted under 37 C.F.R. § 1.821, entitled 1499-11 ST25.txt, 408,234 bytes in size, generated on Feb. 2, 2021 and filed via EFS-Web, is provided in lieu of a paper copy. This Sequence Listing is hereby incorporated herein by reference into the specification for its disclosures.

FIELD OF THE INVENTION

This invention relates to recombinant nucleic acid constructs encoding a DNA binding polypeptide, an endonuclease and/or a reverse transcriptase and to methods of modifying a nucleic acid in a plant.

BACKGROUND OF THE INVENTION

Base editing has been shown to be an efficient way to change cytosine and adenine residues to thymine and guanine, respectively. These tools, while powerful, do have some limitations such as bystander bases, small base editing windows that give limited accessibility to trait-relevant targets unless enzymes with high PAM density are available to compensate, limited ability to convert cytosines and adenines to residues other than thymine and guanine, respectively, and no ability to edit thymine or guanine residues. Thus, the current tools available for base editing are limited, particularly in plants. Therefore, to make nucleic acid editing more useful across a greater number of organisms, including plants, new editing tools are needed.

SUMMARY OF THE INVENTION

A first aspect of the present invention is directed to a method of modifying a target nucleic acid in a plant cell, the method comprising: contacting the target nucleic acid with (a) a DNA binding domain (e.g., a first DNA binding domain); (b) a DNA endonuclease (e.g., a first DNA endonuclease); and (c) a reverse transcriptase (e.g., a first reverse transcriptase), thereby modifying the target nucleic acid in the plant cell.

Another aspect of the present invention is directed to an expression cassette codon optimized for expression in a plant, comprising 5' to 3' (a) polynucleotide encoding a plant specific promoter sequence (e.g., ZmUbi1, MtUb2, RNA polymerase II (Pol II)), (b) a plant codon-optimized polynucleotide encoding a CRISPR-Cas nuclease (e.g. nCas9, dCas9, Cpf1 (Cas12a), dCas12a and the like); (c) a linker sequence; and (d) a plant codon-optimized polynucleotide encoding a reverse transcriptase.

A further aspect of the present invention is directed to an expression cassette codon optimized for expression in a plant, comprising: (a) a polynucleotide encoding a plant specific promoter sequence (e.g., ZmUbi1, MtUb2), and (b) an extended guide nucleic acid, wherein the extended guide nucleic acid comprises an extended portion comprising at its 3' end a primer binding site and an edit to be incorporated into the target nucleic acid (e.g., reverse transcriptase template), optionally wherein the extended guide nucleic acid is comprised in an expression cassette, optionally wherein the extended guide nucleic acid is operably linked to a Pol II promoter.

An additional aspect of the present invention is directed to a method of modifying a target nucleic acid in a plant cell, comprising contacting the target nucleic acid with a DNA binding domain and a DNA endonuclease domain targeted to a first site on the target nucleic acid and the same or a different DNA binding domain and DNA endonuclease domain targeted to a second site on the target nucleic acid, wherein the first site and the second site are proximal to one another on the same (nontarget) strand, thereby nicking the target nucleic acid at the first and second site; a reverse transcriptase; and a nucleic acid encoded repair template encoding a modification to be incorporated into the target nucleic acid, thereby modifying the target nucleic acid in the plant.

Another aspect of the present invention is directed to a method of modifying a target nucleic acid in a plant cell, the method comprising: contacting the target nucleic acid with (a) a CRISPR-Cas nuclease comprising a first DNA binding domain and a first DNA endonuclease (a nickase); (b) a reverse transcriptase; (c) a CRISPR RNA (crRNA) comprising a spacer having substantial homology to a first site on the target nucleic acid; (d) a trans-activating crRNA (tracrRNA) that interacts (recruits/binds) with the crRNA and the CRISPR-Cas nuclease; and (e) a nucleic acid encoded repair template (e.g., an RNA encoded repair template) comprising a primer binding site and an template encoding the modification to be incorporated into the target nucleic acid, wherein the tracrRNA comprises a sequence at the 5' or 3' end that is complementary to a sequence at the 5' end or 3' end of the reverse transcriptase template, thereby modifying the target nucleic acid.

A further aspect of the present invention is directed to a method of modifying a target nucleic acid in a plant cell, the method comprising: contacting the target nucleic acid with (a) a CRISPR-Cas nuclease comprising a first DNA binding domain and a first DNA endonuclease (a nickase); (b) a reverse transcriptase; (c) a CRISPR RNA (crRNA) comprising a spacer having substantial homology to a first site on the target nucleic acid; (d) a trans-activating crRNA (tracrRNA) that interacts (recruits/binds) with the crRNA and the CRISPR-Cas nuclease; and (e) a nucleic acid encoded repair template (e.g., an RNA encoded repair template) comprising a primer binding site and an template encoding the modification to be incorporated into the target nucleic acid, thereby modifying the target nucleic acid.

Another aspect of the present invention is directed to a method of modifying a target nucleic acid in a plant cell, the method comprising: contacting the target nucleic acid with (a) a CRISPR-Cas nuclease comprising a first DNA binding domain and a first DNA endonuclease (a nickase); (b) a reverse transcriptase; (c) a CRISPR RNA (crRNA) guide that interacts (recruits/binds) with the CRISPR-Cas nuclease and comprises a spacer having substantial homology to a first site on the target nucleic acid; and (e) a nucleic acid encoded repair template (e.g., an RNA encoded repair template) comprising a primer binding site and an RNA template (that encodes the modification to be incorporated into the target nucleic acid), wherein the crRNA comprises a sequence at its 5' end or 3' end that is complementary to the primer binding site, thereby modifying the target nucleic acid.

A further aspect of the present invention is directed to a method of modifying a target nucleic acid in a plant cell, the method comprising: contacting the target nucleic acid with (a) a CRISPR-Cas nuclease comprising a first DNA binding domain and a first DNA endonuclease (e.g., a nickase); (b) a reverse transcriptase; (c) an extended guide nucleic acid comprising a sequence that interacts that interacts (recruits/binds) with the CRISPR-Cas nuclease and a spacer having substantial homology to a first site on the target nucleic acid (e.g., CRISPR RNA (crRNA) (a first crRNA) and/or tracrRNA+crRNA (sgRNA)) and a nucleic acid encoded repair template (e.g., an RNA encoded repair template) comprising a primer binding site and an RNA template (that encodes the modification to be incorporated into the target nucleic acid), thereby modifying the target nucleic acid.

An additional aspect of the present invention is directed to a method of modifying a target nucleic acid in a plant cell, the method comprising: contacting the target nucleic acid with (a) a first CRISPR-Cas nuclease (a nickase) comprising a first DNA binding domain and a first DNA endonuclease; (b) an extended guide nucleic acid comprising a CRISPR RNA (crRNA) comprising a spacer having substantial homology to a first site on the target nucleic acid, a trans-activating crRNA (tracrRNA) that recruits the first CRISPR-Cas nuclease and an RNA template comprising the modification to be incorporated into the target nucleic acid, wherein the first CRISPR-Cas nuclease nicks the target nucleic acid at a first site (on the non-target strand); (c) a second CRISPR Cas-nuclease (a nickase) comprising a first DNA binding domain and a first DNA endonuclease (a nickase); (d) a guide nucleic acid comprising a CRISPR RNA (crRNA) comprising a spacer having substantial homology to a second site on the target nucleic acid that is proximal to (and on the same strand as) the first site on the target nucleic acid, a trans-activating crRNA (tracrRNA) that recruits the second CRISPR-Cas nuclease, thereby nicking the DNA at the second site (on the non-target strand); and (e) a reverse transcriptase fused or recruited to the first CRISPR Cas-nuclease and/or the second CRISPR Cas-nuclease, thereby modifying the target nucleic acid.

A further aspect of the present invention is directed to a method of releasing a portion of a double stranded nucleic acid, comprising: (a) targeting a first DNA endonuclease to a first site of the nucleic acid; (b) making a nick at in a first strand of the nucleic acid at the first site; (c) targeting the first DNA endonuclease or a second DNA endonuclease to a second site on the first strand; and (d) making a nick in the first strand at the second site, wherein the portion of the first strand of the nucleic acid between the first site and second site can be released from the nucleic acid.

The invention further provides expression cassettes and/or vectors comprising a nucleic acid construct of the present invention, and cells comprising a polypeptide, fusion protein and/or nucleic acid construct of the present invention. Additionally, the invention provides kits comprising a nucleic acid construct of the present invention and expression cassettes, vectors and/or cells comprising the same.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 12 is a diagram of two target sites for testing of reverse transcriptase recruitment through MS2 loops. Spacer binding sites are shown with arrows and designed changes shown in boxes. WT sequence for site O2 (SEQ ID NO:77); Edit sequence for site O2 (SEQ ID NO:78); WT sequence for site O3 (SEQ ID NO:79); and Edit sequence for site O3 (SEQ ID NO:80).

DETAILED DESCRIPTION

Figure 1:
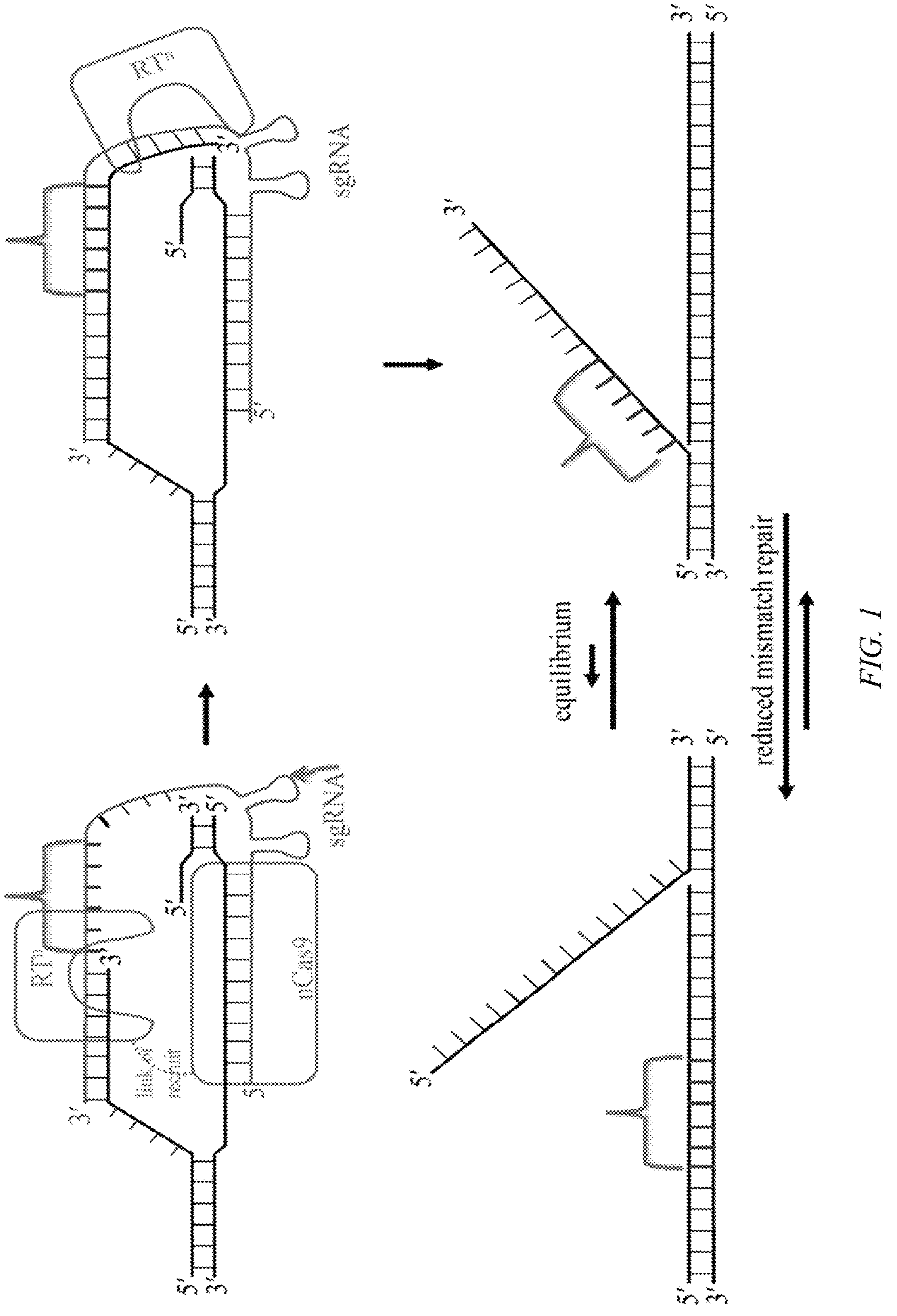
FIG. 1 provides a schematic showing the generation of DNA sequences from reverse transcription off the sgRNA and subsequent integration into the nick site. The extended sgRNA is shown in light gray and is bound to the non-target strand nickase Cas9 (nCas9, upper left). The 3' end of the sgRNA is complimentary to the DNA at the nick site (black pairing lines, upper left). The RT then polymerizes DNA from the 3' end of the DNA nick generating a DNA sequence with non-complimentary nucleotides (pairing lines indicated by bracket, upper right) followed by complimentary nucleotides (black pairing lines, upper right). Upon dissociation, the resultant DNA has an extended ssDNA with a 3' overhang which is largely the same sequence as the original DNA (black pairing lines, lower right) but with some non-native nucleotides (pairing lines indicated by bracket, lower right). This flap is in equilibrium with a structure having a 5' overhang (lower left) where there are mismatched nucleotides incorporated into the DNA.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "recombinant nucleic acid," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., "substantially complementary" such as about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence or polypeptide will be understood to mean a nucleotide sequence or polypeptide of reduced length (e.g., reduced by 1, 2, 3, 4, 5, 6, 7, 8, 9, 10, 11, 12, 13, 14, 15, 16, 17, 18, 19, 20 or more residue(s) (e.g., nucleotide(s) or peptide(s)) relative to a reference nucleotide sequence or polypeptide, respectively, and comprising, consisting essentially of and/or consisting of contiguous residues identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleotide sequence or polypeptide. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part 1 chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention can be codon optimized for expression. In some embodiments, a polynucleotide, nucleic acid construct, expression cassette, and/or vector of the invention (e.g., comprising/encoding a DNA binding domain, a DNA endonuclease, a reverse transcriptase, a flap endonuclease, and/or the like) are codon optimized for expression in an organism (e.g., an animal, a plant (e.g., in a particular plant species), a fungus, an archaeon, or a bacterium). In some embodiments, the codon optimized nucleic acid constructs, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acid constructs, polynucleotides, expression cassettes, and/or vectors but which have not been codon optimized.

In any of the embodiments described herein, a polynucleotide or nucleic acid construct of the invention may be operatively associated with a variety of promoters and/or other regulatory elements for expression in an organism or cell thereof (e.g., a plant and/or a cell of a plant). Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron may be referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked" or "fused" in reference to polypeptides, refers to the attachment of one polypeptide to another. A polypeptide may be linked (e.g., fused) to another polypeptide (at the N-terminus or the C-terminus) directly (e.g., via a peptide bond) or through a linker (e.g., a peptide linker).

The term "linker" in reference to polypeptides is art-recognized and refers to a chemical group, or a molecule linking two molecules or moieties, e.g., two domains of a fusion protein, such as, for example, a fusion protein comprising a DNA binding polypeptide (e.g., a DNA binding domain) and a peptide tag (e.g., a peptide repeat unit), a fusion protein comprising a a reverse transcriptase and an affinity polypeptide that binds to the peptide tag, a fusion protein comprising a DNA endonuclease polypeptide (e.g., a DNA binding domain) and peptide tag, and/or a fusion protein comprising a reverse transcriptase and an affinity polypeptide that binds to the peptide tag. A linker may be comprised of a single linking molecule (e.g., a single amino acid) or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g. extension of the hairpin structure in guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NOs:1 or 2).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in European patent publication EP0342926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, incorporated herein by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); European patent EP0452269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2 USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), $PLA_2$-δ promoter from *arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHES) (Kim et al, *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-metinorine synthetase (S AMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., a DNA binding polypeptide or domain (e.g. a CRISPR-Cas nuclease, a transcription activator-like effector (TALE) protein domain or polypeptide, and/or a zinc finger protein domain or polypeptide), an endonuclease polypeptide or domain (e.g., a CRISPR-Cas nuclease, and/or a Fok1 endonuclease), a reverse transcriptase polypeptide or domain, and/or a flap endonuclease polypeptide or domain (e.g., FEN)), wherein the nucleic acid construct is operably associated with at one or more control sequences (e.g., a promoter, terminator and the like). Thus, some embodiments of the invention provide expression cassettes designed to express, for example, a nucleic acid construct of the invention (e.g., a nucleic acid construct of the invention encoding a DNA binding polypeptide or domain, an endonuclease polypeptide or domain, a reverse transcriptase polypeptide or domain, a flap endonuclease polypeptide or domain and/or nucleic acid modifying polypeptide or domain. When an expression cassette comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter or they may be different promoters. Thus, a polynucleotide encoding a DNA binding polypeptide or domain, a polynucleotide encoding an endonuclease polypeptide or domain, a polynucleotide encoding a reverse transcriptase polypeptide or domain, a polynucleotide encoding a flap endonuclease polypeptide or domain and/or a polynucleotide encoding a nucleic acid modifying polypeptide or domain comprised in an expression cassette may each be operably linked to a separate promoter or they may be operably linked to two or more promoters in any combination.

In some embodiments, an expression cassette and the polynucleotides comprised therein in may be optimized for expression in an organism (e.g., an animal, a plant, a bacterium and the like).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to a gene encoding a DNA binding polypeptide, a gene encoding an endonuclease polypeptide, a gene encoding a reverse transcriptase, a gene encoding a flap endonuclease, and/or a gene encoding a nucleic acid modifying polypeptide nuclease, may be native to a host cell, or may be native to another source (e.g., foreign or heterologous to the promoter, to a gene encoding the DNA binding polypeptide, to the gene encoding an endonuclease polypeptide, to the gene encoding a reverse transcriptase, to the gene encoding a flap endonuclease, to the gene encoding a nucleic acid modifying polypeptide nuclease, to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

The expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or Agrobacterium binary vectors in double or single stranded linear or circular form which may or may not be self transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a nucleic acid binding domain (e.g., a DNA binding domain such as a sequence-specific DNA binding protein (e.g., polynucleotide-guided endonuclease, a CRISPR-Cas effector protein (e.g., CRISPR-Cas endonuclease), a zinc finger nuclease, a transcription activator-like effector nuclease (TALEN) and/or an Argonaute protein), and a reverse transcriptase or a nucleic acid construct encoding the same, under conditions whereby the nucleic acid binding domain (e.g., CRISPR-Cas nuclease) and the reverse transcriptase are expressed and the nucleic acid binding domain binds to the target nucleic acid, and the reverse transcriptase is either fused to the nucleic acid binding domain or is recruited to the nucleic acid binding domain (e.g., via a peptide tag (e.g., peptide repeat unit) fused to the nucleic acid binding domain and an affinity tag fused to the reverse transcriptase) (and thus, the reverse transcriptase is positioned in the vicinity of the target nucleic acid), thereby modifying the target nucleic acid. In some embodiments, the reverse transcriptase and the nucleic acid binding domain (e.g., CRISPR-Cas endonuclease) localize at the target nucleic acid, optionally through covalent and/or non-covalent interactions.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid. In some embodiments, a modification may include an indel of any size and/or a single base change (SNP) of any type.

"Recruit," "recruiting" or "recruitment" as used herein refer to attracting one or more polypeptide(s) or polynucleotide(s) to another polypeptide or polynucleotide (e.g., to a particular location in a genome) using protein-protein interactions, RNA-protein interactions, and/or chemical interactions. Protein-protein interactions can include, but are not limited to, peptide tags (epitopes, multimerized epitopes) and corresponding affinity polypeptides, RNA recruiting motifs and corresponding affinity polypeptides, and/or chemical interactions. Example chemical interactions that may be useful with polypeptides and polynucleotides for the purpose of recruitment can include, but are not limited to, rapamycin-inducible dimerization of FRB-FKBP; Biotin-streptavidin interaction; SNAP tag (Hussain et al. *Curr Pharm Des.* 19(30):5437-42 (2013)); Halo tag (Los et al. *ACS Chem Biol.* 3(6):373-82 (2008)); CLIP tag (Gautier et al. *Chemistry & Biology* 15:128-136 (2008)); DmrA-DmrC heterodimer induced by a compound (Tak et al. *Nat Methods* 14(12):1163-1166 (2017)); Bifunctional ligand approaches (fuse two protein-binding chemicals together) (Voβ et al. *Curr Opin Chemical Biology* 28:194-201 (2015)) (e.g. dihyrofolate reductase (DHFR) (Kopyteck et al. Cell Chem Biol 7(5):313-321 (2000)).

"Introducing," "introduce," "introduced" (and grammatical variations thereof) in the context of a polynucleotide of interest means presenting a nucleotide sequence of interest (e.g., polynucleotide, a nucleic acid construct, and/or a guide nucleic acid) to a host organism or cell of said organism (e.g., host cell; e.g., a plant cell) in such a manner that the nucleotide sequence gains access to the interior of a cell. Thus, for example, a nucleic acid construct of the invention encoding a DNA binding domain, a DNA endonuclease, and/or a reverse transcriptase may be introduced into a cell of an organism, thereby transforming the cell with the DNA binding domain, the DNA endonuclease, and/or the reverse transcriptase.

The terms "transformation" or transfection" may be used interchangeably and as used herein refer to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromosomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes encoding a DNA binding polypeptide or domain, an endonuclease polypeptide or domain, a reverse transcriptase polypeptide or domain, a flap endonuclease polypeptide or domain and/or nucleic acid modifying polypeptide or domain) may be transiently introduced into a cell with a guide nucleic acid and as such, no DNA maintained in the cell.

A nucleic acid construct of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence can be incorporated into a plant, for example, as part of a breeding protocol.

Base editing has been shown to be an efficient way to change cytosine and adenine residues to thymine and guanine, respectively. These tools, while powerful, do have some limitations such as bystander bases, small base editing windows, and limited PAMs.

To perform precise templated editing in cells there are several essential steps, each of which has rate limitations that together can severely hamper the ability to effectively perform editing due to low efficiencies. For example, one step requires inducing the cell to initiate a repair event at the target site. This is typically performed by causing a double-strand break (DSB) or nick by an exogenously provided, sequence-specific nuclease or nickase. Another step requires local availability of a homologous template to be used for the repair. This step requires the template to be in the proximity of the DSB at exactly the right time when the DSB is competent to commit to a templated editing pathway. In particular, this step is widely regarded to be the rate limiting step with current editing technologies. A further step is the efficient incorporation of sequence from the template into the broken or nicked target. Prior to the present invention, this step was typically provided by the cell's endogenous DNA repair enzymes. The efficiency of this step is probably low and is very difficult to manipulate. The present invention bypasses many of the major obstacles to the efficiency of the process of templated editing by co-localizing, in a coordinate fashion, the functionalities required to carry out the steps described above.

FIG. 1 shows the generation of DNA sequences from reverse transcription off the sgRNA and subsequent integration into the nick site using methods and constructs of the present invention. An extended sgRNA is shown in light gray and is bound to the non-target strand nickase Cas9 (nCas9, upper left) (e.g., a binding domain and a DNE endonuclease domain (e.g. H840A)). As described in more detail herein, the nCas9 may be either covalently linked via, for example, a peptide to a reverse transcriptase (RT) or the RT may be recruited to the nCas9 (e.g., via the use of a peptide repeat unit motif/affinity polypeptide that binds to the peptide repeat unit as described herein), in which case multiple reverse transcriptase proteins (RP) may be recruited. The 3' end of the sgRNA is complimentary to the DNA at the nick site (black pairing lines, upper left). The RT then polymerizes DNA from the 3' end of the DNA nick generating a DNA sequence with non-complimentary nucleotides (pairing lines indicated by bracket, upper right) followed by complimentary nucleotides (black pairing lines, upper right). Upon dissociation, the resultant DNA has an extended ssDNA with a 3' overhang which is largely the same sequence as the original DNA (black pairing lines, lower right) but with some non-native nucleotides (pairing lines indicated by bracket, lower right). This flap is in equilibrium with a structure having a 5' overhang (lower left) where there are mismatched nucleotides incorporated into the DNA. This equilibrium lies more to the favorable perfect pairing on the right, but can be driven may be reduced in a variety of ways including, for example, nicking the target strand. The structure on the left is preferentially cleaved by cellular flap endonucleases involved in DNA lagging strand synthesis, which are highly conserved between mammalian and plant cells (the amino acid sequence of *Homo sapiens* FEN1 is over 50% identical to both *Zea mays* and *Glycine max* FEN1). Thus, a flap endonuclease may be introduced to drive the equilibrium in the direction of the 3' flap comprising the non-native/mismatched nucleotides.

Figure 2:
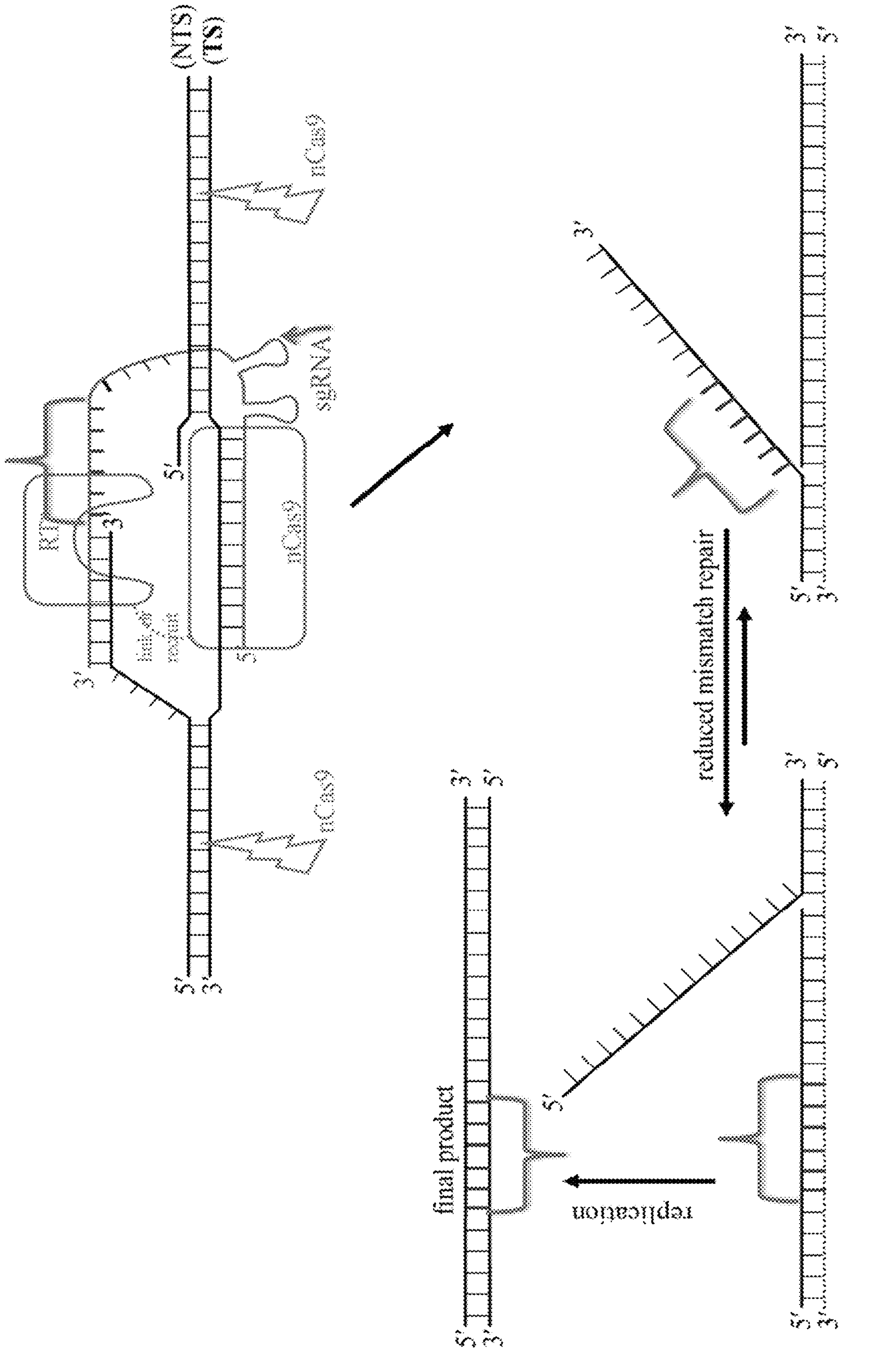
FIG. 2 provides a schematic of reducing mismatch repair. In order to drive the equilibrium more in favor of forming the final product with the modified nucleotides (indicated by bracket), a target strand (TS) nickase is targeted to regions outside of the RT-editing bubble (lightning bolts). The nCas9:sgRNA molecules may be on either side or both sides of the editing bubble. Nicking the target strand (dashed line) indicates to the cell that the newly incorporated nucleotides are the correct nucleotides during mismatch repair and replication, thus favoring a final product with the new nucleotides.

Further in the process of the present invention, and as exemplified in FIG. 2, to reduce mismatch repair and to drive the equilibrium more in favor of forming the final product with the modified nucleotides (indicated by bracket), a target strand (TS) nickase, for example, Cas9-D10A, is targeted to regions outside of the RT-editing bubble (lightning bolts). The nCas9:sgRNA molecules may be on either side or both sides of the editing bubble. Nicking the target strand (dashed line) indicates to the cell that the newly incorporated nucleotides are the correct nucleotides during mismatch repair and replication, thus favoring a final product with the new nucleotides.

Variants of the reverse transcriptase (RT) enzyme can have significant effects on the temperature-sensitivity and processivity of the editing system. Natural and rationally- and irrationally-engineered (i.e., directed evolution) variants of the RT may be useful in optimizing activity in plant-preferred temperatures and for optimizing processivity profiles.

Protein domain fusions to the RT enzyme can have significant effects on the temperature-sensitivity and processivity of the editing system. The RT enzyme can be improved for temperature-sensitivity, processivity, and template affinity through fusions to ssRNA binding domains (RBDs). These RBDs may have sequence specificity, non-specificity or sequence preferences. A range of affinity distributions may be beneficial to editing in different cellular and in vitro environments. RBDs can be modified in both specificity and binding free energy through increasing or decreasing the size of the RBD in order to recognize more or fewer nucleotides. Multiple RBDs result in proteins with affinity distributions that are a combination of the individual RBDs. Adding one or more RBD to the RT enzyme can result in increased affinity, increased or decreased sequence specificity, and/or promote cooperativity.

After reverse transcriptase incorporates the edit into the genome, a sequence redundancy exists between the newly synthesized edited sequence and the original WT sequence it is intended to replace. This leads to either a 5' or 3' flap at the target site, which has to be repaired by the cell. The two states exist in an equilibrium. Binding energy favors the 3' flap because more base pairs are available when the WT sequence is paired with its complement than when the edited strand is paired with its complement. This is unfavorable for efficient editing because processing (removal) of the 3' flap would remove the edited residues and revert the target back to WT sequence. However, cellular flap endonucleases such as FEN1 can efficiently process 5' flaps. Thus, instead of relying on the function of 5'-flap endonucleases native to the cell, in some embodiments of this invention the concentration of flap endonucleases at the target may be increased to further favor the desirable equilibrium outcome (removal of the WT sequence in the 5' flap so that the edited sequence becomes stably incorporated at the target site). This may be achieved by overexpression of a 5' flap endonuclease as a free protein in the cell. Alternatively, FEN may be actively recruited to the target site by association with the CRISPR complex, either by direct protein fusion or by non-covalent recruitment such as with a peptide tag (e.g., a peptide repeat unit) and affinity polypeptide pair (e.g., a SunTag antibody/epitope pair).

Thus, in some embodiments, a method of modifying a target nucleic acid in a plant cell is provided, the method comprising: contacting the target nucleic acid with (a) a DNA binding domain (e.g., a first DNA binding domain); (b) a DNA endonuclease (e.g., a first DNA endonuclease); and (c) a reverse transcriptase (e.g., a first reverse transcriptase), thereby modifying the target nucleic acid. In some embodiments, the (a) DNA binding domain; (b) the DNA endonuclease; and (c) the reverse transcriptase are comprised in a complex. In some embodiments, the DNA binding protein is a DNA binding fusion protein comprising a DNA binding protein domain fused (linked) to a peptide tag (e.g., peptide repeat unit, an epitope or a multimerized epitope) and/or the DNA endonuclease is a DNA endonuclease fusion protein comprising a DNA endonuclease domain fused (linked) to a peptide tag (e.g., a peptide repeat unit, an epitope or a multimerized epitope) and the reverse transcriptase is a reverse transcriptase fusion protein comprising a reverse transcriptase domain fused (e.g., linked) to an affinity polypeptide that binds to the peptide tag, optionally wherein the target nucleic acid is contacted with two or more reverse transcriptase fusion proteins.

In some embodiments, the DNA binding domain may be a CRISPR-Cas nuclease domain, a transcription activator-like effector (TALE) protein domain, and/or a zinc finger protein domain. In some embodiments, the DNA endonuclease may be a CRISPR-Cas nuclease, and/or a Fok1 endonuclease. In some embodiments, a DNA binding domain (a) and/or a DNA endonuclease (b) may be comprised in a CRISPR-Cas nuclease. In some embodiments, the CRISPR-Cas nuclease is a Cas9 nickase (nCas9). In some embodiments, the DNA binding domain may be a CRISPR-Cas nuclease comprising a mutation in one or more nuclease active sites (e.g., in the RuvC domain, in the HNH domain) (e.g., deactivated or deadCas (dCas)), optionally a dCas9 or dCas12a. In some embodiments, the DNA endonuclease is a Fok1 endonuclease.

In some embodiments, a method of the invention may further comprise contacting the target nucleic acid with an extended guide nucleic acid (e.g., a pegRNA), wherein the extended guide nucleic acid comprises an extended portion comprising a primer binding site and a reverse transcriptase template, wherein the reverse transcriptase template comprises the edit to be incorporated into the target nucleic acid, optionally wherein the extended guide nucleic acid is comprised in an expression cassette, optionally wherein the extended guide nucleic acid is operably linked to a Pol II promoter.

In some embodiments, an extended guide RNA may comprise, 5'-3', a spacer sequence, a repeat sequence, and an extended portion, the extended portion comprising, 5' to 3', a reverse transcriptase template and a primer binding site. In some embodiments, an extended guide RNA may comprise, 5'-3', a spacer sequence, a repeat sequence and an extended portion, the extended portion comprising, 5' to 3', a primer binding site and a reverse transcriptase template. In some embodiments, an extended guide RNA may comprise, 5'-3', an extended portion, a spacer sequence, and a repeat sequence, wherein the extended portion comprises, 5' to 3', a reverse transcriptase template and a primer binding site. In some embodiments, an extended guide RNA may comprise, 5'-3', an extended portion, a spacer sequence, and a repeat sequence, wherein the extended portion comprises, 5' to 3', a primer binding site and a reverse transcriptase template.

In some embodiments, an extended guide nucleic acid may be linked to an RNA recruiting motif, and the reverse transcriptase may be a reverse transcriptase fusion protein comprising a reverse transcriptase domain fused (linked) to an affinity polypeptide that binds to the RNA recruiting motif, optionally wherein the target nucleic acid is contacted with two or more reverse transcriptase fusion proteins. In some embodiments, a reverse transcriptase may be recruited through RNA recruitment, which may direct the reverse transcriptase to the exact template location on the extended guide nucleic acid. In some embodiment, the extended guide nucleic acid comprises a peptide tag (e.g., a protein-recruitment scaffold such as, but not limited to, a MS2 phage operator stem-loop, a PP7 phage operator stem-loop or a SfMu phage Com stem-loop) that can be used to recruit the reverse transcriptase as the reverse transcriptase comprises an affinity polypeptide that corresponds to the peptide tag (e.g., a protein recruitment domain such as, but not limited to, a MS2 Coat Protein (MCP) polypeptide, a PP7 Coat Protein (PCP) polypeptide, or a Com RNA binding protein polypeptide).

According to some embodiments, an extended guide nucleic acid (e.g., a pegRNA) may have a structure and/or be designed as described in Anzalone et al., *Nature,* 2019 December; 576(7785): 149-157. In some embodiments, an extended guide nucleic acid comprises a primer binding site (PBS) optionally having a sequence of 1, 2, 3, 4, or 5 to 6, 7, 8, 9, 10, 11, 12, 13, 14, or 15 nucleotides and a reverse transcriptase template (RT template) sequence optionally having a sequence of 65 nucleotides or more. In some embodiments, the PBS of the extended guide nucleic acid has a sequence of less than 15 nucleotides and has a sequence of 1, 2, 3, 4, 5, 6, 7, 8, 9, 10, 11, 12, 13, or 14 nucleotides (e.g., a sequence of 5 or 6 nucleotides in length). The RT template sequence may be after the PBS sequence in the 5' to 3' direction. In some embodiments, the RT template sequence of the extended guide nucleic acid has a length of greater than 65 nucleotides and may comprise about 50 or more nucleotides of heterology relative to the target site (e.g., target nucleic acid), followed by about 15 or more nucleotides of homology relative to the target site. In some embodiments, the RT template sequence of the extended guide nucleic acid is after the PBS sequence and the RT template sequence has a length of greater than 65 nucleotides with the sequence including more than 50 nucleotides of heterology relative to the target site, followed by more than 15 nucleotides of homology relative to the target site. Accordingly, in some embodiments, when the extended guide nucleic acid is reverse transcribed, the resulting newly transcribed sequence may hybridize and/or is configured to hybridize with the unnicked strand of the target site, which may thereby create a heteroduplex DNA with a large insertion into the newly synthesized strand. Upon repair of this mismatched DNA, the resultant repaired DNA may contain a large insertion (e.g., greater than 50 nucleotides) of DNA sequence. In some embodiments, the method may provide a large deletion (e.g., greater than 50 nucleotides) of DNA sequence. In some embodiments, the PBS and the 15 or more nucleotides of homology to the target site may comprise homology arms, which may serve to insert the heterology into the target site optionally using homology directed repair. The inserted DNA may correspond to any functional sequence of DNA such as, but not limited to: a functional transgene; a fragment of DNA that is inserted into a gene in a way that, when the gene is transcribed, would produce a hairpin RNA that is sufficient to silence homologous genes through RNAi; and/or one or more functional site-specific recombination sites, e.g. lox, frt, which could then be used in subsequent Cre or Flp mediated site-specific recombination processes. In some embodiments, an extended guide nucleic acid may be too large to produce using a PolIII promoter in vivo. In some embodiments, an extended guide nucleic acid may be operatively associated with and/or produced using a PolII promoter. In some embodiments, the DNA binding domain and/or DNA endonuclease may have a structure and/or be designed as described in Anzalone et al., Nature, 2019 December; 576(7785): 149-157. In some embodiment, the DNA binding domain and/or DNA endonuclease is a CRISPR Cas polypeptide such as a Cas9 nickase or a similar nicking variant of another CRISPR Cas polypeptide such as, but not limited to, Cas12a.

In some embodiments, a polypeptide, polynucleotide, complex, composition, system, kit, and/or method of the present invention may be used to make and/or may make large edits (e.g., greater than 50 nucleotides in length) using homology directed repair. Exemplary large edits include, but are not limited to; large deletions, large inversions, inter-chromosomal recombinations, and/or intra-chromosomal recombinations. In some embodiments, a polypeptide, polynucleotide, complex, composition, system, kit, and/or method of the present invention may be used in and/or may be configured for use in a one cross editing (1XE) method and/or system in which modifying a target nucleic acid occurs during the step of haploid induction.

In some embodiments, two extended guide nucleic acids (e.g., pegRNAs) may be used. One or both of the extended guide nucleic acids may have a structure and/or be designed as described in Anzalone et al., Nature, 2019 December; 576(7785): 149-157. The extended guide nucleic acids may comprise a primer binding site (PBS) optionally having a sequence of 1, 2, 3, 4, or 5 to 6, 7, 8, 9, 10, 11, 12, 13, 14, or 15 nucleotides and a reverse transcriptase template (RT template) sequence optionally having a sequence of 50 nucleotides or more. The RT template sequences of the two extended guide nucleic acids are complementary to each other and as such the polynucleotides that are respectively reverse transcribed from each the RT templates will be complementary to each other and will be able to hybridize with each other. This may allow for the intermediates that are produced by this system and/or method to join together two sections of DNA that are otherwise separated by more than 50 nucleotides, e.g. within a chromosome, or that are positioned on two separate pieces of DNA, e.g. on two different chromosomes. After repair of the intermediates, the resultant products may produce, depending on the design of the RT template, large deletions, large inversions, or inter-chromosomal recombinations. Since all of these products are produced by homology directed repair, the products may be predictably precise and/or reproducible. In some embodiments, the DNA binding domain and/or DNA endonuclease may have a structure and/or be designed as described in Anzalone et al., Nature, 2019 December; 576(7785): 149-157. In some embodiment, the DNA binding domain and/or DNA endonuclease is a CRISPR Cas polypeptide such as a Cas9 nickase or a similar nicking variant of another CRISPR Cas polypeptide such as, but not limited to, Cas12a. In some embodiments, the DNA binding domain and/or DNA endonuclease is a Cas9 nuclease or a similar nuclease from another CRISPR Cas polypeptide such as, but not limited to, Cas12a. Using a nuclease (rather than a nickase) may facilitate the intra- or intrachromosomal recombination processes through single-strand annealing of the more than 50 nucleotide 3' overhangs that would be produced at each of the two target sites corresponding to the two pegRNA target nucleic acids.

In some embodiments, a polypeptide, polynucleotide, complex, composition, system, kit, and/or method of the present invention may be directed by homology to modify a target nucleic acid. In some embodiments, a polypeptide, polynucleotide, complex, composition, system, kit, and/or method of the present invention may be used to make and/or may make identical modifications (e.g., edits) in a target nucleic acid. In some embodiments, a polypeptide, polynucleotide, complex, composition, system, kit, and/or method of the present invention may be used to make and/or may make identical modifications (e.g., edits) in a target nucleic acid that are produced independently multiple times optionally in multiple germplasms.

In some embodiments, a DNA binding domain may be encoded by a polynucleotide, a DNA endonuclease may be encoded by a polynucleotide and a reverse transcriptase may be encoded by a polynucleotide. In some embodiments, the polynucleotide encoding the DNA binding domain, the polynucleotide encoding the DNA endonuclease and the polynucleotide encoding the reverse transcriptase may be comprised in the same or separate expression cassettes, optionally wherein when present in the same expression cassette, the polynucleotide encoding the DNA binding domain, the polynucleotide encoding the DNA endonuclease and the polynucleotide encoding the reverse transcriptase may be operably linked to a single promoter or they may be linked to two or more separate promoters in any combination.

In some embodiments, the expression cassettes of the invention may be comprised in one or more vectors. In some embodiments, the expression cassettes and/or the one or more vectors of the invention may comprise a guide RNA and/or an extended guide RNA.

In some embodiments, the methods of the invention may further comprises contacting the target nucleic acid with a second DNA binding domain, a second DNA endonuclease, and an RNA encoded template, optionally wherein the second DNA binding domain, the second DNA endonuclease, and the second reverse transcriptase are comprised in a complex.

In some embodiments, the second DNA binding protein may be a second DNA binding fusion protein comprising a second DNA binding protein domain fused (linked) to a peptide tag (e.g., a peptide repeat unit, an epitope or a multimerized epitope) and/or the second DNA endonuclease may be a second DNA endonuclease fusion protein comprising a second DNA endonuclease domain fused (linked) to a peptide tag (e.g., a peptide repeat unit, an epitope or a multimerized epitope), and the second reverse transcriptase may be a second reverse transcriptase fusion protein comprising a second reverse transcriptase domain fused (linked) to an affinity polypeptide that binds to the peptide tag, optionally wherein the target nucleic acid may be contacted with two or more second reverse transcriptase fusion proteins. In some embodiments, the methods of the invention may further comprise contacting the target nucleic acid with a guide nucleic acid. In some embodiments, the guide nucleic acid is linked to an RNA recruiting motif, and the second reverse transcriptase is a second reverse transcriptase fusion protein comprising a second reverse transcriptase domain fused (linked) to an affinity polypeptide that binds to the RNA recruiting motif, optionally wherein the target nucleic acid is contacted with two or more second reverse transcriptase fusion proteins.

In some embodiments, the second DNA binding domain may be a CRISPR-Cas nuclease domain, a transcription activator-like effector (TALE) protein domain, and/or a zinc finger protein domain. In some embodiments, the second DNA endonuclease may be a CRISPR-Cas nuclease, and/or a Fok1 endonuclease. In some embodiments, the second DNA binding domain and the second DNA endonuclease may be comprised in a CRISPR-Cas nuclease. In some embodiments, the CRISPR-Cas nuclease may be a Cas9 nickase (nCas9), optionally wherein the Cas9 nickase is encoded by a polynucleotide that is optionally comprised in an expression cassette. In some embodiments, the second DNA binding domain may be encoded by a polynucleotide and the second DNA endonuclease may be encoded by a polynucleotide.

In some embodiments, a polynucleotide encoding the second DNA binding domain and a polynucleotide encoding the second DNA endonuclease may be comprised in the same or separate expression cassettes, optionally wherein when present in the same expression cassette, the polynucleotide encoding the second DNA binding domain and the polynucleotide encoding the second DNA endonuclease may be operably linked to a single promoter or to two or more separate promoters in any combination. In some embodiments, the expression cassettes of the invention may be comprised in one or more vectors, optionally wherein the expression cassettes and/or vectors of the invention may further comprise a guide RNA. In some embodiments, a guide nucleic acid and/or extended guide nucleic acid may be operably linked to a PolIII or PolII promoter.

In some embodiments, the methods of the invention may further comprise contacting a target nucleic acid with a 5' flap endonuclease (FEN), optionally an FEN1 polypeptide. In some embodiments, the FEN may be overexpressed in the plant or plant cell. In some embodiments, the FEN may be fusion protein comprising an FEN domain fused to the DNA binding domain and/or the DNA endonuclease. In some embodiments, the DNA binding protein may be a DNA binding fusion protein comprising a DNA binding protein domain fused (linked) to a peptide tag (e.g., a peptide repeat unit, an epitope or a multimerized epitope) and/or the DNA endonuclease may be a DNA endonuclease fusion protein comprising a DNA endonuclease domain fused (linked) to a peptide tag (e.g., a peptide repeat unit, an epitope or a multimerized epitope) and the FEN may be an FEN fusion protein comprising an FEN domain fused (linked) to an affinity polypeptide that binds to the peptide repeat unit, optionally wherein the target nucleic acid is contacted with two or FEN fusion proteins, thereby recruiting the FEN to the DNA binding protein and/or DNA endonuclease, and the target nucleic acid.

In some embodiments of the invention, a reverse transcriptase (e.g., a first reverse transcriptase, a second reverse transcriptase and the like) may be fused to one or more ssRNA binding domains (RBDs).

In some embodiments of the invention, polynucleotides encoding DNA binding domains, DNA endonucleases, reverse transcriptase, flap endonucleases, extended guide nucleic acids, guide nucleic acids, expression cassettes and/or vectors may be codon optimized for expression in a plant, optionally wherein the polynucleotides may be codon optimized for expression in a dicot plant or for expression in a monocot plant.

In some embodiments, a peptide tag (e.g., a peptide repeat unit) may comprise 1 or 2 or more copies of a peptide repeat unit (e.g., an epitope, multimerized epitope) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, the peptide repeat unit may include, but is not limited to, a GCN4 peptide repeat unit (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope.

In some embodiments, an affinity polypeptide that binds to a peptide tag (e.g., a peptide repeat unit) may be an antibody, optionally wherein the antibody is a scFv antibody.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein and/or a synthetic RNA-aptamer and the aptamer ligand as the corresponding affinity polypeptide.

In some embodiments, the present invention provides a method of modifying a target nucleic acid in a plant cell, comprising contacting the nucleic acid with a DNA binding domain and a DNA endonuclease domain targeted to a first site on the target nucleic acid and the same or a different DNA binding domain and DNA endonuclease domain targeted to a second site on the target nucleic acid, wherein the first site and the second site are proximal to one another on the same (nontarget) strand, thereby nicking the target nucleic acid at the first and second site; a reverse transcriptase; and a nucleic acid encoded repair template encoding a modification to be incorporated into the target nucleic acid, thereby modifying the target nucleic acid in the plant.

In some embodiments, a method of modifying a target nucleic acid in a plant cell is provided, the method comprising: contacting the target nucleic acid with (a) a CRISPR-Cas nuclease comprising a first DNA binding domain and a first DNA endonuclease (a nickase); (b) a reverse transcriptase; (c) a CRISPR RNA (crRNA) comprising a spacer having substantial homology to a first site on the target nucleic acid; (d) a trans-activating crRNA (tracrRNA) that interacts (recruits/binds) with the crRNA and the CRISPR-Cas nuclease; and (e) a nucleic acid encoded repair template (e.g., an RNA encoded repair template) comprising a primer binding site and an template encoding the modification to be incorporated into the target nucleic acid, wherein the tracrRNA comprises a sequence at the 5' or 3' end that is complementary to a sequence at the 5' end or 3' end of the reverse transcriptase template, thereby modifying the target nucleic acid. In some embodiments, the methods of the invention further comprise contacting the target nucleic acid with two or more crRNAs, two or more tracrRNAs, two or more nucleic acid encoded repair templates and/or two or more CRISPR-Cas nucleases. In some embodiments, a method of the invention further comprises contacting the target nucleic acid (e.g., target DNA) with a second crRNA comprising a spacer having substantial homology to a second site on the target nucleic acid that is proximal to and on the same strand (non-target strand) as the first site and a second tracrRNA, wherein the second tracrRNA may or may not comprise a sequence at the 5' or 3' end that is complementary to a sequence at the 5' end or 3' end of the reverse transcriptase template (for a double nick to remove the wild type nucleic acid). In some embodiments, a method of the invention further comprises contacting the target nucleic acid (e.g., target DNA) with a second crRNA comprising a spacer having substantial homology to a third site on the target nucleic acid that is on a different strand from the first site (e.g., for improved mismatch repair).

In some embodiments, the present invention provides a method of modifying a target nucleic acid in a plant cell, the method comprising: contacting the target nucleic acid with (a) a CRISPR-Cas nuclease comprising a first DNA binding domain and a first DNA endonuclease (a nickase); (b) a reverse transcriptase; (c) a CRISPR RNA (crRNA) comprising a spacer having substantial homology to a first site on the target nucleic acid; (d) a trans-activating crRNA (tracrRNA) that interacts (recruits/binds) with the crRNA and the CRISPR-Cas nuclease; and a nucleic acid encoded repair template (e.g., an RNA encoded repair template) comprising a primer binding site and a template encoding the modification to be incorporated into the target nucleic acid, thereby modifying the target nucleic acid. In some embodiments, the methods of the invention further comprise contacting the target nucleic acid with two or more crRNAs, two or more tracrRNAs and/or two or more CRISPR-Cas nucleases. In some embodiments, a method of the invention further comprises contacting the target nucleic acid (e.g., target DNA) with a second crRNA comprising a spacer having substantial homology to a second site on the target nucleic acid that is proximal to and on the same strand (non-target strand) as the first site and a second tracrRNA that interacts (recruits/binds) with the second crRNA and either the first CRISPR-Cas nuclease or a different CRISPR-Cas nuclease thereby providing a double nick for removing the wild type nucleic acid. In some embodiments, a method of the invention further comprises contacting the target nucleic acid (e.g., target DNA) with a third crRNA comprising a spacer having substantial homology to a third site on the target nucleic acid that is on a different strand (target strand) from the first site and a third tracrRNA that interacts (recruits/binds) with the third crRNA and either the first CRISPR-Cas nuclease or a different CRISPR-Cas nuclease thereby improving mismatch repair.

In some embodiments, a method of modifying a target nucleic acid in a plant cell is provided, the method comprising: contacting the target nucleic acid with (a) a CRISPR-Cas nuclease comprising a first DNA binding domain and a first DNA endonuclease (e.g., a nickase); (b) a reverse transcriptase; (c) a CRISPR RNA (crRNA) guide that interacts (recruits/binds) with the CRISPR-Cas nuclease and comprises a spacer having substantial homology to a first site on the target nucleic acid; (e) a nucleic acid encoded repair template (e.g., an RNA encoded repair template) comprising a primer binding site and an RNA template (that encodes the modification to be incorporated into the target nucleic acid), wherein the crRNA comprises a sequence at its 5' end or 3' end that is complementary to the primer binding site, thereby modifying the target nucleic acid. In some embodiments, a method of the invention further comprises contacting the target nucleic acid with two or more crRNAs, two or more nucleic acid encoded repair templates and/or two or more CRISPR-Cas nucleases. In some embodiments, a method of the invention further comprises contacting the target nucleic acid (e.g., target DNA) with a second crRNA that interacts (recruits/binds) with the either the first CRISPR-Cas nuclease or a different CRISPR-Cas nuclease and comprises a spacer having substantial homology to a second site on the target nucleic acid that is proximal to and on the same strand (non-target strand) as the first site, thereby providing a double nick for removing the wild type nucleic acid. In some embodiments, a method of the invention further comprises contacting the target nucleic acid (e.g., target DNA) with a third crRNA that interacts (recruits/binds) with either the first CRISPR-Cas nuclease or a different CRISPR-Cas nuclease and comprises a spacer having substantial homology to a third site on the target nucleic acid that is on a different strand (target strand) from the first site, thereby improving mismatch repair.

In some embodiments, a method of modifying a target nucleic acid in a plant cell is provided, the method comprising contacting the target nucleic acid with (a) a CRISPR-Cas nuclease comprising a first DNA binding domain and a first DNA endonuclease (e.g., a nickase); (b) a reverse transcriptase; (c) an extended guide nucleic acid comprising a sequence that interacts that interacts (recruits/binds) with the CRISPR-Cas nuclease and a spacer having substantial homology to a first site on the target nucleic acid (e.g., CRISPR RNA (crRNA) (a first crRNA) and/or tracrRNA+crRNA (sgRNA)) and a nucleic acid encoded repair template (e.g., an RNA encoded repair template) comprising a primer binding site and an RNA template (that encodes the modification to be incorporated into the target nucleic acid), thereby modifying the target nucleic acid. In some embodiments, a method of the invention further comprises contacting the target nucleic acid with two or more extended guide nucleic acids and/or two or more CRISPR-Cas nucleases. In some embodiments, a method of the invention further comprises contacting the target nucleic acid (e.g., target DNA) with a crRNA (e.g., a second crRNA) that interacts (recruits/binds) with the either the first CRISPR-Cas nuclease or a different CRISPR-Cas nuclease and comprises a spacer having substantial homology to a second site on the target nucleic acid that is proximal to and on the same strand (non-target strand) as the first site, thereby providing a double nick for removing the wild type nucleic acid. In some embodiments, a method of the invention further comprises contacting the target nucleic acid (e.g., target DNA) with a second crRNA (e.g. a third crRNA) that interacts (recruits/binds) with either the first CRISPR-Cas nuclease or a different CRISPR-Cas nuclease and comprises a spacer having substantial homology to a third site on the target nucleic acid that is on a different strand (target strand) from the first site, thereby improving mismatch repair.

Figure 3:
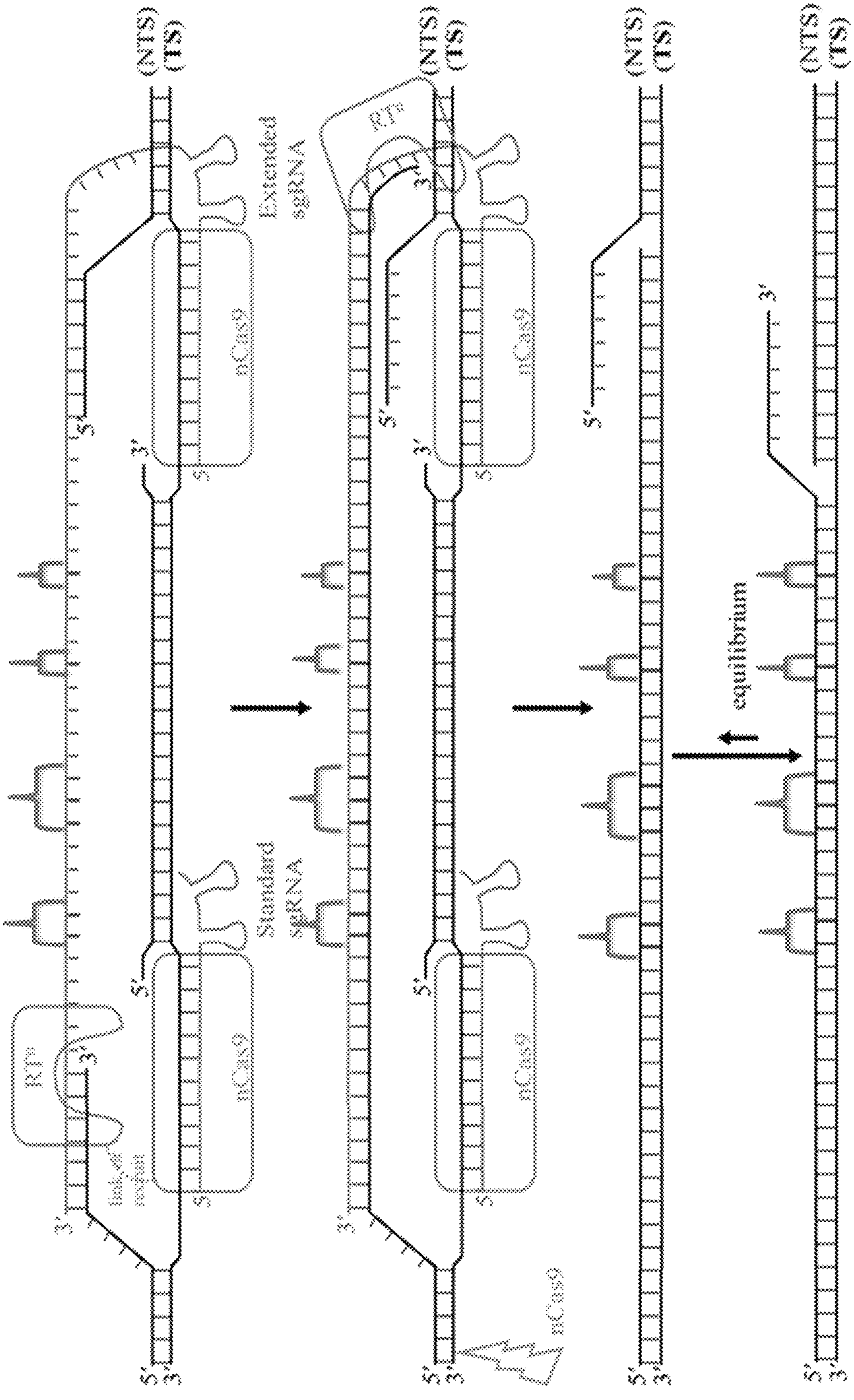
FIG. 3 shows alternative methods of modifying nucleic acids using the compositions of the present invention, wherein in two nicks are introduced in the PAM-containing strand and the sequence introduced by the RT displaces the double-nicked WT sequence and thereby, is more efficiently incorporated into the genome.

In some embodiments, the invention provides a method of modifying a target nucleic acid in a plant cell, the method comprising contacting the target nucleic acid with (a) a first CRISPR-Cas nuclease (a nickase) comprising a first DNA binding domain and a first DNA endonuclease; (b) an extended guide nucleic acid comprising a CRISPR RNA (crRNA) comprising a spacer having substantial homology to a first site on the target nucleic acid, a trans-activating crRNA (tracrRNA) that recruits the first CRISPR-Cas nuclease and an RNA template comprising the modification to be incorporated into the target nucleic acid, wherein the first CRISPR-Cas nuclease nicks the target nucleic acid at a first site (on the non-target strand); (c) a second CRISPR-Cas nuclease (e.g., a nickase) comprising a first DNA binding domain and a first DNA endonuclease (e.g., a nickase); (d) a guide nucleic acid comprising a CRISPR RNA (crRNA) comprising a spacer having substantial homology to a second site on the target nucleic acid that is proximal to (and on the same strand as) the first site on the target nucleic acid, a trans-activating crRNA (tracrRNA) that recruits the second CRISPR-Cas nuclease, thereby nicking the target nucleic acid at the second site (on the non-target strand); and (e) a reverse transcriptase fused or recruited to the first CRISPR Cas-nuclease and/or the second CRISPR Cas-nuclease, thereby modifying the target nucleic acid. See e.g., FIG. 3.

In some embodiments, a method of releasing a portion of a double stranded nucleic acid is provided, comprising: (a) targeting a first DNA endonuclease to a first site of the nucleic acid; (b) making a nick at in a first strand of the nucleic acid at the first site; (c) targeting the first DNA endonuclease or a second DNA endonuclease to a second site on the first strand; and (d) making a nick in the first strand at the second site, wherein the portion of the first strand of the nucleic acid between the first site and second site can be released from the nucleic acid. In some embodiments, the method further comprises contacting the nucleic acid with a reverse transcriptase. In some embodiments, the method further comprises contacting the nucleic acid with a reverse transcriptase template. In some embodiments, a transcriptase template may comprise a sequence substantially similar to the released portion of the nucleic acid and additionally comprises at least one nucleotide insertion, deletion or substitution. In some embodiments, the reverse transcriptase template may replace the released portion and become part of the double stranded nucleic acid.

In some embodiments, the invention provides an insertion of one or more nucleotide(s) in an organism (e.g., a plant). The insertion may comprise a recombination site or a whole gene at a specific genomic locus in the organism. In some embodiments, a reverse transcriptase template within an extended guide nucleic acid includes the insertion sequence such as, but not limited to, a recombination site (e.g., a wild type or mutated loxP, FRT, RS, attP and attB site) or a coding sequence of a gene and/or a regulatory element (e.g., promoter, 5'UTR sequence, and/or 3'UTR sequence). Exemplary recombination site sequences include, but are not limited to, those listed in Table 1. In some embodiments of the invention, the 3' end of a guide nucleic acid (e.g., a sgRNA) may comprise a sequence that is complimentary a region comprising the target nucleic acid, optionally the 3' end of a target nucleic acid. In some embodiments of the invention, the 3' end of a guide nucleic acid (e.g., a sgRNA) may comprise a microhomology region (e.g., a small region of homology such as 5-25 nucleotides in length) that binds to the 3' end of a target nucleic acid, which may optionally provide microhomolgy mediated end joining (MMEJ) and/or a repair mechanism.

TABLE 1

Exemplary recombination site sequences.

| Recombination site | Sequence |
|---|---|
| loxP | 5'-ATAACTTCGTATA ATGTATGC TATACGAAGTTAT-3' (SEQ ID NO: 148) |
| lox75 | 5'-ATAACTTCGTATA ATGTATGC TATACGcccggta-3' (SEQ ID NO: 149) |
| lox76 | 5'-taccgggCGTATA ATGTATGC TATACGAAGTTAT-3' (SEQ ID NO: 150) |
| lox66 | 5'-taccgTTCGTATA ATGTATGC TATACGAAGTTAT-3' (SEQ ID NO: 151) |
| lox71 | 5'-ATAACTTCGTATA ATGTATGC TATACGAAcggta-3' (SEQ ID NO: 152) |
| lox78 | 5'-taccgggCGTATA ATGTATGC TATACGcccggta-3' (SEQ ID NO: 153) |
| lox72 | 5'-taccgTTCGTATA ATGTATGC TATACGAAcggta-3' (SEQ ID NO: 154) |
| FRT | 5'-GAAGTTCCTATTC TCTAGAAA GTATAGGAACTTC-3' (SEQ ID NO: 155) |
| RS | 5'-TTGATGAAAGAA TACGTTA TTCTTTCATCAA-3' (SEQ ID NO: 156) |
| phiC31-attP | 5'-CCCCAACTGGGGTAACCTTTGAGTTCTCTCAGTTGGGGG-3' (SEQ ID NO: 157) |
| phiC31-attB | 5'-GTGCCAGGGCGTGCCCTTGGGCTCCCCGGGCGCG-3' (SEQ ID NO: 158) |
| Bxb1-attP | 5'-GGTTTGTCTGGTCAACCACCGCGGTCTCAGTGGTGTACGGTACAAACC-3'(SEQ ID NO: 159) |
| Bxb1-attB | 5'-CCGGCTTGTCGACGACGGCGGTCTCCGTCGTCAGGATCATCC-3' (SEQ ID NO: 160) |

In some embodiments, polynucleotides, nucleic acid constructs, expression cassettes and vectors may be provided for carrying out the methods of the invention. Thus, in some embodiments an expression cassette is provided that is codon optimized for expression in a plant, comprising 5' to 3' (a) polynucleotide encoding a plant specific promoter sequence (e.g. ZmUbi1, MtUb2, RNA polymerase II (Pol II)), (b) a plant codon-optimized polynucleotide encoding a CRISPR-Cas nuclease (e.g. nCas9, dCas9, Cpf1 (Cas12a), dCas12a and the like), (c) a linker sequence; and (d) a plant codon-optimized polynucleotide encoding a reverse transcriptase.

In some embodiments of the invention, a reverse transcriptase may be fused to one or more ssRNA binding domains (RBDs).

In some embodiments, polypeptides of the invention may be fusion proteins comprising one or more polypeptides linked to one another via a linker. In some embodiments, the linker may be an amino acid or peptide linker. In some embodiments, a peptide linker may be about 2 to about 100 amino acids (residues) in length. In some embodiments, a peptide linker may be a GS linker.

In some embodiments, the invention provides an expression cassette that is codon optimized for expression in a plant, comprising: (a) a polynucleotide encoding a plant specific promoter sequence (e.g. ZmUbi1, MtUb2), and (b) an extended guide nucleic acid, wherein the extended guide nucleic acid comprises an extended portion comprising at its 3' end a primer binding site and an edit to be incorporated into the target nucleic acid (e.g., reverse transcriptase template), optionally wherein the extended guide nucleic acid is comprised in an expression cassette, optionally wherein the extended guide nucleic acid is operably linked to a Pol II promoter.

In some embodiments, a plant specific promoter may be associated with an intron or may be a promoter region comprising an intron (e.g., ZmUbi1 comprising an intron; MtUb2 comprising an intron).

In some embodiments, an expression cassette of the invention may be codon optimized for expression in a dicot plant or for expression in a monocot plant. In some embodiments, the expression cassettes of the invention may be used in a method of modifying a target nucleic acid in a plant or plant cell, the method comprising introducing one or more expression cassettes of the invention into a plant or plant cell, thereby modifying the target nucleic acid in the plant or plant cell to produce a plant or plant cell comprising the modified target nucleic acid. In some embodiments, the method may further comprise regenerating the plant cell comprising the modified target nucleic acid to produce a plant comprising the modified target nucleic acid.

In some embodiments, the present invention provides a nucleic acid molecule comprising (a) a sequence that interacts (e.g., binds, recruits) with a CRISPR-Cas nuclease (tracrRNA), (b) a sequence that directs the CRISPR-Cas nuclease to a target nucleic acid (e.g., a crRNA), and (c) a sequence encoding a template for introducing a modification into the target nucleic acid, or (a) a sequence that that interacts (e.g., binds, recruits) with a CRISPR-Cas nuclease and directs the CRISPR-Cas nuclease to a target nucleic acid (crRNA) and (b) a sequence encoding a template for introducing a modification into the target nucleic acid.

In some embodiments of the invention, a CRISPR-Cas nuclease, a DNA binding domain, and/or a DNA endonuclease may be from a Type I CRISPR-Cas system, a Type II CRISPR-Cas system, a Type III CRISPR-Cas system, a Type IV CRISPR-Cas system or a Type V CRISPR-Cas system. In some embodiments, the CRISPR-Cas nuclease is from a Type II CRISPR-Cas system or a Type V CRISPR-Cas system. In some embodiments, a CRISPR-Cas effector protein may be a Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments of the invention, a CRISPR-Cas nuclease, a DNA binding domain, and/or a DNA endonuclease may be a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas nuclease may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c nuclease.

In some embodiments, a CRISPR-Cas nuclease, a DNA binding domain, and/or a DNA endonuclease may be a Cas9 nickase or a Cas12a nickase.

In some embodiments, a polynucleotide encoding a DNA binding polypeptide or domain, a polynucleotide encoding a DNA endonuclease polypeptide or domain, a polynucleotide encoding a reverse transcriptase polypeptide or domain, and/or a polynucleotide encoding a flap endonuclease polypeptide or domain may be operably linked to at least one regulatory sequence, optionally, wherein the at least one regulatory sequence may be codon optimized for expression in a plant. In some embodiments, the at least one regulatory sequence may be, for example, a promoter, an operon, a terminator, or an enhancer. In some embodiments, the at least one regulatory sequence may be a promoter. In some embodiments, the regulatory sequence may be an intron. In some embodiments, the at least one regulatory sequence may be, for example, a promoter operably associated with an intron or a promoter region comprising an intron. In some embodiments, the at least one regulatory sequence may be, for example a ubiquitin promoter and its associated intron (e.g., *Medicago truncatula* and/or *Zea mays* and their associated introns). In some embodiments, the at least one regulatory sequence may be a terminator nucleotide sequence and/or an enhancer nucleotide sequence.

In some embodiments, the present invention provides a polynucleotide encoding a DNA binding polypeptide or domain, a polynucleotide encoding an endonuclease polypeptide or domain, a polynucleotide encoding a reverse transcriptase polypeptide or domain, and/or a polynucleotide encoding a flap endonuclease polypeptide or domain operably associated with one or more promoter regions, wherein one or more of the promoter regions may comprises an intron, optionally wherein the promoter region may be a ubiquitin promoter and intron (e.g., a *Medicago* or a maize ubiquitin promoter and intron, e.g., SEQ ID NOs:1 or 2). In some embodiments, the CRISPR-Cas nuclease operably associated with a promoter region comprising an intron may be codon optimized for expression in a plant.

A CRISPR-Cas nuclease useful with this invention can include, but is not limited, to Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas nuclease may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas nuclease useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas nuclease having a mutation in its nuclease active site, and therefore, no longer comprising nuclease activity, is commonly referred to as "dead," e.g., dCas such as dCas9. In some embodiments, a CRISPR-Cas nuclease domain or polypeptide having a mutation in its nuclease active site may have impaired activity or reduced activity as compared to the same CRISPR-Cas nuclease without the mutation, e.g., a nickase, e.g, Cas9 nickase, Cas12a nickase.

A CRISPR Cas9 polypeptide or CRISPR Cas9 domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophiles*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. In some embodiments, a CRISPR-Cas nuclease may be a Cas9 polypeptide or domain thereof and optionally may have a nucleotide sequence of any one of SEQ ID NOs:3-13 and/or an amino acid sequence of any one of SEQ ID NOs:14-15.

In some embodiments, the CRISPR-Cas nuclease may be a Cas9 polypeptide derived from *Streptococcus pyogenes* and recognizes the PAM sequence motif NGG, NAG, NGA (Mali et al, *Science* 2013; 339(6121): 823-826). In some embodiments, the CRISPR-Cas nuclease may be a Cas9 polypeptide derived from *Streptococcus* thermophiles and recognizes the PAM sequence motif NGGNG and/or NNAGAAW (W=A or T) (See, e.g., Horvath et al, *Science,* 2010; 327(5962): 167-170, and Deveau et al, *J Bacteriol* 2008; 190(4): 1390-1400). In some embodiments, the CRISPR-Cas nuclease may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas nuclease may be a Cas9 polypeptide derived from *Streptococcus aureus* and recognizes the PAM sequence motif NNGRR (R=A or G). In some embodiments, the CRISPR-Cas nuclease may be a Cas9 protein derived from *S. aureus*, which recognizes the PAM sequence motif N GRRT (R=A or G). In some embodiments, the CRISPR-Cas nuclease may be a Cas9 polypeptide derived from *S. aureus*, which recognizes the PAM sequence motif N GRRV (R=A or G). In some embodiments, the CRISPR-Cas nuclease may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas nuclease may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

A Type V CRISPR-Cas nuclease useful with embodiments of the invention may be any Type V CRISPR-Cas nuclease. A Type V CRISPR-Cas nuclease useful with this invention as an effector protein can include, but is not limited, to Cas12a (Cpf1), Cas12b, Cas12c (C2c3), Cas12d (CasY), Cas12e (CasX), Cas12g, Cas12h, Cas12i, C2c1, C2c4, C2c5, C2c8, C2c9, C2c10, Cas14a, Cas14b, and/or Cas14c nuclease. In some embodiments, a Type V CRISPR-Cas nuclease polypeptide or domain useful with embodiments of the invention may be a Cas12a polypeptide or domain. In some embodiments, a Type V CRISPR-Cas nuclease or domain useful with embodiments of the invention may be a nickase, optionally, a Cas12a nickase.

In some embodiments, the CRISPR-Cas nuclease may be derived from Cas12a, which is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a polypeptide or CRISPR Cas12a domain useful with this invention may be any known or later identified Cas12a nuclease (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

In some embodiments, a CRISPR-Cas nuclease may be optimized for expression in an organism, for example, in an animal, a plant, a fungus, an archaeon, or a bacterium. In some embodiments, a CRISPR-Cas nuclease (e.g., Cas12a polypeptide/domain or a Cas9 polypeptide/domain) may be optimized for expression in a plant. In some embodiments, a Cas12a polypeptide/domain that may be optimized according to the present invention can include, but is not limited to, the amino acid sequence of any one of SEQ ID NOs:16-32 (e.g., SEQ ID NOs: 16, 17, 18, 19, 20, 21, 22, 23, 24, 25, 26, 27, 28, 29, 30, 31, or 32), or a polynucleotide encoding the same such as, but not limited to, the polynucleotide of any one of SEQ ID NOs:33-35.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. In some embodiments, the guide nucleic acid comprises DNA. In some embodiments, the guide nucleic acid comprises RNA (e.g., is a guide RNA). The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer. In some embodiments, as described herein, a guide RNA may include a template for editing and a primer binding site. In some embodiments, a guide RNA may include a region or sequence on its 5' end or 3' end that is complementary to an editing template (a reverse transcriptase template), thereby recruiting the editing template to the target nucleic acid.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas nuclease encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 23 nucleotides in length.

In some embodiments, the 5' region of a spacer sequence of a guide nucleic acid (e.g., guide RNA) may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA. A recruiting guide RNA further comprises one or more recruiting motifs as described herein, which may be linked to the 5' end of the guide or the 3' end or it may be inserted into the recruiting guide nucleic acid (e.g., within the hairpin loop).

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refer to a region of an organism's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid (e.g., guide RNA) of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
  5'-NNNNNNNNNNNNNNNNNNN-3'  RNA Spacer (SEQ ID NO: 36)
     ||||||||||||||||||||
3'AAANNNNNNNNNNNNNNNNNNN-5'  Target strand (SEQ ID NO: 37)
  ||||
5'TTTNNNNNNNNNNNNNNNNNNN-3'  Non-target strand (SEQ ID NO: 38
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. Appl. *Environ. Microbiol.* 80:994-1001; Mojica et al. 2009. *Microbiology* 155:733-740).

Fusion proteins of the invention may comprise a DNA binding domain, DNA endonuclease, guide nucleic acid, or reverse transcriptase fused to a peptide tag or an affinity polypeptide. In some embodiments, a DNA binding domain is fused to a peptide tag or an affinity polypeptide that interacts with the peptide tag, as known in the art, for use in recruiting the DNA binding domain to the target nucleic acid, and/or an DNA endonuclease is fused to a peptide tag or an affinity polypeptide that interacts with the peptide tag, as known in the art, for use in recruiting the DNA endonuclease to the target nucleic acid. In some embodiments, a method of recruiting may comprise a guide nucleic acid linked to an RNA recruiting motif and a reverse transcriptase fused to an affinity polypeptide capable of interacting with the RNA recruiting motif, thereby recruiting the reverse transcriptase to the target nucleic acid. Alternatively, chemical interactions may be used to recruit a polypeptide (e.g., a reverse transcriptase) to a target nucleic acid.

As described herein, a "peptide tag" may be employed to recruit one or more polypeptides. A peptide tag may be any polypeptide that is capable of being bound by a corresponding affinity polypeptide. A peptide tag may also be referred to as an "epitope" and when provided in multiple copies, a "multimerized epitope." Example peptide tags can include, but are not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. In some embodiments, a peptide tag may also include phosphorylated tyrosines in specific sequence contexts recognized by SH2 domains, characteristic consensus sequences containing phosphoserines recognized by 14-3-3 proteins, proline rich peptide motifs recognized by SH3 domains, PDZ protein interaction domains or the PDZ signal sequences, and an AGO hook motif from plants. Peptide tags are disclosed in WO2018/136783 and U.S. Patent Application Publication No. 2017/0219596, which are incorporated by reference for their disclosures of peptide tags. Peptide tags that may be useful with this invention can include, but are not limited to, SEQ ID NO:39 and SEQ ID NO:40. An affinity polypeptide useful with peptide tags includes, but is not limited to, SEQ ID NO:41.

A peptide tag may comprise or be present in one copy or in 2 or more copies of the peptide tag (e.g., multimerized peptide tag or multimerized epitope) (e.g., about 2, 3, 4, 5, 6, 7, 8, 9, 10, 11, 12, 13, 14, 15, 16, 17, 18, 9, 20, 21, 22, 23, 24, or 25 or more peptide tags). When multimerized, the peptide tags may be fused directly to one another or they may be linked to one another via one or more amino acids (e.g., 1, 2, 3, 4, 5, 6, 7, 8, 9, 10, 11, 12, 13, 14, 15, 16, 17, 18, 19, 20 or more amino acids, optionally about 3 to about 10, about 4 to about 10, about 5 to about 10, about 5 to about 15, or about 5 to about 20 amino acids, and the like, and any value or range therein. Thus, in some embodiments, a CRISPR-Cas nuclease of the invention may comprise a CRISPR-Cas nuclease domain fused to one peptide tag or to two or more peptide tags, optionally wherein the two or more peptide tags are fused to one another via one or more amino acid residues. In some embodiments, a peptide tag useful with the invention may be a single copy of a GCN4 peptide tag or epitope or may be a multimerized GCN4 epitope comprising about 2 to about 25 or more copies of the peptide tag (e.g., about 2, 3, 4, 5, 6, 7, 8, 9, 10, 11, 12, 13, 14, 15, 16, 17, 18, 19, 20, 21, 22, 23, 24, 25 or more copies of a GCN4 epitope or any range therein).

Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5):910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a reverse transcriptase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., reverse transcriptase). In some embodiments, two or more polypeptides may be recruited to a guide nucleic acid, thereby contacting the target nucleic acid with two or more polypeptides.

In some embodiments of the invention, a guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF). Exemplary RNA recruiting motifs and corresponding affinity polypeptides that may be useful with this invention can include, but are not limited to, SEQ
Id Nos:42-52.

In some embodiments, the components for recruiting polypeptides and nucleic acids may include those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g. dihyrofolate reductase (DHFR)).

In some embodiments, a peptide tag may be fused to a CRISPR-Cas polypeptide or domain. In some embodiments, a peptide tag may be fused or linked to the C-terminus of a CRISPR-Cas nuclease to form a CRISPR-Cas fusion protein. In some embodiments, a peptide tag may be fused or linked to the N-terminus of a CRISPR-Cas nuclease to form a CRISPR-Cas fusion protein. In some embodiments, a peptide tag may be fused within a CRISPR-Cas nuclease (e.g., a peptide tag may be in a loop region of a CRISPR-Cas effector protein).

In some embodiments, when a peptide tag comprises more than one peptide tag, the quantity and spacing of each peptide tag may be optimized to maximize occupation of the peptide tags and minimize steric interference of, for example, polypeptide portions, with each other.

An "affinity polypeptide" (e.g., "recruiting polypeptide") refers to any polypeptide that is capable of binding to its corresponding peptide tag, peptide tag, or RNA recruiting motif. An affinity polypeptide for a peptide tag may be, for example, an antibody and/or a single chain antibody that specifically binds the peptide tag, respectively. In some embodiments, an antibody for a peptide tag may be, but is not limited to, a scFv antibody. In some embodiments, an affinity polypeptide may be fused or linked to the N-terminus of a reverse transcriptase. In some embodiments, the affinity polypeptide is stable under the reducing conditions of a cell or cellular extract.

The nucleic acid constructs of the invention and/or guide nucleic acids may be comprised in one or more expression cassettes as described herein. In some embodiments, a nucleic acid construct of the invention may be comprised in the same or in a separate expression cassette or vector from that comprising a guide nucleic acid and/or a recruiting guide nucleic acid.

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same but which have not been codon optimized for expression in a plant.

In some embodiments, the invention provides cells (e.g., plant cells, animal cells, bacterial cells, archaeon cells, and the like) comprising one or more polynucleotides, guide nucleic acids, nucleic acid constructs, expression cassettes or vectors of the invention.

When used in combination with guide nucleic acids, the nucleic acid constructs of the invention (and expression cassettes and vectors comprising the same) may be used to modify a target nucleic acid. A target nucleic acid may be contacted with a nucleic acid construct of the invention and/or expression cassettes and/or vectors comprising the same prior to, concurrently with or after contacting the target nucleic acid with the guide nucleic acid. In some embodiments, the nucleic acid constructs of the invention and a guide nucleic acid may be comprised in the same expression cassette or vector and therefore, a target nucleic acid may be contacted concurrently with the nucleic acid constructs of the invention and guide nucleic acid. In some embodiments, the nucleic acid constructs of the invention and a guide nucleic acid may be in different expression cassettes or vectors and thus, a target nucleic acid may be contacted with the nucleic acid constructs of the invention prior to, concurrently with, or after contact with a guide nucleic acid.

In some embodiments, after contacting a target nucleic acid with a polypeptide, composition, complex (e.g., an assembled ribonucleoprotein complex), nucleic acid construct, expression cassette, and/or vector of the present invention, the cell and/or organism comprising the target nucleic acid may be exposed to and/or provided in an environment having a temperature of greater than 25° C. for a period of time (e.g., 1, 2, 3, 4, 5, 6, 7, 8, 9, 10, 11, 12, 13, 14, 15, 20, 30, 40, 50, 60 or more minutes, hours, or days). In some embodiments, the cell and/or organism is exposed to (e.g., provided, incubated, cultured, grown, or the like in an environment at) a temperature in a range of about 26° C., 28° C., 30° C., or 32° C. to about 34° C., 36° C., 38° C., 40° C., or 42° C. for a period of time (e.g., 1, 2, 3, 4, 5, 6, 7, 8, 9, 10, 11, 12, 13, 14, 15, 20, 30, 40, 50, 60 or more minutes, hours, or days). Exposing the cell and/or organism to a temperature of greater than 25° C. for a period of time may increase editing efficiency optionally by increasing reverse transcriptase activity and/or breaking RNA secondary structure elements in the extended guide nucleic acid. In some embodiments, exposing the cell and/or organism to a temperature of greater than 25° C. may improve performance of a polypeptide, composition, complex (e.g., an assembled ribonucleoprotein complex), nucleic acid construct, expression cassette, and/or vector of the present invention. In some embodiments, the organism is a plant tissue and after contacting and/or transforming a plant cell of the plant tissue with a polypeptide, composition, complex (e.g., an assembled ribonucleoprotein complex), nucleic acid construct, expression cassette, and/or vector of the present invention, the plant tissue is incubated at a temperature of greater than 25° C. fora period of time (e.g., 1, 2, 3, 4, 5, 6, 7, 8, 9, 10, 11, 12, 13, 14, 15, 20, 30, 40, 50, 60 or more minutes, hours, or days). In some embodiments, a method of the present invention comprises exposing a cell and/or organism to two or more different temperatures. For example, before, during, and/or after contacting and/or transforming a cell of an organism with a polypeptide, composition, complex (e.g., an assembled ribonucleoprotein complex), nucleic acid construct, expression cassette, and/or vector of the present invention, the cell is exposed to a first temperature of about 25° C. or less and then a second temperature of greater than 25° C. (e.g., about 26° C. to about 42° C.) or vice versa. In some embodiments, the first temperature is before and/or during the contacting and/or transforming step and the second temperature is after the contacting and/or transforming step.

According to some embodiments of the present invention, a polypeptide, polynucleotide, complex, composition, system, kit, and/or method of the present invention may be used and/or configured to modify (e.g., edit) one or more locus (loci) in a genome to alter gene function. In some embodiments, this may be achieved through a modification to a promoter, enhancer, 5' UTR, exon, intron, 3' UTR, terminator, miRNA binding site, and/or other functional element and/or junction between such elements. In some embodiments, a polypeptide, polynucleotide, complex, composition, system, kit, and/or method of the present invention may be used and/or configured to provide one or more targeted promoter sequence change(s). Targeted promoter sequence changes could be designed in a rational way to increase or decrease gene expression at any spatio-temporal point through insertion or deletion of known regulatory sequences. Targeted sequence changes may also be used in non-rational designs to develop allelic diversity that is screened to phenotypically determine a favorable allele. In some embodiments, a method of the present invention comprises generating allelic diversity to be screened such as by targeting a promoter region in a promoter bashing type approach. A library may be generated that includes 2 to 5, 10, 25, 50, 100, 200, 300, 400, 500, or more extended guide nucleic acids that are targeted against a gene promoter or coding sequence, which may aid in introducing and/or which may introduce a large amount of allelic variation that may be useful for screening for optimized phenotypes.

In some embodiments, a polynucleotide, complex, composition, system, kit, and/or method of the present invention comprises a crRNA (e.g., 1, 2, 3, 4, or more crRNA(s)) that has an extended 3' extension, and the crRNA may aid in and/or be configured to aid in creating allelic diversity in an organism. The crRNA may be delivered with a DNA binding domain and/or DNA endonuclease (e.g., a CRISPR Cas polypeptide) or may be delivered separately. In some embodiments, the crRNA may be delivered assembled and/or in the same complex as a DNA binding domain and/or DNA endonuclease (e.g., a CRISPR Cas polypeptide). In some embodiments, a crRNA and a DNA binding domain and/or DNA endonuclease are delivered separately to a cell (e.g., a plant cell). In some embodiments, a first organism (e.g., a first plant or line (A)) may be transformed with a DNA binding domain and/or DNA endonuclease (e.g., a CRISPR Cas polypeptide) and optionally 0, 1, 2, or 3 crRNA(s), and a second organism (e.g., a second plant or line (B)) may be transformed with one or more crRNA(s). The first organism (e.g., line A) may be modified (e.g., edited) at a first target nucleic acid (e.g., a first loci) that is targeted by the crRNA(s) in line A, if at least one crRNA is present. The second organism (e.g., line B) would not be modified by the crRNA(s) in the second organism due to lack of a DNA binding domain and/or DNA endonuclease. The method may further comprise crossing the first and second organisms, which may result in modifications in progeny resulting from the cross at a second target nucleic acid (e.g., a second loci) that is unmodified in the first and second organisms, but which may be modified in progeny due to the new combination of unmodified target nucleic acids and the editing machinery. A variety of modifications and/or repair outcomes may be inherited by the progeny of the cross, which may result in allelic diversity that may be phenotypically screened for desirable outcomes. This method may provide a high density of allelic variation that is introduced at a target nucleic acid and may allow for phenotyping to be used as the primary screen.

According to some embodiments of the present invention, a polypeptide, polynucleotide, complex, composition, system, kit, and/or method of the present invention may be used and/or configured to co-modify (e.g., co-edit) genes that confer phenotypes aiding in the isolation of modified plants. This application has high value for crops with low efficiency transformation systems and applies in regard to the requirement for modifying without integration of a transgenic DNA sequence. This may be particularly useful for crops such as cane berries, stonefruits, and other clonally propagated hybrid crops with long generation times. In some embodiments, at least two pegRNAs or a pegRNA and a guide RNA are delivered that are directed to two different target nucleic acids (e.g., two different genes). The first target nucleic acid may be in a trait gene of interest and may be modified using an editing system such as described herein (e.g., such as with a prime editor or any other type of genome editing tool to confer an economically valuable phenotype. The second target nucleic acid may be a different target nucleic acid (e.g., a different gene) that is modified using an editing system (e.g., a prime editor) to confer a phenotype that assists in the identification and/or isolation of cells, tissues, or plants that obtain this edit. For example, the phenotype may be a visual phenotype (e.g., thornless, glossy), a herbicide-resistant phenotype (e.g., ALS inhibitors, glyphosate, PPO inhibitors, etc), and/or an antibiotic-resistant phenotype. A modification conferring such a phenotype may enable the identification and/or isolation of a cell, tissue, or plant that had received the editing machinery. In this way, the provided phenotype acts similar to a selectable marker cassette as a tool to aid in the recovery of modified plants. However, a key difference is that the method does not require the genomic integration of a transgenic marker cassette. Because both pegRNAs may be delivered by the same mechanism, cells that obtain the modification in the second target nucleic acid may have a much greater than random probability of obtaining a modification in the first target nucleic acid. Thus, they may be used to assist in the recovery of non-transgenic, modified organisms (e.g., plants) obtained via transient delivery of the editing tools. A difficulty in trying to obtain non-transgenic, modified plants is the inability to prevent regeneration of untreated cells, requiring handling and screening of thousands or millions of explants. Thus, embodiments of the present invention have major economic benefits and can enable a pipeline of non-transgenic, modified organisms (e.g., plants) that would be impractical to implement without a selection tool.

A target nucleic acid of any plant or plant part may be modified (e.g., mutated, e.g., base edited, cleaved, nicked, etc.) using the nucleic acid constructs of the invention (e.g., SEQ ID NOs:1-129). Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), Cannabis (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

The present invention further comprises a kit or kits to carry out the methods of this invention. A kit of this invention can comprise reagents, buffers, and apparatus for mixing, measuring, sorting, labeling, etc, as well as instructions and the like as would be appropriate for modifying a target nucleic acid.

In some embodiments, the invention provides a kit comprising one or more nucleic acid constructs of the invention and/or expression cassettes and/or vectors and/or cells comprising the same as described herein, with optional instructions for the use thereof. In some embodiments, a kit may further comprise a CRISPR-Cas guide nucleic acid (corresponding to the CRISPR-Cas nuclease encoded by the polynucleotide of the invention) and/or expression cassette and/or vector comprising the same. In some embodiments, the guide nucleic acid may be provided on the same expression cassette and/or vector as a nucleic acid construct of the invention. In some embodiments, the guide nucleic acid may be provided on a separate expression cassette or vector from that comprising the nucleic acid construct of the invention.

Accordingly, in some embodiments, kits are provided comprising a nucleic acid construct comprising (a) a polynucleotide(s) as provided herein and (b) a promoter that drives expression of the polynucleotide(s) of (a). In some embodiments, the kit may further comprise a nucleic acid construct encoding a guide nucleic acid, wherein the construct comprises a cloning site for cloning of a nucleic acid sequence identical or complementary to a target nucleic acid sequence into backbone of the guide nucleic acid.

In some embodiments, the nucleic acid construct of the invention may be an mRNA that may encode one or more introns within the encoded polynucleotide(s). In some embodiments, a nucleic acid construct of the invention and/or an expression cassette and/or vector comprising the same, may further encode one or more selectable markers useful for identifying transformants (e.g., a nucleic acid encoding an antibiotic resistance gene, herbicide resistance gene, and the like).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1: Prime Editing Through Recruitment

Previously published strategies for prime editing rely on the use of a reverse transcriptase that is linked to an effector protein through a polypeptide linker. This will naturally restrict the reverse transcriptase to a region accessible by this linker length. To alleviate this issue, methods were developed to recruit reverse transcriptase (RT) to the genomic region, thereby causing a localized concentration increase at the site of editing. Two methods were tested to achieve this goal, recruitment to the Cas effector protein by the addition of peptide epitopes (Suntag), and recruitment to the guide through the addition of hairpin loops.

Methods:

Human Cell Testing

Eukaryotic HEK293T (ATCC CRL-3216) cells were cultured in Dulbecco's Modified Eagle's Medium plus GlutaMax (ThermoFisher) supplemented with 10% (v/v) FBS (FBS), at 37° C. with 5% CO2. Cas and reverse transcriptase components were synthesized using solid-state synthesis and subsequently cloned into plasmids behind a CMV promoter. CRISPR RNAs (crRNAs) and pegRNAs (e.g., extended guide nucleic acids) were cloned behind a human U6 promoter. HEK293T cells were seeded on 48-well collagen-coated BioCoat plates (Corning). Cells were transfected at −70% confluency. 750 ng of protein plasmid and 250 ng of crRNA expression plasmids were transfected using 1.5 μl of Lipofectamine 3000 (ThermoFisher Scientific) per well according to the manufacturer's protocol. Genomic DNA from transfected cells were obtained after 3 days and indels were detected and quantified using high-throughput Illumina amplicon sequencing.

Recruitment of RT for Editing Through Epitope Tags

To test the strategy of reverse transcriptase recruitment, a three-plasmid system was designed for expression in human cells. As a control, a PE2 architecture, which consists of a nCas9 protein that is directly fused to the MuLV (5M) (Murine leukemia virus reverse transcriptase with five mutations-D200N+L603W+T330P+T306K+W313F) (Anzalone et al. 2019) reverse transcriptase that is co-delivered with a single pegRNA, was tested alongside the recruitment designs.

Figure 4:
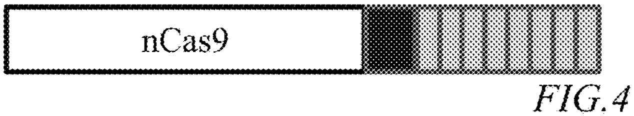
FIG. 4 is an illustration of an exemplary effector sequence including a nickase (Cas9 (H840A)) (white) followed by a linker (black) which is followed by eight repeats of the GCN4 epitope motif.

To enable recruitment of the reverse transcriptase to the Cas protein, a set of eight GCN4 epitope motifs was added to the C terminus of a nickase Cas9 protein sequence with a linker between the nCas9 (H840A) and eight GCN4 epitope motifs (nCas9::GCN4) as shown in FIG. 4. The nCas9::GCN4 expression plasmid consists of a CMV promoter driving the nCas9::GCN4 transcription unit, which is separated from an EGFP marker by the P2A ribosomal cleavage sequence. Transcription is terminated by the bGH polyA signal motif. A nucleotide sequence including nCas9::GCN4::P2A::EGFP is provided in SEQ ID NO:53.

Figure 5:
FIG. 5 is an illustration of an exemplary sequence including a scFv fragment (grey) that is fused to the reverse transcriptase MuLV-5M followed by the guanine nucleotide-binding protein subunit beta sequence.

On a separate plasmid the reverse transcriptase is delivered. The reverse transcriptase MuLV-5M is fused to a single-chain variable fragment (scFv) which is an antibody that will bind to the GCN4 epitopes that are fused to nickase Cas9. The reverse transcriptase is followed by the guanine nucleotide-binding protein subunit beta (GB1) sequence for increased solubility (scFV::RT::GB1) as shown in FIG. 5. The scFV::RT::GB1 expression plasmid consists of a CMV promoter driving the scFV::RT::GB1 transcription unit, which is separated from an EGFP marker by the P2A ribosomal cleavage sequence. Transcription is terminated by the bGH polyA signal motif. A nucleotide sequence including scFV::MuLV (5M)::GB1::P2A::EGFP is provided in SEQ ID NO:54.

Figure 6:
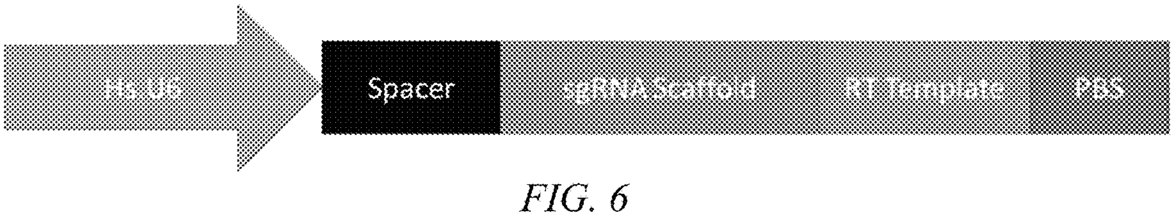
FIG. 6 is an illustration of an exemplary pegRNA structure where the promoter (Hs.U6) is promoting the transcription of a spacer, followed by the sgRNA scaffold, reverse transcriptase template (RT Template), and primer binding site (PBS).
Figure 7:
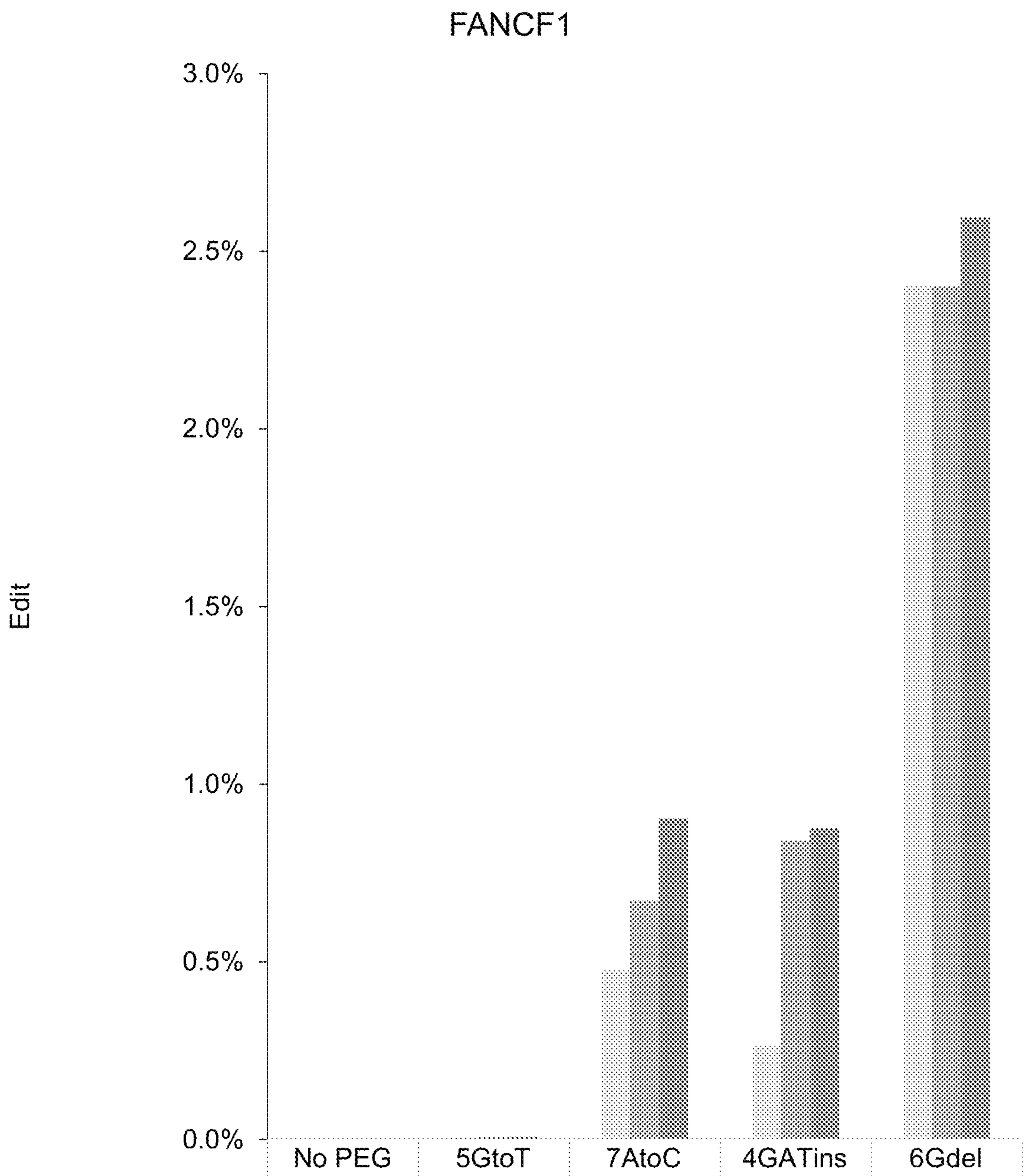
FIG. 7 is a graph showing the results of editing at the FANCF1 locus using the recruitment (Suntag) strategy or published PE2 strategy.
Figure 8:
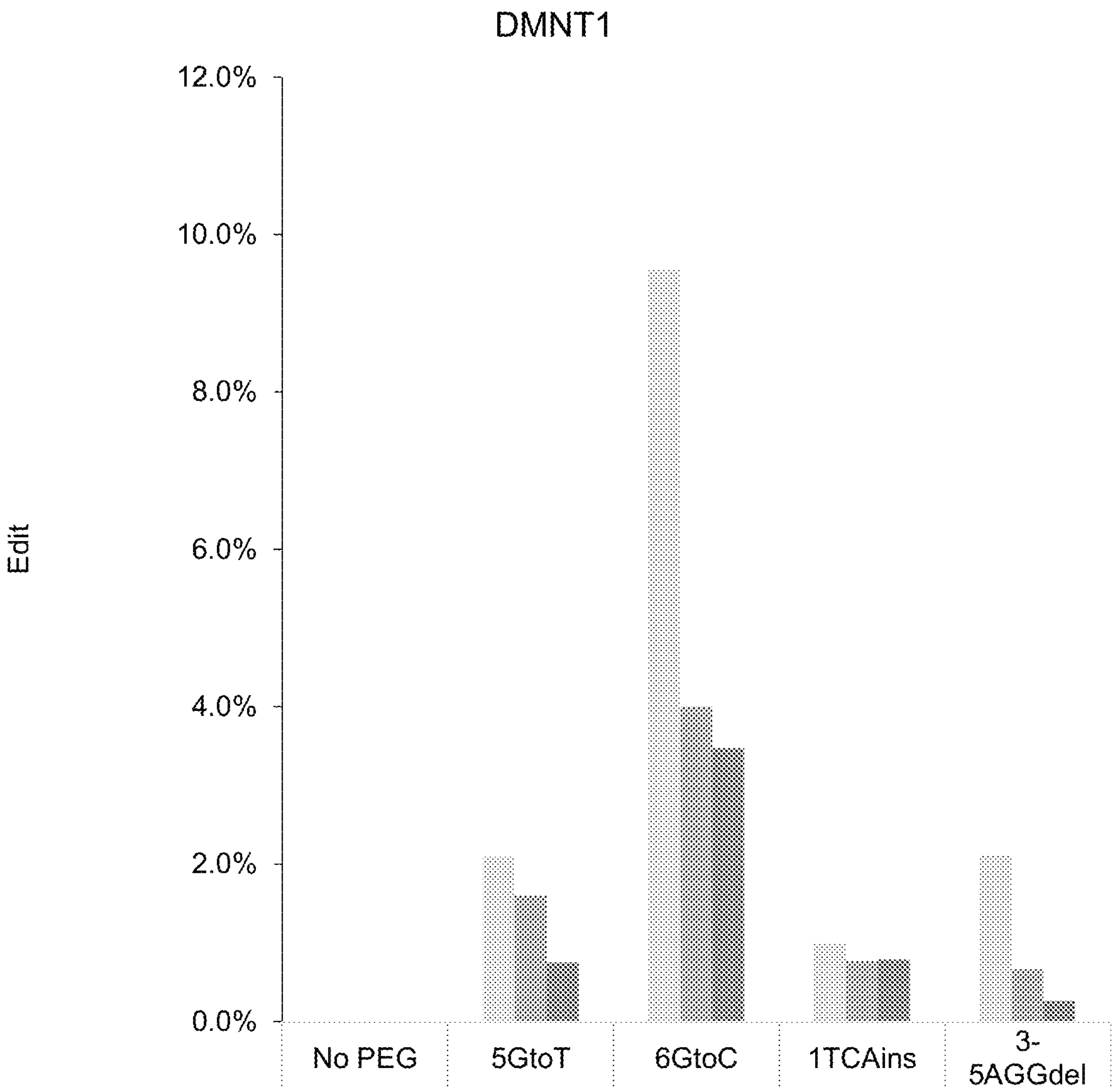
FIG. 8 is a graph showing the results of editing at the DMNT1 locus using the recruitment (Suntag) strategy or published PE2 strategy.
Figure 9:
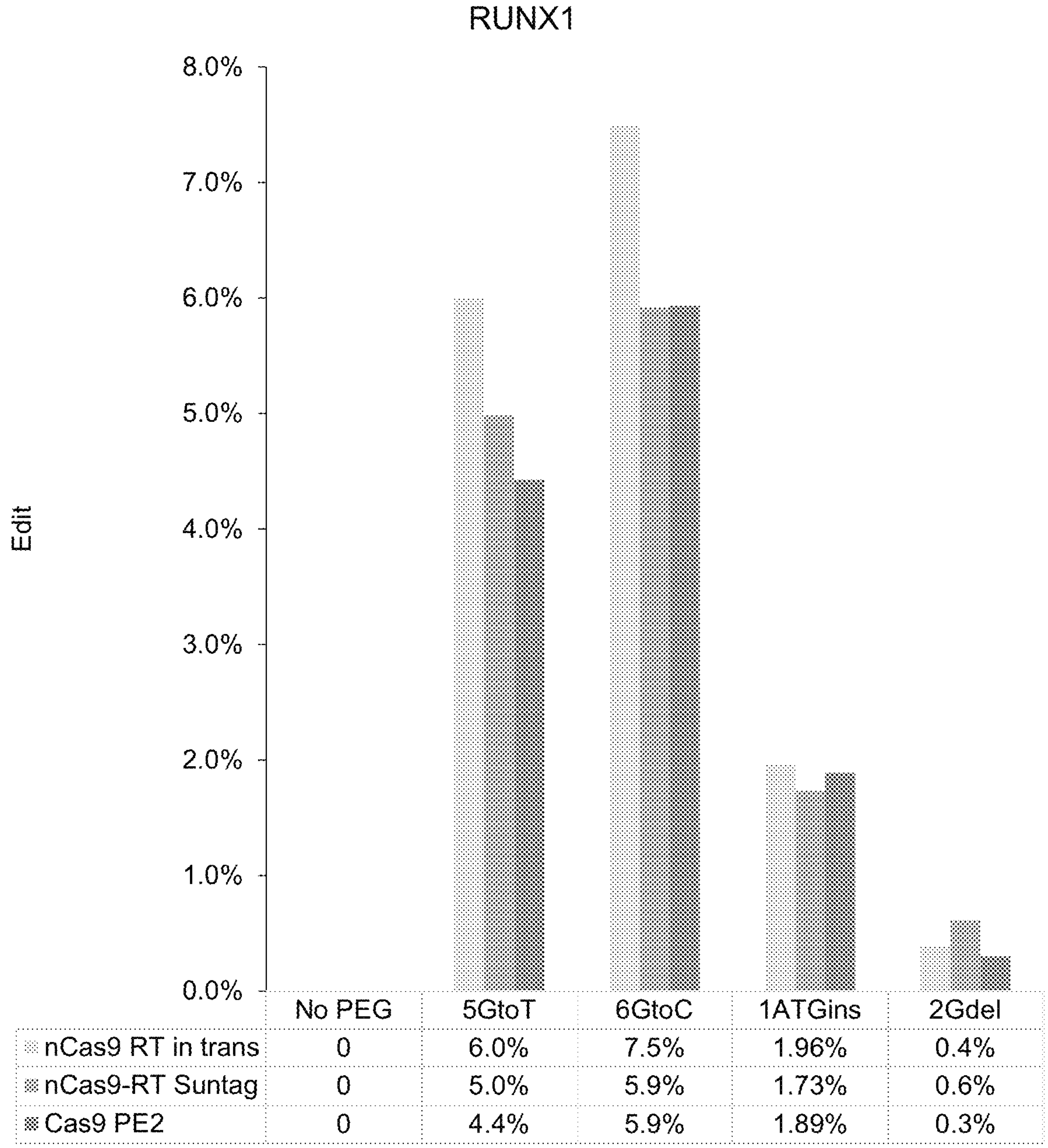
FIG. 9 is a graph showing the results of editing at the RUNX1 locus using the recruitment (Suntag) strategy or published PE2 strategy.
Figure 10:
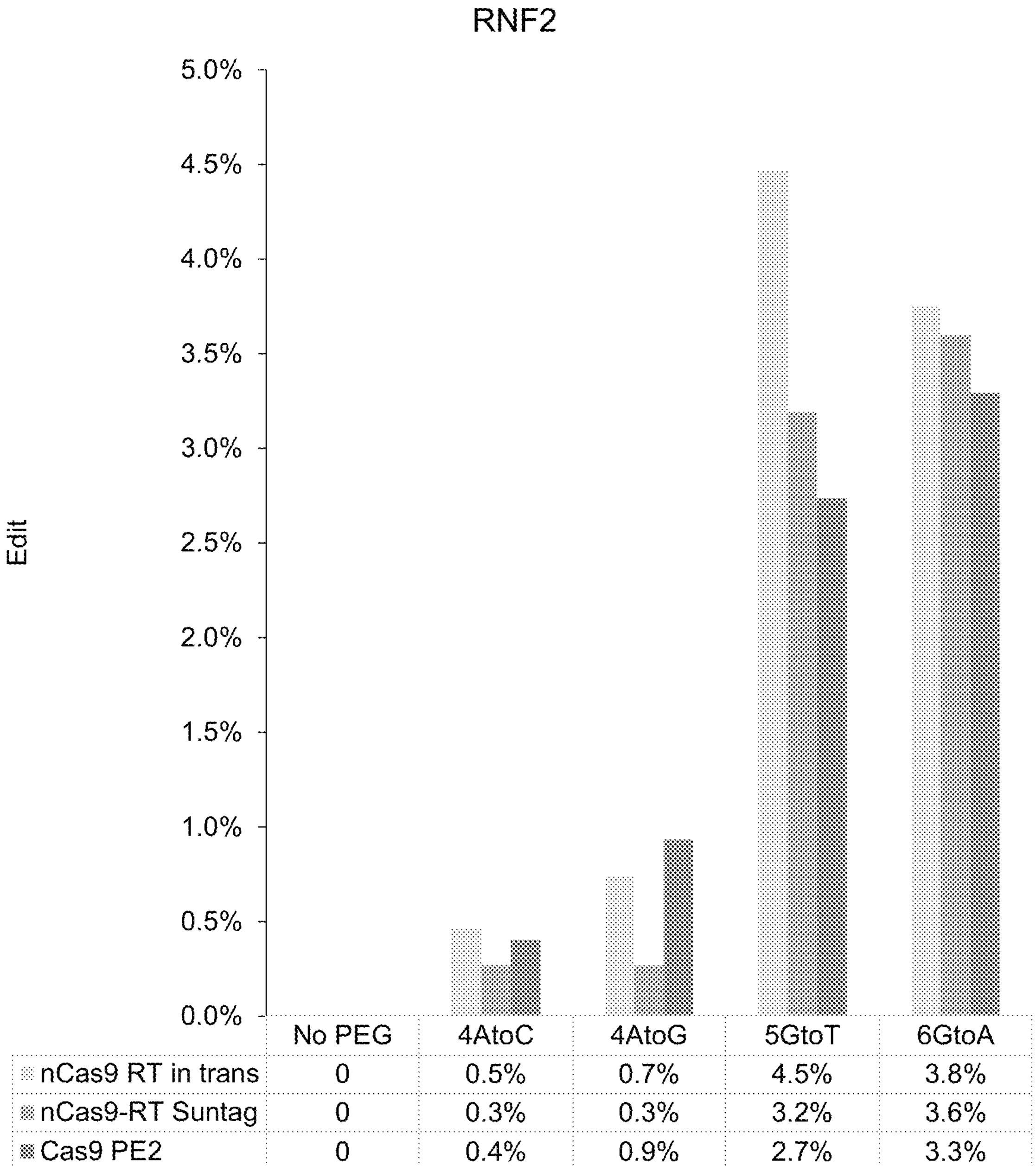
FIG. 10 is a graph showing the results of editing at the RNF2 locus using the recruitment (Suntag) strategy or published PE2 strategy.

Additionally, a third plasmid is delivered that contains the pegRNA (sgRNA scaffold) in the form of a guide scaffold and sequence for Cas9 behind the *Homo sapiens* U6 promoter (Hs. U6). The sequence for the pegRNA was designed to contain a reverse transcriptase template, and primer binding sequence (PBS) for the purpose of designed edits from the reverse transcriptase, as previously described for prime editing. The pegRNA structure with promoter is shown in FIG. 6. For the purpose of this test, 16 separate guide plasmids were utilized to target 4 separate sites in the human genome as provided in Table 2.

TABLE 2

Guide plasmids for reverse transcriptase recruitment testing.

| Guide Plasmid | Target | Designed Change | pegRNA Sequence |
|---|---|---|---|
| pWISE1580 | FANCF | 5GtoT | GGAATCCCTTCTGCAGCACCGTTTTAGAGCTAGAAATAGCAAGTTAAAATAAGGCTAGTCCGTTATCAACTTGAAAAAGTGGCACCGAGTCGGTGCGGAAAAGCGATCAAGGTGCTGCAGAAGGGA (SEQ ID NO: 55) |
| pWISE1581 | | 7AtoC | GGAATCCCTTCTGCAGCACCGTTTTAGAGCTAGAAATAGCAAGTTAAAATAAGGCTAGTCCGTTATCAACTTGAAAAAGTGGCACCGAGTCGGTGCGGAAAAGCGAGCCAGGTGCTGCAGAAGGGAT (SEQ ID NO: 56) |
| pWISE1582 | | 4GATins | GGAATCCCTTCTGCAGCACCGTTTTAGAGCTAGAAATAGCAAGTTAAAATAAGGCTAGTCCGTTATCAACTTGAAAAAGTGGCACCGAGTCGGTGCGGAAAAGCGATCCAATCGGTGCTGCAGAAGGGAT (SEQ ID NO: 57) |
| pWISE1583 | | 6Gdel | GGAATCCCTTCTGCAGCACCGTTTTAGAGCTAGAAATAGCAAGTTAAAATAAGGCTAGTCCGTTATCAACTTGAAAAAGTGGCACCGAGTCGGTGCGGAAAAGCGATCAGGTGCTGCAGAAGGGAT (SEQ ID NO: 58) |
| pWISE1584 | RNF2 | 4AtoC | GTCATCTTAGTCATTACCTGGTTTTAGAGCTAGAAATAGCAAGTTAAAATAAGGCTAGTCCGTTATCAACTTGAAAAAGTGGCACCGAGTCGGTGCAACGAACACCGCAGGTAATGACTAAGATG (SEQ ID NO: 59) |
| pWISE1585 | | 4AtoG | GTCATCTTAGTCATTACCTGGTTTTAGAGCTAGAAATAGCAAGTTAAAATAAGGCTAGTCCGTTATCAACTTGAAAAAGTGGCACCGAGTCGGTGCAACGAACACCCCAGGTAATGACTAAGATG (SEQ ID NO: 60) |
| pWISE1586 | | 5GtoT | GTCATCTTAGTCATTACCTGGTTTTAGAGCTAGAAATAGCAAGTTAAAATAAGGCTAGTCCGTTATCAACTTGAAAAAGTGGCACCGAGTCGGTGCAACGAACACATCAGGTAATGACTAAGATG (SEQ ID NO: 61) |
| pWISE1587 | | 6GtoA | GTCATCTTAGTCATTACCTGGTTTTAGAGCTAGAAATAGCAAGTTAAAATAAGGCTAGTCCGTTATCAACTTGAAAAAGTGGCACCGAGTCGGTGCAACGAACATCTCAGGTAATGACTAAGATG (SEQ ID NO: 62) |
| pWISE1589 | RUNX1 | 5GtoT | GCATTTTCAGGAGGAAGCGAGTTTTAGAGCTAGAAATAGCAAGTTAAAATAAGGCTAGTCCGTTATCAACTTGAAAAAGTGGCACCGAGTCGGTGCTGTCTGAAGCAATCGCTTCCTCCTGAAAAT (SEQ ID NO: 63) |
| pWISE1590 | | 6GtoC | GCATTTTCAGGAGGAAGCGAGTTTTAGAGCTAGAAATAGCAAGTTAAAATAAGGCTAGTCCGTTATCAACTTGAAAAAGTGGCACCGAGTCGGTGCTGTCTGAAGGCATCGCTTCCTCCTGAAAAT (SEQ ID NO: 64) |
| pWISE1591 | | 1ATGins | GCATTTTCAGGAGGAAGCGAGTTTTAGAGCTAGAAATAGCAAGTTAAAATAAGGCTAGTCCGTTATCAACTTGAAAAAGTGGCACCGAGTCGGTGCTGTCTGAAGCCATCCATGCTTCCTCCTGAAAAT (SEQ ID NO: 65) |
| pWISE1592 | | 2Gdel | GCATTTTCAGGAGGAAGCGAGTTTTAGAGCTAGAAATAGCAAGTTAAAATAAGGCTAGTCCGTTATCAACTTGAAAAAGTGGCACCGAGTCGGTGCTGTCTGAAGCCATGCTTCCTCCTGAAAAT (SEQ ID NO: 66) |

TABLE 2-continued

| Guide plasmids for reverse transcriptase recruitment testing. | | | |
|---|---|---|---|
| Guide Plasmid | Target | Designed Change | pegRNA Sequence |
| pWISE1594 | DMNT1 | 5GtoT | GATTCCTGGTGCCAGAAACAGTTTTAGAGCTAGAAATAGCAAGTTAAAATAAGGCTAGTCCGTTATCAACTTGAAAAAGTGGCACCGAGTCGGTGCGTCACCACTGTTTCTGGCACCAGG (SEQ ID NO: 67) |
| pWISE1595 | | 6GtoC | GATTCCTGGTGCCAGAAACAGTTTTAGAGCTAGAAATAGCAAGTTAAAATAAGGCTAGTCCGTTATCAACTTGAAAAAGTGGCACCGAGTCGGTGCGTCACGCCTGTTTCTGGCACCAGG (SEQ ID NO: 68) |
| pWISE1596 | | 1TCAins | GATTCCTGGTGCCAGAAACAGTTTTAGAGCTAGAAATAGCAAGTTAAAATAAGGCTAGTCCGTTATCAACTTGAAAAAGTGGCACCGAGTCGGTGCTCCCGTCACCCCTGTGATTTCTGGCACCAGG (SEQ ID NO: 69) |
| pWISE1597 | | 3-5AGGdel | GATTCCTGGTGCCAGAAACAGTTTTAGAGCTAGAAATAGCAAGTTAAAATAAGGCTAGTCCGTTATCAACTTGAAAAAGTGGCACCGAGTCGGTGCTCCCGTCACCGTTTCTGGCACCAGG (SEQ ID NO: 70) |

To examine whether editing could be enabled without recruitment, and thus through overexpression of the reverse transcriptase, an in trans treatment was performed utilizing the same scFV::Reverse Transcriptase::GB1 plasmid, but with a standard nCas9 that did not contain the GCN4 motif.

Following delivery to cells, genomic DNA was extracted and the target regions sequenced via amplicon sequencing. As shown in FIGS. 7-10, the recruitment strategy is shown to be equivalent to the previously published PE2 strategy.

Recruitment of RT to an Upstream Template

Figure 11:
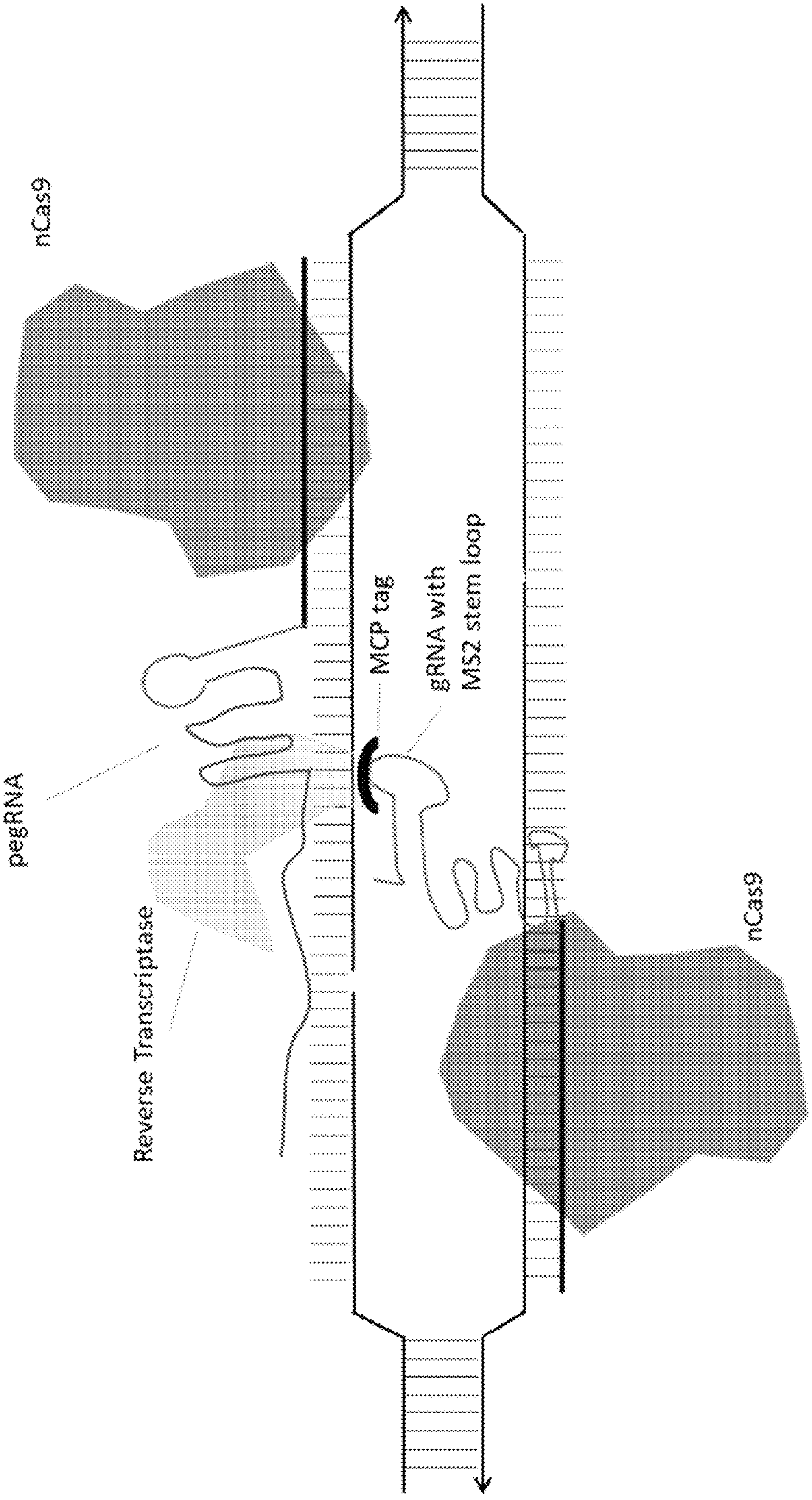
FIG. 11 is an illustration of the strategy to recruit the reverse transcriptase to an upstream template through a guide on the opposite strand. The reverse transcriptase is recruited to the pegRNA through a secondary guide containing a MS2 stem loop.

Another method of recruiting the reverse transcriptase to the edit site is to recruit it to the guide itself. To examine this architecture, a strategy was designed wherein one guide would recruit the reverse transcriptase so that it could be positioned nearby the template that is attached to a second guide. As shown in FIG. 11, the recruitment is achieved by utilizing an MS2 RNA stem-loop sequence as a 3' extension after the sgRNA scaffold. This then recruits the reverse transcriptase which has been engineered to contain the MCP coat protein sequence that will bind to the MS2 loop on the RNA, thus recruiting the reverse transcriptase to the guide RNA. A nucleotide sequence including MCP::MuLV (5M) is provided in SEQ ID NO:71. The gRNA is positioned to be upstream at a nearby genomic location, the template and primer binding sites designed to be positioned nearby the recruited reverse transcriptase. Nucleotides sequences for the FANCF gRNAs are provided in SEQ ID NOs:72-73.

The components were separately introduced to human cells on plasmid vectors using the CMV promoter for nCas9 and the reverse transcriptase, and the human U6 promoter for the guide RNAs. A nucleotide sequence including nCas9 (H840A)::P2A::EGFP is provided in SEQ ID NO:74. As a control, the same edits were attempted with a PE3 strategy, where the reverse transcriptase is linked to the nCas9 and the guide originally containing the MS2 loop is exchanged for a pegRNA containing the template for editing. Nucleotides sequences for the FANCF pegRNAs are provided in SEQ ID NOs:75-76.

Figure 13:
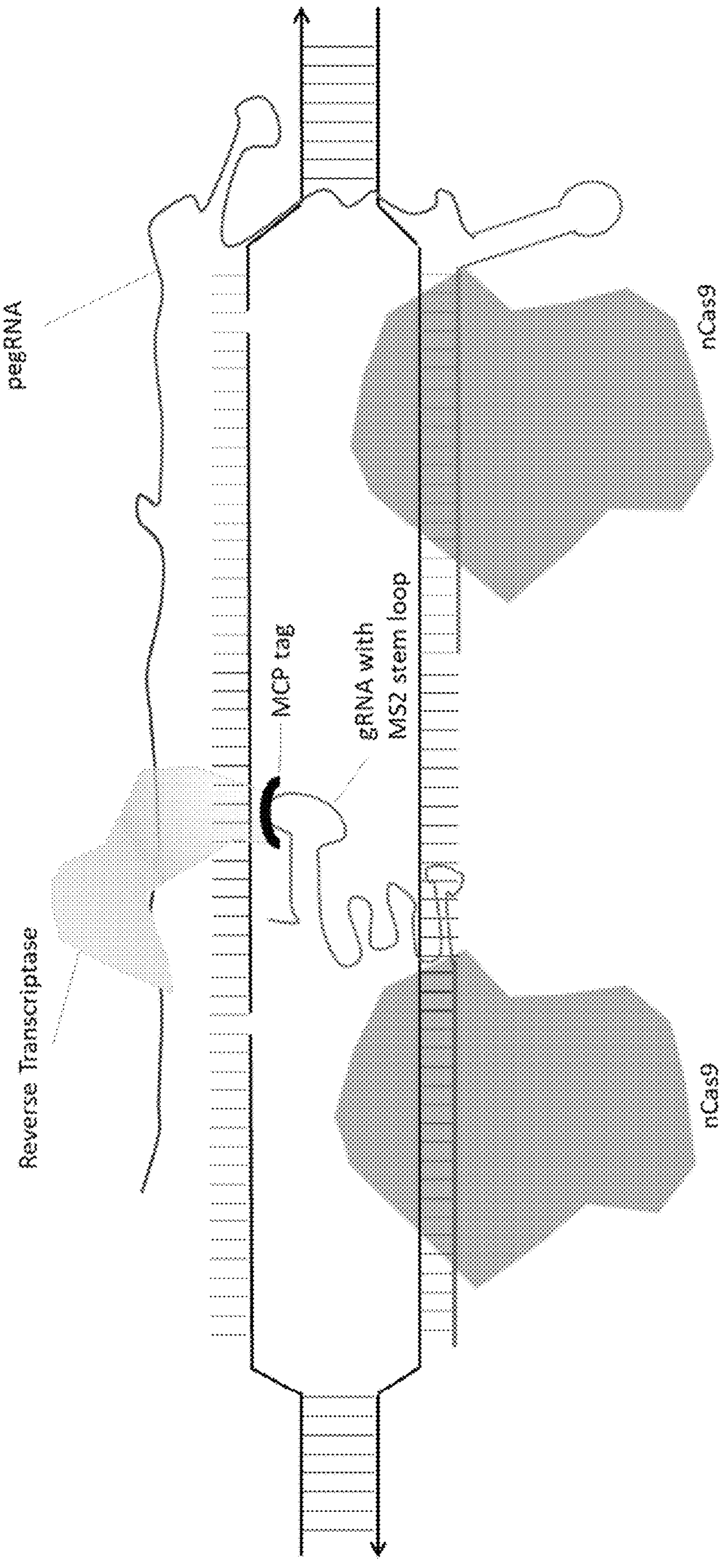
FIG. 13 is an illustration of the strategy to recruit the reverse transcriptase to an upstream template through a guide on the same strand. The reverse transcriptase is recruited to the pegRNA through a secondary guide containing a MS2 stem loop.

To examine if the recruitment strategy could edit through recruitment two targets at the FANCF locus in human cells were examined that had designed changes between two separate spacers. These targets represent multiple changes, and also a wide window, which is expected to be possible with this strategy. An example of the edits attempted is shown in FIG. 12 for the opposite strand strategy (WT sequence for site O2 (SEQ ID NO:77); Edit sequence for site O2 (SEQ ID NO:78); WT sequence for site O3 (SEQ ID NO:79); and Edit sequence for site O3 (SEQ ID NO:80). The design is similar for the same-strand strategy as shown in FIG. 13.

Figure 14:
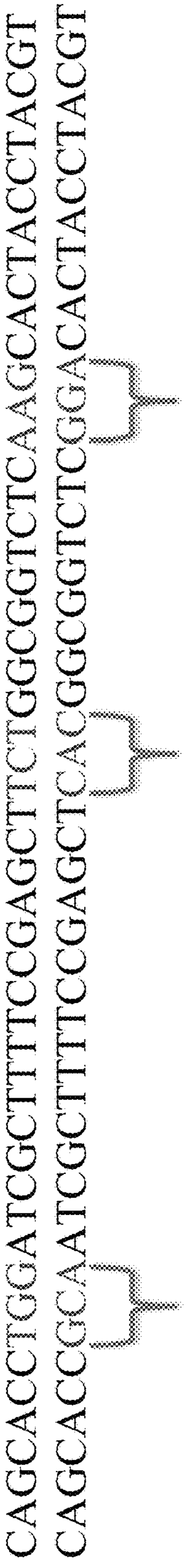
FIG. 14 is a diagram showing evidence of recruitment reverse transcriptase editing at the O2 site. Edits are shown in light gray and indicated by brackets. Top line: SEQ ID NO:81; Bottom line: SEQ ID NO:82.
Figure 15:
FIG. 15 is a diagram showing evidence of recruitment reverse transcriptase editing at the O3 site. Edits are shown in light gray and indicated by brackets. Top line: SEQ ID NO:83; Middle line: SEQ ID NO:84; Bottom line: SEQ ID NO:85.

Following delivery of the reagents, the target was sequenced via amplicon sequencing. The PE3 positive control showed editing at both sites for both the opposite and same strand strategies. In the experimental positive edits were only obtained with the opposite strand strategy where editing was observed at both the 02 and 03 sites (FIG. 12), as can be seen in the alignments provided in FIG. 14 (Top line: SEQ ID NO:81; Bottom line: SEQ ID NO:82) and FIG. 15 (Top line: SEQ ID NO:83; Middle line: SEQ ID NO:84; Bottom line: SEQ ID NO:85). Edits were not observed when the reverse transcriptase was not introduced to the system.

Example 2: Evidence of Prime Editing in Plants

Methods

Tobacco Infiltration:

Briefly, 4 week old *Nicotiana benthamiana* plants were used for infiltration with editing constructs. Prior to infiltration, all side shoots and flower buds were removed from plants and plants watered. Constructs were inoculated into LB liquid media with appropriate antibiotics and shaken for 2 days at 28 centigrade. The morning of infiltration, cultures were resuspended in infiltration buffer (10 mM MgCl2, 10 mM MES, pH5.6) and diluted to reach a final OD of 0.7. Prime constructs were mixed at a 3:1 editor to reporter ratio with pWISE711, which contained a ZsGreen fluorescent reporter. Leaves were infiltrated with a needless syringe into the underside of a leaf. Following infiltration, plants were allowed to rest for 1 hour on the lab bench before being moved to a growth chamber. After 5-δ days, plants were collected from growth chamber and treated leaves visualized with a bluelight flashlight. Leaf samples were collected from areas showing fluorescence, and thus presence of introduced constructs. Genomic DNA was collected from these samples before being used for amplicon sequencing.

Experimental Design:

To adapt the previously published prime editing experiments performed in human cells to plants, an experiment was designed to interrogate different reverse transcriptases and codon optimizations. First, the MuMLV (5M) reverse transcriptase was codon optimized for monocots and dicots. Additionally, the soybean chlorotic mottle virus (SbCMV) (Uniprot ID P15629) and cauliflower mosaic virus (CaMV) (Uniprot ID P03556) reverse transcriptases were optimized for dicots as well as using the native sequence. The various reverse transcriptases used in the experiment are listed in Table 3.

TABLE 3

Reverse Transcriptases Used for Experiment

| Name | Reverse Transcriptase | Codon Optimization Target |
|---|---|---|
| MMLV_MO1 (SEQ ID NO: 86) | MuMLV(5M) | Monocot |
| MMLV_MO2 (SEQ ID NO: 87) | MuMLV(5M) | Monocot |
| MMLV_MO3 (SEQ ID NO: 88) | MuMLV(5M) | Monocot |
| MMLV_DO1 (SEQ ID NO: 89) | MuMLV(5M) | Dicot |
| MMLV_DO2 (SEQ ID NO: 90) | MuMLV(5M) | Dicot |
| SbCMV_Native_Fragment (SEQ ID NO: 91) | SbCMV | Native Sequence |
| SbCMV_DO1 (SEQ ID NO: 92) | SbCMV | Dicot |
| CaMV_Native_Fragment (SEQ ID NO: 93) | CaMV | Native Sequence |
| CaMV_DO1 (SEQ ID NO: 94) | CaMV | Dicot |

Figure 16:
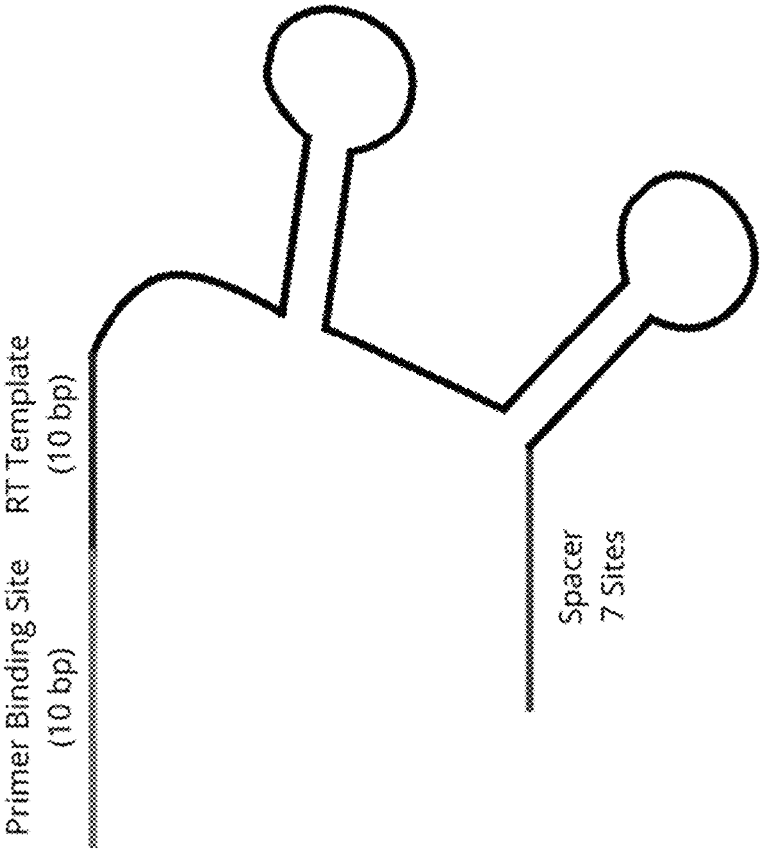
FIG. 16 is an illustration of a structure of pegRNA for the experiment in tobacco.

These reverse transcriptases were linked to the nickase variant of SpCas9 (H840A) by the XTEN linker. To examine the impact of expression, each of these editors was placed behind either a double viral promoter consisting of an enhancer from banana streak virus, and promoter and 5' UTR from dahlia mosaic virus, or ubiquitin 2 promoter from *Medicago truncatula*. These 18 editor cassettes (9 reverse transcriptase sequences driven by 2 promoters) were then combined with a double guide cassette targeting either the PDS or actin locus of tobacco in the PE3 architecture, containing a pegRNA containing the template for editing with the reverse transcriptase, and a standard sgRNA that will introduce a nick near the target site of the pegRNA; the nicking sequence being one of SEQ ID NOs:122-128. The pegRNA sequences are provided in Table 4. Each of the pegRNAs have a sequence of one of SEQ ID NOs:95-101, which was used behind a glycine max 7SL pol III promoter, and included a spacer having a sequence of one of SEQ ID NOs:102-108, a sgRNA scaffold having a sequence of SEQ ID NO:129, a primer binding site having a sequence of one of SEQ ID NOs:115-121, and a reverse transcriptase template having a sequence of one of SEQ ID NOs:109-114 or SEQ ID NO:161 that encodes the desired change as shown in FIG. 16. The sgRNA cassette sequences are also provided in Table 4. Each of the sgRNAs have a sequence of one of SEQ ID NOs:130-136 and included a spacer having a sequence of one of SEQ ID NOs:137-143 and a sgRNA scaffold having a sequence of SEQ ID NO:129. For this experiment, all reverse transcriptase templates and primer binding sites were 10 bp in length, and the encoded change was a 6 bp deletion. These 126 constructs were then infiltrated into tobacco leaves as described in the methods section.

TABLE 4 pegRNA and sgRNA sequences.

| Full Sequence | Spacer | Target | Reverse Transcriptase Target | Primer Binding Site | Nicking Spacer |
|---|---|---|---|---|---|
| AGATGAAACCAAAAGAAGAGGTTTTAGA GCTAGAAATAGCAAGTTAAAATAAGGCT AGTCCGTTATCAACTTGAAAAAGTGGCA CCGAGTCGGTGCATGGCAATGGTTCTTTT GGTT (SEQ ID NO: 95) | AGATGAAACCAAAA GAAGAG (SEQ ID NO: 102) | Actin | ATGGCAATGG (SEQ ID NO: 109) | TTCTTTTGGTT (SEQ ID NO: 115) | CTGGCCCCTCCA TTGTGCAT (SEQ ID NO: 122) |
| CACTTCCTATGCACAATGGAGTTTTAGAG CTAGAAATAGCAAGTTAAAATAAGGCTA GTCCGTTATCAACTTGAAAAAGTGGCACC GAGTCGGTGCTGAGTCTGGCATTGTGCAT AG (SEQ ID NO: 96) | CACTTCCTATGCAC AATGGA (SEQ ID NO: 103) | Actin | TGAGTCTGGC (SEQ ID NO: 161) | ATTGTGCATAG (SEQ ID NO: 116) | TAATTATCATTA TAATTCTT (SEQ ID NO: 123) |
| TTGGTAGTAGCGACTCCATGGTTTTAGAG CTAGAAATAGCAAGTTAAAATAAGGCTA GTCCGTTATCAACTTGAAAAAGTGGCACC GAGTCGGTGCTTAACTTATGGGAGTCGCT AC (SEQ ID NO: 97) | TTGGTAGTAGCGAC TCCATG (SEQ ID NO: 104) | PDS | TTAACTTATG (SEQ ID NO: 110) | GGAGTCGCTAC (SEQ ID NO: 117) | CATTCAAAACAA ACCTTTAA (SEQ ID NO: 124) |
| GCTCTTCCTGCGCCATTAAAGTTTTAGAG CTAGAAATAGCAAGTTAAAATAAGGCTA GTCCGTTATCAACTTGAAAAAGTGGCACC GAGTCGGTGCTAAGTACTTAAATGGCGC AGG (SEQ ID NO: 98) | GCTCTTCCTGCGCC ATTAAA (SEQ ID NO: 105) | PDS | TAAGTACTTA (SEQ ID NO: 111) | AATGGCGCAGG (SEQ ID NO: 118) | TTTGCATAATCA ACGCTGAA (SEQ ID NO: 125) |

TABLE 4-continued pegRNA and sgRNA sequences.

| Full Sequence | Spacer | Target | Reverse Transcriptase Target | Primer Binding Site | Nicking Spacer |
|---|---|---|---|---|---|
| GCCGTTAATTTGAGAGTCCAGTTTTAGAGCTAGAAATAGCAAGTTAAAATAAGGCTAGTCCGTTATCAACTTGAAAAAGTGGCACCGAGTCGGTGCAGCTGAATTAACTCTCAAATT (SEQ ID NO: 99) | GCCGTTAATTTGAGAGTCCA (SEQ ID NO: 106) | PDS | AGCTGAATTA (SEQ ID NO: 112) | ACTCTCAAATT (SEQ ID NO: 119) | AATCCTTAACTTATGCCCCA (SEQ ID NO: 126) |
| GAGATTGTTATTGCTGGTGCGTTTTAGAGCTAGAAATAGCAAGTTAAAATAAGGCTAGTCCGTTATCAACTTGAAAAAGTGGCACCGAGTCGGTGCGAAAAAATCACAGCAATAACA (SEQ ID NO: 100) | GAGATTGTTATTGCTGGTGC (SEQ ID NO: 107) | PDS | GAAAAAATCA (SEQ ID NO: 113) | CAGCAATAACA (SEQ ID NO: 120) | ATGAAAACTACAAATATAGA (SEQ ID NO: 127) |
| GAGGCAAGAGATGTCCTAGGGTTTTAGAGCTAGAAATAGCAAGTTAAAATAAGGCTAGTCCGTTATCAACTTGAAAAAGTGGCACCGAGTCGGTGCCTTCACCTTTAGGACATCTCT (SEQ ID NO: 101) | GAGGCAAGAGATGTCCTAGG (SEQ ID NO: 108) | PDS | CTTCACCTTT (SEQ ID NO: 114) | AGGACATCTCT (SEQ ID) NO: 121) | GGGAAGGACACAAAAGAAAA (SEQ ID NO: 128) |
| CTGGCCCCTCCATTGTGCATGTTTTAGAGCTAGAAATAGCAAGTTAAAATAAGGCTAGTCCGTTATCAACTTGAAAAAGTGGCACCGAGTCGGTGC (SEQ ID NO: 130) | CTGGCCCCTCCATTGTGCAT (SEQ ID NO: 137) | Actin - sgRNA nicking guide | | | |
| TAATTATCATTATAATTCTTGTTTTAGAGCTAGAAATAGCAAGTTAAAATAAGGCTAGTCCGTTATCAACTTGAAAAAGTGGCACCGAGTCGGTGC (SEQ ID NO: 131) | TAATTATCATTATAATTCTT (SEQ ID NO: 138) | Actin - sgRNA nicking guide | | | |
| CATTCAAAACAAACCTTTAAGTTTTAGAGCTAGAAATAGCAAGTTAAAATAAGGCTAGTCCGTTATCAACTTGAAAAAGTGGCACCGAGTCGGTGC (SEQ ID NO: 132) | CATTCAAAACAAACCTTTAA (SEQ ID NO: 139) | PDS - sgRNA nicking guide | | | |
| TTTGCATAATCAACGCTGAAGTTTTAGAGCTAGAAATAGCAAGTTAAAATAAGGCTAGTCCGTTATCAACTTGAAAAAGTGGCACCGAGTCGGTGC (SEQ ID NO: 133) | TTTGCATAATCAACGCTGAA (SEQ ID NO: 140) | PDS - sgRNA nicking guide | | | |
| AATCCTTAACTTATGCCCCAGTTTTAGAGCTAGAAATAGCAAGTTAAAATAAGGCTAGTCCGTTATCAACTTGAAAAAGTGGCACCGAGTCGGTGC (SEQ ID NO: 134) | AATCCTTAACTTATGCCCCA (SEQ ID NO: 141) | PDS - sgRNA nicking guide | | | |
| ATGAAAACTACAAATATAGAGTTTTAGAGCTAGAAATAGCAAGTTAAAATAAGGCTAGTCCGTTATCAACTTGAAAAAGTGGCACCGAGTCGGTGC (SEQ ID NO: 135) | ATGAAAACTACAAATATAGA (SEQ ID NO: 142) | PDS - sgRNA nicking guide | | | |
| GGGAAGGACACAAAAGAAAAGTTTTAGAGCTAGAAATAGCAAGTTAAAATAAGGCTAGTCCGTTATCAACTTGAAAAAGTGGCACCGAGTCGGTGC (SEQ ID NO: 136) | GGGAAGGACACAAAAGAAAA (SEQ ID NO: 143) | PDS - sgRNA nicking guide | | | |

Results

Figure 17:
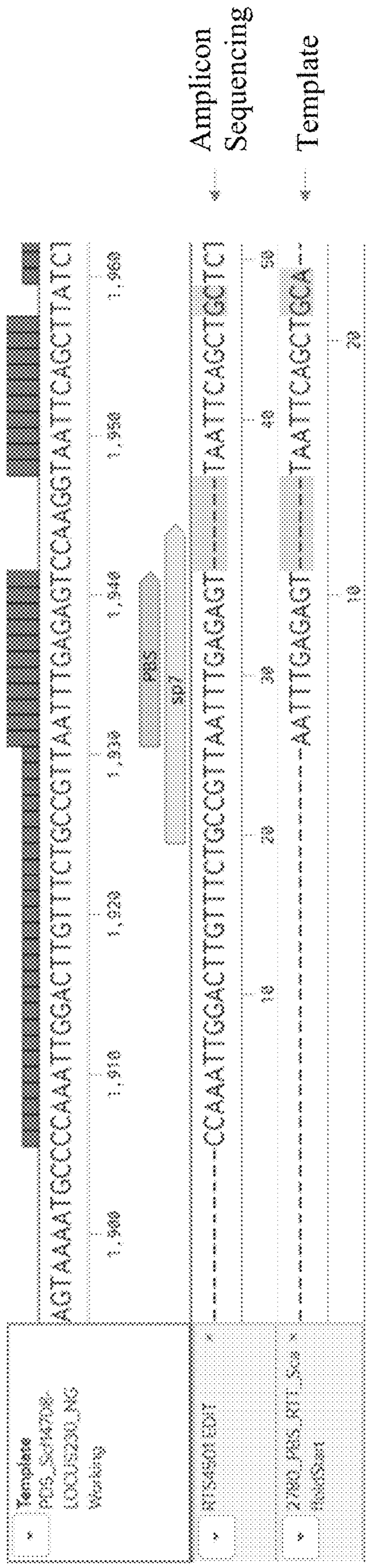
FIG. 17 is a diagram showing evidence of prime editing in plants. The top row is the targeted gene sequence (SEQ ID NO:130) with the spacer and primer binding site annotated. The second row (SEQ ID NO:131) is the amplicon sequencing result aligned to the reference showing the targeted deletion and insertion. The bottom row (SEQ ID NO:132) shows the prime binding site, reverse transcriptase template, and the first three bases of the scaffold, demonstrating the source of the deletion and insertion.

Following amplicon sequencing, positive editing was observed for pWISE2780 (SEQ ID NO:144) where the MMLV_MO1 codon optimization of the MuMLV (5M) reverse transcriptase was used behind the double viral promoter. The desired 6 bp deletion was observed as well as an insertion of 2 bp that incorporated the start of the scaffold sequence following the reverse transcriptase template, the end result being a 6 bp deletion and a 2 bp insertion as shown in FIG. 17 in which the top row is the targeted gene sequence (SEQ ID NO:130) with the spacer and primer binding site annotated. The second row (SEQ ID NO:131) of FIG. 17 is the amplicon sequencing result aligned to the reference showing the targeted deletion and insertion and the bottom row is SEQ ID NO:132.

The foregoing is illustrative of the present invention, and is not to be construed as limiting thereof. The invention is defined by the following claims, with equivalents of the claims to be included therein.

That which is claimed is:

1. A method of modifying a target nucleic acid in a cell, the method comprising:

contacting the target nucleic acid with a DNA binding polypeptide;

a DNA endonuclease;

a guide nucleic acid that comprises an RNA recruiting motif and a first spacer that has substantial complementarity to a first site on a first strand of the target nucleic acid, wherein the guide nucleic acid is devoid of a primer binding site, and wherein the guide nucleic acid binds to the first strand;

an extended guide nucleic acid, wherein the extended guide nucleic acid comprises (a) a second spacer having substantial complementarity to a second site on a second strand of the target nucleic acid and (b) an extended portion that comprises a primer binding site and a reverse transcriptase template encoding a modification to be incorporated into the target nucleic acid, wherein the extended guide nucleic acid binds to the second strand; and a reverse transcriptase that binds to the RNA recruiting motif, thereby modifying the target nucleic acid in the cell, wherein the target nucleic acid comprises the first strand and the second strand that are opposite strands of the target nucleic acid;

wherein the DNA binding polypeptide and the DNA endonuclease bind to the guide nucleic acid on the first strand;

wherein the reverse transcriptase is recruited to the second strand of the target nucleic acid by the RNA recruiting motif of the guide nucleic acid, and wherein the reverse transcriptase polymerizes a first polynucleotide from one end of the second strand.

2. The method of claim 1, wherein the DNA binding polypeptide is comprised in a DNA binding fusion protein comprising the DNA binding protein polypeptide fused to a peptide tag, and/or wherein the DNA endonuclease is a DNA endonuclease fusion protein comprising a DNA endonuclease domain fused to a peptide tag; and the reverse transcriptase is a reverse transcriptase fusion protein comprising a reverse transcriptase domain fused to an affinity polypeptide that binds to the peptide tag.

3. The method of claim 1, wherein the DNA binding polypeptide and the DNA endonuclease are comprised in a CRISPR-Cas nuclease.

4. The method of claim 1, wherein the DNA binding polypeptide is a CRISPR-Cas nuclease domain and the CRISPR-Cas nuclease domain is a Cas9 nickase (nCas9) domain or Cas12a domain.

5. The method of claim 1, wherein the DNA binding polypeptide is a CRISPR-Cas nuclease comprising a mutation in one or more nuclease active sites.

6. The method of claim 1, wherein the extended guide nucleic acid is linked to an RNA recruiting motif, and the reverse transcriptase is a reverse transcriptase fusion protein comprising a reverse transcriptase domain fused to an affinity polypeptide that binds to the RNA recruiting motif.

7. The method of claim 1, further comprising contacting the target nucleic acid with a second DNA binding polypeptide, a second DNA endonuclease, and an RNA encoded template.

8. The method of claim 1, further comprising contacting the target nucleic acid with a 5' flap endonuclease (FEN).

9. The method of claim 8, wherein the FEN is overexpressed in the plant or plant cell.

10. The method of claim 8, wherein the FEN is a fusion protein comprising an FEN domain fused to the DNA binding polypeptide and/or the DNA endonuclease.

11. The method of claim 1, wherein the reverse transcriptase is fused to one or more ssRNA binding domains (RBDs).

12. The method of claim 1, wherein a second polynucleotide encodes the DNA binding polypeptide, the DNA endonuclease, and the reverse transcriptase.

13. An expression cassette codon optimized for expression in a plant, comprising 5' to 3':

a polynucleotide encoding a plant specific promoter sequence; and a plant codon-optimized polynucleotide encoding a reverse transcriptase, the plant codon-optimized polynucleotide having at least 90% sequence identity to one of SEQ ID NOs: 86-94.

14. The expression cassette of claim 13, wherein the reverse transcriptase is fused to one or more ssRNA binding domains (RBDs).

15. An expression cassette codon optimized for expression in a plant, comprising:

a polynucleotide encoding a plant specific promoter sequence;

a guide nucleic acid that comprises a first spacer having substantial complementary to a first site on a first strand of a target nucleic acid, wherein the guide nucleic acid is devoid of a primer binding site;

an extended guide nucleic acid, wherein the extended guide nucleic acid comprises (a) a second spacer having substantial complementary to a second site on a second strand of the target nucleic acid, wherein the second strand is opposite the first strand and (b) an extended portion that comprises at its 3' end a primer binding site and a reverse transcriptase template, and polynucleotide encoding a DNA binding polypeptide.

16. The method of claim 1, wherein the extended guide nucleic acid is a first extended guide nucleic acid, the primer binding site is a first primer binding site and the reverse transcriptase template is a first reverse transcriptase template that is more than 50 nucleotides in length.

17. The method of claim 16, wherein the first primer binding site is 1 to 15 nucleotides in length.

18. The method of claim 16, wherein the first reverse transcriptase template is more than 65 nucleotides in length and/or the first reverse transcriptase template is after the first primer binding site.

19. The method of claim 16, wherein the first extended guide nucleic acid is comprised in an expression cassette.

20. The method of claim 16, further comprising contacting a second target nucleic acid with a second extended guide nucleic acid.

21. The method of claim 20, wherein the second extended guide nucleic acid comprises a second primer binding site and a second reverse transcriptase template that is more than 50 nucleotides in length.

22. The method of claim 21, wherein the second primer binding site is 1 to 15 nucleotides in length.

23. The method of claim 21, wherein the second reverse transcriptase template is more than 65 nucleotides in length and/or the second reverse transcriptase template is after second first primer binding site.

24. The method of claim 21, wherein the second reverse transcriptase template has more than 50 nucleotides of heterology relative to the second target nucleic acid and/or more than 15 nucleotides of homology relative to the second target nucleic acid.

25. The method of claim 20, wherein at least a portion of the first and second extended guide nucleic acids are complementary.

26. The method of claim 1, wherein a second polynucleotide encodes the DNA binding polypeptide, the DNA endonuclease, and/or the reverse transcriptase, and the second polynucleotide is codon optimized for expression in a plant.

27. The method of claim 1, wherein the reverse transcriptase is recruited to a location upstream of an edit site of the second strand.

28. The method of claim 1, wherein the RNA recruiting motif is at the 3' end of the guide nucleic acid.

29. A method of modifying a target nucleic acid in a cell, the method comprising:

contacting the target nucleic acid with:

a guide nucleic acid that comprises a first spacer having substantial complementarity to a first site on a first strand of the target nucleic acid, wherein the guide nucleic acid is devoid of a primer binding site;

an extended guide nucleic acid, wherein the extended guide nucleic acid comprises (a) a second spacer having substantial complementarity to a second site on the first strand, wherein a second strand of the target nucleic acid is opposite the first strand and (b) an extended portion that comprises at its 3' end a primer binding site and a reverse transcriptase template;

a first DNA binding polypeptide;

a first DNA endonuclease;

a second DNA binding polypeptide;

a second DNA endonuclease; and a reverse transcriptase, thereby modifying the target nucleic acid in the cell, wherein the first DNA binding polypeptide and the first DNA endonuclease are targeted to the first site of the target nucleic acid and the second DNA binding polypeptide and the second DNA endonuclease are targeted to the second site of the target nucleic acid;

wherein the first site and the second site are on the same strand of the target nucleic acid; and wherein the first DNA endonuclease and the second DNA endonuclease each nick the second strand of the target nucleic acid to provide a first nick and second nick that are on the same strand and the reverse transcriptase polymerizes a polynucleotide from one end of the second strand.

* * * * *

UNITED STATES PATENT AND TRADEMARK OFFICE
CERTIFICATE OF CORRECTION

PATENT NO. : 12,331,330 B2
APPLICATION NO. : 17/078919
DATED : June 17, 2025
INVENTOR(S) : Hummel et al.

It is certified that error appears in the above-identified patent and that said Letters Patent is hereby corrected as shown below:

In the Specification

Column 15, Lines 8-9: Please correct “ZmSTK2 USP” to read --ZmSTK2_USP--

Column 15, Line 17: Please correct “(RHES)” to read --(RHEs)--

Column 15, Line 24: Please correct “(S AMS)” to read --(SAMS)--

Column 21, Line 32: Please correct “(RP)” to read --(RT$^n$)--

Column 33, Line 58: Please correct “Cash” to read --Cas6--

Column 34, Line 44: Please correct “Cash” to read --Cas6--

Column 36, Line 60: Please correct “Cash” to read --Cas6--

Column 42, Lines 36-37: Please remove the paragraph break between “SEQ” and “Id”

Column 42, Lines 36-37: Please correct “SEQ Id Nos:42-52.” to read --SEQ ID NOs:42-52.--

Column 44, Line 10: Please correct “fora” to read --for a--

Column 48, Line 17: Please correct “-70%” to read ---~70%--

Column 48, Line 55: Please correct “scFV::MuLV (5M)::GB1::P2A::EGFP” to read --scFV::MuLV(5M)::GB1::P2A::EGFP--

Signed and Sealed this
Thirtieth Day of December, 2025

John A. Squires
*Director of the United States Patent and Trademark Office*

Column 52, Line 43: Please correct “02 and 03” to read --O2 and O3--

Column 52, Line 67: Please correct “5-δ days” to read --5-6 days--

SEQUENCE LISTING

<160> NUMBER OF SEQ ID NOS: 161

<210> SEQ ID NO 1
<211> LENGTH: 1592
<212> TYPE: DNA
<213> ORGANISM: Medicago truncatula

<400> SEQUENCE: 1
actgttaata atttttaaac gtcagcgcac taaaaaaacg aaaagacgga cacgtgaaaa 60
taaaaaacac acactagttt atgacgcaat actattttac ttatgatttg ggtacattag 120
acaaaaccgt gaaagagatg tatcagctat gaaacctgta tacttcaata cagagactta 180
ctcatatcgg atacgtacgc acgaagtatc atattaatta ttttaatttt taataaatat 240
tttatcggat acttatgtga tactctacat atacacaagg atatttctaa gatactttat 300
agatacgtat cctagaaaaa catgaagagt aaaaaagtga gacaatgttg taaaaattca 360
ttataaatgt atatgattca attttagata tgcatcagta taattgattc tcgatgaaac 420
acttaaaatt atatttcttg tggaagaacg tagcgagaga ggtgattcag ttagacaaca 480
ttaaataaaa ttaatgttaa gttcttttaa tgatgtttct ctcaatatca catcatatga 540
aaatgtaata tgatttataa gaaaattttt aaaaaattta ttttaataat cacatgtact 600
attttttaaa aattgtatct tttataataa tacaataata aagagtaatc agtgttaatt 660
tttcttcaaa tataagtttt attataaatc attgttaacg tatcataagt cattaccgta 720
tcgtatctta attttttttt aaaaaccgct aattcacgta cccgtattgt attgtacccg 780
cacctgtatc acaatcgatc ttagttagaa gaattgtctc gaggcggtgc aagacagcat 840
ataatagacg tggactctct tataccaaac gttgtcgtat cacaaagggt taggtaacaa 900
gtcacagttt gtccacgtgt cacgttttaa ttggaagagg tgccgttggc gtaatataac 960
agccaatcga tttttgctat aaaagcaaat caggtaaact aaacttcttc attcttttct 1020
tccccatcgc tacaaaaccg gttcctttgg aaaagagatt cattcaaacc tagcacccaa 1080
ttccgtttca aggtataatc tactttctat tcttcgatta ttttattatt attagctact 1140
atcgtttaat cgatcttttc ttttgatccg tcaaatttaa attcaattag ggttttgttc 1200
ttttctttca tctgattgaa atccttctga attgaaccgt ttacttgatt ttactgttta 1260
ttgtatgatt taatcctttg tttttcaaag acagtcttta gattgtgatt aggggttcat 1320
ataaattttt agatttggat ttttgtattg tatgattcaa aaaatacgtc ctttaattag 1380
attagtacat ggatattttt tacccgattt attgattgtc agggagaatt tgatgagcaa 1440 gttttttga tgtctgttgt aaattgaatt gattataatt gctgatctgc tgcttccagt 1500
tttcataacc catattcttt taaccttgtt gtacacacaa tgaaaaattg gtgattgatt 1560
catttgtttt tctttgtttt ggattataca gg 1592

<210> SEQ ID NO 2
<211> LENGTH: 2000
<212> TYPE: DNA
<213> ORGANISM: Zea mays

<400> SEQUENCE: 2
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240

-continued ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccottta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccoct ccacaccctc tttccccaac ctcgtgttcg ttcggagcgc 900
acacacacgc aaccagatct cccccaaatc cagccgtcgg cacctccgct tcaaggtacg 960
ccgctcatcc tccccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc tttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgtttg gtgatacttc 2000

<210> SEQ ID NO 3
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 3
gacaagaagt acagcatcgg gctggcgatc gggaccaact ccgtcggctg ggctgtgatt 60
accgacgagt acaaggtgcc atccaagaag ttcaaggtcc tcggcaacac tgaccggcac 120
agcattaaga agaacctgat tggggcgctg ctgttcgatt cgggggagac tgcggaggcg 180
accaggctga agcggactgc gcgccggagg tacaccagga ggaagaatcg gatctgctac 240

-continued

```
ctccaggaga ttttctcgaa tgagatggcc aaggtggacg attccttctt ccatcgcctg    300
gaggagtcgt tcctcgttga ggaggacaag aagcatgaga ggcatcccat tttcgggaat    360
atcgttgacg aggtggctta ccatgagaag tacccgacca tctaccatct gcggaagaag    420
ctcgtcgatt cgaccgataa ggccgacctg cggctgatct acctggccct cgcgcacatg    480
attaagttcc ggggccattt cctcatcgag ggcgacctca acccggacaa ctcggacgtg    540
gataagctct tcattcagct cgtgcagaca tacaaccagc tcttcgagga gaatcccatt    600
aacgcctcgg gggtcgacgc taaggctatt ctctcggctc ggctgtcgaa gtcgcgccgg    660
ctggagaatc tcattgccca gctcccaggc gagaagaaga acggcctctt cggcaacctg    720
attgccctgt cgctggggct cacaccgaat ttcaagtcga acttcgacct cgccgaggac    780
gctaagctcc agctcagcaa ggatacttac gatgatgacc tcgataacct gctcgcccag    840
attggggatc agtacgcgga tctgttcctc gcggccaaga atctcagcga tgctattctc    900
ctgtcggaca ttctccgcgt caacacagag attactaagg ccccactgtc ggcgagcatg    960
attaagaggt acgatgagca tcatcaggac ctgacactgc tcaaggcgct ggtccggcag   1020
cagctccccg agaagtacaa ggagattttc ttcgatcagt caaagaatgg gtacgcgggc   1080
tacattgatg gcggcgcgtc ccaggaggag ttctacaagt tcattaagcc catcctggag   1140
aagatggacg ggaccgagga gctgctggtg aagctcaatc gggaggacct gctccggaag   1200
cagcgcacat tcgacaatgg ctcgattcct caccagattc acctgggcga gctgcacgcc   1260
attctccgca ggcaggagga cttctacccg ttcctcaagg acaaccgcga gaagatcgag   1320
aagatcctga ccttccggat tccatactac gtggggccgc tcgcgcgggg gaactcccgg   1380
ttcgcgtgga tgactcgcaa gtccgaagaa acgattacac cgtggaattt cgaggaggtc   1440
gtcgacaagg gcgctagtgc gcagtcattc attgagagga tgaccaattt cgataagaac   1500
ctgcctaacg agaaggtgct gccgaagcat tcgctgctct acgagtactt caccgtttac   1560
aatgagctga ccaaggtgaa gtatgtgact gagggcatga ggaagccagc gttcctgagc   1620
ggcgagcaga agaaggctat cgtggacctg ctcttcaaga ctaaccggaa ggtgactgtg   1680
aagcagctca aggaggacta cttcaagaag attgagtgct tcgattccgt tgagattagc   1740
ggggtggagg atcggttcaa tgcttcgctc gggacatacc acgatctcct gaagatcatt   1800
aaggataagg acttcctcga caacgaggag aacgaggaca ttctcgaaga tattgtcctg   1860
accctcaccc tcttcgagga tcgggagatg atcgaggaga ggctcaagac atacgctcat   1920
ctgttcgatg ataaggtcat gaagcagctg aagcgcaggc ggtacacagg gtgggggcgg   1980
ctgagccgga agctgatcaa cgggattcgg gataagcagt ccgggaagac aattctcgac   2040
ttcctcaagt ccgacgggtt cgctaaccgg aacttcatgc agctcattca tgatgactcg   2100
ctgacattca aggaggatat tcagaaggcg caggtttcgg ggcagggcga ctcgctccac   2160
gagcatattg cgaatctggc gggctccccc gcgattaaga agggcattct gcaaaccgtc   2220
aaggtggttg atgagctggt caaggtcatg ggcggcata agccagagaa tattgtcatc   2280
gagatggcgc gggagaatca gaccacacag aaggggcaga agaactcacg ggagcggatg   2340
aagcgcatcg aggagggcat caaggagctg gggtcgcaga tcctgaagga gcatcccgtg   2400
gagaacactc agctgcaaaa tgagaagctg tacctctact acctccagaa cgggagggac   2460
atgtatgtgg atcaggagct ggatattaat aggctgagcg attacgatgt cgaccacatt   2520
gtcccacagt cgttcctgaa ggacgacagc attgacaaca aggtgctgac ccgctcggat   2580
aagaacaggg gcaagagcga taatgttcca agcgaggagg ttgtgaagaa gatgaagaac   2640
```

```
tactggcggc agctcctgaa cgcgaagctc atcacacagc ggaagttcga caacctcacc   2700

aaggctgagc gcgggggcct gagcgagctg gacaaggcgg ggttcattaa gaggcagctg   2760

gtcgagacac ggcagattac aaagcatgtt gcgcagattc tcgattcccg gatgaacacc   2820

aagtacgatg agaacgataa gctgattcgg gaggtcaagg taattaccct gaagtccaag   2880

ctggtgtccg acttcaggaa ggacttccag ttctacaagg ttcgggagat caacaactac   2940

caccacgcgc atgatgccta cctcaacgcg gtcgtgggga ccgctctcat caagaagtac   3000

ccaaagctgg agtcagagtt cgtctacggg gattacaagg tttacgacgt gcggaagatg   3060

atcgctaaga gcgagcagga gattggcaag gctaccgcta agtacttctt ctactccaac   3120

atcatgaact tcttcaagac agagattacc ctcgcgaatg gcgagatccg gaagaggccc   3180

ctcatcgaga caaatgggga gacaggggag attgtctggg ataaggggcg ggatttcgcg   3240

accgtccgga aggtcctgtc gatgccccag gttaatattg tcaagaagac tgaggtccag   3300

actggcggct tctcaaagga gtcgattctc ccaaagagga actccgataa gctcattgct   3360

cggaagaagg attgggaccc caagaagtac gggggattcg actcccccac tgttgcttac   3420

tctgttctgg ttgttgctaa ggtggagaag gggaagtcga agaagctgaa gagcgtgaag   3480

gagctgctcg ggattacaat tatggagagg tcatccttcg agaagaatcc catcgacttc   3540

ctggaggcca agggctacaa ggaggtgaag aaggacctga ttattaagct gcccaagtac   3600

tcgctcttcg agctggagaa tgggcggaag cggatgctgg cgtccgcggg ggagctgcaa   3660

aaggggaacg agctggcgct cccctccaag tatgtgaact tcctctacct ggcgtcgcac   3720

tacgagaagc tgaaggggtc cccagaggat aatgagcaga agcagctctt cgtcgagcag   3780

cataagcact acctggacga gattatcgag cagattagcg agttctcgaa gcgggtcatc   3840

ctcgcggatg cgaacctgga taaggtgctc agcgcctaca ataagcaccg ggacaagccg   3900

attcgggagc aggcggagaa tattattcac ctcttcacac tcaccaacct cggggcacca   3960

gctgcgttca agtacttcga cactactatc gaccggaagc ggtacacctc gacgaaggag   4020

gtgctcgacg ccaccctcat tcaccagtcg atcacaggcc tgtacgagac acggattgac   4080

ctgtcccagc tcgggggcga c                                             4101
```

<210> SEQ ID NO 4
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 4

```
gacaagaagt actccattgg cctggcgatt gggacaaact cggtggggtg ggccgtgatt     60

acggatgagt acaaggttcc aagcaagaag ttcaaggtcc tcgggaacac agatcggcat    120

tcgattaaga agaatctcat tggggcgctc ctcttcgact cgggggagac agcggaggct    180

accaggctca agcggacagc caggcggcgg tacacaaggc ggaagaatcg catctgctac    240

ctccaggaga ttttctcgaa tgagatggcg aaggtggacg acagcttctt ccatcggctg    300

gaggagtcct tcctggtgga ggaggataag aagcacgaga ggcatccaat tttcgggaac    360

atcgtggacg aggttgcgta ccatgagaag taccctacaa tctaccatct gcggaagaag    420

ctggttgact ccacagacaa ggcggacctg aggctgatct acctcgctct ggcccacatg    480

attaagttcc gcgggcattt cctgatcgag gggaacctga atcccgacaa ttcggatgtg    540
```

-continued

```
gacaagctct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga atgggctctt cgggaatctg    720
attgcgctct ccctggggct gacaccgaac ttcaagagca atttcgatct ggctgaggac    780
gcgaagctcc agctctcgaa ggacacttac gacgatgacc tcgataacct cctcgcgcag    840
atcggggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg ggacagagga gctgctggtg aagctcaacc gggaggatct gctcaggaag   1200
cagcggacgt tcgacaacgg gtcgattccc catcagatcc acctggggga gctgcacgcg   1260
atcctgcgcc ggcaggagga tttctaccct ttcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagcg gccagggcga ctcgctgcat   2160
gagcacatcg ctaacctggc gggcagccca gccatcaaga agggcatcct ccagacagtg   2220
aaggtcgtgg atgagctggt gaaggtcatg ggccggcata agcccgagaa tattgtgatt   2280
gagatggcgc gggagaatca gaccactcag aagggccaga agaactcgcg ggagcgcatg   2340
aagaggatcg aggaggggat taaggagctg ggcagccaga ttctcaagga gcaccccgtg   2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtcaaag   2880
ctcgttagcg atttccggaa ggacttccag ttctacaagg tgcgggagat taacaactac   2940
```

```
catcatgcgc acgatgcgta cctcaatgcg gtggtgggca cagccctgat taagaagtac   3000

cccaagctgg agagcgagtt cgtctacggg gactacaagg tgtacgatgt tcggaagatg   3060

atcgccaaga gcgagcagga gattgggaag gccaccgcta agtacttctt ctactcgaat   3120

attatgaatt tcttcaagac cgagatcaca ctcgctaatg gggagattcg gaagcggccc   3180

ctcatcgaga ctaacgggga gactggcgag attgtgtggg acaaggggcg cgacttcgct   3240

accgtgcgca aggtcctctc gatgccccag gttaatattg ttaagaagac agaggtgcag   3300

acgggcgggt tctccaagga gtctatcctg ccgaagcgga actcggacaa gctgatcgcc   3360

cgcaagaagg attgggaccc caagaagtac gggggattcg atagcccaac cgtggcttac   3420

agcgtcctgg tggtcgccaa ggttgagaag ggaaagtcga agaagctcaa gagcgttaag   3480

gagctgctgg gcatcaccat catggagcgg tccagcttcg agaagaatcc tatcgacttc   3540

ctggaggcta aggggtacaa ggaggtcaag aaggacctga tcattaagct gcccaagtac   3600

tctctgttcg agctggagaa cgggaggaag cggatgctgg cgtctgctgg cgagctacag   3660

aagggcaatg agctggcgct cccctcgaag tatgtcaact tcctctacct ggcttcccat   3720

tacgagaagc tgaagggctc gcccgaggat aatgagcaga agcagctctt cgtggagcag   3780

cacaagcact acctcgacga gatcattgag cagatttcgg agttctcgaa gcgggtcatt   3840

ctcgcggacg cgaacctcga caaggtcctc tcggcgtaca acaagcaccg ggacaagccc   3900

atccgggagc aggccgagaa cattatccac ctcttcacac tgaccaacct cggcgctccc   3960

gccgcgttca agtacttcga caccaccatt gaccgcaaga gatacacatc caccaaggag   4020

gtgctggacg cgaccctcat ccaccagagc atcacaggcc tctacgagac acggatcgac   4080

ctctcgcagc tcgggggcga t                                               4101
```

```
<210> SEQ ID NO 5
<211> LENGTH: 4092
<212> TYPE: DNA
<213> ORGANISM: Artificial
<220> FEATURE:
<223> OTHER INFORMATION: Cas9 nucleic acid sequence

<400> SEQUENCE: 5

gacaagaagt actcgatcgg cctggcgatt ggcacaaaca gcgtggggtg ggctgtgatc     60

actgatgagt acaaggtgcc atcgaagaag ttcaaggtgc tggggaatac agaccggcat    120

tcgatcaaga agaatctcat tggcgctctc ctcttcgatt ccggcgagac tgctgaggcg    180

acccgcctga agcgcaccgc ccggcggcgc tacactcggc ggaagaatag gatttgctac    240

ctccaggaga ttttctcgaa tgagatggcc aaggtggatg acagcttctt ccaccgcctg    300

gaggagtcgt tcctggtcga ggaggacaag aagcatgagc ggcaccctat cttcgggaat    360

atcgttgatg aggtcgccta ccacgagaag taccccacta tctaccatct ccgcaagaag    420

ctcgtggaca gcacagataa ggccgacctc cgcctgatct acctcgccct cgcgcacatg    480

attaagttcc gggggcactt cctcattgag ggggatctga atcccgataa ctccgacgtg    540

gacaagctgt tcatccagct ggtgcagaca tacaaccagc tgttcgagga gaatcccatc    600

aacgcgagcg gcgtggacgc taaggccatt ctgtcggcta ggctctcgaa gtcgaggcgg    660

ctggagaacc tgattgcgca gctccccggc gagaagaaga acgggctgtt cgggaatctc    720

atcgccctct ccctcggcct cacaccaaac ttcaagagca atttcgacct ggctgaggac    780

gctaagctgc aactctcaaa ggatacatac gatgacgacc tggacaatct cctggctcag    840
```

```
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag   1020
cagctgcccg agaagtacaa ggagattttc ttcgatcaga gcaagaatgg ctacgccggc   1080
tacatcgacg ggggcgcgag ccaggaggag ttctacaagt tcatcaagcc catcctggag   1140
aagatggacg gcaccgagga gctactcgtg aagctcaatc gggaggatct cctccggaag   1200
cagcggacat tcgataacgg gtctatccca caccagatcc acctcggcga gctgcatgcg   1260
attctgcggc ggcaggagga tttctaccct ttcctgaagg acaaccggga gaagatcgag   1320
aagatcctca cattccggat tccatactac gtcggccccc tggcgagggg caatagccgg   1380
ttcgcgtgga tgacaaggaa gtccgaggag actattaccc cgtggaattt cgaggaggtg   1440
gttgacaagg gcgcttccgc gcagagcttc attgagcgga tgacaaactt cgacaagaat   1500
ctccccaacg agaaggtcct gccgaagcat agcctcctgt acgagtactt caccgtctac   1560
aatgagctaa ctaaggtcaa gtatgtgaca gagggcatga ggaagccagc cttcctctca   1620
ggcgagcaga agaaggccat tgtggacctc ctgttcaaga caaaccgcaa ggtgacagtg   1680
aagcagctga aggaggatta cttcaagaag attgagtgct tcgactcagt ggagatttca   1740
ggcgtggagg atcggttcaa cgcgagcctg ggacttaccc acgacctgct gaagattatt   1800
aaggacaagg acttcctgga taacgaggag aatgaggaca tcctggagga tattgtgctc   1860
accctcaccc tgttcgagga cagggagatg attgaggaga ggctcaagac ctacgcgcac   1920
ctgttcgatg acaaggtcat gaagcagctg aagaggcggc gctacactgg gtggggccgc   1980
ctgtcgcgga agctgatcaa cggcattcgg gataagcagt ccgggaagac cattctggat   2040
ttcctgaagt cggacggctt cgccaacagg aatttcatgc agctgatcca cgacgactcc   2100
ctcaccttca aggaggacat tcagaaggcc caggttagcg gccaggggga ctcactccac   2160
gagcatattg ccaatctggc cggctctcca gctatcaaga agggcatcct gcaaacagtt   2220
aaggttgttg acgagctggt taaggtcatg gggcggcata agcccgagaa cattgtcatc   2280
gagatggctc gggagaacca gacaactcag aagggccaga agaactccag ggagcgcatg   2340
aagcggattg aggagggcat taaggagctg gggtcccaga tcctcaagga gcaccctgtc   2400
gagaacactc agctgcaaaa cgagaagctc tacctgtact acctccagaa cgggcgggat   2460
atgtatgtgg atcaggagct ggacatcaac aggctctccg actacgacgt ggatcacatt   2520
gtcccacagt cttccctcaa ggatgattcc atcgacaaca aggtgctgac gcgcagcgac   2580
aagaataggg ggaagtcgga caacgttccg agcgaggagg tcgtgaagaa gatgaagaat   2640
tactggaggc agctcctgaa tgcgaagctg atcactcaga ggaagttcga caatctgaca   2700
aaggcggaga ggggcgggct ctcggagctg gataaggcgg gcttcatcaa gcggcagctc   2760
gttgaaaccc ggcagatcac caagcatgtc gcccagatcc tcgatagccg catgaacacc   2820
aagtacgatg agaacgacaa gctcattcgg gaggttaagg tcattacgct gaagtccaag   2880
ctcgtcagcg acttcaggaa ggatttccag ttctacaagg ttcgggagat taacaactac   2940
caccacgcgc atgatgcgta cctgaacgct gttgtcggca ctgctctcat caagaagtac   3000
ccaaagctgg agtccgagtt cgtctacggg gactacaagg tctacgatgt ccggaagatg   3060
atcgccaagt cggagcagga gatcgggaag gctactgcga agtacttctt ctacagcaac   3120
attatgaatt tcttcaagac ggagattacg ctggcgaacg gggagattag gaagaggccc   3180
ctcattgaga ctaatgggga gacaggcgag attgtttggg acaagggccg cgacttcgcg   3240
```

```
actgtgcgga aggtcctgtc catgccacag gtgaatattg ttaagaagac agaggtgcag   3300

actgggggct tctcgaagga gagcattctc ccaaagcgga acagcgataa gctcatcgcg   3360

cgcaagaagg attgggaccc taagaagtac ggcggcttcg attctcccac tgtggcctac   3420

tccgttctcg tggttgccaa ggttgagaag gggaagtcga agaagctgaa gtcggtcaag   3480

gagctgctcg ggattacaat catggagcgg agcagcttcg agaagaaccc tattgatttc   3540

ctggaggcca agggctacaa ggaggttaag aaggatctca ttatcaagct ccctaagtac   3600

tctctgttcg agctggagaa tggccggaag aggatgctgg cctcggctgg cgagctacag   3660

aaggggaatg agctggccct cccgtcgaag tatgtgaatt tcctgtacct cgcgtcgcac   3720

tacgagaagc tcaagggcag cccggaggat aatgagcaga agcagctctt cgtggagcag   3780

cataagcact acctggacga gatcattgag cagatcagcg agttctcgaa gcgggttatt   3840

ctggctgatg ctaacctgga caaggttctg agcgcctaca ataagcatcg cgacaagccg   3900

attcgcgagc aggcggagaa tattatccac ctgttcaccc tcactaacct cggggctccc   3960

gcggccttca agtacttcga taccacaata gataggaagc ggtacacctc gacgaaggag   4020

gtcctcgacg ccacactcat ccatcagtcg attacaggcc tgtacgagac acggattgac   4080

ctctcgcagc tg                                                       4092
```

<210> SEQ ID NO 6
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 6

```
gacaagaagt attccatagg cctggctatc ggcaccaaca gcgtgggctg ggccgtcatc     60

accgacgagt acaaagtgcc gagtaaaaag ttcaaagtgc tcggcaacac cgaccgccac    120

tccataaaga aaaacctgat cggggcgctc ctgttcgaca gcggcgagac ggcggaggcc    180

acccgcttga aacgcacggc ccgacggcgc tacacgcggc gcaagaaccg gatctgttac    240

ctacaggaga ttttctctaa cgagatggcg aaggtggacg actcgttctt tcaccgcctc    300

gaagagtcct tcctcgtgga ggaggacaag aaacacgagc gccacccgat cttcggcaac    360

atcgtggacg aggtggccta ccacgagaag tacccgacca tctaccacct ccggaagaaa    420

ctcgtggaca gcacggacaa ggccgacctg aggctcatct acctcgccct ggcgcacatg    480

attaagttcc ggggccactt cctgatcgag ggcgacctga acccggacaa cagcgacgtg    540

gacaagctgt tcatccagct agtccagacc tacaaccagc ttttcgagga aaaccccatc    600

aacgccagcg gggtggacgc gaaggcgatc ctgtccgccc ggctgagcaa gtcccggcgg    660

ctggagaacc tcatcgcgca gttgcccggc gagaagaaga acgggctgtt cgggaacctg    720

atcgccctct ccctggggct caccccgaac ttcaagtcca acttcgacct cgccgaggac    780

gccaaactac agctgagcaa ggacacctac gacgacgacc tcgacaacct gctggcccag    840

atcggggacc agtacgcaga cctgttcctc gccgccaaga acctctccga cgccatcctg    900

ctgtcggaca tcctgcgggt gaacacggag atcacgaagg ccccgctctc ggcctcgatg    960

attaaacgct acgacgagca ccaccaggac ttgaccctcc tcaaggcgct ggtccgccag   1020

cagcttcccg agaagtacaa ggaaatcttt ttcgatcaga gcaagaacgg gtacgccggg   1080

tacatcgacg gcggggcgtc ccaggaggag ttctacaagt tcatcaagcc catcctggag   1140
```

-continued

```
aaaatggacg ggaccgagga gctgctcgtg aagctcaacc gcgaagattt gctccgcaag   1200
cagcgcacgt tcgacaacgg gtcgatcccg caccagatcc acctgggcga gctgcacgcg   1260
atcctcaggc gtcaggaaga cttctacccc ttcctcaagg acaaccgcga gaagatagag   1320
aagattctga ccttcagaat tccttattac gtgggcccgc tggctcgggg caactcgcgc   1380
ttcgcctgga tgacgcgcaa gtccgaggag accatcaccc cgtggaactt cgaggaggtg   1440
gtggataagg gtgcctcggc ccagtccttc atcgagcgga tgaccaactt cgacaagaac   1500
ctgccgaacg agaaggtgct ccccaagcac agcctgctct acgaatattt cacggtgtac   1560
aacgagctga cgaaggtcaa gtacgtgacc gagggaatga ggaaacctgc attcctctcc   1620
ggggagcaga agaaagccat agtcgacctc ctgttcaaga ccaaccggaa ggtcaccgtc   1680
aagcagctca aggaggacta cttcaagaag atcgagtgct tcgattcagt ggagatcagc   1740
ggcgtcgagg accggttcaa cgccagcctg ggcacctacc acgacctgct caagatcatc   1800
aaggacaagg acttcctcga caacgaggag aacgaggaca tcctggagga catcgtgctg   1860
accctgacgc tcttcgagga ccgcgagatg atcgaggagc gcctcaagac ctacgcccac   1920
ctgttcgacg acaaggtgat gaagcagctc aagcggcgga gatatactgg gtgggggccgc   1980
ctctcccgga agctcattaa cggtatcagg gataagcagt ccgggaagac gatcctcgac   2040
ttcctcaagt cggacgggtt cgccaaccgc aacttcatgc agctcatcca cgacgactcc   2100
ctgacgttca aggaggacat ccagaaggcc caagtgtctg gtcaaggtga ctcgctccac   2160
gagcacatcg ccaacctcgc gggcagcccg gccatcaaga agggaatact ccagaccgtc   2220
aaggtggtgg acgagctggt gaaggtcatg ggccgccaca agccggagaa catcgtcatc   2280
gagatggcgc gggagaacca gaccacgcag aaggggcaga aaaatagccg tgagcgcatg   2340
aagcgcatcg aggaggggat taaggagttg ggcagccaga tcctcaagga gcaccctgtg   2400
gagaacacgc agttgcaaaa cgagaagctc tacctgtact acctccagaa cgggagggat   2460
atgtacgtgg accaagaact ggacatcaac cgcctgtccg actacgacgt ggaccacatc   2520
gtgccgcaga gcttcctcaa ggacgacagc atcgacaaca aggtgctcac ccggtccgac   2580
aagaatcggg gcaagtccga caacgtgccc agcgaggagg tcgtcaaaaa gatgaaaaac   2640
tactggcgac aactactgaa cgccaagctc atcacccagc gcaagttcga caacctcaca   2700
aaagccgagc gcggcgggtt gagcgagctg gacaaggccg ggttcatcaa gcgccagctc   2760
gtcgagacgc gccagatcac gaagcacgtc gcgcagatac tcgacagccg gatgaacacc   2820
aagtacgacg agaacgacaa gctcatccgg gaggtgaagg tcatcaccct caagtcgaag   2880
ctcgtgagcg acttccgcaa ggacttccag ttctacaagg tccgggagat caacaactac   2940
caccacgccc acgatgctta tcttaacgcc gtggtgggga cggccctcat taagaaatac   3000
ccgaagctgg agtcggagtt cgtgtacggc gactacaagg tgtacgacgt caggaagatg   3060
atcgccaagt ccgaacagga gatcgggaag gccacggcga aatacttctt ctacagcaac   3120
atcatgaact tcttcaagac cgagatcacc ctcgccaacg gcgagatccg caagcgcccg   3180
ctcatcgaga cgaacgggga gaccggcgag atcgtctggg acaaggggcg cgacttcgcc   3240
actgtgcgga aggtgctgtc gatgccccag gtcaacatcg tcaagaagac ggaggtccag   3300
acgggcgggt tcagcaagga gagcatcctg ccgaagcgca acagcgacaa gctgatcgcc   3360
cgcaaaaagg actgggatcc aaaaaagtac ggcggcttcg acagccccac cgtcgcctac   3420
agcgtcctcg tcgtcgctaa agtcgagaag ggcaagtcca aaaagctcaa gagcgtcaag   3480
gagctgctcg ggatcaccat catggagcgg tccagcttcg agaagaaccc aattgatttc   3540
```

ctggaggcga agggctacaa ggaggtcaag aaagacctca tcataaagct gccgaagtac 3600
tcactcttcg agctggagaa cgggcgcaag cggatgctgg cgtcggccgg agagctccaa 3660
aagggcaacg agctggcgct gccgagcaag tacgtgaact tcctctacct ggcgtcccac 3720
tacgagaagc tcaagggcag tccagaggat aacgagcaga agcagctatt cgtggagcag 3780
cacaagcact acctggacga gatcatcgag cagatcagcg agttctccaa gcgcgtcatc 3840
ctggcggacg ccaacctgga caaggtgctg tccgcgtaca acaagcaccg cgacaagccg 3900
atccgcgagc aagccgagaa catcatccac ctgttcaccc tcacgaacct cggggcaccc 3960
gccgccttca aatatttcga cacgaccatc gaccgcaagc gctacaccag cacgaaggag 4020
gtgctcgacg ccaccctgat ccaccagagc atcaccgggc tgtacgagac ccgcatcgac 4080
ctctcgcagc tcggcgggga c 4101

<210> SEQ ID NO 7
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 7
gacaagaagt acagtattgg attggccatc gggacgaaca gcgtgggctg ggccgtcatc 60
accgacgagt acaaggtgcc atccaagaag tttaaggttc tggggaatac cgaccgccac 120
tcgatcaaga aaaatctcat cggggcgctg cttttcgaca gcggcgagac ggcggaagcg 180
acgcggctca agcggacggc tcgtcgccgt tacacccggc gtaagaaccg catctgttac 240
ctccaggaga tattcagcaa cgagatggcg aaggtggacg actccttttt ccaccgtctt 300
gaggagtcct tcctggtcga ggaggacaag aagcacgagc gccacccgat cttcgggaac 360
atcgtggacg aggtggccta ccacgagaag taccccacga tctaccacct ccgcaaaaaa 420
ctcgtggact caactgacaa ggccgatttg aggcttatct acctcgccct cgcccacatg 480
attaagttcc gtgggcactt cctaatcgag ggtgacctca accccgacaa ctctgacgtg 540
gacaagctgt tcatccagct tgtgcagacc tacaatcagc tctttgagga gaatccgatc 600
aacgcatctg gtgtggacgc aaaggccatc ctcagcgcgc ggctgagcaa gtctaggcgg 660
ttggagaacc tgatcgccca actgcccggc gagaagaaaa atggcctctt cggcaacctg 720
atcgccctgt cgctggggct cacgccgaac ttcaagagta actttgacct ggcggaggac 780
gctaagctcc agctatctaa ggacacatac gacgacgacc tggacaacct gctggcccag 840
atcggcgacc agtacgccga cctcttccta gccgccaaga acctgtccga cgccatcctc 900
ctcagcgaca tcctgcgcgt gaacacggag atcacgaagg ctccgctcag cgcctccatg 960
attaagcggt acgacgagca ccaccaagac ctaactttac tcaaagccct cgtgcggcag 1020
cagcttcccg agaagtacaa agagatattt tttgatcagt ccaagaacgg ttatgcgggc 1080
tacatcgacg gcggcgcgag ccaggaggag ttctacaagt tcatcaagcc catcctggag 1140
aagatggacg gcacggagga gctgctcgtg aagctcaacc gtgaagacct cctgcgaaag 1200
cagcgaacct tcgacaacgg ttcgatcccg caccagatcc acctcgggga gctgcacgcc 1260
atcctgaggc gacaggagga cttctaccct ttcctaaagg acaaccgcga gaagattgaa 1320
aaaatcctga cgtttcgcat accctactac gtcggcccgc tggcgcgcgg caactcccgg 1380
ttcgcctgga tgacccgtaa gagcgaggag acgatcaccc cgtggaactt cgaggaggtc 1440

-continued

```
gtggacaagg gcgcgagcgc gcagagcttc atcgagcgca tgaccaactt cgacaagaac   1500
ctcccgaacg agaaggtgct cccaaagcac tccctcctgt acgagtattt caccgtgtac   1560
aacgagttga caaaggtgaa gtacgtgacg gagggaatgc ggaagcctgc gttcctctcg   1620
ggcgagcaga agaaggcaat cgtggacctg ctcttcaaga ccaaccggaa ggtgacggtg   1680
aagcagctca aggaggacta cttcaaaaaa atcgagtgct tcgactccgt ggagataagc   1740
ggcgtggagg accgattcaa cgcctccctc ggcacctacc acgacctcct taagatcatc   1800
aaggacaagg acttcctgga caacgaggag aacgaggaca tcctggagga catcgtgctc   1860
accctgaccc tcttcgagga ccgggagatg atcgaggagc gcctcaagac gtacgcccac   1920
ttgttcgacg acaaggtgat gaagcagctc aagcggcggc gatacaccgg gtggggccgc   1980
ctatcccgca aacttatcaa cggcatccgc gacaagcagt ccggcaagac gatcctggat   2040
ttcctcaagt cggacgggtt cgccaaccgg aacttcatgc agctcatcca cgacgacagc   2100
ctcacgttca aggaggacat ccagaaggcc caagtgagcg gtcaagggga cagcctccac   2160
gagcacattg cgaaccttgc tgggagccct gcgatcaaga aggggatatt gcaaaccgtg   2220
aaggtcgtgg acgagttggt gaaggtcatg gggcgacaca agcccgagaa catcgtgatc   2280
gagatggcca gggaaaatca gaccacgcag aagggccaaa aaaacagccg cgagcggatg   2340
aagcggatcg aggagggcat caaggagctg gggtcgcaga tcctcaagga gcacccggtg   2400
gagaacacgc agctccagaa cgagaagctg tacctctatt acctacagaa cgggcgggat   2460
atgtacgtgg accaggagct agacatcaac cgcctgtccg actacgacgt ggaccatatc   2520
gtcccgcagt cgttcttgaa ggacgacagc atcgacaaca aggtgctcac aagatcggat   2580
aagaatcgag gcaagtccga caacgtgccc tcggaggagg tggtcaagaa aatgaaaaac   2640
tactggcggc agttgctgaa cgccaagctc attacgcagc ggaagttcga caacctgacg   2700
aaggctgaac gtggtgggct cagcgagcta gacaaggcgg ggttcatcaa gcggcagctc   2760
gtcgagaccc ggcagatcac caagcacgtg gcgcagatcc tggactcgcg catgaacacc   2820
aagtacgacg agaacgacaa gctcatccgt gaggtgaagg tcatcaccct taagtctaag   2880
ctggtcagtg acttccgcaa ggacttccag ttctacaagg tccgggagat caacaactac   2940
caccacgcgc acgacgccta cctcaacgcg gtggtgggga cggcgcttat taagaaatat   3000
cccaagctgg aaagcgagtt cgtttacggc gactacaagg tgtacgacgt ccgcaagatg   3060
atcgcaaagt cggaacagga aatcggaaag gcgacggcca aatatttctt ttactccaac   3120
atcatgaatt tttttaagac ggagatcacc ctggcgaacg gggagatccg caagcggccc   3180
ctcatcgaga ccaacgggga gacgggcgag atcgtctggg acaagggccg ggacttcgcc   3240
accgtgcgga aggtgctttc tatgcctcaa gtcaatatcg tcaaaaagac agaggtgcag   3300
accggcgggt tcagcaagga gtctatcctg ccgaagcgca actcggacaa gctcatcgcg   3360
cgcaagaaag actgggaccc caaaaaatat ggcgggttcg actcgccgac cgtcgcctac   3420
agcgtcctcg tggtggctaa ggtcgagaag ggcaagagca aaaagctaaa gtcggtgaag   3480
gagctgctgg gcatcaccat catggagcgc tcgtctttcg agaagaatcc aatcgacttc   3540
ctagaggcga aggggtacaa ggaggtcaaa aaggatctta tcatcaaact gccgaagtac   3600
agtctgttcg agctggagaa cgggcggaag cggatgctgg ctagtgcggg cgagttgcag   3660
aagggcaacg agttggcact gccctccaag tacgtgaact tcctgtacct ggcctcccac   3720
tacgagaagc tcaaggggag ccccgaggac aacgagcaga agcagctatt cgtcgagcag   3780
cacaagcact acctggacga gatcatcgag cagatcagtg agttctccaa gcgggtcatc   3840
```

```
ctcgcggacg ccaacctgga caaggtgctg agcgcgtaca acaagcacag ggacaagcca   3900

atcagggaac aggccgagaa catcatccac ctgttcaccc tgaccaacct gggtgcaccg   3960

gctgccttca agtactttga cacgaccatc gaccggaagc gctacacctc cacgaaggag   4020

gtgctggacg ccacgctgat ccaccagagc atcaccgggc tctacgagac acggatcgac   4080

ctgagccagc ttggcgggga c                                             4101


<210> SEQ ID NO 8
<211> LENGTH: 4092
<212> TYPE: DNA
<213> ORGANISM: Artificial
<220> FEATURE:
<223> OTHER INFORMATION: Cas9 nucleic acid sequence

<400> SEQUENCE: 8

gacaaaaagt attccattgg actcgctatc ggcacgaaca gcgtcgggtg ggcggtcatc     60

actgacgagt acaaggtgcc gagcaagaag tttaaggtgc tgggaaacac cgacaggcac    120

tcgatcaaga aaaatcttat cggggcccta ctcttcgact ccggagaaac cgccgaggcc    180

acccggttga agcgcacggc ccgccgtcgc tacaccaggc gcaagaaccg gatctgctac    240

ctccaggaga tattcagcaa tgagatggcg aaggtggacg actcgttttt tcacaggcta    300

gaggagtctt tcctcgtgga ggaggacaag aaacacgagc gccaccccat cttcggcaac    360

atcgtggatg aggtggcata tcacgagaag tacccaacca tctaccacct ccgcaaaaag    420

ctcgtggact ctaccgacaa ggccgacctc cgtctgatct acctcgcgct ggcccacatg    480

attaagttcc gaggacactt tctgatcgag ggcgacctga acccagacaa cagcgacgtg    540

gacaagctgt tcatccaact tgtccagacc tacaatcagc tcttcgagga gaaccctatc    600

aacgcctcgg gcgtggacgc gaaggccatc ctgtccgccc gcctgagcaa gtcgcggcgg    660

ctggagaacc tgatcgccca gctccccggc gaaaaaaaga acggcctctt cggcaacctc    720

atcgcgttgt cgctggggct caccccgaac ttcaagtcca acttcgacct ggccgaggac    780

gctaaactcc agctctcgaa ggatacctac gacgacgacc tcgacaacct gctggcccag    840

atcggcgacc agtacgcgga ccttttcctg gcggccaaga acctgagcga cgcgatcctc    900

cttagcgaca tactccgtgt gaacaccgag atcacgaagg ccccgctctc cgcgtccatg    960

attaagcgct acgacgagca ccaccaagac cttaccctgc ttaaggcgct ggtcaggcag   1020

cagttaccgg agaagtacaa ggagatcttt tttgatcaat ctaagaacgg ttacgccggg   1080

tacatcgacg gcggcgcgtc ccaggaggag ttctacaagt tcatcaagcc gatcttggag   1140

aaaatggacg ggaccgagga gctgctcgtg aagctcaacc gcgaagacct cctccgcaag   1200

cagcgcacct tcgacaacgg gagcatcccg caccagatcc acctgggaga gctgcacgcg   1260

atcctgcgga gacaagagga cttctacccc ttcctcaagg acaaccggga gaagattgaa   1320

aaaatactta cttttcgtat cccgtactac gtcgggcccc ttgcgagggg caactccaga   1380

ttcgcgtgga tgacccgcaa gtccgaggag accatcaccc cgtggaactt cgaggaggtg   1440

gtggacaagg gcgcgtcggc ccagtcgttc atcgagcgca tgaccaactt cgacaagaac   1500

cttccgaacg agaaggtgct cccgaagcac agcctgctct acgaatattt tactgtgtac   1560

aacgagctga cgaaggtcaa gtacgttacg gaggggatga ggaagcccgc cttcctctcc   1620

ggcgagcaga agaaagccat tgtggatctc ctgttcaaga ccaaccgcaa ggtgacggtg   1680

aaacagctca aagaggacta cttcaagaag atcgagtgct tcgactccgt agagatcagc   1740
```

-continued

```
ggggtcgagg accgcttcaa cgcctcgctg ggcacgtacc acgacctgct aaagattatc   1800
aaggacaaag acttcctaga caatgaggag aacgaggaca ttctggagga catcgtgctg   1860
actctgacgc tgttcgaaga ccgcgagatg atcgaggagc ggcttaagac gtacgcccac   1920
ctgttcgacg acaaggtgat gaagcagttg aaacggcggc gctacaccgg gtggggccgc   1980
ctctcccgca agctcatcaa cggcatccgc gacaagcagt cggggaagac gatcctggac   2040
ttcctcaaga gcgacggctt cgccaaccga aacttcatgc agctaatcca cgacgacagc   2100
ctgacgttca aggaggacat ccagaaggcc caagtgagcg gccagggaga ctcgctacac   2160
gagcatatcg ccaacctggc tggcagcccg gcgattaaga aaggaatcct ccaaaccgtc   2220
aaagtggtgg acgagctggt gaaggtgatg ggccgccaca agcccgagaa cattgtgatc   2280
gagatggcgc gggagaacca gacgacgcag aagggccaaa aaaatagcag ggaaaggatg   2340
aagcgaatag aggaggggat caaggagctg gggagccaga ttctcaaaga gcacccggtc   2400
gagaacacac agctccagaa cgagaagctg tacctctact acctccaaaa cggccgcgat   2460
atgtacgtgg accaggaact agacatcaac cggctgagcg actatgacgt ggaccacatc   2520
gtgccgcagt ccttcctcaa ggacgactcg attgacaaca aagtgctcac tagatccgac   2580
aagaacagag gcaagagcga taacgtcccg tcggaggagg tcgtcaagaa aatgaaaaac   2640
tactggcggc agctcctaaa cgccaagctc atcacgcagc gtaagttcga caacctgacg   2700
aaggcggagc ggggcgggct gagcgagctg gacaaagcgg ggttcatcaa gcggcagctc   2760
gttgagacgc ggcagatcac aaagcacgtc gcgcaaatcc tcgactcccg catgaacacc   2820
aagtacgacg agaacgacaa gctcatccgg gaggtgaagg tcattaccct taaatcgaag   2880
ctcgtcagcg actttcgtaa ggacttccag ttctacaagg tcagagagat caacaactac   2940
caccacgccc acgacgccta tctgaacgcc gtggtgggca ccgcgcttat taagaagtac   3000
cccaagctgg agtccgagtt cgtgtacggc gactacaagg tttatgacgt caggaagatg   3060
atcgccaagt cggaacagga gatcggaaaa gctaccgcca aatatttctt ctatagcaac   3120
atcatgaact tcttcaaaac cgagatcacc ctcgccaacg gcgagatccg gaagcgcccg   3180
ctcatcgaga ccaacgggga gaccggggag atcgtctggg acaaggggcg ggacttcgct   3240
actgtccgaa aggtgctctc catgccacaa gtgaatatcg tcaagaaaac agaggtgcag   3300
accggagggt tcagtaagga gtccatcctg cccaagcgga actccgacaa gctaattgct   3360
cgcaaaaagg attgggatcc taaaaaatat ggcggcttcg actcgcccac ggtcgcctac   3420
tctgtgctgg tcgtggcgaa ggtggagaag ggcaagtcca agaagctcaa gagcgtcaag   3480
gagctgctgg ggatcacgat catggagcgt agttcgtttg agaagaatcc catcgacttc   3540
ctggaggcta agggctacaa ggaggtcaaa aaggacctca tcattaagct gccgaagtac   3600
agcctcttcg agctggagaa cgggcggaag cgtatgctcg cctccgctgg ggagttacaa   3660
aaggggaacg agctggcgct gccgtctaag tacgtcaact tcctgtacct ggcctcccac   3720
tacgagaagc tcaaggggtc gccggaggac aacgagcaga agcagctctt cgtagagcag   3780
cacaagcact acctggacga gatcatcgag cagatttcag agttctcaaa gcgggtcatc   3840
ctcgccgacg ccaacctgga caaggtgctc tcggcctaca acaagcaccg ggacaagccg   3900
atccgcgaac aggccgaaaa catcatccac ctgttcacgc tcaccaacct cggtgccccg   3960
gcggccttca agtactttga cacgaccatc gaccggaagc gctatacctc gacgaaggag   4020
gtgctggacg ccaccctgat ccaccagtcc atcaccgggc tttacgagac ccggatcgac   4080
ctctcgcagc ta                                                       4092
```

<210> SEQ ID NO 9
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 9
gacaagaagt atagtattgg actcgccatc ggaaccaact ctgtggggtg ggctgttatt 60
acagatgaat ataaggtgcc atccaaaaag tttaaagttc tgggcaatac tgatagacac 120
tcaatcaaga agaatctgat aggtgcactt ctgtttgata gtggagagac tgccgaggca 180
accagactta aaaggactgc aagaagaaga tataccagaa gaaagaatag gatttgctat 240
ttgcaggaaa tcttcagcaa cgaaatggcc aaggttgatg actcattttt ccataggttg 300
gaggagagtt ttcttgtgga ggaagataag aagcacgaaa gacacccaat tttcgggaat 360
atagtggacg aggtggctta tcatgagaag tatcccacta tctaccacct gagaaagaaa 420
cttgtggact caaccgataa ggctgatctt aggcttatat acttggccct tgcacatatg 480
atcaaattca ggggccattt tcttatcgaa ggcgatctta atcccgataa ctcagatgtg 540
gacaagctgt ttatacaact tgtgcaaacc tacaatcaac tcttcgagga gaatcccatt 600
aacgcctccg gcgtggatgc aaaagccata ctgtcagcca gactgagcaa aagtaggaga 660
ctggagaatc ttatagccca actgcccggt gaaaagaaga atgggctctt cggaaatctg 720
atcgctcttt cattggggtt gacacccaac tttaagagta actttgactt ggcagaagat 780
gcaaagttgc agctcagtaa agacacatat gacgatgacc ttgacaatct cttggcacaa 840
ataggggatc aatacgctga ccttttcctc gctgccaaga acctcagcga cgctatactg 900
ttgtccgaca ttcttagggt taataccgaa attacaaagg cccctcttag tgcaagtatg 960
atcaaaaggt atgatgagca tcaccaagac cttacactgc tgaaggctct ggttagacag 1020
caactccctg aaaagtataa ggaaatattc ttcgaccaaa gtaagaacgg gtacgccggt 1080
tatattgatg gggcgcaag tcaagaagaa ttttacaaat tcatcaagcc aattcttgaa 1140
aagatggacg ggactgagga attgctggtg aaactgaata gagaggacct tcttagaaaa 1200
cagaggacat ttgacaatgg gtccatccca caccagattc atctggggga actccacgca 1260
atattgagga gacaagaaga cttttaccca ttccttaagg ataatagaga gaaaatcgaa 1320
aaaatcctga ctttcaggat tccttactat gttgggccac tggccagggg gaactcaaga 1380
ttcgcttgga tgacaaggaa gtcagaagaa accataaccc cttggaattt tgaagaggtg 1440
gttgataagg gggcatcagc ccagtctttc atagagagga tgaccaactt tgataaaaat 1500
cttccaaatg agaaggtttt gccaaaacat agtcttttgt acgagtactt tactgtttat 1560
aacgaattga ccaaggtgaa gtatgtgacc gagggaatga ggaagccagc atttttgtcc 1620
ggggagcaaa agaaagcaat cgttgatctt ctcttcaaga ccaacagaaa agtgaccgtg 1680
aaacaactga aggaagacta cttcaaaaag atagaatgtt tcgattcagt ggaaattagc 1740
ggtgttgaag acaggttcaa tgcttcattg ggtacttacc acgacctgtt gaagataatc 1800
aaagacaagg actttctcga taatgaggag aacgaagaca tcttggaaga cattgtgctt 1860
acactcactt tgtttgagga cagggaaatg attgaggaaa gactcaaaac ttacgctcat 1920
ttgtttgatg ataaggttat gaaacaacta aaaagaagaa ggtacaccgg ctggggaaga 1980
ttgagtagga aactgatcaa cggtattaga gataaacaat ccggaaagac tatcctcgat 2040

-continued

```
ttccttaaga gtgatggctt tgcaaatagg aattttatgc agctgattca tgacgactca   2100
cttaccttca aagaagacat ccaaaaagct caggtgtctg ggcaaggcga cagtctgcat   2160
gaacatatag ctaacttggc tgggagtccc gccatcaaga aggggatact tcaaacagtt   2220
aaagttgtgg acgaattggt gaaggtaatg ggaaggcaca agcctgaaaa tatagtgata   2280
gaaatggcaa gggaaaatca aacaacccag aagggacaga agaacagtag ggaaaggatg   2340
aaaaggatag aagaggggat caaagagctt ggtagccaga tcctcaagga acatccagtg   2400
gagaataccc aacttcaaaa cgagaaactc tatttgtact acttgcagaa cggaagagat   2460
atgtatgtgg accaagagct tgatattaac aggctgagcg attatgacgt tgaccacata   2520
gtgccccaat cattcctcaa ggatgactct attgataata aggtgctgac aaggagtgac   2580
aagaatagag ggaaatccga caacgttcca tccgaggaag ttgtgaagaa gatgaagaac   2640
tactggaggc agttgctgaa cgctaagctc attacccaga ggaaattcga taacctgacc   2700
aaagcagaga gaggcgggct gagcgaactc gataaagcag gtttcatcaa gagacaactc   2760
gtggagacta ggcaaattac taagcacgtg gctcaaatac tcgacagcag gatgaacaca   2820
aagtacgacg agaacgacaa gctcattaga gaggttaagg ttattactct gaaaagtaaa   2880
ttggttagcg atttcagaaa ggatttccaa ttctataagg ttagagagat caacaattat   2940
catcatgcac atgatgccta tctgaatgct gtggttggta cagcccttat caagaagtac   3000
cctaagctag agagcgagtt tgtgtacgga gattataagg tgtatgatgt gaggaaaatg   3060
atcgctaaaa gtgagcaaga gattggaaag gctaccgcca aatacttctt ttattccaat   3120
attatgaatt tcttcaagac agaaatcacc ctggctaacg gcgagataag gaagaggccg   3180
cttatcgaaa ctaatgggga gacaggcgaa atagtgtggg acaaagggag ggatttcgca   3240
actgtgagga aggttttgag catgcctcag gtgaatatcg ttaagaaaac cgaagttcaa   3300
actggagggt tctctaagga aagcattctc cccaagagga actccgacaa gctgattgct   3360
agaaagaaag actgggaccc caagaagtat ggcggattcg actcacccac tgtggcatat   3420
agcgttctcg tggtggcaaa ggttgaaaag ggtaaatcca aaaaactcaa atccgtgaag   3480
gaactccttg gcataactat tatggaaagg agtagctttg aaaagaatcc catcgacttt   3540
ctcgaagcta agggctataa ggaagttaag aaggacctta taatcaaact tccaaaatac   3600
tccctttttg agttggaaaa cggcagaaag agaatgttgg ccagtgccgg ggagcttcaa   3660
aagggcaacg aactggctct gcctagcaaa tatgtgaact tttgtatct ggcatcacac    3720
tacgagaaac ttaaaggctc tcctgaggac aacgagcaaa aacagctctt tgttgaacag   3780
cataagcact acctcgacga gattattgag cagatcagcg agttctcaaa gagagttatt   3840
ctggctgacg ctaatcttga caaggttttg tccgcttaca acaaacacag ggataagcca   3900
atcagggagc aggcagaaaa cataatccat ctctttaccc tgacaaacct cggtgccccc   3960
gctgctttca agtattttga tactaccatt gacaggaaga gatatacttc cactaaggaa   4020
gtgctcgacg caaccctcat acaccaaagt atcacaggcc tctatgaaac taggatagat   4080
ttgtctcaac ttgggggcga t                                             4101
```

<210> SEQ ID NO 10
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 10

-continued gacaaaaagt attccatcgg gcttgctatc ggaaccaact ctgtggggtg ggcagttatt 60
accgacgaat acaaggtgcc cagcaagaag tttaaggttc tggggaacac agatagacat 120
agcataaaga aaaacctgat aggcgcactg ttgttcgact ccggggaaac agccgaagct 180
accaggctga agagaactgc aagaagaagg tacaccagaa gaaaaaacag aatatgttat 240
ctccaagaga ttttctctaa cgagatggcc aaggtggacg actcattctt tcacagactg 300
gaagaatctt tccttgtgga agaagataag aaacacgaga ggcaccctat ttttggcaat 360
atcgtggatg aggtggctta ccacgaaaaa taccctacaa tataccacct caggaaaaaa 420
ttggttgata gtacagacaa ggccgacctc aggctcatct atttggccct ggcccatatg 480
attaaattca gggggcactt tctcatcgag ggagatttga accccgacaa cagtgatgtt 540
gataagctct ttattcagct cgtgcagact tacaatcagt tgtttgagga aaaccccatt 600
aatgcttccg gggtggacgc caaggcaatc ctttctgcaa gactctcaaa gtcaaggaga 660
ctcgaaaatc tgatagcaca gcttccagga gagaagaaga acgggctctt tggaaacctg 720
atcgctctgt cactcggact cacacccaat ttcaaaagca attttgattt ggcagaggac 780
gctaagctgc aactcagtaa ggatacctac gacgatgact tggataatct gctcgcacaa 840
attggggacc agtatgcaga cctgtttctc gcagctaaga acttgagtga cgccatattg 900
ctcagtgaca tcctcagggt taataccgag attacaaaag ctccactctc tgcaagcatg 960
atcaagaggt atgacgagca ccatcaagac ctgacactcc ttaaggcgtt ggttaggcag 1020
caacttcctg aaaagtataa ggaaatcttc ttcgatcaaa gcaaaaacgg ctacgccggc 1080
tatatagacg gggagcatc ccaagaagaa ttttataagt tcataaaacc tatattggag 1140
aagatggacg ggacagagga attgctcgtg aaactgaaca gggaggatct cctcaggaag 1200
caaaggacct tcgacaatgg ctccatccca catcagattc acctcggcga actgcacgca 1260
atactgagaa gacaagagga cttttatcct ttcctgaagg acaacaggga gaaaatcgag 1320
aaaatcttga cattcagaat cccatactac gttgggcctc tggccagagg taacagtagg 1380
ttcgcctgga tgactaggaa atcagaggag actattacac cctggaactt tgaagaagtt 1440
gttgataagg gagcttcagc acaatcattc atcgaaagaa tgacaaactt tgacaaaaat 1500
ctgcctaatg agaaagtgct cccaaaacat tccctgctgt atgagtattt taccgtttat 1560
aacgagctta ccaaggtgaa atacgttact gaaggtatga gaaagccagc ttttctttca 1620
ggggagcaaa agaaggctat cgtggatctt ctctttaaga ccaacagaaa ggttaccgtg 1680
aagcagctta aggaagacta ctttaaaaag atcgagtgtt ttgactcagt ggaaataagc 1740
ggtgttgaag atagattcaa cgcatccttg ggaacttatc atgatcttct taagataatc 1800
aaggataaag actttctcga caacgaggaa aacgaagata tactggagga catagttctg 1860
acacttactt tgttcgagga tagggagatg atcgaggaaa gactgaaaac atatgctcac 1920
cttttcgacg acaaagttat gaaacaactc aagagaagga gatatacagg gtgggggaga 1980
ttgagcagga aactgattaa tggtatcaga gacaaacagt caggaaaaac aatactcgac 2040
tttttgaaat cagacgggtt cgcaaatagg aatttcatgc agcttataca cgacgattca 2100
cttactttta aagaggacat tcaaaaggct caagttagtg gacaaggtga ctccctccac 2160
gaacacatcg caaatctcgc tggcagccct gcaattaaga agggtatact ccagacagtt 2220
aaggttgttg acgagctggt taaagtgatg ggaagacaca aacccgagaa catagtgata 2280
gagatggcca gggaaaacca aaccactcaa aaagggcaga aaaattccag agagaggatg 2340

-continued

```
aaaaggattg aagaaggtat caaggagctg ggtagccaaa ttctgaaaga acatcctgtg   2400

gaaaacactc aactccagaa tgagaaactc tatctgtact atctgcaaaa tgggagagat   2460

atgtatgtgg accaggaact ggacataaac aggctctcag attacgatgt ggatcatatc   2520

gtgccacagt cctttcttaa ggatgatagc atcgacaata aggtgcttac caggtccgac   2580

aagaacaggg gaaagtcaga taacgtgcct tctgaagaag ttgttaaaaa gatgaagaac   2640

tactggagac agctgcttaa cgctaagctc ataacacaga ggaagtttga caacttgacc   2700

aaggccgaga gaggcggact ctcagaattg gataaggcag ggttcataaa aaggcagctg   2760

gtggaaacaa ggcagataac taaacatgtg gctcagatcc tcgatagtag gatgaataca   2820

aaatacgatg agaacgacaa gctcataagg gaggttaaag tgataactct gaaatccaaa   2880

ctggttagcg attttaggaa ggatttccag ttttacaaag ttagggagat caacaattat   2940

catcacgccc acgatgccta cttgaacgca gttgtgggta ctgcacttat caaaaagtac   3000

cctaagctgg aatccgagtt tgtttatgga gactataagg tgtacgacgt tagaaaaatg   3060

attgcaaagt cagagcagga gatagggaaa gccactgcaa aatatttctt ttatagcaat   3120

atcatgaatt tctttaagac agaaatcaca ctggccaatg gggaaataag gaagaggccc   3180

ctgatcgaaa ctaatggcga gacaggggag attgtgtggg ataaaggtag ggactttgca   3240

acagtgagga aagtgctgag catgccccaa gttaatatcg ttaaaaagac cgaggttcaa   3300

acagggggct ttagtaagga aagcattttg cccaagagga atagtgacaa attgattgct   3360

aggaaaaaag attgggaccc caaaaagtat ggcggatttg atagccccac tgttgcttac   3420

tccgtgctcg tggttgcaaa ggtggagaag ggaaagagca agaaactgaa gtcagttaag   3480

gaactccttg gtatcactat catggaaaga agctcctttg agaagaaccc tattgacttc   3540

ctggaggcta aagggtacaa agaggttaag aaagacctta tcattaaatt gcccaaatat   3600

agtcttttcg agcttgaaaa cggaagaaag aggatgcttg catccgctgg cgaattgcaa   3660

aagggcaatg agcttgctct cccttccaag tatgtgaact tcctttatct tgcctcacac   3720

tatgaaaaac tcaaaggttc acccgaagac aacgaacaaa agcaactatt tgtggaacaa   3780

cacaagcact acctggacga aatcattgag caaatttctg agttttcaaa aagggtaatc   3840

ttggctgacg caaatctcga caaagttttg tcagcttaca acaaacatag agataagcca   3900

attagagagc aagctgagaa tatcatccat ctgtttaccc tgactaacct tggagcgcct   3960

gctgctttta aatatttcga caccacaatc gacaggaaga ggtacactag cactaaggaa   4020

gttctcgacg ccaccctcat ccaccagagt attacaggcc tgtacgagac aagaattgat   4080

ctttctcaac ttggtggtga c                                             4101
```

<210> SEQ ID NO 11
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 11

```
gataagaagt actcaatcgg tctggcaatc ggaaccaact ctgtgggttg ggcagtgatt     60

acagatgagt ataaggtgcc aagcaaaaaa ttcaaggtgc tgggtaatac cgacagacac    120

agcattaaga agaatttgat tggagcactc ctctttgact caggggaaac agcagaggca    180

acaaggctga agaggacagc aaggcggagg tacacaaggc ggaaaaacag gatatgctac    240

ctccaggaaa tctttagcaa cgagatggct aaagtggatg atagcttttt ccatagactc    300
```

```
gaagaatcct ttcttgttga agaggacaaa aagcatgaaa ggcatcccat cttcggcaat    360
atagttgatg aggttgcata ccatgagaag taccccacaa tctaccacct cagaaagaaa    420
cttgtggact ccacagataa agcagacctg aggctcatat acctcgcact cgcacacatg    480
atcaagttca gagggcactt tctcatcgaa ggtgacctga atccagataa ttcagatgtg    540
gataaactgt ttatacagct ggtgcaaaca tacaaccaac ttttcgagga aaacccaatc    600
aatgcctccg gtgttgatgc aaaggccatc ctgtcagcaa gactcagcaa aagcaggcgg    660
ctcgaaaacc tcatcgccca gcttcccggt gaaaagaaga acgggctctt tggtaatctc    720
atcgcattga gccttggtct tactccaaac ttcaagagca attttgatct ggcagaggat    780
gctaaactgc aactctcaaa ggacacatat gacgatgacc ttgacaatct gttggcccag    840
atcggggacc aatatgcaga cctcttcctg gccgcaaaga atctgtcaga tgcaatcctc    900
ttgtccgaca tactgagagt taacactgag atcacaaagg cacctctgtc cgcctccatg    960
attaagagat acgatgagca tcaccaggat ctgactttgc tcaaagccct cgttagacag   1020
cagttgccag aaaagtacaa agaaatattc tttgatcaat caaaaaacgg atatgcaggg   1080
tacatcgacg gtggggcaag ccaggaagag ttctacaaat tcatcaaacc tatcctggaa   1140
aagatggatg ggacagaaga gctgctggtt aagctgaata gggaagacct cctcagaaag   1200
cagaggacat ttgataacgg gagcatccct catcaaatcc acctcggtga actccatgct   1260
atcctgagaa ggcaggaaga cttttatcca tttttgaagg acaataggga gaaaatcgaa   1320
aaaatcctga cattcagaat cccatactac gttggtcctc tggcaagagg taacagtagg   1380
ttcgcatgga tgacaaggaa aagcgaggag acaatcacac cctggaattt tgaggaagtt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga ggaagccagc attcctttcc   1620
ggggaacaga agaaagctat tgtggacctc ctgttcaaga caaatagaaa agtgacagtt   1680
aagcaactca aagaggatta cttcaaaaag atcgaatgtt ttgactctgt ggagatcagc   1740
ggggtggagg atagattcaa cgccagcctg ggtacatatc atgatctcct gaaaatcatt   1800
aaagacaagg acttccttga caacgaggag aacgaggaca ttctggaaga cattgttctg   1860
accctcacac tctttgagga tagggagatg attgaggaaa gactgaagac ctacgcccac   1920
ctctttgacg ataaagtgat gaaacagctc aagagaagaa ggtatacagg ttgggggaga   1980
ctgagcagga agttgatcaa tgggattagg gacaaacagt ccgggaaaac aatcctcgat   2040
tttctgaagt cagacggttt cgcaaacaga aattttatgc agctcattca cgatgacagc   2100
ttgacattca aggaagacat ccaaaaggct caagtgagcg gccaagggga tagcctccac   2160
gagcatattg caaatctggc aggttcacca gccatcaaaa agggcatact tcagacagtt   2220
aaggttgtgg acgaattggt taaagttatg ggcaggcata agccagagaa tatcgttatc   2280
gaaatggcaa gggagaacca aacaactcaa aaagggcaga aaaatagcag agagaggatg   2340
aaaagaatcg aggaagggat caaggaactt gggtcccaaa tcctcaagga gcacccagtt   2400
gaaaatactc aactgcaaaa cgagaagctc tatctctact atctccaaaa cgggagggat   2460
atgtatgttg accaggagct ggatattaac agactgtcag attatgatgt tgatcatatc   2520
gtgccccagt cattcctgaa ggacgattcc atcgacaaca aagttctcac aaggtccgat   2580
aaaaacaggg gcaagtccga taacgttcca agcgaagaag tggtgaaaaa gatgaaaaac   2640
```

-continued

```
tattggagac aacttctgaa tgcaaagttg attactcaga gaaagtttga caacctcaca   2700

aaagcagaaa gaggcgggct tagcgaactc gataaggcag ggtttatcaa aagacagctg   2760

gttgagacaa ggcagatcac aaaacatgtg gcacagatcc ttgactcaag gatgaatacc   2820

aagtatgatg agaatgataa gttgatcagg gaggttaaag ttatcacact caaatccaaa   2880

ctggtgtcag acttcaggaa agactttcaa ttttataagg tgagggagat caataactac   2940

caccatgcac atgacgccta cctgaacgca gtggtgggta cagcattgat taaaaaatac   3000

cctaagctgg agtctgagtt tgtgtacggg gactacaagg tgtacgacgt gaggaaaatg   3060

atagccaagt ccgagcagga gatcgggaaa gcaacagcta agtatttctt ttacagtaat   3120

atcatgaatt tctttaaaac tgagattact ctggcaaacg gggagatcag gaaaagaccc   3180

ctcatcgaga ctaatggtga aacaggtgag atcgtttggg acaaggggag ggattttgct   3240

actgttagaa aagttctgag tatgccacaa gtgaatattg tgaaaaagac agaagttcag   3300

acaggtgggt tctccaaaga atccatcctg cccaagagaa attcagacaa gctcatcgca   3360

agaaagaagg actgggaccc taagaagtac ggaggatttg acagccccac cgtggcctat   3420

tccgtgcttg ttgtggcaaa ggtggagaaa gggaagagca aaaaactgaa atccgtgaaa   3480

gaactgctgg gaattaccat catggaaaga agctcctttg agaagaaccc aatcgacttc   3540

ctggaagcaa aaggatataa ggaagtgaaa aaggacctca ttatcaagct cccaaaatac   3600

tcacttttcg agttggagaa cggtagaaag aggatgctgg caagcgcagg ggaacttcag   3660

aaaggcaatg agctggcatt gccatcaaag tatgtgaact tcctctactt ggccagccat   3720

tacgagaaac ttaaaggtag cccagaagat aacgagcaaa aacagctctt tgtggaacag   3780

cataagcatt atctggatga gatcatagaa caaatctcag agttttccaa gagagttatc   3840

ctcgcagatg caaacctgga taaggttctc tcagcctata ataagcatag agacaagcca   3900

attagagagc aagcagagaa cattatccac ttgttcactc ttacaaacct gggggcacca   3960

gccgccttca aatatttcga tacaacaata gacagaaaga ggtataccag caccaaagaa   4020

gttctcgacg ccacactgat ccatcaatca atcacaggcc tttacgaaac taggatcgac   4080

ttgtcacaac tgggtgggga t                                             4101
```

```
<210> SEQ ID NO 12
<211> LENGTH: 3307
<212> TYPE: DNA
<213> ORGANISM: Artificial
<220> FEATURE:
<223> OTHER INFORMATION: Cas9 nucleic acid sequence

<400> SEQUENCE: 12

gagcaaggac acctacgacg acgacttgga caacctattg gcccagatag gtgaccagta     60

tgcagacctc ttccttgcgg ccaagaactt gagtgacgct atactgctca gtgacatcct    120

gagggtgaac actgagatca ctaaggcccc tctctctgcc tcaatgatta agcgttacga    180

cgagcatcac caggatctca ccctgcttaa ggcccttgtt cggcagcagc tccctgagaa    240

gtacaaggag atatttttg accagtctaa gaacggctac gccggttaca ttgacggtgg     300

ggcaagccag gaggagttct acaagttcat caagccgatc cttgagaaga tggacggcac    360

cgaggagcta cttgtcaagt tgaaccggga agacctgctc cggaaacagc gtacattcga    420

caacggcagc atccctcacc agatccacct gggcgaacta cacgccatcc tccgacgtca    480

ggaggacttc tatccattct tgaaagataa cagggaaaaa atcgaaaaaa tacttacgtt    540

tcgaatacct tactacgtgg ggccccttgc tcggggaaac tccagattcg catggatgac    600
```

caggaagtca gaggagacca tcacaccctg gaactttgag gaggtggttg acaaaggtgc 660
ttctgcccag tccttcattg agcggatgac taacttcgac aagaacctgc ccaacgagaa 720
ggtgctgcca aagcacagcc tgctctacga atactttact gtgtacaatg agctgacgaa 780
ggtgaagtac gtgacagagg ggatgcggaa gcccgctttc ctgagcggcg agcaaaaaaa 840
agcaatcgtg gacctactgt tcaagaccaa ccgaaaggtg acagtgaagc agctcaagga 900
ggactacttc aaaaaaatcg agtgcttcga ctctgttgag ataagcggcg tggaggaccg 960
attcaacgcc tcattgggaa cctatcacga cctgctcaag atcattaagg acaaggactt 1020
cctggataat gaggagaatg aggacatcct ggaggatatt gtgctgaccc ttactctatt 1080
cgaggacagg gagatgatcg aggagcgact caagacctac gctcacctgt tcgacgacaa 1140
ggttatgaag caattgaagc gtaggcgata cacggggtgg ggaagactct cccgaaaact 1200
gataaacggc atcagggaca agcagtcagg gaagacgatc ttggacttcc tgaaatccga 1260
cgggttcgcc aaccgcaact tcatgcagct cattcacgac gactcactaa cgttcaaaga 1320
ggacattcag aaggctcaag tcagtggaca aggcgactcc ctgcacgagc acattgcaaa 1380
ccttgcgggc tccccggcga ttaaaaaggg cattctccaa acggttaagg tggtggacga 1440
gctggtgaag gtgatgggcc gacacaagcc tgagaacatc gtgatcgaga tggccaggga 1500
gaaccagact acccagaagg gtcagaagaa ctctcgggaa cgtatgaagc gtattgagga 1560
ggggattaag gagttgggct ctcaaatcct caaggagcac cctgtggaga acactcagct 1620
ccaaaacgag aagctgtacc tgtactacct gcaaaacggg cgcgatatgt acgtggatca 1680
ggagttggac atcaacaggc ttagcgatta cgacgtggac cacatcgtgc cacagtcatt 1740
cttaaaggac gacagcatcg acaacaaggt tctgacgagg agcgacaaga atcgagggaa 1800
aagtgacaat gttccatccg aggaggtggt caagaaaatg aagaactatt ggcgtcagct 1860
tctgaacgcc aagctcatca cccagcggaa attcgacaac ctgactaagg ctgagcgagg 1920
cggactctcc gagcttgaca aggctggctt catcaagcgg cagttggtcg aaacccgaca 1980
gataacgaag cacgttgccc agatacttga ctcccgtatg aacaccaagt acgacgagaa 2040
cgacaagctc atcagggagg tgaaggtcat taccctaag tccaaactcg tcagcgactt 2100
tcgtaaggac ttccagttct acaaggtgcg cgagatcaat aactaccacc acgcacacga 2160
cgcctacctg aacgcagtgg ttggaaccgc gttgattaaa aagtacccca agttggagtc 2220
ggagttcgtt tacggggact acaaggtgta cgacgttcgg aagatgatcg ccaagtctga 2280
acaggagatc gggaaagcaa ccgccaagta tttcttctat agcaacatca tgaacttctt 2340
taaaaccgag atcacacttg ccaatggcga gatccgtaag aggccgctga tcgagacaaa 2400
tggggagact ggcgagatcg tgtgggacaa gggccgcgac ttcgcaaccg ttcggaaagt 2460
cttgtccatg cctcaagtca acatcgtcaa gaagactgag gtgcaaacag gcgggttctc 2520
gaaggagtcc atactgccca agaggaactc agacaagctc atagcacgca aaaaagactg 2580
ggatccaaag aaatacggcg ggttcgactc gccgacagtc gcatactccg tgttagtggt 2640
ggctaaagtg gaaaagggga agtccaagaa gctcaagtcc gtcaaggagt tgctcgggat 2700
caccattatg gaacggtcct cattcgagaa gaatcccatt gacttcctag aggcgaaggg 2760
ctacaaagag gtcaaaaagg acctaattat taagctcccc aagtattcac tcttcgaact 2820
tgaaaatggt cgtaagcgga tgttggcaag cgctggagag cttcagaagg ggaacgagct 2880
tgcactgcct tccaagtacg tgaacttcct gtacctcgcc tctcattacg agaagttgaa 2940

-continued

```
gggctcaccg gaggacaacg agcagaagca gttgttcgtg gagcagcaca agcactacct   3000

cgacgagatc attgagcaga taagtgagtt cagcaaacgg gtgatccttg ccgacgctaa   3060

cctggacaag gtgctgagcg cctacaacaa gcacagagac aagccgatcc gagagcaagc   3120

ggagaacatc atacacctgt tcaccctcac gaacctcggg gctcccgcag ccttcaaata   3180

ttttgacacg accatcgacc gtaaacgcta cactagcacg aaggaggtgc tggacgctac   3240

ccttatccac cagtccatca ccggcctgta cgagacgaga atcgacttgt cgcagctcgg   3300

tggtgac                                                             3307
```

<210> SEQ ID NO 13
<211> LENGTH: 4101
<212> TYPE: DNA
<213> ORGANISM: Artificial
<220> FEATURE:
<223> OTHER INFORMATION: Cas9 nucleic acid sequence

<400> SEQUENCE: 13

```
gacaaaaaat actcaattgg tctggcaatt gggaccaaca gtgtcggatg ggccgtgatt     60

accgacgagt acaaggtgcc gtccaaaaaa ttcaaggtgc ttgggaacac cgaccgccac    120

tcgatcaaga aaaacctaat cggtgcgttg cttttcgaca gtggggagac cgccgaggca    180

acacgcttaa aacgcacagc taggaggaga tatacacggc gcaagaaccg aatatgctac    240

ttacaggaga tattctccaa tgagatggcg aaggtggacg actctttctt ccatcggctt    300

gaggaatcct tcctggtcga ggaggacaag aagcacgagc gacacccgat attcgggaac    360

atcgttgatg aggtggcgta ccacgagaag tacccaacga tataccactt acgcaagaag    420

ctcgtggact ctacggacaa ggccgacttg cgccttatct acttggcact ggcccacatg    480

attaagttcc gaggccactt ccttatcgag ggtgacctga accccgataa ctccgacgtg    540

gacaagctct tcatccaact cgtccagaca tacaaccagc tattcgagga gaatcctatc    600

aacgcctctg ggtggacgc taaagctatc ctctcagccc gcctgtcaaa gtcgaggagg    660

ttggagaacc taatcgccca gcttccaggc gagaagaaaa atgggctgtt cggaaacctt    720

atcgcactct cactgggcct aaccccgaac ttcaagtcca acttcgacct ggcagaggac    780

gcgaaattgc agttgtcgaa agacacctat gacgatgacc tggacaacct gttggcccag    840

atagggggacc agtacgccga cctgttccta gcggccaaga acctgtccga cgccatcttg    900

ctgtcggata tactgcgggt gaacaccgag atcactaaag cacctctctc cgccagcatg    960

attaagcgtt acgacgagca ccaccaagat ttgaccctgc taaaggcact tgtacggcag   1020

cagcttcccg agaagtacaa ggagatcttt ttcgaccaaa gcaagaacgg ctacgccggg   1080

tacatcgacg gaggtgccag ccaggaggag ttctacaagt tcattaagcc catcctggag   1140

aagatggacg ggactgagga actacttgtg aagctgaacc gggaagactt actacggaag   1200

cagcgtacct tcgacaacgg ttctatccca catcagatcc atcttgggga gttgcacgcg   1260

atcctgcgac gccaggagga cttttacccc ttcctgaaag acaaccgcga gaaaatcgag   1320

aagatactga ccttcagaat accttactac gtcggacccc ttgcgcgagg caactcaaga   1380

ttcgcgtgga tgaccaggaa atcagaggag accatcacac cctggaattt cgaggaggtg   1440

gttgacaagg gtgcctccgc ccagtccttt atcgaacgaa tgaccaactt cgacaagaac   1500

ttgcccaacg agaaggtgct ccccaaacac agcctcctct acgaatattt cacagtgtac   1560

aacgagctta ctaaagttaa gtatgttact gagggcatga ggaaacccgc cttcctgtca   1620

ggcgagcaga agaaagctat tgtggacctc cttttcaaga ccaaccggaa ggtgacagtg   1680
```

```
aagcagctca aggaggacta cttcaagaag atagagtgct tcgacagcgt ggagatcagc   1740
ggggtggagg acagattcaa tgcctctctc ggaacatacc acgacttgct taagatcatc   1800
aaggacaagg acttcctcga caacgaggaa aacgaggata ttctggagga tattgttctg   1860
actcttaccc tgttcgagga ccgggagatg atcgaggagc gtctcaagac ctacgcccac   1920
ctgttcgacg acaaagttat gaagcagctc aagcgtcgga gatataccgg atggggccgt   1980
ctgtctcgga agctcatcaa cgggatcagg gacaagcagt cagggaagac gatcttagac   2040
ttccttaagt ctgacggctt cgccaacagg aacttcatgc agttgatcca cgacgacagc   2100
cttaccttca aggaggacat ccagaaggcc caagtgagtg gccagggtga cagcctccac   2160
gagcatattg ctaatcttgc gggttcccca gcgattaaaa agggcatact tcaaaccgtt   2220
aaggtggtgg acgagcttgt caaggtgatg gggcgacaca agcccgagaa catcgtgatc   2280
gagatggcca gggagaacca gaccacccag aaggggcaga agaatagccg agaacgcatg   2340
aagcgcatcg aggaggggat taaggagcta gggagccaga tcctcaagga acatcccgtc   2400
gagaacaccc agctccagaa cgagaagcta tacctctact acttgcaaaa cgggagggat   2460
atgtacgtgg atcaggagtt ggacattaac cgcctaagcg actacgacgt agatcacatc   2520
gtgcctcagt cattcctcaa agacgacagc attgacaaca aagtcttgac ccgatccgac   2580
aagaaccgag gaaaatccga caatgtgccc tcagaggagg tcgtcaagaa aatgaagaac   2640
tattggaggc agctacttaa cgccaaactc ataacccagc ggaagttcga caacctgaca   2700
aaggctgagc ggggtgggct cagcgagctt gacaaggctg gcttcatcaa gcggcagttg   2760
gtggagacaa gacagataac gaagcacgtg gctcagatcc tggactctcg catgaacacg   2820
aagtacgacg agaacgacaa attgatccgc gaggtcaagg ttattacgct caagagcaaa   2880
cttgtcagcg atttccgcaa ggacttccag ttctacaagg tgagggagat taacaactac   2940
caccatgcac atgatgccta cttgaacgca gtggtgggga ccgcgcttat taaaaagtac   3000
cctaagttgg agtcagagtt cgtttatggg gactacaagg tgtacgacgt ccggaagatg   3060
attgcaaagt ctgaacagga aatcgggaag gccaccgcca aatatttctt ctacagtaac   3120
attatgaatt tttttaagac tgaaattact ctcgcaaacg gcgagatcag gaagcgtccc   3180
ctcatcgaga caaacgggga gaccggggag atagtctggg acaaggggcg ggacttcgct   3240
acggtgagga aggtgctctc gatgccacaa gtgaacatcg tcaaaaagac agaggtgcag   3300
accggtggct tctcaaagga gtcaatcctg ccaaaacgta acagcgacaa gctcatcgcc   3360
cgcaagaaag actgggaccc taagaagtat ggtgggttcg actcaccgac ggtcgcatac   3420
tccgttctgg tcgtggcaaa ggtggaaaag ggcaagtcca aaaaactgaa atccgtgaag   3480
gagttgcttg gcattaccat catggaacgc agcagcttcg agaagaaccc cattgacttc   3540
ctggaggcta aagggtacaa ggaggtcaag aaagatttaa ttattaagct acctaagtac   3600
agcttgttcg agctggagaa cggccgaaaa cgaatgctcg catccgccgg ggaacttcaa   3660
aagggcaacg agcttgcgct gccctccaag tacgtgaact tcctgtactt ggcatcccac   3720
tacgagaaac tcaagggtag cccagaggac aacgagcaga agcagctatt cgtggagcag   3780
cacaagcact acctcgacga gataatcgag cagatcagtg agttcagtaa gcgggtgata   3840
ctcgcggacg ccaacttgga caaggtgctt agtgcctaca acaagcaccg tgacaagccc   3900
atccgagaac aggctgagaa catcatccac cttttcactc tgacaaacct cggtgctccc   3960
gccgccttca aatacttcga cactaccatc gacaggaagc gctacacatc tacgaaggaa   4020
```

gttcttgacg ctacgcttat tcatcagtct atcacagggc tgtacgagac aaggatcgac 4080
cttagccaac tcggcgggga t 4101

<210> SEQ ID NO 14
<211> LENGTH: 1367
<212> TYPE: PRT
<213> ORGANISM: Artificial
<220> FEATURE:
<223> OTHER INFORMATION: nCas9

<400> SEQUENCE: 14

Asp Lys Lys Tyr Ser Ile Gly Leu Ala Ile Gly Thr Asn Ser Val Gly
1 5 10 15

Trp Ala Val Ile Thr Asp Glu Tyr Lys Val Pro Ser Lys Lys Phe Lys
20 25 30

Val Leu Gly Asn Thr Asp Arg His Ser Ile Lys Lys Asn Leu Ile Gly
35 40 45

Ala Leu Leu Phe Asp Ser Gly Glu Thr Ala Glu Ala Thr Arg Leu Lys
50 55 60

Arg Thr Ala Arg Arg Arg Tyr Thr Arg Arg Lys Asn Arg Ile Cys Tyr
65 70 75 80

Leu Gln Glu Ile Phe Ser Asn Glu Met Ala Lys Val Asp Asp Ser Phe
85 90 95

Phe His Arg Leu Glu Glu Ser Phe Leu Val Glu Glu Asp Lys Lys His
100 105 110

Glu Arg His Pro Ile Phe Gly Asn Ile Val Asp Glu Val Ala Tyr His
115 120 125

Glu Lys Tyr Pro Thr Ile Tyr His Leu Arg Lys Lys Leu Val Asp Ser
130 135 140

Thr Asp Lys Ala Asp Leu Arg Leu Ile Tyr Leu Ala Leu Ala His Met
145 150 155 160

Ile Lys Phe Arg Gly His Phe Leu Ile Glu Gly Asp Leu Asn Pro Asp
165 170 175

Asn Ser Asp Val Asp Lys Leu Phe Ile Gln Leu Val Gln Thr Tyr Asn
180 185 190

Gln Leu Phe Glu Glu Asn Pro Ile Asn Ala Ser Gly Val Asp Ala Lys
195 200 205

Ala Ile Leu Ser Ala Arg Leu Ser Lys Ser Arg Arg Leu Glu Asn Leu
210 215 220

Ile Ala Gln Leu Pro Gly Glu Lys Lys Asn Gly Leu Phe Gly Asn Leu
225 230 235 240

Ile Ala Leu Ser Leu Gly Leu Thr Pro Asn Phe Lys Ser Asn Phe Asp
245 250 255

Leu Ala Glu Asp Ala Lys Leu Gln Leu Ser Lys Asp Thr Tyr Asp Asp
260 265 270

Asp Leu Asp Asn Leu Leu Ala Gln Ile Gly Asp Gln Tyr Ala Asp Leu
275 280 285

Phe Leu Ala Ala Lys Asn Leu Ser Asp Ala Ile Leu Leu Ser Asp Ile
290 295 300

Leu Arg Val Asn Thr Glu Ile Thr Lys Ala Pro Leu Ser Ala Ser Met
305 310 315 320

Ile Lys Arg Tyr Asp Glu His His Gln Asp Leu Thr Leu Leu Lys Ala
325 330 335

Leu Val Arg Gln Gln Leu Pro Glu Lys Tyr Lys Glu Ile Phe Phe Asp
340 345 350

-continued

```
Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765
```

```
Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
```

```
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365


<210> SEQ ID NO 15
<211> LENGTH: 1367
<212> TYPE: PRT
<213> ORGANISM: Artificial
<220> FEATURE:
<223> OTHER INFORMATION: enCas9

<400> SEQUENCE: 15

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
```

-continued

```
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590
```

-continued

```
Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Ala Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Ala Leu Glu Ser  Glu Phe Val
        995                 1000                1005
```

```
Tyr Gly  Asp Tyr Lys Val Tyr  Asp Val Arg Lys Met  Ile Ala Lys
    1010                 1015                 1020

Ser Glu  Gln Glu Ile Gly Lys  Ala Thr Ala Lys Tyr  Phe Phe Tyr
    1025                 1030                 1035

Ser Asn  Ile Met Asn Phe Phe  Lys Thr Glu Ile Thr  Leu Ala Asn
    1040                 1045                 1050

Gly Glu  Ile Arg Lys Ala Pro  Leu Ile Glu Thr Asn  Gly Glu Thr
    1055                 1060                 1065

Gly Glu  Ile Val Trp Asp Lys  Gly Arg Asp Phe Ala  Thr Val Arg
    1070                 1075                 1080

Lys Val  Leu Ser Met Pro Gln  Val Asn Ile Val Lys  Lys Thr Glu
    1085                 1090                 1095

Val Gln  Thr Gly Gly Phe Ser  Lys Glu Ser Ile Leu  Pro Lys Arg
    1100                 1105                 1110

Asn Ser  Asp Lys Leu Ile Ala  Arg Lys Lys Asp Trp  Asp Pro Lys
    1115                 1120                 1125

Lys Tyr  Gly Gly Phe Asp Ser  Pro Thr Val Ala Tyr  Ser Val Leu
    1130                 1135                 1140

Val Val  Ala Lys Val Glu Lys  Gly Lys Ser Lys Lys  Leu Lys Ser
    1145                 1150                 1155

Val Lys  Glu Leu Leu Gly Ile  Thr Ile Met Glu Arg  Ser Ser Phe
    1160                 1165                 1170

Glu Lys  Asn Pro Ile Asp Phe  Leu Glu Ala Lys Gly  Tyr Lys Glu
    1175                 1180                 1185

Val Lys  Lys Asp Leu Ile Ile  Lys Leu Pro Lys Tyr  Ser Leu Phe
    1190                 1195                 1200

Glu Leu  Glu Asn Gly Arg Lys  Arg Met Leu Ala Ser  Ala Gly Glu
    1205                 1210                 1215

Leu Gln  Lys Gly Asn Glu Leu  Ala Leu Pro Ser Lys  Tyr Val Asn
    1220                 1225                 1230

Phe Leu  Tyr Leu Ala Ser His  Tyr Glu Lys Leu Lys  Gly Ser Pro
    1235                 1240                 1245

Glu Asp  Asn Glu Gln Lys Gln  Leu Phe Val Glu Gln  His Lys His
    1250                 1255                 1260

Tyr Leu  Asp Glu Ile Ile Glu  Gln Ile Ser Glu Phe  Ser Lys Arg
    1265                 1270                 1275

Val Ile  Leu Ala Asp Ala Asn  Leu Asp Lys Val Leu  Ser Ala Tyr
    1280                 1285                 1290

Asn Lys  His Arg Asp Lys Pro  Ile Arg Glu Gln Ala  Glu Asn Ile
    1295                 1300                 1305

Ile His  Leu Phe Thr Leu Thr  Asn Leu Gly Ala Pro  Ala Ala Phe
    1310                 1315                 1320

Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365
```

<210> SEQ ID NO 16
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 16

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu

-continued

```
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Ala
            820                 825                 830
```

-continued

```
Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His
    1220                1225
```

<210> SEQ ID NO 17
<211> LENGTH: 1307
<212> TYPE: PRT
<213> ORGANISM: Acidaminococcus sp.

<400> SEQUENCE: 17

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380
```

-continued

Leu Arg Asn Ala Leu Tyr Glu Arg Arg Ile Ser Glu Leu Thr Gly Lys
385 390 395 400

Ile Thr Lys Ser Ala Lys Glu Lys Val Gln Arg Ser Leu Lys His Glu
405 410 415

Asp Ile Asn Leu Gln Glu Ile Ile Ser Ala Ala Gly Lys Glu Leu Ser
420 425 430

Glu Ala Phe Lys Gln Lys Thr Ser Glu Ile Leu Ser His Ala His Ala
435 440 445

Ala Leu Asp Gln Pro Leu Pro Thr Thr Leu Lys Lys Gln Glu Glu Lys
450 455 460

Glu Ile Leu Lys Ser Gln Leu Asp Ser Leu Leu Gly Leu Tyr His Leu
465 470 475 480

Leu Asp Trp Phe Ala Val Asp Glu Ser Asn Glu Val Asp Pro Glu Phe
485 490 495

Ser Ala Arg Leu Thr Gly Ile Lys Leu Glu Met Glu Pro Ser Leu Ser
500 505 510

Phe Tyr Asn Lys Ala Arg Asn Tyr Ala Thr Lys Lys Pro Tyr Ser Val
515 520 525

Glu Lys Phe Lys Leu Asn Phe Gln Met Pro Thr Leu Ala Ser Gly Trp
530 535 540

Asp Val Asn Lys Glu Lys Asn Asn Gly Ala Ile Leu Phe Val Lys Asn
545 550 555 560

Gly Leu Tyr Tyr Leu Gly Ile Met Pro Lys Gln Lys Gly Arg Tyr Lys
565 570 575

Ala Leu Ser Phe Glu Pro Thr Glu Lys Thr Ser Glu Gly Phe Asp Lys
580 585 590

Met Tyr Tyr Asp Tyr Phe Pro Asp Ala Ala Lys Met Ile Pro Lys Cys
595 600 605

Ser Thr Gln Leu Lys Ala Val Thr Ala His Phe Gln Thr His Thr Thr
610 615 620

Pro Ile Leu Leu Ser Asn Asn Phe Ile Glu Pro Leu Glu Ile Thr Lys
625 630 635 640

Glu Ile Tyr Asp Leu Asn Asn Pro Glu Lys Glu Pro Lys Lys Phe Gln
645 650 655

Thr Ala Tyr Ala Lys Lys Thr Gly Asp Gln Lys Gly Tyr Arg Glu Ala
660 665 670

Leu Cys Lys Trp Ile Asp Phe Thr Arg Asp Phe Leu Ser Lys Tyr Thr
675 680 685

Lys Thr Thr Ser Ile Asp Leu Ser Ser Leu Arg Pro Ser Ser Gln Tyr
690 695 700

Lys Asp Leu Gly Glu Tyr Tyr Ala Glu Leu Asn Pro Leu Leu Tyr His
705 710 715 720

Ile Ser Phe Gln Arg Ile Ala Glu Lys Glu Ile Met Asp Ala Val Glu
725 730 735

Thr Gly Lys Leu Tyr Leu Phe Gln Ile Tyr Asn Lys Asp Phe Ala Lys
740 745 750

Gly His His Gly Lys Pro Asn Leu His Thr Leu Tyr Trp Thr Gly Leu
755 760 765

Phe Ser Pro Glu Asn Leu Ala Lys Thr Ser Ile Lys Leu Asn Gly Gln
770 775 780

Ala Glu Leu Phe Tyr Arg Pro Lys Ser Arg Met Lys Arg Met Ala His
785 790 795 800

-continued

```
Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065

Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
```

```
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305


<210> SEQ ID NO 18
<211> LENGTH: 1241
<212> TYPE: PRT
<213> ORGANISM: Utyrivibrio proteoclasticus

<400> SEQUENCE: 18

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
            20                  25                  30

Glu Leu Asn Leu Leu Glu Gln Asp Lys Ala Ile Tyr Ala Leu Leu Glu
        35                  40                  45

Arg Leu Lys Pro Val Ile Asp Glu Gly Ile Lys Asp Ile Ala Arg Asp
    50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110

Lys Ile Ser Glu Ile Asn Ser Ala Lys Tyr Leu Asn Gly Val Leu Tyr
        115                 120                 125

Asp Phe Ile Asp Lys Thr His Lys Asp Ser Glu Glu Lys Gln Asn Ile
    130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
            180                 185                 190

Asp Ala Leu Glu Arg Gly Ala Val Ser Phe Ala Ile Glu Tyr Glu Ser
        195                 200                 205

Ile Cys Ser Val Asp Tyr Tyr Asn Gln Ile Leu Ser Gln Glu Asp Ile
    210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
            260                 265                 270
```

-continued

```
His Lys Gln Ile Leu Glu Glu Arg Glu Lys Ala Phe Thr Ile Asp His
        275                 280                 285

Ile Asp Ser Asp Glu Glu Val Val Gln Val Thr Lys Glu Ala Phe Glu
    290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala
    370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
    450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525

His Trp Trp Asn Gly Glu Glu Asn Phe Ala Ile Asn Asp Val Ala Met
    530                 535                 540

Ile Arg Arg Gly Asp Glu Tyr Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575

Val Gln Arg Lys Gly Ala Lys Ser Phe Leu Gly Leu Pro Lys Ala Leu
            580                 585                 590

Phe Lys Cys Ile Leu Glu Pro Tyr Phe Glu Ser Pro Glu His Lys Asn
        595                 600                 605

Asp Lys Asn Cys Val Ile Glu Glu Tyr Val Ser Lys Pro Leu Thr Ile
    610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
            660                 665                 670

Tyr Ser Cys Phe Asn Met Ser Gly Leu Lys Arg Ala Asp Glu Tyr Asn
        675                 680                 685

Asp Ile Gly Glu Phe Phe Ser Asp Val Asp Thr Arg Leu Cys Thr Met
```

-continued

```
    690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
            740                 745                 750

Asn Met Glu His Thr Ser Met Leu Leu Asn Ser Arg Ala Met Ile Gln
        755                 760                 765

Tyr Arg Ala Ala Ser Leu Pro Arg Arg Val Thr His Lys Lys Gly Ser
    770                 775                 780

Ile Leu Val Ala Leu Arg Asp Ser Asn Gly Glu His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
            820                 825                 830

Ile Lys Lys Ala Asn Glu Asp Ile Ile Arg Asn Arg Arg Tyr Thr Glu
        835                 840                 845

Asp Lys Phe Phe Leu Ser Leu Ser Tyr Thr Lys Asn Ala Asp Ile Ser
    850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
            900                 905                 910

Leu Asn Glu Ile Asp Gly Val Asn Tyr Arg Glu Leu Leu Lys Glu Arg
        915                 920                 925

Thr Lys Ile Lys Tyr His Asp Lys Thr Arg Leu Trp Gln Tyr Asp Val
    930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Val Glu Ser
                965                 970                 975

Met Ser Ser Thr Phe Lys Asp Lys Phe Ser Phe Leu Asp Glu Gln Ile
            980                 985                 990

Phe Lys Ala Phe Glu Ala Arg Leu  Cys Ala Arg Met Ser  Asp Leu Ser
        995                 1000                1005

Phe Asn  Thr Ile Lys Glu Gly  Glu Ala Gly Ser Ile  Ser Asn Pro
    1010                 1015                 1020

Ile Gln  Val Ser Asn Asn Asn  Gly Asn Ser Tyr Gln  Asp Gly Val
    1025                 1030                 1035

Ile Tyr  Phe Leu Asn Asn Ala  Tyr Thr Arg Thr Leu  Cys Pro Asp
    1040                 1045                 1050

Thr Gly  Phe Val Asp Val Phe  Asp Lys Thr Arg Leu  Ile Thr Met
    1055                 1060                 1065

Gln Ser  Lys Arg Gln Phe Phe  Ala Lys Met Lys Asp  Ile Arg Ile
    1070                 1075                 1080

Asp Asp  Gly Glu Met Leu Phe  Thr Phe Asn Leu Glu  Glu Tyr Pro
    1085                 1090                 1095

Thr Lys  Arg Leu Leu Asp Arg  Lys Glu Trp Thr Val  Lys Ile Ala
    1100                 1105                 1110
```

```
Gly Asp  Gly Ser Tyr Phe Asp  Lys Asp Lys Gly Glu  Tyr Val Tyr
    1115                 1120                 1125

Val Asn  Asp Ile Val Arg Glu  Gln Ile Ile Pro Ala  Leu Leu Glu
    1130                 1135                 1140

Asp Lys  Ala Val Phe Asp Gly  Asn Met Ala Glu Lys  Phe Leu Asp
    1145                 1150                 1155

Lys Thr  Ala Ile Ser Gly Lys  Ser Val Glu Leu Ile  Tyr Lys Trp
    1160                 1165                 1170

Phe Ala  Asn Ala Leu Tyr Gly  Ile Ile Thr Lys Lys  Asp Gly Glu
    1175                 1180                 1185

Lys Ile  Tyr Arg Ser Pro Ile  Thr Gly Thr Glu Ile  Asp Val Ser
    1190                 1195                 1200

Lys Asn  Thr Thr Tyr Asn Phe  Gly Lys Lys Phe Met  Phe Lys Gln
    1205                 1210                 1215

Glu Tyr  Arg Gly Asp Gly Asp  Phe Leu Asp Ala Phe  Leu Asn Tyr
    1220                 1225                 1230

Met Gln  Ala Gln Asp Ile Ala  Val
    1235                 1240
```

<210> SEQ ID NO 19
<211> LENGTH: 1238
<212> TYPE: PRT
<213> ORGANISM: Candidatus Methanoplasma termitum

<400> SEQUENCE: 19

```
Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Ile Val Phe Ser
    210                 215                 220

Leu Glu Tyr Phe Asn Lys Val Leu Asn Gln Glu Gly Ile Gln Arg Tyr
```

-continued

```
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
    370                 375                 380

Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
        435                 440                 445

Ser Ile His Ile Ile Lys Thr Leu Leu Asp Ser Val Gln Gln Phe Leu
    450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
        515                 520                 525

Gly Trp Asp Gln Asn Lys Val Tyr Asp Tyr Ala Ser Leu Ile Phe Leu
    530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Arg Pro Val
            580                 585                 590

Phe Leu Thr Ser Thr Lys Gly Lys Lys Glu Tyr Lys Pro Ser Lys Glu
        595                 600                 605

Ile Ile Glu Gly Tyr Glu Ala Asp Lys His Ile Arg Gly Asp Lys Phe
    610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655
```

-continued

```
Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
        675                 680                 685

Tyr Val Glu Lys Gly Asp Leu Phe Leu Phe Gln Ile Tyr Asn Lys Asp
    690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
    770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
    850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
    930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
            980                 985                 990

Tyr Gln Leu Thr Asn Pro Leu Glu  Ser Phe Ala Lys Leu  Gly Lys Gln
        995                 1000                1005

Thr Gly  Ile Leu Phe Tyr Val  Pro Ala Ala Tyr Thr  Ser Lys Ile
    1010                1015                1020

Asp Pro  Thr Thr Gly Phe Val  Asn Leu Phe Asn Thr  Ser Ser Lys
    1025                1030                1035

Thr Asn  Ala Gln Glu Arg Lys  Glu Phe Leu Gln Lys  Phe Glu Ser
    1040                1045                1050

Ile Ser  Tyr Ser Ala Lys Asp  Gly Gly Ile Phe Ala  Phe Ala Phe
    1055                1060                1065
```

-continued

```
Asp Tyr  Arg Lys Phe Gly Thr  Ser Lys Thr Asp His  Lys Asn Val
    1070                1075                1080

Trp Thr  Ala Tyr Thr Asn Gly  Glu Arg Met Arg Tyr  Ile Lys Glu
    1085                1090                1095

Lys Lys  Arg Asn Glu Leu Phe  Asp Pro Ser Lys Glu  Ile Lys Glu
    1100                1105                1110

Ala Leu  Thr Ser Ser Gly Ile  Lys Tyr Asp Gly Gly  Gln Asn Ile
    1115                1120                1125

Leu Pro  Asp Ile Leu Arg Ser  Asn Asn Asn Gly Leu  Ile Tyr Thr
    1130                1135                1140

Met Tyr  Ser Ser Phe Ile Ala  Ala Ile Gln Met Arg  Val Tyr Asp
    1145                1150                1155

Gly Lys  Glu Asp Tyr Ile Ile  Ser Pro Ile Lys Asn  Ser Lys Gly
    1160                1165                1170

Glu Phe  Phe Arg Thr Asp Pro  Lys Arg Arg Glu Leu  Pro Ile Asp
    1175                1180                1185

Ala Asp  Ala Asn Gly Ala Tyr  Asn Ile Ala Leu Arg  Gly Glu Leu
    1190                1195                1200

Thr Met  Arg Ala Ile Ala Glu  Lys Phe Asp Pro Asp  Ser Glu Lys
    1205                1210                1215

Met Ala  Lys Leu Glu Leu Lys  His Lys Asp Trp Phe  Glu Phe Met
    1220                1225                1230

Gln Thr  Arg Gly Asp
    1235


<210> SEQ ID NO 20
<211> LENGTH: 1281
<212> TYPE: PRT
<213> ORGANISM: Eubacterium eligens

<400> SEQUENCE: 20

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
        115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190
```

-continued

```
His Glu Asn Ser Leu Ile Phe Leu Ala Asn Met Thr Ser Tyr Lys Lys
        195                 200                 205

Ile Ser Glu Lys Ala Leu Asp Glu Ile Glu Val Ile Glu Lys Asn Asn
    210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
        275                 280                 285

Leu Ala Tyr Thr Ser Thr Ser Phe Glu Val Pro Lys Met Phe Glu Asp
    290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
            340                 345                 350

Leu Ser Cys Phe Met Ser Gly Asn Trp Asn Leu Ile Thr Gly Cys Val
        355                 360                 365

Glu Asn Phe Tyr Asp Glu Asn Ile His Ala Lys Gly Lys Ser Lys Glu
    370                 375                 380

Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                405                 410                 415

Glu Phe Lys Asn Ser Asn Ala Lys Gln Tyr Ile Arg Glu Ile Ser Asn
            420                 425                 430

Ile Ile Thr Asp Thr Glu Thr Ala His Leu Glu Tyr Asp Asp His Ile
        435                 440                 445

Ser Leu Ile Glu Ser Glu Glu Lys Ala Asp Glu Met Lys Lys Arg Leu
    450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
        515                 520                 525

Gln Ser Pro Thr Leu Ala Asn Gly Trp Ser Gln Ser Lys Glu Phe Asp
    530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
        595                 600                 605
```

-continued

```
Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
            740                 745                 750

Tyr Arg Arg Ala Ser Val Lys Asn Pro Val Lys His Lys Lys Asp Ser
        755                 760                 765

Val Leu Val Asn Lys Thr Tyr Lys Asn Gln Leu Asp Asn Gly Asp Val
    770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
        835                 840                 845

Ile Asn Tyr Lys Val Thr Ala Arg Asn Asn Val Asn Asp Met Val Val
    850                 855                 860

Lys Tyr Ile Ala Gln Asn Asp Asp Ile His Val Ile Gly Ile Asp Arg
865                 870                 875                 880

Gly Glu Arg Asn Leu Ile Tyr Ile Ser Val Ile Asp Ser His Gly Asn
                885                 890                 895

Ile Val Lys Gln Lys Ser Tyr Asn Ile Leu Asn Asn Tyr Asp Tyr Lys
            900                 905                 910

Lys Lys Leu Val Glu Lys Glu Lys Thr Arg Glu Tyr Ala Arg Lys Asn
        915                 920                 925

Trp Lys Ser Ile Gly Asn Ile Lys Glu Leu Lys Glu Gly Tyr Ile Ser
    930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                965                 970                 975

Val Glu Arg Gln Val Tyr Gln Lys Phe Glu Ser Met Leu Ile Asn Lys
            980                 985                 990

Leu Asn Tyr Phe Ala Ser Lys Glu  Lys Ser Val Asp Glu  Pro Gly Gly
        995                 1000                1005

Leu Leu  Lys Gly Tyr Gln Leu  Thr Tyr Val Pro Asp  Asn Ile Lys
    1010                1015                1020

Asn Leu  Gly Lys Gln Cys Gly  Val Ile Phe Tyr Val  Pro Ala Ala
```

1025 1030 1035

Phe Thr Ser Lys Ile Asp Pro Ser Thr Gly Phe Ile Ser Ala Phe
1040 1045 1050

Asn Phe Lys Ser Ile Ser Thr Asn Ala Ser Arg Lys Gln Phe Phe
1055 1060 1065

Met Gln Phe Asp Glu Ile Arg Tyr Cys Ala Glu Lys Asp Met Phe
1070 1075 1080

Ser Phe Gly Phe Asp Tyr Asn Asn Phe Asp Thr Tyr Asn Ile Thr
1085 1090 1095

Met Gly Lys Thr Gln Trp Thr Val Tyr Thr Asn Gly Glu Arg Leu
1100 1105 1110

Gln Ser Glu Phe Asn Asn Ala Arg Arg Thr Gly Lys Thr Lys Ser
1115 1120 1125

Ile Asn Leu Thr Glu Thr Ile Lys Leu Leu Leu Glu Asp Asn Glu
1130 1135 1140

Ile Asn Tyr Ala Asp Gly His Asp Ile Arg Ile Asp Met Glu Lys
1145 1150 1155

Met Asp Glu Asp Lys Lys Ser Glu Phe Phe Ala Gln Leu Leu Ser
1160 1165 1170

Leu Tyr Lys Leu Thr Val Gln Met Arg Asn Ser Tyr Thr Glu Ala
1175 1180 1185

Glu Glu Gln Glu Asn Gly Ile Ser Tyr Asp Lys Ile Ile Ser Pro
1190 1195 1200

Val Ile Asn Asp Glu Gly Glu Phe Phe Asp Ser Asp Asn Tyr Lys
1205 1210 1215

Glu Ser Asp Asp Lys Glu Cys Lys Met Pro Lys Asp Ala Asp Ala
1220 1225 1230

Asn Gly Ala Tyr Cys Ile Ala Leu Lys Gly Leu Tyr Glu Val Leu
1235 1240 1245

Lys Ile Lys Ser Glu Trp Thr Glu Asp Gly Phe Asp Arg Asn Cys
1250 1255 1260

Leu Lys Leu Pro His Ala Glu Trp Leu Asp Phe Ile Gln Asn Lys
1265 1270 1275

Arg Tyr Glu
1280

<210> SEQ ID NO 21
<211> LENGTH: 1300
<212> TYPE: PRT
<213> ORGANISM: Francisella novicida

<400> SEQUENCE: 21

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

-continued

```
Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
```

```
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940
```

Gly Asn Asp Arg Met Lys Thr Asn Tyr His Asp Lys Leu Ala Ala Ile
945 950 955 960

Glu Lys Asp Arg Asp Ser Ala Arg Lys Asp Trp Lys Lys Ile Asn Asn
965 970 975

Ile Lys Glu Met Lys Glu Gly Tyr Leu Ser Gln Val Val His Glu Ile
980 985 990

Ala Lys Leu Val Ile Glu Tyr Asn Ala Ile Val Val Phe Glu Asp Leu
995 1000 1005

Asn Phe Gly Phe Lys Arg Gly Arg Phe Lys Val Glu Lys Gln Val
1010 1015 1020

Tyr Gln Lys Leu Glu Lys Met Leu Ile Glu Lys Leu Asn Tyr Leu
1025 1030 1035

Val Phe Lys Asp Asn Glu Phe Asp Lys Thr Gly Gly Val Leu Arg
1040 1045 1050

Ala Tyr Gln Leu Thr Ala Pro Phe Glu Thr Phe Lys Lys Met Gly
1055 1060 1065

Lys Gln Thr Gly Ile Ile Tyr Tyr Val Pro Ala Gly Phe Thr Ser
1070 1075 1080

Lys Ile Cys Pro Val Thr Gly Phe Val Asn Gln Leu Tyr Pro Lys
1085 1090 1095

Tyr Glu Ser Val Ser Lys Ser Gln Glu Phe Phe Ser Lys Phe Asp
1100 1105 1110

Lys Ile Cys Tyr Asn Leu Asp Lys Gly Tyr Phe Glu Phe Ser Phe
1115 1120 1125

Asp Tyr Lys Asn Phe Gly Asp Lys Ala Ala Lys Gly Lys Trp Thr
1130 1135 1140

Ile Ala Ser Phe Gly Ser Arg Leu Ile Asn Phe Arg Asn Ser Asp
1145 1150 1155

Lys Asn His Asn Trp Asp Thr Arg Glu Val Tyr Pro Thr Lys Glu
1160 1165 1170

Leu Glu Lys Leu Leu Lys Asp Tyr Ser Ile Glu Tyr Gly His Gly
1175 1180 1185

Glu Cys Ile Lys Ala Ala Ile Cys Gly Glu Ser Asp Lys Lys Phe
1190 1195 1200

Phe Ala Lys Leu Thr Ser Val Leu Asn Thr Ile Leu Gln Met Arg
1205 1210 1215

Asn Ser Lys Thr Gly Thr Glu Leu Asp Tyr Leu Ile Ser Pro Val
1220 1225 1230

Ala Asp Val Asn Gly Asn Phe Phe Asp Ser Arg Gln Ala Pro Lys
1235 1240 1245

Asn Met Pro Gln Asp Ala Asp Ala Asn Gly Ala Tyr His Ile Gly
1250 1255 1260

Leu Lys Gly Leu Met Leu Leu Gly Arg Ile Lys Asn Asn Gln Glu
1265 1270 1275

Gly Lys Lys Leu Asn Leu Val Ile Lys Asn Glu Glu Tyr Phe Glu
1280 1285 1290

Phe Val Gln Asn Arg Asn Asn
1295 1300

<210> SEQ ID NO 22
<211> LENGTH: 1206
<212> TYPE: PRT
<213> ORGANISM: Unknown
<220> FEATURE:

<223> OTHER INFORMATION: Lachnospiraceae bacterium

<400> SEQUENCE: 22

```
Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
    290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Val Ile Val Phe Glu Asn
                325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Ser Leu Glu His Leu Cys Asn Leu Ser
    370                 375                 380

Glu Asp Ser Cys Asn Leu Ile Glu Asn Tyr Ile His Gln Ile Ser Asp
385                 390                 395                 400
```

Asp Ile Glu Asn Ile Ile Ile Asn Asn Glu Thr Phe Leu Arg Ile Val
405 410 415

Ile Asn Glu His Asp Arg Ser Arg Lys Leu Ala Lys Asn Arg Lys Ala
420 425 430

Val Lys Ala Ile Lys Asp Phe Leu Asp Ser Ile Lys Val Leu Glu Arg
435 440 445

Glu Leu Lys Leu Ile Asn Ser Ser Gly Gln Glu Leu Glu Lys Asp Leu
450 455 460

Ile Val Tyr Ser Ala His Glu Glu Leu Leu Val Glu Leu Lys Gln Val
465 470 475 480

Asp Ser Leu Tyr Asn Met Thr Arg Asn Tyr Leu Thr Lys Lys Pro Phe
485 490 495

Ser Thr Glu Lys Val Lys Leu Asn Phe Asn Arg Ser Thr Leu Leu Asn
500 505 510

Gly Trp Asp Arg Asn Lys Glu Thr Asp Asn Leu Gly Val Leu Leu Leu
515 520 525

Lys Asp Gly Lys Tyr Tyr Leu Gly Ile Met Asn Thr Ser Ala Asn Lys
530 535 540

Ala Phe Val Asn Pro Pro Val Ala Lys Thr Glu Lys Val Phe Lys Lys
545 550 555 560

Val Asp Tyr Lys Leu Leu Pro Val Pro Asn Gln Met Leu Pro Lys Val
565 570 575

Phe Phe Ala Lys Ser Asn Ile Asp Phe Tyr Asn Pro Ser Ser Glu Ile
580 585 590

Tyr Ser Asn Tyr Lys Lys Gly Thr His Lys Lys Gly Asn Met Phe Ser
595 600 605

Leu Glu Asp Cys His Asn Leu Ile Asp Phe Phe Lys Glu Ser Ile Ser
610 615 620

Lys His Glu Asp Trp Ser Lys Phe Gly Phe Lys Phe Asp Thr Gln Ala
625 630 635 640

Ser Tyr Asn Asp Ile Ser Glu Phe Tyr Arg Glu Val Glu Lys Gln Gly
645 650 655

Tyr Lys Leu Thr Tyr Thr Asp Ile Asp Glu Thr Tyr Ile Asn Asp Leu
660 665 670

Ile Glu Arg Asn Glu Leu Tyr Leu Phe Gln Ile Tyr Asn Lys Asp Phe
675 680 685

Ser Met Tyr Ser Lys Gly Lys Leu Asn Leu His Thr Leu Tyr Phe Met
690 695 700

Met Leu Phe Asp Gln Arg Asn Ile Asp Asp Val Val Tyr Lys Leu Asn
705 710 715 720

Gly Glu Ala Glu Val Phe Tyr Arg Pro Ala Ser Ile Ser Glu Asp Glu
725 730 735

Leu Ile Ile His Lys Ala Gly Glu Glu Ile Lys Asn Lys Asn Pro Asn
740 745 750

Arg Ala Arg Thr Lys Glu Thr Ser Thr Phe Ser Tyr Asp Ile Val Lys
755 760 765

Asp Lys Arg Tyr Ser Lys Asp Lys Phe Thr Leu His Ile Pro Ile Thr
770 775 780

Met Asn Phe Gly Val Asp Glu Val Lys Arg Phe Asn Asp Ala Val Asn
785 790 795 800

Ser Ala Ile Arg Ile Asp Glu Asn Val Asn Val Ile Gly Ile Asp Arg
805 810 815

Gly Glu Arg Asn Leu Leu Tyr Val Val Val Ile Asp Ser Lys Gly Asn

-continued

```
            820                 825                 830

Ile Leu Glu Gln Ile Ser Leu Asn Ser Ile Ile Asn Lys Glu Tyr Asp
        835                 840                 845

Ile Glu Thr Asp Tyr His Ala Leu Leu Asp Glu Arg Glu Gly Gly Arg
    850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Asp Lys Leu Asn Tyr Leu Val Ile Asp Lys Ser Arg
    930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr  Met Lys Cys Glu Asn  Val Glu Lys
        995                 1000                1005

Ser Lys  Arg Phe Phe Asp Gly  Phe Asp Phe Ile Arg  Phe Asn Ala
    1010                1015                1020

Leu Glu  Asn Val Phe Glu Phe  Gly Phe Asp Tyr Arg  Ser Phe Thr
    1025                1030                1035

Gln Arg  Ala Cys Gly Ile Asn  Ser Lys Trp Thr Val  Cys Thr Asn
    1040                1045                1050

Gly Glu  Arg Ile Ile Lys Tyr  Arg Asn Pro Asp Lys  Asn Asn Met
    1055                1060                1065

Phe Asp  Glu Lys Val Val Val  Val Thr Asp Glu Met  Lys Asn Leu
    1070                1075                1080

Phe Glu  Gln Tyr Lys Ile Pro  Tyr Glu Asp Gly Arg  Asn Val Lys
    1085                1090                1095

Asp Met  Ile Ile Ser Asn Glu  Glu Ala Glu Phe Tyr  Arg Arg Leu
    1100                1105                1110

Tyr Arg  Leu Leu Gln Gln Thr  Leu Gln Met Arg Asn  Ser Thr Ser
    1115                1120                1125

Asp Gly  Thr Arg Asp Tyr Ile  Ile Ser Pro Val Lys  Asn Lys Arg
    1130                1135                1140

Glu Ala  Tyr Phe Asn Ser Glu  Leu Ser Asp Gly Ser  Val Pro Lys
    1145                1150                1155

Asp Ala  Asp Ala Asn Gly Ala  Tyr Asn Ile Ala Arg  Lys Gly Leu
    1160                1165                1170

Trp Val  Leu Glu Gln Ile Arg  Gln Lys Ser Glu Gly  Glu Lys Ile
    1175                1180                1185

Asn Leu  Ala Met Thr Asn Ala  Glu Trp Leu Glu Tyr  Ala Gln Thr
    1190                1195                1200

His Leu  Leu
    1205
```

<210> SEQ ID NO 23

<211> LENGTH: 1233
<212> TYPE: PRT
<213> ORGANISM: Unknown
<220> FEATURE:
<223> OTHER INFORMATION: Lachnospiraceae bacterium

<400> SEQUENCE: 23

```
Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
        355                 360                 365

Arg Lys Glu Ser Lys Lys Arg Leu Glu Gly Leu Glu Glu His Ile Arg
    370                 375                 380
```

Lys Ser Thr Tyr Thr Phe Asp Glu Leu Asn Arg Tyr Ala Glu Lys Asn
385 390 395 400

Val Met Ala Ala Tyr Ile Ala Ala Val Glu Glu Ser Cys Ala Glu Ile
405 410 415

Met Arg Lys Glu Lys Asp Leu Arg Thr Leu Leu Ser Lys Glu Asp Val
420 425 430

Lys Ile Arg Gly Asn Arg His Asn Thr Leu Ile Val Lys Asn Tyr Phe
435 440 445

Asn Ala Trp Thr Val Phe Arg Asn Leu Ile Arg Ile Leu Arg Arg Lys
450 455 460

Ser Glu Ala Glu Ile Asp Ser Asp Phe Tyr Asp Val Leu Asp Asp Ser
465 470 475 480

Val Glu Val Leu Ser Leu Thr Tyr Lys Gly Glu Asn Leu Cys Arg Ser
485 490 495

Tyr Ile Thr Lys Lys Ile Gly Ser Asp Leu Lys Pro Glu Ile Ala Thr
500 505 510

Tyr Gly Ser Ala Leu Arg Pro Asn Ser Arg Trp Trp Ser Pro Gly Glu
515 520 525

Lys Phe Asn Val Lys Phe His Thr Ile Val Arg Arg Asp Gly Arg Leu
530 535 540

Tyr Tyr Phe Ile Leu Pro Lys Gly Ala Lys Pro Val Glu Leu Glu Asp
545 550 555 560

Met Asp Gly Asp Ile Glu Cys Leu Gln Met Arg Lys Ile Pro Asn Pro
565 570 575

Thr Ile Phe Leu Pro Lys Leu Val Phe Lys Asp Pro Glu Ala Phe Phe
580 585 590

Arg Asp Asn Pro Glu Ala Asp Glu Phe Val Phe Leu Ser Gly Met Lys
595 600 605

Ala Pro Val Thr Ile Thr Arg Glu Thr Tyr Glu Ala Tyr Arg Tyr Lys
610 615 620

Leu Tyr Thr Val Gly Lys Leu Arg Asp Gly Glu Val Ser Glu Glu Glu
625 630 635 640

Tyr Lys Arg Ala Leu Leu Gln Val Leu Thr Ala Tyr Lys Glu Phe Leu
645 650 655

Glu Asn Arg Met Ile Tyr Ala Asp Leu Asn Phe Gly Phe Lys Asp Leu
660 665 670

Glu Glu Tyr Lys Asp Ser Ser Glu Phe Ile Lys Gln Val Glu Thr His
675 680 685

Asn Thr Phe Met Cys Trp Ala Lys Val Ser Ser Ser Gln Leu Asp Asp
690 695 700

Leu Val Lys Ser Gly Asn Gly Leu Leu Phe Glu Ile Trp Ser Glu Arg
705 710 715 720

Leu Glu Ser Tyr Tyr Lys Tyr Gly Asn Glu Lys Val Leu Arg Gly Tyr
725 730 735

Glu Gly Val Leu Leu Ser Ile Leu Lys Asp Glu Asn Leu Val Ser Met
740 745 750

Arg Thr Leu Leu Asn Ser Arg Pro Met Leu Val Tyr Arg Pro Lys Glu
755 760 765

Ser Ser Lys Pro Met Val Val His Arg Asp Gly Ser Arg Val Val Asp
770 775 780

Arg Phe Asp Lys Asp Gly Lys Tyr Ile Pro Pro Glu Val His Asp Glu
785 790 795 800

-continued

```
Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
    850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
    930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Lys Leu Ala Lys  Leu Ser Asp Leu His  Phe Arg Gly
        995                 1000                1005

Ile Lys  Asp Gly Glu Pro Cys  Ser Phe Thr Asn Pro  Leu Gln Leu
    1010                1015                1020

Cys Gln  Asn Asp Ser Asn Lys  Ile Leu Gln Asp Gly  Val Ile Phe
    1025                1030                1035

Met Val  Pro Asn Ser Met Thr  Arg Ser Leu Asp Pro  Asp Thr Gly
    1040                1045                1050

Phe Ile  Phe Ala Ile Asn Asp  His Asn Ile Arg Thr  Lys Lys Ala
    1055                1060                1065

Lys Leu  Asn Phe Leu Ser Lys  Phe Asp Gln Leu Lys  Val Ser Ser
    1070                1075                1080

Glu Gly  Cys Leu Ile Met Lys  Tyr Ser Gly Asp Ser  Leu Pro Thr
    1085                1090                1095

His Asn  Thr Asp Asn Arg Val  Trp Asn Cys Cys Cys  Asn His Pro
    1100                1105                1110

Ile Thr  Asn Tyr Asp Arg Glu  Thr Lys Lys Val Glu  Phe Ile Glu
    1115                1120                1125

Glu Pro  Val Glu Glu Leu Ser  Arg Val Leu Glu Glu  Asn Gly Ile
    1130                1135                1140

Glu Thr  Asp Thr Glu Leu Asn  Lys Leu Asn Glu Arg  Glu Asn Val
    1145                1150                1155

Pro Gly  Lys Val Val Asp Ala  Ile Tyr Ser Leu Val  Leu Asn Tyr
    1160                1165                1170

Leu Arg  Gly Thr Val Ser Gly  Val Ala Gly Gln Arg  Ala Val Tyr
    1175                1180                1185

Tyr Ser  Pro Val Thr Gly Lys  Lys Tyr Asp Ile Ser  Phe Ile Gln
    1190                1195                1200

Ala Met  Asn Leu Asn Arg Lys  Cys Asp Tyr Tyr Arg  Ile Gly Ser
```

1205 1210 1215

Lys Glu Arg Gly Glu Trp Thr Asp Phe Val Ala Gln Leu Ile Asn
1220 1225 1230

<210> SEQ ID NO 24
<211> LENGTH: 1227
<212> TYPE: PRT
<213> ORGANISM: Unknown
<220> FEATURE:
<223> OTHER INFORMATION: Lachnospiraceae bacterium

<400> SEQUENCE: 24

Met Ser Lys Leu Glu Lys Phe Thr Asn Cys Tyr Ser Leu Ser Lys Thr
1 5 10 15

Leu Arg Phe Lys Ala Ile Pro Val Gly Lys Thr Gln Glu Asn Ile Asp
20 25 30

Asn Lys Arg Leu Leu Val Glu Asp Glu Lys Arg Ala Glu Asp Tyr Lys
35 40 45

Gly Val Lys Lys Leu Leu Asp Arg Tyr Tyr Leu Ser Phe Ile Asn Asp
50 55 60

Val Leu His Ser Ile Lys Leu Lys Asn Leu Asn Asn Tyr Ile Ser Leu
65 70 75 80

Phe Arg Lys Lys Thr Arg Thr Glu Lys Glu Asn Lys Glu Leu Glu Asn
85 90 95

Leu Glu Ile Asn Leu Arg Lys Glu Ile Ala Lys Ala Phe Lys Gly Asn
100 105 110

Glu Gly Tyr Lys Ser Leu Phe Lys Lys Asp Ile Ile Glu Thr Ile Leu
115 120 125

Pro Glu Phe Leu Asp Asp Lys Asp Glu Ile Ala Leu Val Asn Ser Phe
130 135 140

Asn Gly Phe Thr Thr Ala Phe Thr Gly Phe Phe Asp Asn Arg Glu Asn
145 150 155 160

Met Phe Ser Glu Glu Ala Lys Ser Thr Ser Ile Ala Phe Arg Cys Ile
165 170 175

Asn Glu Asn Leu Thr Arg Tyr Ile Ser Asn Met Asp Ile Phe Glu Lys
180 185 190

Val Asp Ala Ile Phe Asp Lys His Glu Val Gln Glu Ile Lys Glu Lys
195 200 205

Ile Leu Asn Ser Asp Tyr Asp Val Glu Asp Phe Phe Glu Gly Glu Phe
210 215 220

Phe Asn Phe Val Leu Thr Gln Glu Gly Ile Asp Val Tyr Asn Ala Ile
225 230 235 240

Ile Gly Gly Phe Val Thr Glu Ser Gly Glu Lys Ile Lys Gly Leu Asn
245 250 255

Glu Tyr Ile Asn Leu Tyr Asn Gln Lys Thr Lys Gln Lys Leu Pro Lys
260 265 270

Phe Lys Pro Leu Tyr Lys Gln Val Leu Ser Asp Arg Glu Ser Leu Ser
275 280 285

Phe Tyr Gly Glu Gly Tyr Thr Ser Asp Glu Glu Val Leu Glu Val Phe
290 295 300

Arg Asn Thr Leu Asn Lys Asn Ser Glu Ile Phe Ser Ser Ile Lys Lys
305 310 315 320

Leu Glu Lys Leu Phe Lys Asn Phe Asp Glu Tyr Ser Ser Ala Gly Ile
325 330 335

Phe Val Lys Asn Gly Pro Ala Ile Ser Thr Ile Ser Lys Asp Ile Phe

```
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765
```

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp  Leu Thr Ser Lys Ile  Asp Pro Ser
        995                 1000                1005

Thr Gly  Phe Val Asn Leu Leu  Lys Thr Lys Tyr Thr  Ser Ile Ala
    1010                1015                1020

Asp Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

-continued

Ile Leu Pro Lys Asn Ala Asp Ala Asn Gly Ala Tyr Asn Ile Ala
1175 1180 1185

Arg Lys Val Leu Trp Ala Ile Gly Gln Phe Lys Lys Ala Glu Asp
1190 1195 1200

Glu Lys Leu Asp Lys Val Lys Ile Ala Ser Asn Lys Glu Trp Leu
1205 1210 1215

Glu Tyr Ala Gln Thr Ser Val Lys His
1220 1225

<210> SEQ ID NO 25
<211> LENGTH: 1264
<212> TYPE: PRT
<213> ORGANISM: Leptospira inadai

<400> SEQUENCE: 25

Met Glu Asp Tyr Ser Gly Phe Val Asn Ile Tyr Ser Ile Gln Lys Thr
1 5 10 15

Leu Arg Phe Glu Leu Lys Pro Val Gly Lys Thr Leu Glu His Ile Glu
20 25 30

Lys Lys Gly Phe Leu Lys Lys Asp Lys Ile Arg Ala Glu Asp Tyr Lys
35 40 45

Ala Val Lys Lys Ile Ile Asp Lys Tyr His Arg Ala Tyr Ile Glu Glu
50 55 60

Val Phe Asp Ser Val Leu His Gln Lys Lys Lys Lys Asp Lys Thr Arg
65 70 75 80

Phe Ser Thr Gln Phe Ile Lys Glu Ile Lys Glu Phe Ser Glu Leu Tyr
85 90 95

Tyr Lys Thr Glu Lys Asn Ile Pro Asp Lys Glu Arg Leu Glu Ala Leu
100 105 110

Ser Glu Lys Leu Arg Lys Met Leu Val Gly Ala Phe Lys Gly Glu Phe
115 120 125

Ser Glu Glu Val Ala Glu Lys Tyr Asn Lys Asn Leu Phe Ser Lys Glu
130 135 140

Leu Ile Arg Asn Glu Ile Glu Lys Phe Cys Glu Thr Asp Glu Glu Arg
145 150 155 160

Lys Gln Val Ser Asn Phe Lys Ser Phe Thr Thr Tyr Phe Thr Gly Phe
165 170 175

His Ser Asn Arg Gln Asn Ile Tyr Ser Asp Glu Lys Lys Ser Thr Ala
180 185 190

Ile Gly Tyr Arg Ile Ile His Gln Asn Leu Pro Lys Phe Leu Asp Asn
195 200 205

Leu Lys Ile Ile Glu Ser Ile Gln Arg Arg Phe Lys Asp Phe Pro Trp
210 215 220

Ser Asp Leu Lys Lys Asn Leu Lys Lys Ile Asp Lys Asn Ile Lys Leu
225 230 235 240

Thr Glu Tyr Phe Ser Ile Asp Gly Phe Val Asn Val Leu Asn Gln Lys
245 250 255

Gly Ile Asp Ala Tyr Asn Thr Ile Leu Gly Gly Lys Ser Glu Glu Ser
260 265 270

Gly Glu Lys Ile Gln Gly Leu Asn Glu Tyr Ile Asn Leu Tyr Arg Gln
275 280 285

Lys Asn Asn Ile Asp Arg Lys Asn Pro Leu Asn Val Lys Ile Leu Phe
290 295 300

Lys Gln Ile Leu Gly Asp Arg Glu Thr Lys Ser Phe Ile Pro Glu Ala
305 310 315 320

-continued

```
Phe Pro Asp Asp Gln Ser Val Leu Asn Ser Ile Thr Glu Phe Ala Lys
                325                 330                 335

Tyr Leu Lys Leu Asp Lys Lys Lys Lys Ser Ile Ile Ala Glu Leu Lys
            340                 345                 350

Lys Phe Leu Ser Ser Phe Asn Arg Tyr Glu Leu Asp Gly Ile Tyr Leu
        355                 360                 365

Ala Asn Asp Asn Ser Leu Ala Ser Ile Ser Thr Phe Leu Phe Asp Asp
    370                 375                 380

Trp Ser Phe Ile Lys Lys Ser Val Ser Phe Lys Tyr Asp Glu Ser Val
385                 390                 395                 400

Gly Asp Pro Lys Lys Lys Ile Lys Ser Pro Leu Lys Tyr Glu Lys Glu
                405                 410                 415

Lys Glu Lys Trp Leu Lys Gln Lys Tyr Tyr Thr Ile Ser Phe Leu Asn
            420                 425                 430

Asp Ala Ile Glu Ser Tyr Ser Lys Ser Gln Asp Glu Lys Arg Val Lys
        435                 440                 445

Ile Arg Leu Glu Ala Tyr Phe Ala Glu Phe Lys Ser Lys Asp Asp Ala
    450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
            500                 505                 510

Lys Ser Leu Gln Phe Phe Leu Lys Pro Leu Leu Ser Ala Glu Ile Phe
        515                 520                 525

Asp Glu Lys Asp Leu Gly Phe Tyr Asn Gln Leu Glu Gly Tyr Tyr Glu
    530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
                565                 570                 575

Ser Thr Leu Leu Lys Gly Trp Asp Glu Asn Arg Glu Val Ala Asn Leu
            580                 585                 590

Cys Val Ile Phe Arg Glu Asp Gln Lys Tyr Tyr Leu Gly Val Met Asp
        595                 600                 605

Lys Glu Asn Asn Thr Ile Leu Ser Asp Ile Pro Lys Val Lys Pro Asn
    610                 615                 620

Glu Leu Phe Tyr Glu Lys Met Val Tyr Lys Leu Ile Pro Thr Pro His
625                 630                 635                 640

Met Gln Leu Pro Arg Ile Ile Phe Ser Ser Asp Asn Leu Ser Ile Tyr
                645                 650                 655

Asn Pro Ser Lys Ser Ile Leu Lys Ile Arg Glu Ala Lys Ser Phe Lys
            660                 665                 670

Glu Gly Lys Asn Phe Lys Leu Lys Asp Cys His Lys Phe Ile Asp Phe
        675                 680                 685

Tyr Lys Glu Ser Ile Ser Lys Asn Glu Asp Trp Ser Arg Phe Asp Phe
    690                 695                 700

Lys Phe Ser Lys Thr Ser Ser Tyr Glu Asn Ile Ser Glu Phe Tyr Arg
705                 710                 715                 720

Glu Val Glu Arg Gln Gly Tyr Asn Leu Asp Phe Lys Lys Val Ser Lys
                725                 730                 735
```

-continued

```
Phe Tyr Ile Asp Ser Leu Val Glu Asp Gly Lys Leu Tyr Leu Phe Gln
            740                 745                 750

Ile Tyr Asn Lys Asp Phe Ser Ile Phe Ser Lys Gly Lys Pro Asn Leu
        755                 760                 765

His Thr Ile Tyr Phe Arg Ser Leu Phe Ser Lys Glu Asn Leu Lys Asp
    770                 775                 780

Val Cys Leu Lys Leu Asn Gly Glu Ala Glu Met Phe Phe Arg Lys Lys
785                 790                 795                 800

Ser Ile Asn Tyr Asp Glu Lys Lys Lys Arg Glu Gly His His Pro Glu
                805                 810                 815

Leu Phe Glu Lys Leu Lys Tyr Pro Ile Leu Lys Asp Lys Arg Tyr Ser
            820                 825                 830

Glu Asp Lys Phe Gln Phe His Leu Pro Ile Ser Leu Asn Phe Lys Ser
        835                 840                 845

Lys Glu Arg Leu Asn Phe Asn Leu Lys Val Asn Glu Phe Leu Lys Arg
    850                 855                 860

Asn Lys Asp Ile Asn Ile Ile Gly Ile Asp Arg Gly Glu Arg Asn Leu
865                 870                 875                 880

Leu Tyr Leu Val Met Ile Asn Gln Lys Gly Glu Ile Leu Lys Gln Thr
                885                 890                 895

Leu Leu Asp Ser Met Gln Ser Gly Lys Gly Arg Pro Glu Ile Asn Tyr
            900                 905                 910

Lys Glu Lys Leu Gln Glu Lys Glu Ile Glu Arg Asp Lys Ala Arg Lys
        915                 920                 925

Ser Trp Gly Thr Val Glu Asn Ile Lys Glu Leu Lys Glu Gly Tyr Leu
    930                 935                 940

Ser Ile Val Ile His Gln Ile Ser Lys Leu Met Val Glu Asn Asn Ala
945                 950                 955                 960

Ile Val Val Leu Glu Asp Leu Asn Ile Gly Phe Lys Arg Gly Arg Gln
                965                 970                 975

Lys Val Glu Arg Gln Val Tyr Gln Lys Phe Glu Lys Met Leu Ile Asp
            980                 985                 990

Lys Leu Asn Phe Leu Val Phe Lys  Glu Asn Lys Pro Thr  Glu Pro Gly
        995                 1000                1005

Gly Val  Leu Lys Ala Tyr Gln  Leu Thr Asp Glu Phe  Gln Ser Phe
    1010                1015                1020

Glu Lys  Leu Ser Lys Gln Thr  Gly Phe Leu Phe Tyr  Val Pro Ser
    1025                1030                1035

Trp Asn  Thr Ser Lys Ile Asp  Pro Arg Thr Gly Phe  Ile Asp Phe
    1040                1045                1050

Leu His  Pro Ala Tyr Glu Asn  Ile Glu Lys Ala Lys  Gln Trp Ile
    1055                1060                1065

Asn Lys  Phe Asp Ser Ile Arg  Phe Asn Ser Lys Met  Asp Trp Phe
    1070                1075                1080

Glu Phe  Thr Ala Asp Thr Arg  Lys Phe Ser Glu Asn  Leu Met Leu
    1085                1090                1095

Gly Lys  Asn Arg Val Trp Val  Ile Cys Thr Thr Asn  Val Glu Arg
    1100                1105                1110

Tyr Phe  Thr Ser Lys Thr Ala  Asn Ser Ser Ile Gln  Tyr Asn Ser
    1115                1120                1125

Ile Gln  Ile Thr Glu Lys Leu  Lys Glu Leu Phe Val  Asp Ile Pro
    1130                1135                1140

Phe Ser  Asn Gly Gln Asp Leu  Lys Pro Glu Ile Leu  Arg Lys Asn
```

1145 1150 1155

Asp Ala Val Phe Phe Lys Ser Leu Leu Phe Tyr Ile Lys Thr Thr
1160 1165 1170

Leu Ser Leu Arg Gln Asn Asn Gly Lys Lys Gly Glu Glu Glu Lys
1175 1180 1185

Asp Phe Ile Leu Ser Pro Val Val Asp Ser Lys Gly Arg Phe Phe
1190 1195 1200

Asn Ser Leu Glu Ala Ser Asp Asp Glu Pro Lys Asp Ala Asp Ala
1205 1210 1215

Asn Gly Ala Tyr His Ile Ala Leu Lys Gly Leu Met Asn Leu Leu
1220 1225 1230

Val Leu Asn Glu Thr Lys Glu Glu Asn Leu Ser Arg Pro Lys Trp
1235 1240 1245

Lys Ile Lys Asn Lys Asp Trp Leu Glu Phe Val Trp Glu Arg Asn
1250 1255 1260

Arg

<210> SEQ ID NO 26
<211> LENGTH: 1373
<212> TYPE: PRT
<213> ORGANISM: Moraxella bovoculi

<400> SEQUENCE: 26

Met Leu Phe Gln Asp Phe Thr His Leu Tyr Pro Leu Ser Lys Thr Val
1 5 10 15

Arg Phe Glu Leu Phe Ile Asp Arg Thr Leu Glu His Ile His Ala Lys
20 25 30

Asn Phe Leu Ser Gln Asp Glu Thr Met Ala Asp Met His Gln Lys Val
35 40 45

Lys Val Ile Leu Asp Asp Tyr His Arg Asp Phe Ile Ala Asp Met Met
50 55 60

Gly Glu Val Lys Leu Thr Lys Leu Ala Glu Phe Tyr Asp Val Tyr Leu
65 70 75 80

Lys Phe Arg Lys Asn Pro Lys Asp Asp Glu Leu Gln Lys Ala Gln Leu
85 90 95

Lys Asp Leu Gln Ala Val Leu Arg Lys Glu Ile Val Lys Pro Ile Gly
100 105 110

Asn Gly Gly Lys Tyr Lys Ala Gly Tyr Asp Arg Leu Phe Gly Ala Lys
115 120 125

Leu Phe Lys Asp Gly Lys Glu Leu Gly Asp Leu Ala Lys Phe Val Ile
130 135 140

Ala Gln Glu Gly Glu Ser Ser Pro Lys Leu Ala His Leu Ala His Phe
145 150 155 160

Glu Lys Phe Ser Thr Tyr Phe Thr Gly Phe His Asp Asn Arg Lys Asn
165 170 175

Met Tyr Ser Asp Glu Asp Lys His Thr Ala Ile Ala Tyr Arg Leu Ile
180 185 190

His Glu Asn Leu Pro Arg Phe Ile Asp Asn Leu Gln Ile Leu Thr Thr
195 200 205

Ile Lys Gln Lys His Ser Ala Leu Tyr Asp Gln Ile Ile Asn Glu Leu
210 215 220

Thr Ala Ser Gly Leu Asp Val Ser Leu Ala Ser His Leu Asp Gly Tyr
225 230 235 240

His Lys Leu Leu Thr Gln Glu Gly Ile Thr Ala Tyr Asn Thr Leu Leu

-continued

```
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670
```

-continued

```
Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
    770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Lys
    930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
        995                 1000                1005

Ser Leu  Asn Asp Ile Thr Thr  Ala Ser Ala Asn Gly  Thr Gln Met
    1010                1015                1020

Thr Thr  Pro Tyr His Lys Ile  Leu Asp Lys Arg Glu  Ile Glu Arg
    1025                1030                1035

Leu Asn  Ala Arg Val Gly Trp  Gly Glu Ile Glu Thr  Ile Lys Glu
    1040                1045                1050

Leu Lys  Ser Gly Tyr Leu Ser  His Val Val His Gln  Ile Ser Gln
    1055                1060                1065

Leu Met  Leu Lys Tyr Asn Ala  Ile Val Val Leu Glu  Asp Leu Asn
    1070                1075                1080
```

Phe Gly Phe Lys Arg Gly Arg Phe Lys Val Glu Lys Gln Ile Tyr
1085 1090 1095

Gln Asn Phe Glu Asn Ala Leu Ile Lys Lys Leu Asn His Leu Val
1100 1105 1110

Leu Lys Asp Lys Ala Asp Asp Glu Ile Gly Ser Tyr Lys Asn Ala
1115 1120 1125

Leu Gln Leu Thr Asn Asn Phe Thr Asp Leu Lys Ser Ile Gly Lys
1130 1135 1140

Gln Thr Gly Phe Leu Phe Tyr Val Pro Ala Trp Asn Thr Ser Lys
1145 1150 1155

Ile Asp Pro Glu Thr Gly Phe Val Asp Leu Leu Lys Pro Arg Tyr
1160 1165 1170

Glu Asn Ile Gln Ala Ser Gln Ala Phe Phe Gly Lys Phe Asp Lys
1175 1180 1185

Ile Cys Tyr Asn Ala Asp Lys Asp Tyr Phe Glu Phe His Ile Asp
1190 1195 1200

Tyr Ala Lys Phe Thr Asp Lys Ala Lys Asn Ser Arg Gln Ile Trp
1205 1210 1215

Thr Ile Cys Ser His Gly Asp Lys Arg Tyr Val Tyr Asp Lys Thr
1220 1225 1230

Ala Asn Gln Asn Lys Gly Ala Ala Lys Gly Ile Asn Val Asn Asp
1235 1240 1245

Ile Leu Lys Ser Leu Phe Ala Arg His His Ile Asn Glu Lys Gln
1250 1255 1260

Pro Asn Leu Val Met Asp Ile Cys Gln Asn Asn Asp Lys Glu Phe
1265 1270 1275

His Lys Ser Leu Met Tyr Leu Leu Lys Thr Leu Leu Ala Leu Arg
1280 1285 1290

Tyr Ser Asn Ala Ser Ser Asp Glu Asp Phe Ile Leu Ser Pro Val
1295 1300 1305

Ala Asn Asp Glu Gly Val Phe Phe Asn Ser Ala Leu Ala Asp Asp
1310 1315 1320

Thr Gln Pro Gln Asn Ala Asp Ala Asn Gly Ala Tyr His Ile Ala
1325 1330 1335

Leu Lys Gly Leu Trp Leu Leu Asn Glu Leu Lys Asn Ser Asp Asp
1340 1345 1350

Leu Asn Lys Val Lys Leu Ala Ile Asp Asn Gln Thr Trp Leu Asn
1355 1360 1365

Phe Ala Gln Asn Arg
1370

<210> SEQ ID NO 27
<211> LENGTH: 1352
<212> TYPE: PRT
<213> ORGANISM: Unknown
<220> FEATURE:
<223> OTHER INFORMATION: Parcubacteria bacterium

<400> SEQUENCE: 27

Met Glu Asn Ile Phe Asp Gln Phe Ile Gly Lys Tyr Ser Leu Ser Lys
1 5 10 15

Thr Leu Arg Phe Glu Leu Lys Pro Val Gly Lys Thr Glu Asp Phe Leu
20 25 30

Lys Ile Asn Lys Val Phe Glu Lys Asp Gln Thr Ile Asp Asp Ser Tyr
35 40 45

-continued

```
Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
```

-continued

```
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Asp Val
        755                 760                 765

Gln Lys Tyr Gly Tyr Lys Ile Ser Phe Arg Asp Ile Asp Asp Glu Tyr
    770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
            820                 825                 830

Phe Lys Leu Ser Gly Met Ala Glu Ile Phe Gln Arg Gln Pro Ser Val
        835                 840                 845

Asn Glu Arg Glu Lys Ile Thr Thr Gln Lys Asn Gln Cys Ile Leu Asp
    850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895
```

-continued

```
Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
    930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
            980                 985                 990

Lys Ile Cys Gln Leu Ile Glu Lys  Tyr Ser Ala Ile Val  Val Leu Glu
        995                 1000                1005

Asp Leu  Asn Met Arg Phe Lys  Gln Ile Arg Gly Gly  Ile Glu Arg
    1010                1015                1020

Ser Val  Tyr Gln Gln Phe Glu  Lys Ala Leu Ile Asp  Lys Leu Gly
    1025                1030                1035

Tyr Leu  Val Phe Lys Asp Asn  Arg Asp Leu Arg Ala  Pro Gly Gly
    1040                1045                1050

Val Leu  Asn Gly Tyr Gln Leu  Ser Ala Pro Phe Val  Ser Phe Glu
    1055                1060                1065

Lys Met  Arg Lys Gln Thr Gly  Ile Leu Phe Tyr Thr  Gln Ala Glu
    1070                1075                1080

Tyr Thr  Ser Lys Thr Asp Pro  Ile Thr Gly Phe Arg  Lys Asn Val
    1085                1090                1095

Tyr Ile  Ser Asn Ser Ala Ser  Leu Asp Lys Ile Lys  Glu Ala Val
    1100                1105                1110

Lys Lys  Phe Asp Ala Ile Gly  Trp Asp Gly Lys Glu  Gln Ser Tyr
    1115                1120                1125

Phe Phe  Lys Tyr Asn Pro Tyr  Asn Leu Ala Asp Glu  Lys Tyr Lys
    1130                1135                1140

Asn Ser  Thr Val Ser Lys Glu  Trp Ala Ile Phe Ala  Ser Ala Pro
    1145                1150                1155

Arg Ile  Arg Arg Gln Lys Gly  Glu Asp Gly Tyr Trp  Lys Tyr Asp
    1160                1165                1170

Arg Val  Lys Val Asn Glu Glu  Phe Glu Lys Leu Leu  Lys Val Trp
    1175                1180                1185

Asn Phe  Val Asn Pro Lys Ala  Thr Asp Ile Lys Gln  Glu Ile Ile
    1190                1195                1200

Lys Lys  Ile Lys Ala Gly Asp  Leu Gln Gly Glu Lys  Glu Leu Asp
    1205                1210                1215

Gly Arg  Leu Arg Asn Phe Trp  His Ser Phe Ile Tyr  Leu Phe Asn
    1220                1225                1230

Leu Val  Leu Glu Leu Arg Asn  Ser Phe Ser Leu Gln  Ile Lys Ile
    1235                1240                1245

Lys Ala  Gly Glu Val Ile Ala  Val Asp Glu Gly Val  Asp Phe Ile
    1250                1255                1260

Ala Ser  Pro Val Lys Pro Phe  Phe Thr Thr Pro Asn  Pro Tyr Ile
    1265                1270                1275

Pro Ser  Asn Leu Cys Trp Leu  Ala Val Glu Asn Ala  Asp Ala Asn
    1280                1285                1290
```

-continued

```
Gly Ala  Tyr Asn Ile Ala Arg  Lys Gly Val Met Ile  Leu Lys Lys
    1295                1300                1305

Ile Arg  Glu His Ala Lys Lys  Asp Pro Glu Phe Lys  Lys Leu Pro
    1310                1315                1320

Asn Leu  Phe Ile Ser Asn Ala  Glu Trp Asp Glu Ala  Ala Arg Asp
    1325                1330                1335

Trp Gly  Lys Tyr Ala Gly Thr  Thr Ala Leu Asn Leu  Asp His
    1340                1345                1350


<210> SEQ ID NO 28
<211> LENGTH: 1260
<212> TYPE: PRT
<213> ORGANISM: Porphyromonas crevioricanis

<400> SEQUENCE: 28

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45

Arg Val Lys Lys Ile Ile Asp Thr Tyr His Lys Val Phe Ile Asp Ser
    50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320
```

```
Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
            420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
    450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510

Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
    530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Met Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735
```

```
Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys  Arg Pro Glu Asp Ile  Gly Gly Leu
        995                 1000                 1005

Leu Arg  Ala Tyr Gln Phe Thr  Ala Pro Phe Lys Ser  Phe Lys Glu
    1010                 1015                 1020

Met Gly  Lys Gln Asn Gly Phe  Leu Phe Tyr Ile Pro  Ala Trp Asn
    1025                 1030                 1035

Thr Ser  Asn Ile Asp Pro Thr  Thr Gly Phe Val Asn  Leu Phe His
    1040                 1045                 1050

Val Gln  Tyr Glu Asn Val Asp  Lys Ala Lys Ser Phe  Phe Gln Lys
    1055                 1060                 1065

Phe Asp  Ser Ile Ser Tyr Asn  Pro Lys Lys Asp Trp  Phe Glu Phe
    1070                 1075                 1080

Ala Phe  Asp Tyr Lys Asn Phe  Thr Lys Lys Ala Glu  Gly Ser Arg
    1085                 1090                 1095

Ser Met  Trp Ile Leu Cys Thr  His Gly Ser Arg Ile  Lys Asn Phe
    1100                 1105                 1110

Arg Asn  Ser Gln Lys Asn Gly  Gln Trp Asp Ser Glu  Glu Phe Ala
    1115                 1120                 1125

Leu Thr  Glu Ala Phe Lys Ser  Leu Phe Val Arg Tyr  Glu Ile Asp
    1130                 1135                 1140

Tyr Thr  Ala Asp Leu Lys Thr  Ala Ile Val Asp Glu  Lys Gln Lys
```

1145 1150 1155

Asp Phe Phe Val Asp Leu Leu Lys Leu Phe Lys Leu Thr Val Gln
1160 1165 1170

Met Arg Asn Ser Trp Lys Glu Lys Asp Leu Asp Tyr Leu Ile Ser
1175 1180 1185

Pro Val Ala Gly Ala Asp Gly Arg Phe Phe Asp Thr Arg Glu Gly
1190 1195 1200

Asn Lys Ser Leu Pro Lys Asp Ala Asp Ala Asn Gly Ala Tyr Asn
1205 1210 1215

Ile Ala Leu Lys Gly Leu Trp Ala Leu Arg Gln Ile Arg Gln Thr
1220 1225 1230

Ser Glu Gly Gly Lys Leu Lys Leu Ala Ile Ser Asn Lys Glu Trp
1235 1240 1245

Leu Gln Phe Val Gln Glu Arg Ser Tyr Glu Lys Asp
1250 1255 1260

<210> SEQ ID NO 29
<211> LENGTH: 1324
<212> TYPE: PRT
<213> ORGANISM: Prevotella disiens

<400> SEQUENCE: 29

Met Glu Asn Tyr Gln Glu Phe Thr Asn Leu Phe Gln Leu Asn Lys Thr
1 5 10 15

Leu Arg Phe Glu Leu Lys Pro Ile Gly Lys Thr Cys Glu Leu Leu Glu
20 25 30

Glu Gly Lys Ile Phe Ala Ser Gly Ser Phe Leu Glu Lys Asp Lys Val
35 40 45

Arg Ala Asp Asn Val Ser Tyr Val Lys Lys Glu Ile Asp Lys Lys His
50 55 60

Lys Ile Phe Ile Glu Glu Thr Leu Ser Ser Phe Ser Ile Ser Asn Asp
65 70 75 80

Leu Leu Lys Gln Tyr Phe Asp Cys Tyr Asn Glu Leu Lys Ala Phe Lys
85 90 95

Lys Asp Cys Lys Ser Asp Glu Glu Glu Val Lys Lys Thr Ala Leu Arg
100 105 110

Asn Lys Cys Thr Ser Ile Gln Arg Ala Met Arg Glu Ala Ile Ser Gln
115 120 125

Ala Phe Leu Lys Ser Pro Gln Lys Lys Leu Leu Ala Ile Lys Asn Leu
130 135 140

Ile Glu Asn Val Phe Lys Ala Asp Glu Asn Val Gln His Phe Ser Glu
145 150 155 160

Phe Thr Ser Tyr Phe Ser Gly Phe Glu Thr Asn Arg Glu Asn Phe Tyr
165 170 175

Ser Asp Glu Glu Lys Ser Thr Ser Ile Ala Tyr Arg Leu Val His Asp
180 185 190

Asn Leu Pro Ile Phe Ile Lys Asn Ile Tyr Ile Phe Glu Lys Leu Lys
195 200 205

Glu Gln Phe Asp Ala Lys Thr Leu Ser Glu Ile Phe Glu Asn Tyr Lys
210 215 220

Leu Tyr Val Ala Gly Ser Ser Leu Asp Glu Val Phe Ser Leu Glu Tyr
225 230 235 240

Phe Asn Asn Thr Leu Thr Gln Lys Gly Ile Asp Asn Tyr Asn Ala Val
245 250 255

-continued

```
Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Gln Asn Ala Glu
    370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
        435                 440                 445

Asn Ser Gly Asn Met Pro Arg Lys Val Glu Asp Tyr Phe Ser Leu Met
    450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
            500                 505                 510

Leu Leu Asp Ala Thr Lys Gln Phe Gln His Phe Ile Lys Pro Leu Leu
        515                 520                 525

Gly Thr Gly Glu Glu Ala Asp Arg Asp Leu Val Phe Tyr Gly Asp Phe
    530                 535                 540

Leu Pro Leu Tyr Glu Lys Phe Glu Glu Leu Thr Leu Leu Tyr Asn Lys
545                 550                 555                 560

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
            580                 585                 590

Thr Glu Lys Ser Asp Asn Gly Thr Gln Tyr Gly Gly Tyr Leu Phe Arg
        595                 600                 605

Lys Lys Asn Glu Ile Gly Glu Tyr Asp Tyr Phe Leu Gly Ile Ser Ser
    610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655

Tyr Glu Gly Glu Asn Ser Tyr Lys Glu Asp Lys Lys Arg Leu Asn Lys
            660                 665                 670

Val Ile Ile Ala Tyr Ile Glu Gln Ile Lys Gln Thr Asn Ile Lys Lys
```

-continued

```
        675                 680                 685

Ser Ile Ile Glu Ser Ile Ser Lys Tyr Pro Asn Ile Ser Asp Asp Asp
    690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
                725                 730                 735

Lys Glu Val Ile Asp Asn Leu Leu Lys Thr Ile Ser Pro Leu Lys Asn
            740                 745                 750

Lys Ala Glu Phe Leu Asp Leu Ile Asn Lys Asp Tyr Gln Ile Phe Thr
        755                 760                 765

Glu Val Gln Ala Val Ile Asp Glu Ile Cys Lys Gln Lys Thr Phe Ile
    770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
                805                 810                 815

Ala Lys Thr Phe Ser Ala Asn Leu Arg Lys Lys Arg Gly Ala Glu Asn
            820                 825                 830

Leu His Thr Met Leu Phe Lys Ala Leu Met Glu Gly Asn Gln Asp Asn
        835                 840                 845

Leu Asp Leu Gly Ser Gly Ala Ile Phe Tyr Arg Ala Lys Ser Leu Asp
    850                 855                 860

Gly Asn Lys Pro Thr His Pro Ala Asn Glu Ala Ile Lys Cys Arg Asn
865                 870                 875                 880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
            900                 905                 910

Gln Asn Tyr Lys Ala Ala Asn Asp Ser Ala Gln Leu Asn Ser Ser Ala
        915                 920                 925

Thr Glu Tyr Ile Arg Lys Ala Asp Asp Leu His Ile Ile Gly Ile Asp
    930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys
            980                 985                 990

Ala Asn Arg Gln Asn Trp Glu Ala  Val Glu Gly Ile Lys  Asp Leu Lys
        995                 1000                1005

Lys Gly  Tyr Leu Ser Gln Ala  Val His Gln Ile Ala  Gln Leu Met
    1010                1015                1020

Leu Lys  Tyr Asn Ala Ile Ile  Ala Leu Glu Asp Leu  Gly Gln Met
    1025                1030                1035

Phe Val  Thr Arg Gly Gln Lys  Ile Glu Lys Ala Val  Tyr Gln Gln
    1040                1045                1050

Phe Glu  Lys Ser Leu Val Asp  Lys Leu Ser Tyr Leu  Val Asp Lys
    1055                1060                1065

Lys Arg  Pro Tyr Asn Glu Leu  Gly Gly Ile Leu Lys  Ala Tyr Gln
    1070                1075                1080

Leu Ala  Ser Ser Ile Thr Lys  Asn Asn Ser Asp Lys  Gln Asn Gly
    1085                1090                1095
```

Phe Leu Phe Tyr Val Pro Ala Trp Asn Thr Ser Lys Ile Asp Pro
1100 1105 1110

Val Thr Gly Phe Thr Asp Leu Leu Arg Pro Lys Ala Met Thr Ile
1115 1120 1125

Lys Glu Ala Gln Asp Phe Phe Gly Ala Phe Asp Asn Ile Ser Tyr
1130 1135 1140

Asn Asp Lys Gly Tyr Phe Glu Phe Glu Thr Asn Tyr Asp Lys Phe
1145 1150 1155

Lys Ile Arg Met Lys Ser Ala Gln Thr Arg Trp Thr Ile Cys Thr
1160 1165 1170

Phe Gly Asn Arg Ile Lys Arg Lys Lys Asp Lys Asn Tyr Trp Asn
1175 1180 1185

Tyr Glu Glu Val Glu Leu Thr Glu Glu Phe Lys Lys Leu Phe Lys
1190 1195 1200

Asp Ser Asn Ile Asp Tyr Glu Asn Cys Asn Leu Lys Glu Glu Ile
1205 1210 1215

Gln Asn Lys Asp Asn Arg Lys Phe Phe Asp Asp Leu Ile Lys Leu
1220 1225 1230

Leu Gln Leu Thr Leu Gln Met Arg Asn Ser Asp Asp Lys Gly Asn
1235 1240 1245

Asp Tyr Ile Ile Ser Pro Val Ala Asn Ala Glu Gly Gln Phe Phe
1250 1255 1260

Asp Ser Arg Asn Gly Asp Lys Lys Leu Pro Leu Asp Ala Asp Ala
1265 1270 1275

Asn Gly Ala Tyr Asn Ile Ala Arg Lys Gly Leu Trp Asn Ile Arg
1280 1285 1290

Gln Ile Lys Gln Thr Lys Asn Lys Asp Asp Leu Asn Leu Ser Ile
1295 1300 1305

Ser Ser Thr Glu Trp Leu Asp Phe Val Arg Glu Lys Pro Tyr Leu
1310 1315 1320

Lys

<210> SEQ ID NO 30
<211> LENGTH: 1484
<212> TYPE: PRT
<213> ORGANISM: Unknown
<220> FEATURE:
<223> OTHER INFORMATION: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 30

Met Ser Asn Phe Phe Lys Asn Phe Thr Asn Leu Tyr Glu Leu Ser Lys
1 5 10 15

Thr Leu Arg Phe Glu Leu Lys Pro Val Gly Asp Thr Leu Thr Asn Met
20 25 30

Lys Asp His Leu Glu Tyr Asp Glu Lys Leu Gln Thr Phe Leu Lys Asp
35 40 45

Gln Asn Ile Asp Asp Ala Tyr Gln Ala Leu Lys Pro Gln Phe Asp Glu
50 55 60

Ile His Glu Glu Phe Ile Thr Asp Ser Leu Glu Ser Lys Lys Ala Lys
65 70 75 80

Glu Ile Asp Phe Ser Glu Tyr Leu Asp Leu Phe Gln Glu Lys Lys Glu
85 90 95

-continued

```
Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
    290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
        355                 360                 365

Glu Ile Ile Asn Lys Ala Gln Glu Ala Ile Asn Lys Tyr Phe Lys Ser
    370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
        435                 440                 445

Glu Asp Asp Ile Lys Ile Pro Glu Ala Ile Glu Leu Ser Gly Leu Phe
    450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
            500                 505                 510
```

-continued

```
Met Glu Ser Phe Leu Lys Glu Thr Asn Asp Ile Ile Thr Leu Lys Lys
        515                 520                 525

Tyr Lys Gly Asn Lys Glu Gly Thr Glu Lys Ile Lys Gln Trp Phe Asp
    530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
            580                 585                 590

Ala Leu Arg Asn Tyr Leu Thr Gln Lys Pro Gln Asp Glu Ala Lys Glu
        595                 600                 605

Asn Lys Leu Lys Leu Asn Phe Asp Asn Pro Ser Leu Ala Gly Gly Trp
    610                 615                 620

Asp Val Asn Lys Glu Cys Ser Asn Phe Cys Val Ile Leu Lys Asp Lys
625                 630                 635                 640

Asn Glu Lys Lys Tyr Leu Ala Met Ile Lys Lys Gly Glu Asn Thr Leu
                645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
        675                 680                 685

Glu Tyr Asp Phe Trp Ala Asp Val Ser Lys Met Ile Pro Lys Cys Ser
    690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
        755                 760                 765

Ser Thr Gln Glu Lys Gln Tyr Ile Lys Ala Phe Gln Lys Glu Tyr Trp
    770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
                805                 810                 815

Leu Leu Ser Trp Glu Arg Lys Tyr Lys Asp Ala Leu Thr Asn Trp Ile
            820                 825                 830

Asn Phe Cys Lys Tyr Phe Leu Ser Lys Tyr Pro Lys Thr Thr Leu Phe
        835                 840                 845

Asn Tyr Ser Phe Lys Glu Ser Glu Asn Tyr Asn Ser Leu Asp Glu Phe
    850                 855                 860

Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
                885                 890                 895

Leu Phe Glu Ile Lys Asn Gln Asp Ser Asn Asp Gly Lys Ser Ile Gly
            900                 905                 910

His Lys Asn Asn Leu His Thr Ile Tyr Trp Asn Ala Ile Phe Glu Asn
        915                 920                 925

Phe Asp Asn Arg Pro Lys Leu Asn Gly Glu Ala Glu Ile Phe Tyr Arg
```

-continued

```
    930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
            980                 985                 990

Tyr Val Asn Asp Ile Val Asn Thr  Lys Phe Tyr Asn Phe  Ser Asn Leu
        995                 1000                1005

His Phe  Leu Gly Ile Asp Arg  Gly Glu Lys His Leu  Ala Tyr Tyr
    1010                1015                1020

Ser Leu  Val Asn Lys Asn Gly  Glu Ile Val Asp Gln  Gly Thr Leu
    1025                1030                1035

Asn Leu  Pro Phe Thr Asp Lys  Asp Gly Asn Gln Arg  Ser Ile Lys
    1040                1045                1050

Lys Glu  Lys Tyr Phe Tyr Asn  Lys Gln Glu Asp Lys  Trp Glu Ala
    1055                1060                1065

Lys Glu  Val Asp Xaa Trp Asn  Tyr Asn Asp Leu Leu  Asp Ala Met
    1070                1075                1080

Ala Ser  Asn Arg Asp Met Ala  Arg Lys Asn Trp Gln  Arg Ile Gly
    1085                1090                1095

Thr Ile  Lys Glu Ala Lys Asn  Gly Tyr Val Ser Leu  Val Ile Arg
    1100                1105                1110

Lys Ile  Ala Asp Leu Ala Val  Asn Asn Glu Arg Pro  Ala Phe Ile
    1115                1120                1125

Val Leu  Glu Asp Leu Asn Thr  Gly Phe Lys Arg Ser  Arg Gln Lys
    1130                1135                1140

Ile Asp  Lys Ser Val Tyr Gln  Lys Phe Glu Leu Ala  Leu Ala Lys
    1145                1150                1155

Lys Leu  Asn Phe Leu Val Asp  Lys Asn Ala Lys Arg  Asp Glu Ile
    1160                1165                1170

Gly Ser  Pro Thr Lys Ala Leu  Gln Leu Thr Pro Pro  Val Asn Asn
    1175                1180                1185

Tyr Gly  Asp Ile Glu Asn Lys  Lys Gln Ala Gly Ile  Met Leu Tyr
    1190                1195                1200

Thr Arg  Ala Asn Tyr Thr Ser  Gln Thr Asp Pro Ala  Thr Gly Trp
    1205                1210                1215

Arg Lys  Thr Ile Tyr Leu Lys  Ala Gly Pro Glu Glu  Thr Thr Tyr
    1220                1225                1230

Lys Lys  Asp Gly Lys Ile Lys  Asn Lys Ser Val Lys  Asp Gln Ile
    1235                1240                1245

Ile Glu  Thr Phe Thr Asp Ile  Gly Phe Asp Gly Lys  Asp Tyr Tyr
    1250                1255                1260

Phe Glu  Tyr Asp Lys Gly Glu  Phe Val Asp Glu Lys  Thr Gly Glu
    1265                1270                1275

Ile Lys  Pro Lys Lys Trp Arg  Leu Tyr Ser Gly Glu  Asn Gly Lys
    1280                1285                1290

Ser Leu  Asp Arg Phe Arg Gly  Glu Arg Glu Lys Asp  Lys Tyr Glu
    1295                1300                1305

Trp Lys  Ile Asp Lys Ile Asp  Ile Val Lys Ile Leu  Asp Asp Leu
    1310                1315                1320

Phe Val  Asn Phe Asp Lys Asn  Ile Ser Leu Leu Lys  Gln Leu Lys
    1325                1330                1335
```

Glu Gly Val Glu Leu Thr Arg Asn Asn Glu His Gly Thr Gly Glu
1340 1345 1350

Ser Leu Arg Phe Ala Ile Asn Leu Ile Gln Gln Ile Arg Asn Thr
1355 1360 1365

Gly Asn Asn Glu Arg Asp Asn Asp Phe Ile Leu Ser Pro Val Arg
1370 1375 1380

Asp Glu Asn Gly Lys His Phe Asp Ser Arg Glu Tyr Trp Asp Lys
1385 1390 1395

Glu Thr Lys Gly Glu Lys Ile Ser Met Pro Ser Ser Gly Asp Ala
1400 1405 1410

Asn Gly Ala Phe Asn Ile Ala Arg Lys Gly Ile Ile Met Asn Ala
1415 1420 1425

His Ile Leu Ala Asn Ser Asp Ser Lys Asp Leu Ser Leu Phe Val
1430 1435 1440

Ser Asp Glu Glu Trp Asp Leu His Leu Asn Asn Lys Thr Glu Trp
1445 1450 1455

Lys Lys Gln Leu Asn Ile Phe Ser Ser Arg Lys Ala Met Ala Lys
1460 1465 1470

Arg Lys Lys Lys Arg Pro Ala Ala Thr Lys Lys
1475 1480

<210> SEQ ID NO 31
<211> LENGTH: 1245
<212> TYPE: PRT
<213> ORGANISM: Porphyromonas macacae

<400> SEQUENCE: 31

Met Lys Thr Gln His Phe Phe Glu Asp Phe Thr Ser Leu Tyr Ser Leu
1 5 10 15

Ser Lys Thr Ile Arg Phe Glu Leu Lys Pro Ile Gly Lys Thr Leu Glu
20 25 30

Asn Ile Lys Lys Asn Gly Leu Ile Arg Arg Asp Glu Gln Arg Leu Asp
35 40 45

Asp Tyr Glu Lys Leu Lys Lys Val Ile Asp Glu Tyr His Glu Asp Phe
50 55 60

Ile Ala Asn Ile Leu Ser Ser Phe Ser Phe Ser Glu Glu Ile Leu Gln
65 70 75 80

Ser Tyr Ile Gln Asn Leu Ser Ile Ser Glu Ala Arg Ala Lys Ile Glu
85 90 95

Lys Thr Met Arg Asp Thr Leu Ala Lys Ala Phe Ser Glu Asp Glu Arg
100 105 110

Tyr Lys Ser Ile Phe Lys Lys Glu Leu Val Lys Lys Asp Ile Pro Val
115 120 125

Trp Cys Pro Ala Tyr Lys Ser Leu Cys Lys Lys Phe Asp Asn Phe Thr
130 135 140

Thr Ser Leu Val Pro Phe His Glu Asn Arg Lys Asn Leu Tyr Thr Ser
145 150 155 160

Asn Glu Ile Thr Ala Ser Ile Pro Tyr Arg Ile Val His Val Asn Leu
165 170 175

Pro Lys Phe Ile Gln Asn Ile Glu Ala Leu Cys Glu Leu Gln Lys Lys
180 185 190

Met Gly Ala Asp Leu Tyr Leu Glu Met Met Glu Asn Leu Arg Asn Val
195 200 205

Trp Pro Ser Phe Val Lys Thr Pro Asp Asp Leu Cys Asn Leu Lys Thr

-continued

```
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640
```

Val Asp Ile Tyr Asn Lys Lys Thr Phe Lys Thr Gly Gln Lys Gly Phe
645 650 655

Asn Lys Lys Asp Leu Tyr Arg Leu Ile Asp Phe Tyr Lys Glu Ala Leu
660 665 670

Thr Val His Glu Trp Lys Leu Phe Asn Phe Ser Phe Ser Pro Thr Glu
675 680 685

Gln Tyr Arg Asn Ile Gly Glu Phe Phe Asp Glu Val Arg Glu Gln Ala
690 695 700

Tyr Lys Val Ser Met Val Asn Val Pro Ala Ser Tyr Ile Asp Glu Ala
705 710 715 720

Val Glu Asn Gly Lys Leu Tyr Leu Phe Gln Ile Tyr Asn Lys Asp Phe
725 730 735

Ser Pro Tyr Ser Lys Gly Ile Pro Asn Leu His Thr Leu Tyr Trp Lys
740 745 750

Ala Leu Phe Ser Glu Gln Asn Gln Ser Arg Val Tyr Lys Leu Cys Gly
755 760 765

Gly Gly Glu Leu Phe Tyr Arg Lys Ala Ser Leu His Met Gln Asp Thr
770 775 780

Thr Val His Pro Lys Gly Ile Ser Ile His Lys Lys Asn Leu Asn Lys
785 790 795 800

Lys Gly Glu Thr Ser Leu Phe Asn Tyr Asp Leu Val Lys Asp Lys Arg
805 810 815

Phe Thr Glu Asp Lys Phe Phe Phe His Val Pro Ile Ser Ile Asn Tyr
820 825 830

Lys Asn Lys Lys Ile Thr Asn Val Asn Gln Met Val Arg Asp Tyr Ile
835 840 845

Ala Gln Asn Asp Asp Leu Gln His Gly Ile Asp Arg Gly Glu Arg Asn
850 855 860

Leu Leu Tyr Ile Ser Arg Ile Asp Thr Arg Gly Asn Leu Leu Glu Gln
865 870 875 880

Phe Ser Leu Asn Val Ile Glu Ser Asp Lys Gly Asp Leu Arg Thr Asp
885 890 895

Tyr Gln Lys Ile Leu Gly Asp Arg Glu Gln Glu Arg Leu Arg Arg Arg
900 905 910

Gln Glu Trp Lys Ser Ile Glu Ser Ile Lys Asp Leu Lys Asp Gly Tyr
915 920 925

Met Ser Gln Val Val His Lys Ile Cys Asn Met Val Val Glu His Lys
930 935 940

Ala Ile Val Val Leu Glu Asn Leu Asn Leu Ser Phe Met Lys Gly Arg
945 950 955 960

Lys Lys Val Glu Lys Ser Val Tyr Glu Lys Phe Glu Arg Met Leu Val
965 970 975

Asp Lys Leu Asn Tyr Leu Val Val Asp Lys Lys Asn Leu Ser Asn Glu
980 985 990

Pro Gly Gly Leu Tyr Ala Ala Tyr Gln Leu Thr Asn Pro Leu Phe Ser
995 1000 1005

Phe Glu Glu Leu His Arg Tyr Pro Gln Ser Gly Ile Leu Phe Phe
1010 1015 1020

Val Asp Pro Trp Asn Thr Ser Leu Thr Asp Pro Ser Thr Gly Phe
1025 1030 1035

Val Asn Leu Leu Gly Arg Ile Asn Tyr Thr Asn Val Gly Asp Ala
1040 1045 1050

Arg Lys Phe Phe Asp Arg Phe Asn Ala Ile Arg Tyr Asp Gly Lys
    1055                1060                1065

Gly Asn Ile Leu Phe Asp Leu Asp Leu Ser Arg Phe Asp Val Arg
    1070                1075                1080

Val Glu Thr Gln Arg Lys Leu Trp Thr Leu Thr Thr Phe Gly Ser
    1085                1090                1095

Arg Ile Ala Lys Ser Lys Lys Ser Gly Lys Trp Met Val Glu Arg
    1100                1105                1110

Ile Glu Asn Leu Ser Leu Cys Phe Leu Glu Leu Phe Glu Gln Phe
    1115                1120                1125

Asn Ile Gly Tyr Arg Val Glu Lys Asp Leu Lys Lys Ala Ile Leu
    1130                1135                1140

Ser Gln Asp Arg Lys Glu Phe Tyr Val Arg Leu Ile Tyr Leu Phe
    1145                1150                1155

Asn Leu Met Met Gln Ile Arg Asn Ser Asp Gly Glu Glu Asp Tyr
    1160                1165                1170

Ile Leu Ser Pro Ala Leu Asn Glu Lys Asn Leu Gln Phe Asp Ser
    1175                1180                1185

Arg Leu Ile Glu Ala Lys Asp Leu Pro Val Asp Ala Asp Ala Asn
    1190                1195                1200

Gly Ala Tyr Asn Val Ala Arg Lys Gly Leu Met Val Val Gln Arg
    1205                1210                1215

Ile Lys Arg Gly Asp His Glu Ser Ile His Arg Ile Gly Arg Ala
    1220                1225                1230

Gln Trp Leu Arg Tyr Val Gln Glu Gly Ile Val Glu
    1235                1240                1245

<210> SEQ ID NO 32
<211> LENGTH: 1250
<212> TYPE: PRT
<213> ORGANISM: Smithella sp.

<400> SEQUENCE: 32

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

-continued

```
His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285

Ile Leu Ser Asp Arg Gln Ser Leu Ser Phe Ile Ala Glu Ala Phe Lys
    290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
            340                 345                 350

Tyr Phe Arg Ser Gly Ala Ser Leu Thr Asp Val Ser Arg Lys Val Phe
        355                 360                 365

Gly Glu Trp Ser Ile Ile Asn Arg Ala Leu Asp Asn Tyr Tyr Ala Thr
    370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
            420                 425                 430

Lys Val Ile Ala Asp Tyr Phe Ala Lys Phe Cys Asp Asp Lys Glu Thr
        435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
            500                 505                 510

Glu Thr Phe Tyr Ser Leu Phe Thr Pro Leu Tyr Asp His Leu Thr Gln
        515                 520                 525

Thr Ile Ala Leu Tyr Asn Lys Val Arg Asn Tyr Leu Thr Gln Lys Pro
    530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
            580                 585                 590
```

-continued

```
Arg Ile Phe Arg Asn Val Pro Lys Ala Asp Lys Lys Asp Phe Cys Tyr
        595                 600                 605

Glu Lys Met Val Tyr Lys Leu Leu Pro Gly Ala Asn Lys Met Leu Pro
    610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
    690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
        755                 760                 765

Leu Asn Gly Glu Ala Glu Val Phe Tyr Arg Lys Lys Ser Ile Ala Glu
    770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
        835                 840                 845

Gln Phe Leu Lys Ala Asn Pro Asp Ile Asn Ile Ile Gly Ile Asp Arg
    850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910

Ala Arg Gln Glu Trp Gly Val Ile Glu Thr Ile Lys Glu Leu Lys Glu
        915                 920                 925

Gly Tyr Leu Ser Gln Val Ile His Lys Leu Thr Asp Leu Met Ile Glu
    930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala  Phe Gln Leu Ala Asn  Lys Phe Glu
        995                 1000                1005

Ser Phe  Gln Lys Met Gly Lys  Gln Asn Gly Phe Ile  Phe Tyr Val
```

1010 1015 1020

Pro Ala Trp Asn Thr Ser Lys Thr Asp Pro Ala Thr Gly Phe Ile
1025 1030 1035

Asp Phe Leu Lys Pro Arg Tyr Glu Asn Leu Asn Gln Ala Lys Asp
1040 1045 1050

Phe Phe Glu Lys Phe Asp Ser Ile Arg Leu Asn Ser Lys Ala Asp
1055 1060 1065

Tyr Phe Glu Phe Ala Phe Asp Phe Lys Asn Phe Thr Glu Lys Ala
1070 1075 1080

Asp Gly Gly Arg Thr Lys Trp Thr Val Cys Thr Thr Asn Glu Asp
1085 1090 1095

Arg Tyr Gln Trp Asn Arg Ala Leu Asn Asn Asn Arg Gly Ser Gln
1100 1105 1110

Glu Lys Tyr Asp Ile Thr Ala Glu Leu Lys Ser Leu Phe Asp Gly
1115 1120 1125

Lys Val Asp Tyr Lys Ser Gly Lys Asp Leu Lys Gln Gln Ile Ala
1130 1135 1140

Ser Gln Glu Ser Ala Asp Phe Phe Lys Ala Leu Met Lys Asn Leu
1145 1150 1155

Ser Ile Thr Leu Ser Leu Arg His Asn Asn Gly Glu Lys Gly Asp
1160 1165 1170

Asn Glu Gln Asp Tyr Ile Leu Ser Pro Val Ala Asp Ser Lys Gly
1175 1180 1185

Arg Phe Phe Asp Ser Arg Lys Ala Asp Asp Asp Met Pro Lys Asn
1190 1195 1200

Ala Asp Ala Asn Gly Ala Tyr His Ile Ala Leu Lys Gly Leu Trp
1205 1210 1215

Cys Leu Glu Gln Ile Ser Lys Thr Asp Asp Leu Lys Lys Val Lys
1220 1225 1230

Leu Ala Ile Ser Asn Lys Glu Trp Leu Glu Phe Val Gln Thr Leu
1235 1240 1245

Lys Gly
1250

<210> SEQ ID NO 33
<211> LENGTH: 3987
<212> TYPE: DNA
<213> ORGANISM: Artificial
<220> FEATURE:
<223> OTHER INFORMATION: Cas12a polynucleotide

<400> SEQUENCE: 33
atggccggga gcaagaagcg ccggataaag caggacacgc agttcgaggg cttcaccaac 60
ctgtaccaag tctccaagac gctccggttc gagcttatcc cgcaagggaa gaccctgaaa 120
cacatccagg aacaaggttt catcgaggag gacaaggccc gcaacgacca ctacaaggag 180
ctcaagccca taatcgatcg gatctacaag acgtacgccg accagtgcct ccaactggtg 240
cagctcgact gggagaacct gagcgccgcc attgacagct accgcaagga aaagacggag 300
gagacgcgca acgcccttat tgaggagcaa gccacctacc gcaacgccat ccacgactac 360
ttcatcgggc gcaccgacaa cctgacggac gcgatcaaca agcgccacgc ggaaatctac 420
aagggccttt tcaaggccga gctcttcaac gggaaggtcc taaaacagct cgggactgtc 480
acgacaaccg agcatgagaa cgccctcctt cgcagcttcg acaagttcac cacatacttc 540
tcgggcttct accggaaccg caagaacgtt ttcagcgccg aggacatctc caccgccatc 600

-continued

```
ccgcacagga tcgtccagga caacttcccc aagttcaagg agaactgcca catcttcacg    660
cgcctgatta cagccgtacc ttcacttcgt gagcacttcg agaacgtcaa aaaggccatc    720
gggatcttcg tctccacgtc catcgaggag gtattctctt tcccgttcta taaccagctc    780
ctgacccaga cgcagatcga cctctacaac cagctactgg gcggcatcag ccgggaggcc    840
gggaccgaga aaataaaggg cctcaacgaa gttctcaacc tggccatcca gaagaacgac    900
gagaccgcgc atatcatcgc atccctgccg catcgcttca ttcctttgtt caagcagata    960
ttgagcgacc ggaacaccct ctcgttcatc ctcgaagaat tcaagagcga cgaggaggtc   1020
attcagtctt tctgcaagta caagacgctc ctacggaatg agaatgtgct ggagaccgcg   1080
gaggcactct tcaatgagct gaactccatt gacctgaccc acatcttcat tagccacaag   1140
aaactggaga cgatctccag cgccctgtgc gaccactggg acactctccg caacgccctc   1200
tacgaacgcc ggatctccga acttaccggc aagataacta agtcggctaa ggagaaggtg   1260
caacggagcc tcaagcacga ggacatcaac cttcaggaaa tcatctcagc cgcgggcaag   1320
gagctgagcg aggcgtttaa gcagaaaaca tcggagatac tgagccacgc gcacgcggcc   1380
ctggatcaac cgctgccgac gactctcaag aagcaagagg agaaggaaat ccttaagtcc   1440
cagctcgact cgctgctcgg cctctatcac ttgctcgact ggttcgcggt tgatgagtcc   1500
aacgaggtgg acccggagtt ctccgcgcgc ctcacgggta ttaagctgga gatggagcca   1560
agcttaagct tctacaacaa ggcccgcaac tacgcgacca aaaaaccgta ctcagtcgag   1620
aaattcaagc tgaatttcca gatgcctaca ttggcgaggg ggtgggacgt gaaccgcgag   1680
aagaacaatg gagccatcct gttcgtcaaa aatgggttgt actacctggg catcatgccc   1740
aagcagaagg gccgttacaa ggccctgtca ttcgagccta ccgagaagac ctcggagggc   1800
ttcgacaaga tgtactacga ctatttcccg gacgccgcca agatgatccc gaagtgctcc   1860
acgcagctca aagccgtcac ggcccacttc cagacgcata ccacgccgat acttctgagc   1920
aacaacttca ttgagccgct agagatcacg aaggagatat acgacctaaa caaccccgaa   1980
aaggagccca agaagttcca gacagcctac gctaagaaga caggtgatca gaagggatat   2040
agggaggcac tctgcaagtg gatcgacttc acgcgcgact tcctgtcgaa atatacaaag   2100
acgaccagca ttgacctaag ttctctccgc ccatcctccc agtacaagga tctgggcgag   2160
tattatgcgg agctgaaccc attgctgtac cacatcagct tccagaggat cgccgagaag   2220
gagattatgg acgcggtgga gacggggaaa ctatacctgt tccaaatata taacaaggac   2280
ttcgctaaag ggcaccacgg gaagcccaac ctgcacacac tctactggac gggcttgttt   2340
tcgccagaaa atttggccaa gacttcgatc aagctcaacg gccaggcgga gttgttttac   2400
cgtcccaagt ctcgcatgaa gcgcatggcg catcgcctcg gagagaaaat gcttaacaag   2460
aagctcaagg atcagaagac gcccatacct gatacgttgt accaggaatt gtacgactac   2520
gtgaaccacc gcctatcgca cgacctctca gacgaggccc gcgccctcct cccaaacgtg   2580
attactaagg aggtttccca tgaaataatc aaggaccgac ggttcaccag cgacaaattt   2640
tttttccacg tgcctatcac gctcaattac caggcggcca actccccatc gaagttcaac   2700
cagcgcgtga acgcctacct taaggagcac ccggagaccc caatcatcgg gatcgaccgt   2760
ggcgagcgga acctgatcta tattacggtg atcgatagca ccgggaagat cctggagcag   2820
cgctccctga acacaatcca gcagtttgac taccagaaga aactcgacaa ccgggagaag   2880
gagcgcgtcg cagcccggca agcatggagt gtggtcggca ccataaagga cctgaaacag   2940
```

-continued

```
ggttacctaa gtcaagttat ccacgagatc gttgacctga tgatacacta tcaagccgta   3000

gtcgtgctgg agaacctcaa cttcgggttt aagtccaagc gcaccggcat cgcggagaag   3060

gcggtgtacc agcagttcga gaagatgctg atcgacaagc tgaactgcct ggtgctcaag   3120

gactaccctg cggagaaggt cggcggggtc ttgaacccgt accagctaac cgaccagttc   3180

acgagcttcg ccaaaatggg cacgcagtcc ggattcttgt tttatgtccc ggctccatat   3240

acaagtaaga tcgacccgct gacagggttt gttgacccat tcgtgtggaa gaccatcaag   3300

aaccacgaga gcaggaaaca cttcttagag ggcttcgact tcctgcatta cgacgttaag   3360

acaggcgact tcatcctgca cttcaagatg aaccgcaacc tgtcgttcca gaggggcctg   3420

cccggcttca tgcccgcctg ggatatcgtc tttgagaaga atgagacgca gttcgacgcg   3480

aaggggacgc cgttcatcgc tggaaagcgg atcgtgccgg tcatcgagaa ccaccgcttc   3540

acgggtcgct accgagattt ataccccgcc aacgaactaa ttgcgctgct ggaggagaag   3600

gggatcgtgt tccgagatgg cagcaacatt ctcccgaagc tgctggagaa cgacgactcg   3660

cacgctattg acacgatggt cgccctcata cggagcgtgc ttcagatgcg gaacagtaac   3720

gctgccacgg gcgaggacta cattaactcc cccgtccgcg acctcaacgg ggtctgcttc   3780

gatagccgct tccagaaccc ggagtggcct atggatgcgg acgcgaacgg ggcctaccac   3840

atcgccctca agggccaact cctgctcaac cacttgaagg aaagcaaaga cctcaaattg   3900

cagaatggca tcagtaacca ggactggctc gcgtacatcc aggaactgag aaacgggtcc   3960

aagaagcggc gtatcaagca agattga                                        3987
```

<210> SEQ ID NO 34
<211> LENGTH: 3987
<212> TYPE: DNA
<213> ORGANISM: Artificial
<220> FEATURE:
<223> OTHER INFORMATION: Cas12a polynucleotide

<400> SEQUENCE: 34

```
atggcgggaa gcaaaaagcg ccggattaag caagacacgc agttcgaggg cttcacgaac     60

ctctaccaag tcagcaagac cctccggttc gagctgatac cacagggaaa gacgctcaag    120

cacatccagg aacagggctt catcgaggag gacaaggcgc gcaacgacca ctacaaggag    180

ttgaaaccga tcatcgaccg catctacaag acgtacgccg accagtgcct ccagctcgtg    240

cagctcgact gggagaacct ctccgccgcc attgactcgt accggaagga gaagactgag    300

gagacccgca acgccctgat cgaggagcaa gcaacctacc ggaacgccat ccacgactac    360

ttcatcggcc gcaccgacaa cctcaccgac gcgatcaaca agcggcacgc ggagatatac    420

aaagggctgt tcaaggcgga gctgttcaac ggcaaggtgc tcaagcagct agggacggtg    480

accacgaccg agcacgagaa cgcgctcctc cgcagcttcg acaagttcac cacctacttc    540

agcggcttct accggaaccg caagaatgtg ttcagcgcgg aggacatcag cacggccatc    600

ccgcaccgca tcgtccagga caacttcccg aagttcaagg agaactgcca catcttcacc    660

cgcctgataa ccgccgtccc ctccctgcgg gagcacttcg agaacgtcaa aaaggcaatt    720

gggatcttcg tctcgaccag cattgaggag gtgttcagct tcccctteta caaccagctc    780

ctcacccaga cgcagatcga cctgtacaat cagttgctcg gcgggataag ccgcgaggcg    840

ggaaccgaaa aaatcaaggg gctgaacgaa gtgttgaacc tcgccatcca gaagaacgac    900

gagaccgcgc acatcatcgc ctccctgccc caccggttca tcccgctgtt caagcagatc    960

ctctctgacc ggaacaccct gtccttcatt cttgaggagt tcaagtcgga cgaggaggtc   1020
```

-continued

```
atccagagct tctgcaagta caagacgctg ctacggaacg agaacgtgct ggagacggcg   1080
gaggcactgt tcaacgagct aaacagcatc gacctcacgc acatcttcat cagtcacaag   1140
aaactggaga ccatctcctc cgcgctgtgc gaccactggg acacgctcag gaacgcgctc   1200
tacgagcgcc gaatcagtga gctgacgggc aagatcacga agtccgcgaa ggagaaggtg   1260
cagcggtccc tcaagcacga ggacatcaac ctccaggaga tcatctcagc ggctgggaaa   1320
gagctgtccg aggcgttcaa gcagaaaacg agcgaaatcc tgtcccacgc gcacgcggcc   1380
ctggatcagc ctctgccgac gaccctcaag aaacaagaag aaaaggaaat cctcaagtcg   1440
cagctcgact cgctgctggg cctgtaccat ctcctcgact ggttcgccgt ggacgagagc   1500
aacgaggtgg accccgagtt ctccgcgcgg cttacgggga tcaagctgga gatggagccc   1560
agcctgtcct tctacaacaa ggcgcgcaac tacgccacca agaagcccta cagcgtggag   1620
aagttcaagc tcaacttcca gatgcccact ctcgcacgtg ggtgggacgt caaccgcgaa   1680
aaaaataatg ggcgatcct gttcgtcaag aacggcctgt actacttggg catcatgccg   1740
aaacagaagg gccgctacaa ggccctgagc ttcgaaccga ccgagaaaac gagcgagggg   1800
ttcgacaaga tgtactacga ctacttcccc gacgccgcga agatgattcc aaagtgctcc   1860
acgcagctta aggccgtgac ggcccacttc cagacgcaca cgacccccgat cctcctcagc   1920
aacaacttca tcgagcccct ggagatcacg aaggagatat acgacctgaa caacccggag   1980
aaggagccca agaaattcca gaccgcctac gccaagaaga caggcgacca aaagggttac   2040
agggaggccc tctgcaagtg gatcgacttc actagggact tcctgtccaa gtacaccaag   2100
actacctcta tcgacctgtc cagcctccgc ccgtcgtccc agtacaaaga tttgggcgag   2160
tattacgcgg agctgaaccc actgctctac cacatcagct tccagcgcat cgcggagaag   2220
gagatcatgg acgcagtgga gacgggcaag ctatacctat ttcagatata caacaaagac   2280
ttcgctaagg gacaccacgg caagcctaac ctgcacaccc tctactggac ggggctcttc   2340
agcccggaga acctcgccaa gacctcgatc aagctcaacg gccaggccga gctgttctac   2400
cggcccaagt cccgcatgaa gcggatggcc caccggctcg ggagagaaat gctcaacaag   2460
aaattgaagg accaaaaaac gccgataccc gacaccctat accaggagct gtacgactat   2520
gtgaaccacc gcctgagcca cgacctcagc gacgaggcgc gggccctcct gccgaacgtc   2580
atcacaaagg aggtcagcca cgagatcatc aaggaccggc gcttcacctc cgacaagttt   2640
ttctttcacg tgcccatcac gctcaactac caggccgcca actcgccgtc caagttcaac   2700
cagcgcgtga acgcctacct caaggagcac cccgagaccc cgatcatcgg gattgaccga   2760
ggggagcgga acctcatcta catcaccgtc atcgacagca ccgggaagat ccttgaacag   2820
cggtcgctca acaccatcca gcagttcgac taccagaaga aactcgacaa ccgggagaag   2880
gagagagtgg cggcccgcca ggcttggtcc gtcgtcggga cgattaagga cttgaaacaa   2940
ggttacctgt cgcaagtgat ccacgagatc gttgacctga tgatccacta ccaagccgtc   3000
gtggtcctgg agaacctcaa cttcggcttc aagagcaaac gaaccggcat cgcggagaag   3060
gccgtgtacc agcagttcga aaaaatgctg atcgacaagc tgaactgcct cgtgctcaag   3120
gactaccccg ctgagaaggt cggcggggtg ctgaacccgt accagctcac tgaccagttc   3180
accagcttcg caaagatggg cacccagtcc ggcttcctgt tctacgtgcc tgcgccatac   3240
acctcgaaga tcgacccgct caccgggttc gtggacccct tcgtctggaa gaccatcaag   3300
aaccacgaga gccgcaagca cttcctggag ggcttcgact tcctccacta cgacgtcaag   3360
```

accggggact tcatcctgca cttcaagatg aaccgcaacc tcagtttcca gcgcggcctg 3420
ccggggttca tgcccgcttg ggatatagtc ttcgagaaga atgagacgca gttcgacgcg 3480
aagggcaccc cgttcatcgc cgggaagcgc atcgtgccgg tcatcgagaa ccaccggttc 3540
accgggcgct accgcgacct atacccggcg aacgagttga tcgccctcct ggaggagaag 3600
ggcatcgtgt tccgcgacgg ctccaacatc ctcccgaagc tgctcgaaaa cgacgactcc 3660
cacgccatcg acacgatggt cgcgctgatc cggtcggtgc tccagatgcg gaactccaac 3720
gccgcgacgg gcgaggacta catcaacagt ccggtccgcg atctgaacgg cgtctgcttc 3780
gactcccggt tccagaaccc cgagtggccg atggacgcgg acgcgaacgg cgcataccac 3840
atcgccctaa aagggcaatt gctgctcaac cacctcaagg aatccaaaga cctaaagctc 3900
cagaacggca tctccaacca ggactggctg gcgtacatcc aggaactgcg gaacgggagc 3960
aaaaaacgtc ggatcaagca agattga 3987

<210> SEQ ID NO 35
<211> LENGTH: 3987
<212> TYPE: DNA
<213> ORGANISM: Artificial
<220> FEATURE:
<223> OTHER INFORMATION: Cas12a polynucleotide

<400> SEQUENCE: 35
atggcgggct ccaagaaacg ccggattaag caagataccc agttcgaggg gttcacgaac 60
ctctaccaag tgagcaagac cctccgattc gaactgattc ctcaggggaa gaccctcaag 120
cacatccagg agcaagggtt catcgaggag gacaaggcgc ggaacgacca ctacaaggaa 180
ctcaaaccca tcatcgaccg catctacaag acctacgccg atcagtgcct ccagctcgtg 240
cagttggact gggagaacct cagcgcggcc attgactcct accggaagga gaaaacggag 300
gagacgcgca acgcgctcat cgaggaacag gcaacctatc gcaacgccat ccacgactac 360
ttcatcggga ggactgacaa cctcactgac gcgattaaca agcgccacgc ggagatatac 420
aagggactct tcaaagcgga gctgtttaac ggcaaggttc tcaagcaact cggcactgtg 480
accacgaccg agcatgagaa cgccctgctc cgctccttcg acaagttcac cacctacttc 540
tccgggttct accgcaaccg caagaatgtc ttcagcgcgg aggacatcag cacggccatt 600
ccacatcgaa tcgtccaaga taacttcccg aagttcaagg agaactgcca catcttcacc 660
cgactcatta ctgctgtacc gtcgttacgc gaacacttcg agaacgtcaa gaaggcaatt 720
ggaatcttcg tctctacgtc aatagaggag gtgttcagct tccctttcta caaccagctc 780
cttacgcaga cccagataga cctgtacaat cagctcctcg gtgggatcag ccgggaggcg 840
gggactgaga agattaaagg gctcaacgag gtcttgaacc tggccatcca aaaaaacgat 900
gagacggcgc acatcatcgc ctcgctgccc caccggttca tcccgctgtt caagcagatc 960
ctcagtgaca ggaacacctt gagctttatc ctagaggagt tcaagagcga cgaggaggtg 1020
atccagagct tctgcaagta caaaaccctg ctgaggaacg agaacgtcct ggagacggcg 1080
gaggcgctgt tcaacgagct gaactctatc gacttaactc acatattcat ctcgcacaag 1140
aagctggaga ctattagctc tgcactctgc gaccactggg acaccctccg caacgcgctc 1200
tacgagcgcc gcatctcgga gctgaccggg aagatcacca aatccgcgaa ggaaaaggtc 1260
cagcgttccc tcaaacacga ggatattaac ttacaggaga ttatctcagc ggctgggaag 1320
gagttgtcag aggcgttcaa gcagaaaact tccgagatcc tgagccacgc gcacgcagcg 1380
ctcgaccagc ctctgcccac caccctcaaa aagcaggaag aaaaagagat cctcaagagc 1440

```
cagttggact ccctgctggg gctctatcac cttctcgact ggttcgccgt cgatgagtcg   1500
aacgaggtgg accccgagtt ctccgcccgg ctgaccggca tcaagctaga gatggagccg   1560
tccctcagct tctacaataa ggcccgcaac tacgcgacca aaaaacccta cagcgtggag   1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggccctttcc ttcgagccga cggagaaaac ctccgagggg   1800
ttcgacaaga tgtactacga ctacttcccc gacgccgcca agatgatccc gaagtgctca   1860
acgcagctaa aagccgtgac cgcccacttc cagacccaca cgacgccgat cctgctgagc   1920
aacaacttca tcgagcccct tgagatcact aaggagatat acgacctgaa caaccccgag   1980
aaggagccca agaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgcgg agcttaatcc actactctac cacatctcat tccagcgcat cgctgagaag   2220
gaaatcatgg acgcggtgga gacaggcaaa ctgtacctct tccagatata caacaaagac   2280
ttcgctaagg ggcaccacgg gaagcccaac cttcatacgc tctactggac gggcctattc   2340
agccccgaaa atctggccaa gacctccatc aagctgaacg gccaagcgga gctgttctac   2400
agacccaaga gccggatgaa gcggatggcc cacaggctcg gcgagaaaat gcttaacaaa   2460
aagttgaagg accagaaaac ccctatcccc gacaccctct accaggaact gtacgactac   2520
gtgaaccaca ggctctcgca cgacctttcc gacgaggccc gtgccctact cccgaacgtc   2580
attaccaaag aggtttcgca cgagatcatc aaggaccggc ggttcacgag cgacaagttt   2640
ttctttcacg tccccatcac ccttaactac caggcggcca actccccatc caagttcaac   2700
cagcgtgtga atgcctacct caaggagcac ccagagaccc cgatcattgg gatcgaccgg   2760
ggcgagcgga acctgatcta catcaccgtc atcgactcga cgggcaagat tcttgagcag   2820
agatcgttga ataccataca gcagttcgac taccagaaga aactcgacaa ccgcgagaag   2880
gagcgcgtgg cggcccgcca ggcgtggtcc gtcgttggga cgattaagga cttgaaacaa   2940
ggttatctgt cccaagtcat ccacgagatc gttgatctga tgatccacta tcaggcagtg   3000
gtggtgctgg agaatctcaa cttcggcttc aagagtaagc ggacgggaat cgccgagaag   3060
gccgtgtacc agcagttcga gaagatgctg atcgacaagc tcaactgcct tgtgctgaaa   3120
gactacccgg ccgagaaggt cggcggcgtc ctcaacccgt accaacttac cgaccagttc   3180
acctccttcg ccaagatggg cactcagtcc gggttcttgt tctacgtccc cgcaccttac   3240
acctctaaga tcgaccctct gactggcttc gtagatccat tcgtgtggaa gaccattaag   3300
aaccacgaga gccgcaagca cttcctggag ggcttcgact tcctgcacta cgacgtgaag   3360
accggggact tcatccttca cttcaagatg aaccggaacc tcagcttcca gcggggcctg   3420
ccggggttca tgcccgcctg ggacatcgtg ttcgagaaga acgagaccca gttcgacgcg   3480
aagggcacgc ccttcatcgc cgggaagcgt atcgtgccgg tgatcgagaa ccatcgtttc   3540
acgggtcgct accgtgacct ctacccggcg aacgagctta tcgcactcct ggaggagaag   3600
ggcatcgtct tccgggacgg ctccaacatc ctcccgaaac tgctggaaaa cgacgactct   3660
cacgccatcg acacgatggt ggccctcatc cggtccgtgc tccaaatgcg gaacagcaac   3720
gccgccaccg gtgaggacta catcaacagc ccggtccggg atctgaacgg ggtgtgcttc   3780
```

-continued

```
gattcgcggt tccagaatcc tgagtggccg atggacgcgg atgcaaacgg ggcgtaccac   3840

atcgcgctca agggccagtt acttctgaac caccttaagg agtctaaaga tttgaaactc   3900

cagaacggga tctcgaacca ggactggctg gcctacatcc aagagttgcg gaacggcagc   3960

aagaagcggc ggattaagca agattag                                       3987
```

```
<210> SEQ ID NO 36
<211> LENGTH: 19
<212> TYPE: DNA
<213> ORGANISM: Artificial
<220> FEATURE:
<223> OTHER INFORMATION: RNA Spacer
<220> FEATURE:
<221> NAME/KEY: misc_feature
<222> LOCATION: (1)..(19)
<223> OTHER INFORMATION: wherein n is A, C, T or G

<400> SEQUENCE: 36

nnnnnnnnnn nnnnnnnnn                                                  19
```

```
<210> SEQ ID NO 37
<211> LENGTH: 22
<212> TYPE: DNA
<213> ORGANISM: Artificial
<220> FEATURE:
<223> OTHER INFORMATION: Target strand
<220> FEATURE:
<221> NAME/KEY: misc_feature
<222> LOCATION: (4)..(22)
<223> OTHER INFORMATION: wherein n is A, C, T or G

<400> SEQUENCE: 37

aaannnnnnn nnnnnnnnnn nn                                              22
```

```
<210> SEQ ID NO 38
<211> LENGTH: 22
<212> TYPE: DNA
<213> ORGANISM: Artificial
<220> FEATURE:
<223> OTHER INFORMATION: Non-target strand
<220> FEATURE:
<221> NAME/KEY: misc_feature
<222> LOCATION: (4)..(22)
<223> OTHER INFORMATION: wherein n is A, C, T or G

<400> SEQUENCE: 38

tttnnnnnnn nnnnnnnnnn nn                                              22
```

```
<210> SEQ ID NO 39
<211> LENGTH: 24
<212> TYPE: PRT
<213> ORGANISM: Artificial
<220> FEATURE:
<223> OTHER INFORMATION: GCN4 sequence

<400> SEQUENCE: 39

Glu Glu Leu Leu Ser Lys Asn Tyr His Leu Glu Asn Glu Val Ala Arg
1               5                   10                  15

Leu Lys Lys Gly Ser Gly Ser Gly
            20
```

```
<210> SEQ ID NO 40
<211> LENGTH: 241
<212> TYPE: PRT
<213> ORGANISM: Artificial
<220> FEATURE:
<223> OTHER INFORMATION: GCN4 sequence
```

<400> SEQUENCE: 40

Glu Glu Glu Leu Leu Ser Lys Asn Tyr His Leu Glu Asn Glu Val Ala
1 5 10 15

Arg Leu Lys Lys Gly Ser Gly Ser Gly Glu Glu Leu Leu Ser Lys Asn
20 25 30

Tyr His Leu Glu Asn Glu Val Ala Arg Leu Lys Lys Gly Ser Gly Ser
35 40 45

Gly Glu Glu Leu Leu Ser Lys Asn Tyr His Leu Glu Asn Glu Val Ala
50 55 60

Arg Leu Lys Lys Gly Ser Gly Ser Gly Glu Glu Leu Leu Ser Lys Asn
65 70 75 80

Tyr His Leu Glu Asn Glu Val Ala Arg Leu Lys Lys Gly Ser Gly Ser
85 90 95

Gly Glu Glu Leu Leu Ser Lys Asn Tyr His Leu Glu Asn Glu Val Ala
100 105 110

Arg Leu Lys Lys Gly Ser Gly Ser Gly Glu Glu Leu Leu Ser Lys Asn
115 120 125

Tyr His Leu Glu Asn Glu Val Ala Arg Leu Lys Lys Gly Ser Gly Ser
130 135 140

Gly Glu Glu Leu Leu Ser Lys Asn Tyr His Leu Glu Asn Glu Val Ala
145 150 155 160

Arg Leu Lys Lys Gly Ser Gly Ser Gly Glu Glu Leu Leu Ser Lys Asn
165 170 175

Tyr His Leu Glu Asn Glu Val Ala Arg Leu Lys Lys Gly Ser Gly Ser
180 185 190

Gly Glu Glu Leu Leu Ser Lys Asn Tyr His Leu Glu Asn Glu Val Ala
195 200 205

Arg Leu Lys Lys Gly Ser Gly Ser Gly Glu Glu Leu Leu Ser Lys Asn
210 215 220

Tyr His Leu Glu Asn Glu Val Ala Arg Leu Lys Lys Gly Ser Gly Ser
225 230 235 240

Gly

<210> SEQ ID NO 41
<211> LENGTH: 277
<212> TYPE: PRT
<213> ORGANISM: Artificial
<220> FEATURE:
<223> OTHER INFORMATION: ScFv antibody

<400> SEQUENCE: 41

Met Gly Pro Asp Ile Val Met Thr Gln Ser Pro Ser Ser Leu Ser Ala
1 5 10 15

Ser Val Gly Asp Arg Val Thr Ile Thr Cys Arg Ser Ser Thr Gly Ala
20 25 30

Val Thr Thr Ser Asn Tyr Ala Ser Trp Val Gln Glu Lys Pro Gly Lys
35 40 45

Leu Phe Lys Gly Leu Ile Gly Gly Thr Asn Asn Arg Ala Pro Gly Val
50 55 60

Pro Ser Arg Phe Ser Gly Ser Leu Ile Gly Asp Lys Ala Thr Leu Thr
65 70 75 80

Ile Ser Ser Leu Gln Pro Glu Asp Phe Ala Thr Tyr Phe Cys Ala Leu
85 90 95

Trp Tyr Ser Asn His Trp Val Phe Gly Gln Gly Thr Lys Val Glu Leu 100 105 110

Lys Arg Gly Gly Gly Gly Ser Gly Gly Gly Gly Ser Gly Gly Gly Gly
115 120 125

Ser Ser Gly Gly Gly Ser Glu Val Lys Leu Leu Glu Ser Gly Gly Gly
130 135 140

Leu Val Gln Pro Gly Gly Ser Leu Lys Leu Ser Cys Ala Val Ser Gly
145 150 155 160

Phe Ser Leu Thr Asp Tyr Gly Val Asn Trp Val Arg Gln Ala Pro Gly
165 170 175

Arg Gly Leu Glu Trp Ile Gly Val Ile Trp Gly Asp Gly Ile Thr Asp
180 185 190

Tyr Asn Ser Ala Leu Lys Asp Arg Phe Ile Ile Ser Lys Asp Asn Gly
195 200 205

Lys Asn Thr Val Tyr Leu Gln Met Ser Lys Val Arg Ser Asp Asp Thr
210 215 220

Ala Leu Tyr Tyr Cys Val Thr Gly Leu Phe Asp Tyr Trp Gly Gln Gly
225 230 235 240

Thr Leu Val Thr Val Ser Ser Tyr Pro Tyr Asp Val Pro Asp Tyr Ala
245 250 255

Gly Gly Gly Gly Gly Ser Gly Gly Gly Gly Ser Gly Gly Gly Gly Ser
260 265 270

Gly Gly Gly Gly Ser
275

<210> SEQ ID NO 42
<211> LENGTH: 66
<212> TYPE: DNA
<213> ORGANISM: Saccharomyces bayanus

<400> SEQUENCE: 42
ttcttgtcgt acttatagat cgctacgtta tttcaatttt gaaaatctga gtcctgggag 60
tgcgga 66

<210> SEQ ID NO 43
<211> LENGTH: 609
<212> TYPE: PRT
<213> ORGANISM: Homo sapiens

<400> SEQUENCE: 43

Met Ser Gly Trp Glu Ser Tyr Tyr Lys Thr Glu Gly Asp Glu Glu Ala
1 5 10 15

Glu Glu Glu Gln Glu Glu Asn Leu Glu Ala Ser Gly Asp Tyr Lys Tyr
20 25 30

Ser Gly Arg Asp Ser Leu Ile Phe Leu Val Asp Ala Ser Lys Ala Met
35 40 45

Phe Glu Ser Gln Ser Glu Asp Glu Leu Thr Pro Phe Asp Met Ser Ile
50 55 60

Gln Cys Ile Gln Ser Val Tyr Ile Ser Lys Ile Ile Ser Ser Asp Arg
65 70 75 80

Asp Leu Leu Ala Val Val Phe Tyr Gly Thr Glu Lys Asp Lys Asn Ser
85 90 95

Val Asn Phe Lys Asn Ile Tyr Val Leu Gln Glu Leu Asp Asn Pro Gly
100 105 110

Ala Lys Arg Ile Leu Glu Leu Asp Gln Phe Lys Gly Gln Gln Gly Gln
115 120 125

-continued

```
Lys Arg Phe Gln Asp Met Met Gly His Gly Ser Asp Tyr Ser Leu Ser
    130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Thr Lys Ala Ser Arg Ala Arg Thr Lys Ala Gly Asp
            180                 185                 190

Leu Arg Asp Thr Gly Ile Phe Leu Asp Leu Met His Leu Lys Lys Pro
        195                 200                 205

Gly Gly Phe Asp Ile Ser Leu Phe Tyr Arg Asp Ile Ile Ser Ile Ala
    210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
            260                 265                 270

Ile Tyr Asn Leu Val Gln Lys Ala Leu Lys Pro Pro Pro Ile Lys Leu
        275                 280                 285

Tyr Arg Glu Thr Asn Glu Pro Val Lys Thr Lys Thr Arg Thr Phe Asn
    290                 295                 300

Thr Ser Thr Gly Gly Leu Leu Leu Pro Ser Asp Thr Lys Arg Ser Gln
305                 310                 315                 320

Ile Tyr Gly Ser Arg Gln Ile Ile Leu Glu Lys Glu Glu Thr Glu Glu
                325                 330                 335

Leu Lys Arg Phe Asp Asp Pro Gly Leu Met Leu Met Gly Phe Lys Pro
            340                 345                 350

Leu Val Leu Leu Lys Lys His His Tyr Leu Arg Pro Ser Leu Phe Val
        355                 360                 365

Tyr Pro Glu Glu Ser Leu Val Ile Gly Ser Ser Thr Leu Phe Ser Ala
    370                 375                 380

Leu Leu Ile Lys Cys Leu Glu Lys Glu Val Ala Ala Leu Cys Arg Tyr
385                 390                 395                 400

Thr Pro Arg Arg Asn Ile Pro Pro Tyr Phe Val Ala Leu Val Pro Gln
                405                 410                 415

Glu Glu Glu Leu Asp Asp Gln Lys Ile Gln Val Thr Pro Pro Gly Phe
            420                 425                 430

Gln Leu Val Phe Leu Pro Phe Ala Asp Asp Lys Arg Lys Met Pro Phe
        435                 440                 445

Thr Glu Lys Ile Met Ala Thr Pro Glu Gln Val Gly Lys Met Lys Ala
    450                 455                 460

Ile Val Glu Lys Leu Arg Phe Thr Tyr Arg Ser Asp Ser Phe Glu Asn
465                 470                 475                 480

Pro Val Leu Gln Gln His Phe Arg Asn Leu Glu Ala Leu Ala Leu Asp
                485                 490                 495

Leu Met Glu Pro Glu Gln Ala Val Asp Leu Thr Leu Pro Lys Val Glu
            500                 505                 510

Ala Met Asn Lys Arg Leu Gly Ser Leu Val Asp Glu Phe Lys Glu Leu
        515                 520                 525

Val Tyr Pro Pro Asp Tyr Asn Pro Glu Gly Lys Val Thr Lys Arg Lys
    530                 535                 540

His Asp Asn Glu Gly Ser Gly Ser Lys Arg Pro Lys Val Glu Tyr Ser
```

545 550 555 560

Glu Glu Glu Leu Lys Thr His Ile Ser Lys Gly Thr Leu Gly Lys Phe
565 570 575

Thr Val Pro Met Leu Lys Glu Ala Cys Arg Ala Tyr Gly Leu Lys Ser
580 585 590

Gly Leu Lys Lys Gln Glu Leu Leu Glu Ala Leu Thr Lys His Phe Gln
595 600 605

Asp

<210> SEQ ID NO 44
<211> LENGTH: 482
<212> TYPE: PRT
<213> ORGANISM: Artificial
<220> FEATURE:
<223> OTHER INFORMATION: polypeptide

<400> SEQUENCE: 44

Met Val Arg Ser Gly Asn Lys Ala Ala Trp Leu Cys Met Asp Val Gly
1 5 10 15

Phe Thr Met Ser Asn Ser Ile Pro Gly Ile Glu Ser Pro Phe Glu Gln
20 25 30

Ala Lys Lys Val Ile Thr Met Phe Val Gln Arg Gln Val Phe Ala Glu
35 40 45

Asn Lys Asp Glu Ile Ala Leu Val Leu Phe Gly Thr Asp Gly Thr Asp
50 55 60

Asn Pro Leu Ser Gly Gly Asp Gln Tyr Gln Asn Ile Thr Val His Arg
65 70 75 80

His Leu Met Leu Pro Asp Phe Asp Leu Leu Glu Asp Ile Glu Ser Lys
85 90 95

Ile Gln Pro Gly Ser Gln Gln Ala Asp Phe Leu Asp Ala Leu Ile Val
100 105 110

Ser Met Asp Val Ile Gln His Glu Thr Ile Gly Lys Lys Phe Glu Lys
115 120 125

Arg His Ile Glu Ile Phe Thr Asp Leu Ser Ser Arg Phe Ser Lys Ser
130 135 140

Gln Leu Asp Ile Ile Ile His Ser Leu Lys Lys Cys Asp Ile Ser Glu
145 150 155 160

Arg His Ser Ile His Trp Pro Cys Arg Leu Thr Ile Gly Ser Asn Leu
165 170 175

Ser Ile Arg Ile Ala Ala Tyr Lys Ser Ile Leu Gln Glu Arg Val Lys
180 185 190

Lys Thr Thr Trp Asp Ala Lys Thr Leu Lys Lys Glu Asp Ile Gln Lys
195 200 205

Glu Thr Val Tyr Cys Leu Asn Asp Asp Asp Glu Thr Glu Val Leu Lys
210 215 220

Glu Asp Ile Ile Gln Gly Phe Arg Tyr Gly Ser Asp Ile Val Pro Phe
225 230 235 240

Ser Lys Val Asp Glu Glu Gln Met Lys Tyr Lys Ser Glu Gly Lys Cys
245 250 255

Phe Ser Val Leu Gly Phe Cys Lys Ser Ser Gln Val Gln Arg Arg Phe
260 265 270

Phe Met Gly Asn Gln Val Leu Lys Val Phe Ala Ala Arg Asp Asp Glu
275 280 285

Ala Ala Ala Val Ala Leu Ser Ser Leu Ile His Ala Leu Asp Asp Leu
290 295 300

```
Asp Ile Trp Ala Ile Val Arg Tyr Ala Tyr Asp Lys Arg Ala Asn Pro
305                 310                 315                 320

Gln Val Gly Val Ala Phe Pro His Ile Lys His Asn Tyr Glu Cys Leu
                325                 330                 335

Val Tyr Val Gln Leu Pro Phe Met Glu Asp Leu Arg Gln Tyr Met Phe
            340                 345                 350

Ser Ser Leu Lys Asn Ser Lys Lys Tyr Ala Pro Thr Glu Ala Gln Leu
        355                 360                 365

Asn Ala Val Asp Ala Leu Ile Asp Ser Met Ser Leu Ala Lys Lys Asp
    370                 375                 380

Glu Lys Thr Asp Thr Leu Glu Asp Leu Phe Pro Thr Thr Lys Ile Pro
385                 390                 395                 400

Asn Pro Arg Phe Gln Arg Leu Phe Gln Cys Leu Leu His Arg Ala Leu
                405                 410                 415

His Pro Arg Glu Pro Leu Pro Pro Ile Gln Gln His Ile Trp Asn Met
            420                 425                 430

Leu Asn Pro Pro Ala Glu Val Thr Thr Lys Ser Gln Ile Pro Leu Ser
        435                 440                 445

Lys Ile Lys Thr Leu Phe Pro Leu Ile Glu Ala Lys Lys Lys Asp Gln
    450                 455                 460

Val Thr Ala Gln Glu Ile Phe Gln Asp Asn His Glu Asp Gly Pro Thr
465                 470                 475                 480

Ala Lys
```

<210> SEQ ID NO 45
<211> LENGTH: 10
<212> TYPE: DNA
<213> ORGANISM: Methanobacterium thermoautotrophicum

<400> SEQUENCE: 45
aatttttgga 10

<210> SEQ ID NO 46
<211> LENGTH: 83
<212> TYPE: PRT
<213> ORGANISM: Methanobacterium thermoautotrophicum

<400> SEQUENCE: 46

```
Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro
```

<210> SEQ ID NO 47
<211> LENGTH: 25
<212> TYPE: DNA
<213> ORGANISM: Bacteriophage MS2

<400> SEQUENCE: 47
gcgcacatga ggatcaccca tgtgc 25

<210> SEQ ID NO 48
<211> LENGTH: 116
<212> TYPE: PRT
<213> ORGANISM: Bacteriophage MS2

<400> SEQUENCE: 48

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Gly Ala Trp Arg Ser Tyr Leu Asn Met Glu Leu Thr Ile Pro
65                  70                  75                  80

Ile Phe Ala Thr Asn Ser Asp Cys Glu Leu Ile Val Lys Ala Met Gln
                85                  90                  95

Gly Leu Leu Lys Asp Gly Asn Pro Ile Pro Ser Ala Ile Ala Ala Asn
            100                 105                 110

Ser Gly Ile Tyr
        115
```

<210> SEQ ID NO 49
<211> LENGTH: 26
<212> TYPE: DNA
<213> ORGANISM: Bacteriophage PP7

<400> SEQUENCE: 49
ataaggagtt tatatggaaa ccctta 26

<210> SEQ ID NO 50
<211> LENGTH: 127
<212> TYPE: PRT
<213> ORGANISM: Bacteriophage PP7

<400> SEQUENCE: 50

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Trp Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Ala Thr
            100                 105                 110

Ser Gln Val Glu Asp Leu Val Val Asn Leu Val Pro Leu Gly Arg
        115                 120                 125
```

<210> SEQ ID NO 51
<211> LENGTH: 19

<212> TYPE: DNA
<213> ORGANISM: Shigella flexneri

<400> SEQUENCE: 51
ctgaatgcct gcgagcatc 19

<210> SEQ ID NO 52
<211> LENGTH: 62
<212> TYPE: PRT
<213> ORGANISM: Unknown
<220> FEATURE:
<223> OTHER INFORMATION: Shigella phage

<400> SEQUENCE: 52

Met Lys Ser Ile Arg Cys Lys Asn Cys Asn Lys Leu Leu Phe Lys Ala
1 5 10 15

Asp Ser Phe Asp His Ile Glu Ile Arg Cys Pro Arg Cys Lys Arg His
20 25 30

Ile Ile Met Leu Asn Ala Cys Glu His Pro Thr Glu Lys His Cys Gly
35 40 45

Lys Arg Glu Lys Ile Thr His Ser Asp Glu Thr Val Arg Tyr
50 55 60

<210> SEQ ID NO 53
<211> LENGTH: 6147
<212> TYPE: DNA
<213> ORGANISM: Artificial
<220> FEATURE:
<223> OTHER INFORMATION: nCas9::GCN4::P2A::EGFP

<400> SEQUENCE: 53
atgaaacgga cagccgacgg aagcgagttc gagtcaccaa agaagaagcg gaaagtcgac 60
aagaagtaca gcatcggcct ggacatcggc accaactctg tgggctgggc cgtgatcacc 120
gacgagtaca aggtgcccag caagaaattc aaggtgctgg gcaacaccga ccggcacagc 180
atcaagaaga acctgatcgg agccctgctg ttcgacagcg gcgaaacagc cgaggccacc 240
cggctgaaga gaaccgccag aagaagatac accagacgga agaaccggat ctgctatctg 300
caagagatct tcagcaacga gatggccaag gtggacgaca gcttcttcca cagactggaa 360
gagtccttcc tggtggaaga ggataagaag cacgagcggc accccatctt cggcaacatc 420
gtggacgagg tggcctacca cgagaagtac cccaccatct accacctgag aaagaaactg 480
gtggacagca ccgacaaggc cgacctgcgg ctgatctatc tggccctggc ccacatgatc 540
aagttccggg gccacttcct gatcgagggc gacctgaacc ccgacaacag cgacgtggac 600
aagctgttca tccagctggt gcagacctac aaccagctgt tcgaggaaaa ccccatcaac 660
gccagcggcg tggacgccaa ggccatcctg tctgccagac tgagcaagag cagacggctg 720
gaaaatctga tcgcccagct gcccggcgag aagaagaatg gcctgttcgg aaacctgatt 780
gccctgagcc tgggcctgac ccccaacttc aagagcaact tcgacctggc cgaggatgcc 840
aaactgcagc tgagcaagga cacctacgac gacgacctgg acaacctgct ggcccagatc 900
ggcgaccagt acgccgacct gtttctggcc gccaagaacc tgtccgacgc catcctgctg 960
agcgacatcc tgagagtgaa caccgagatc accaaggccc ccctgagcgc ctctatgatc 1020
aagagatacg acgagcacca ccaggacctg accctgctga aagctctcgt gcggcagcag 1080
ctgcctgaga agtacaaaga gattttcttc gaccagagca agaacggcta cgccggctac 1140
attgacggcg gagccagcca ggaagagttc tacaagttca tcaagcccat cctggaaaag 1200

```
atggacggca ccgaggaact gctcgtgaag ctgaacagag aggacctgct gcggaagcag   1260
cggaccttcg acaacggcag catcccccac cagatccacc tgggagagct gcacgccatt   1320
ctgcggcggc aggaagattt ttacccattc ctgaaggaca accgggaaaa gatcgagaag   1380
atcctgacct tccgcatccc ctactacgtg ggccctctgg ccaggggaaa cagcagattc   1440
gcctggatga ccagaaagag cgaggaaacc atcaccccct ggaacttcga ggaagtggtg   1500
gacaagggcg cttccgccca gagcttcatc gagcggatga ccaacttcga taagaacctg   1560
cccaacgaga aggtgctgcc caagcacagc ctgctgtacg agtacttcac cgtgtataac   1620
gagctgacca aagtgaaata cgtgaccgag ggaatgagaa agcccgcctt cctgagcggc   1680
gagcagaaaa aggccatcgt ggacctgctg ttcaagacca accggaaagt gaccgtgaag   1740
cagctgaaag aggactactt caagaaaatc gagtgcttcg actccgtgga aatctccggc   1800
gtggaagatc ggttcaacgc ctccctgggc acataccacg atctgctgaa aattatcaag   1860
gacaaggact tcctggacaa tgaggaaaac gaggacattc tggaagatat cgtgctgacc   1920
ctgacactgt ttgaggacag agagatgatc gaggaacggc tgaaaaccta tgcccacctg   1980
ttcgacgaca aagtgatgaa gcagctgaag cggcggagat acaccggctg gggcaggctg   2040
agccggaagc tgatcaacgg catccgggac aagcagtccg gcaagacaat cctggatttc   2100
ctgaagtccg acggcttcgc caacagaaac ttcatgcagc tgatccacga cgacagcctg   2160
acctttaaag aggacatcca gaaagcccag gtgtccggcc agggcgatag cctgcacgag   2220
cacattgcca atctggccgg cagccccgcc attaagaagg gcatcctgca gacagtgaag   2280
gtggtggacg agctcgtgaa agtgatgggc cggcacaagc ccgagaacat cgtgatcgaa   2340
atggccagag agaaccagac cacccagaag ggacagaaga acagccgcga gagaatgaag   2400
cggatcgaag agggcatcaa agagctgggc agccagatcc tgaaagaaca ccccgtggaa   2460
aacacccagc tgcagaacga gaagctgtac ctgtactacc tgcagaatgg gcgggatatg   2520
tacgtggacc aggaactgga catcaaccgg ctgtccgact acgatgtgga cgccatcgtg   2580
cctcagagct ttctgaagga cgactccatc gacaacaagg tgctgaccag aagcgacaag   2640
aaccggggca agagcgacaa cgtgccctcc gaagaggtcg tgaagaagat gaagaactac   2700
tggcggcagc tgctgaacgc caagctgatt acccagagaa agttcgacaa tctgaccaag   2760
gccgagagag gcggcctgag cgaactggat aaggccggct tcatcaagag acagctggtg   2820
gaaacccggc agatcacaaa gcacgtggca cagatcctgg actcccggat gaacactaag   2880
tacgacgaga atgacaagct gatccgggaa gtgaaagtga tcaccctgaa gtccaagctg   2940
gtgtccgatt tccggaagga tttccagttt tacaaagtgc gcgagatcaa caactaccac   3000
cacgcccacg acgcctacct gaacgccgtc gtgggaaccg ccctgatcaa aaagtaccct   3060
aagctggaaa gcgagttcgt gtacggcgac tacaaggtgt acgacgtgcg gaagatgatc   3120
gccaagagcg agcaggaaat cggcaaggct accgccaagt acttcttcta cagcaacatc   3180
atgaactttt tcaagaccga gattaccctg gccaacggcg agatccggaa gcggcctctg   3240
atcgagacaa acggcgaaac cggggagatc gtgtgggata agggccggga ttttgccacc   3300
gtgcggaaag tgctgagcat gccccaagtg aatatcgtga aaaagaccga ggtgcagaca   3360
ggcggcttca gcaaagagtc tatcctgccc aagaggaaca gcgataagct gatcgccaga   3420
aagaaggact gggaccctaa gaagtacggc ggcttcgaca gccccaccgt ggcctattct   3480
gtgctggtgg tggccaaagt ggaaaagggc aagtccaaga aactgaagag tgtgaaagag   3540
ctgctgggga tcaccatcat ggaaagaagc agcttcgaga agaatcccat cgactttctg   3600
```

-continued gaagccaagg gctacaaaga agtgaaaaag gacctgatca tcaagctgcc taagtactcc 3660
ctgttcgagc tggaaaacgg ccggaagaga atgctggcct ctgccggcga actgcagaag 3720
ggaaacgaac tggccctgcc ctccaaatat gtgaacttcc tgtacctggc cagccactat 3780
gagaagctga agggctcccc cgaggataat gagcagaaac agctgtttgt ggaacagcac 3840
aagcactacc tggacgagat catcgagcag atcagcgagt tctccaagag agtgatcctg 3900
gccgacgcta atctggacaa agtgctgtcc gcctacaaca agcaccggga taagcccatc 3960
agagagcagg ccgagaatat catccacctg tttaccctga ccaatctggg agcccctgcc 4020
gccttcaagt actttgacac caccatcgac cggaagaggt acaccagcac caaagaggtg 4080
ctggacgcca ccctgatcca ccagagcatc accggcctgt acgagacacg gatcgacctg 4140
tctcagctgg gaggtgacgg aggcggagga tctggaggcg gtgggagcgg aggcggtggg 4200
tctggaccta agaagaagag aaaggtggcc gcagctggct ccgaggaact gctgtccaag 4260
aactatcacc tggagaacga ggttgcaaga ctgaagaagg gatctggctc aggaggctct 4320
ggcagcggtg ggtccggttc agggtctgga ggcagcggtt ccggtgggtc aggatctggt 4380
gaggaactgc tgtctaagaa ctaccatctg gagaacgagg ttgctaggct gaagaagggt 4440
agcgggtccg gaggctcagg atctggtggg agcggatctg gctcaggagg ctctggcagc 4500
ggtgggtccg gttcaggtga agagttgctg agcaagaact accacctgga gaacgaggta 4560
gccagactga agaagggatc tggcagcgga ggctccggat caggtgggtc tggtagcggg 4620
tccggaggct caggctctgg tgggagcgga tctggtgaag agttgttgtc caagaactac 4680
catctggaga acgaggtagc aaggctgaag aagggttcag ggtctggagg cagcggatct 4740
ggaggatctg gatctggcag cggaggctcc ggctcaggtg ggtctggtag cggcgaagag 4800
ttgttgtcta agaactacca cctggagaac gaggtcgcga gactgaagaa gggatctggc 4860
tcaggaggct ctggaagcgg tgggtccggt tcagggtctg gaggcagcgg ctccggtggg 4920
tcaggatctg gagaagagct tttgagcaag aactaccatc tggagaacga ggtcgccagg 4980
ctgaagaagg gtagcgggtc cggaggctca ggatctggtg ggagcggatc tggctcagga 5040
ggctctggca gcggtgggtc cggttcaggc gaagagttgc tttctaagaa ctaccacctg 5100
gagaacgagg tagcgagact gaagaaggga tctggcagcg gaggctccgg atcaggtggg 5160
tctggtagcg ggtccggagg ctcaggctct ggtgggagcg gatctggaga agagctgctg 5220
tctaagaact atcatctgga gaatgaggtt gcaaggctga agaagtctgg cggctcaaaa 5280
agaaccgccg acggcagcga attcgagccc aagaagaaga ggaaagtcgg aagcggagct 5340
actaacttca gcctgctgaa gcaggctgga gacgtggagg agaaccctgg acctatggtg 5400
agcaagggcg aggagctgtt caccggggtg gtgcccatcc tggtcgagct ggacggcgac 5460
gtaaacggcc acaagttcag cgtgtccggc gagggcgagg gcgatgccac ctacggcaag 5520
ctgaccctga agttcatctg caccaccggc aagctgcccg tgccctggcc caccctcgtg 5580
accaccctga cctatggagt gcagtgcttc agccgctacc ccgaccacat gaagcagcac 5640
gacttcttca agtccgccat gcccgaaggc tacgtccagg agcgcaccat cttcttcaag 5700
gacgacggca actacaagac ccgcgccgag gtgaagttcg agggcgacac cctggtgaac 5760
cgcatcgagc tgaagggcat cgacttcaag gaggacggca acatcctggg gcacaagctg 5820
gagtacaact acaacagcca caacgtctat atcatggccg acaagcagaa gaacggcatc 5880
aaggtgaact tcaagatccg ccacaacatc gaggacggca gcgtgcagct cgccgaccac 5940

-continued taccagcaga acaccccccat cggcgacggc cccgtgctgc tgcccgacaa ccactacctg 6000
agcacccagt ccgccctgag caaagacccc aacgagaagc gcgatcacat ggtcctgctg 6060
gagttcgtga ccgccgccgg gatcactctc ggcatggacg agctgtacaa gtctggtggt 6120
tctcccaaga agaagaggaa agtctaa 6147

<210> SEQ ID NO 54
<211> LENGTH: 3996
<212> TYPE: DNA
<213> ORGANISM: Artificial
<220> FEATURE:
<223> OTHER INFORMATION: scFV::MuLV(5M)::GB1::P2A::EGFP

<400> SEQUENCE: 54
atgaaacgga cagccgacgg aagcgagttc gagtcaccaa agaagaagcg gaaagtcggt 60
ccagacatcg ttatgactca atccccctca agcctttcag cctccgtggg cgacagagtt 120
accattacct gccgctcaag cactggagca gtgaccactt ctaactacgc tagctgggtg 180
caggagaagc caggaaagct gttcaagggg ctgattggag gcacaaacaa tagagcccct 240
ggcgtgccat ccaggttttc tggaagcctg attggcgata aggcaacact gaccatctct 300
agcctgcagc ccgaggactt cgctacctac ttttgcgccc tgtggtatag caatcactgg 360
gtgttcggtc aggggactaa ggtggaactg aagagaggtg ggggaggctc cggtggggga 420
ggctcaggtg gggggaggctc ctcaggtggg ggatctgagg tgaagctgct ggaaagcggc 480
ggtgggctgg tgcagcccgg aggctccctg aagctgtcat gtgccgtgtc tggattttca 540
ctgaccgatt acggcgtgaa ctgggtgaga caggcccctg gaaggggact ggagtggatt 600
ggagtgattt ggggagatgg gatcacagac tacaattccg cactgaagga tagattcatt 660
atctcaaagg acaacggaaa gaacaccgtg tatctgcaga tgtctaaggt gaggagcgat 720
gacactgccc tgtactattg cgtgacaggg ctgtttgact attgggggca aggcactctg 780
gttaccgtga gcagctatcc atacgatgtt cccgactacg ctgggtctag cgagacacct 840
ggaacctctg aaagcgccac cccagaggga ggctccggtg ggtccggatc aacacttaat 900
attgaggatg aacatagatt gcacgagacc tctaaggaac ctgatgtttc tcttggatca 960
acttggttgt cagatttccc acaagcatgg gcagagaccg gaggtatggg tcttgctgtt 1020
aggcaggcac cacttattat tcctttgaag gcaacctcta ctcctgtgtc aattaagcaa 1080
tatccaatgt ctcaggaagc taggcttgga attaagcctc acattcaaag acttttggat 1140
cagggtattt tggtgccatg tcaatcacct tggaacacac cacttttgcc tgttaagaag 1200
cctggaacta atgattacag accagtgcaa gatttgaggg aggttaacaa gagagtggaa 1260
gatattcacc caactgttcc aaacccttat aatcttttgt ctggattgcc accttcacat 1320
caatggtaca ctgtgcttga tttgaaggat gcatttttct gccttaggtt gcatccaaca 1380
tctcagcctc tttttgcttt cgagtggaga gatcctgaaa tgggaatttc tggtcaactt 1440
acatggacca ggttgcctca gggtttcaag aactcaccaa ccttgtttaa tgaggcactt 1500
cacagggatt tggctgattt taggattcaa catcctgatc ttatcctttt gcagtatgtt 1560
gatgatcttt tgcttgctgc aacttctgaa ttggattgtc aacagggaac tagggcattg 1620
cttcaaacac ttggaaattt gggttacaga gcttcagcaa agaaggctca gatttgccaa 1680
aagcaggtta agtatcttgg atacttgctt aaggaaggac aaaggtggtt gaccgaggct 1740
agaaaggaaa ctgtgatggg tcaaccaaca cctaagaccc ctaggcagct tagagagttc 1800
ttgggaaagg caggtttttg taggcttttc attccaggat ttgctgaaat ggctgcacca 1860

-continued

```
ctttatcctt tgaccaagcc tggaactttg tttaactggg gtccagatca acagaaggca   1920
taccaagaaa ttaagcaggc tttgcttact gctccagcac ttggtttgcc tgatcttaca   1980
aagccatttg agttgttcgt tgatgaaaag caaggatatg caaagggtgt gcttacccag   2040
aagttgggac cttggagaag gcctgttgct tacctttcta agaaacttga tccagtggct   2100
gcaggttggc caccttgtct tagaatggtt gctgcaattg cagtgcttac aaaggatgct   2160
ggaaagttga ctatgggaca acctcttgtt attttggcac cacacgctgt tgaggcactt   2220
gtgaagcagc cacctgatag gtggttgtca aacgcaagaa tgacccatta tcaagctctt   2280
cttttggata ctgatagggt gcagttcggt cctgttgtgg ctttgaatcc agcaacactt   2340
ttgccacttc ctgaggaagg attgcaacac aactgccttg atattttggc tgaggcacat   2400
ggtacaagac ctgatcttac cgatcagcca ttgcctgatg ctgatcacac ttggtacaca   2460
gatggatctt cacttttgca agaaggacag aggaaggctg gtgctgcagt tactacagag   2520
actgaagtga tttgggctaa ggcacttcca gctggaacat ctgctcaaag agcagagctt   2580
attgctttga cccaggcact taagatggct gaaggaaaga agttgaacgt ttacactgat   2640
tctaggtatg ctttcgcaac agctcatatt cacggagaaa tctatagaag gagaggatgg   2700
ttgacatcag agggaaagga aattaagaac aaggatgaaa ttcttgcact tttgaaggct   2760
ctttttcttc ctaagagatt gtctattatt cattgcccag gacaccaaaa gggtcattca   2820
gcagaagcta ggggaaatag aatggctgat caggctgcaa gaaaggctgc aattactgag   2880
acacctgata cctctactct tttgatcgaa aactcttcac caagcggagg atccggagga   2940
tctggaggca gctacaagct gattctgaac ggaaagaccc tgaagggaga gaccactaca   3000
gaagcagtgg atgctgccac agctgagaag gtgttcaagc agtacgccaa cgataacgga   3060
gtggacggcg agtggaccta tgatgacgca accaagactt ttacagtgac cgaatctggc   3120
ggctcaaaaa gaaccgccga cggcagcgaa ttcgagccca agaagaagag gaaagtcgga   3180
agcggagcta ctaacttcag cctgctgaag caggctggag acgtggagga gaaccctgga   3240
cctatggtga gcaagggcga ggagctgttc accggggtgg tgcccatcct ggtcgagctg   3300
gacggcgacg taaacggcca caagttcagc gtgtccggcg agggcgaggg cgatgccacc   3360
tacggcaagc tgaccctgaa gttcatctgc accaccggca agctgcccgt gccctggccc   3420
accctcgtga ccaccctgac ctatggagtg cagtgcttca gccgctaccc cgaccacatg   3480
aagcagcacg acttcttcaa gtccgccatg cccgaaggct acgtccagga gcgcaccatc   3540
ttcttcaagg acgacggcaa ctacaagacc cgcgccgagg tgaagttcga gggcgacacc   3600
ctggtgaacc gcatcgagct gaagggcatc gacttcaagg aggacggcaa catcctgggg   3660
cacaagctgg agtacaacta caacagccac aacgtctata tcatggccga caagcagaag   3720
aacggcatca aggtgaactt caagatccgc cacaacatcg aggacggcag cgtgcagctc   3780
gccgaccact accagcagaa cacccccatc ggcgacggcc ccgtgctgct gcccgacaac   3840
cactacctga gcacccagtc cgccctgagc aaagacccca acgagaagcg cgatcacatg   3900
gtcctgctgg agttcgtgac cgccgccggg atcactctcg gcatggacga gctgtacaag   3960
tctggtggtt ctcccaagaa gaagaggaaa gtctaa                             3996
```

<210> SEQ ID NO 55
<211> LENGTH: 126
<212> TYPE: DNA
<213> ORGANISM: Artificial
<220> FEATURE:

<223> OTHER INFORMATION: pegRNA

<400> SEQUENCE: 55
ggaatccctt ctgcagcacc gttttagagc tagaaatagc aagttaaaat aaggctagtc 60
cgttatcaac ttgaaaaagt ggcaccgagt cggtgcggaa aagcgatcaa ggtgctgcag 120
aaggga 126

<210> SEQ ID NO 56
<211> LENGTH: 127
<212> TYPE: DNA
<213> ORGANISM: Artificial
<220> FEATURE:
<223> OTHER INFORMATION: pegRNA

<400> SEQUENCE: 56
ggaatccctt ctgcagcacc gttttagagc tagaaatagc aagttaaaat aaggctagtc 60
cgttatcaac ttgaaaaagt ggcaccgagt cggtgcggaa aagcgagcca ggtgctgcag 120
aagggat 127

<210> SEQ ID NO 57
<211> LENGTH: 130
<212> TYPE: DNA
<213> ORGANISM: Artificial
<220> FEATURE:
<223> OTHER INFORMATION: pegRNA

<400> SEQUENCE: 57
ggaatccctt ctgcagcacc gttttagagc tagaaatagc aagttaaaat aaggctagtc 60
cgttatcaac ttgaaaaagt ggcaccgagt cggtgcggaa aagcgatcca atcggtgctg 120
cagaagggat 130

<210> SEQ ID NO 58
<211> LENGTH: 126
<212> TYPE: DNA
<213> ORGANISM: Artificial
<220> FEATURE:
<223> OTHER INFORMATION: pegRNA

<400> SEQUENCE: 58
ggaatccctt ctgcagcacc gttttagagc tagaaatagc aagttaaaat aaggctagtc 60
cgttatcaac ttgaaaaagt ggcaccgagt cggtgcggaa aagcgatcag gtgctgcaga 120
agggat 126

<210> SEQ ID NO 59
<211> LENGTH: 125
<212> TYPE: DNA
<213> ORGANISM: Artificial
<220> FEATURE:
<223> OTHER INFORMATION: pegRNA

<400> SEQUENCE: 59
gtcatcttag tcattacctg gttttagagc tagaaatagc aagttaaaat aaggctagtc 60
cgttatcaac ttgaaaaagt ggcaccgagt cggtgcaacg aacaccgcag gtaatgacta 120
agatg 125

<210> SEQ ID NO 60
<211> LENGTH: 125
<212> TYPE: DNA
<213> ORGANISM: Artificial

<220> FEATURE:
<223> OTHER INFORMATION: pegRNA

<400> SEQUENCE: 60
gtcatcttag tcattacctg gttttagagc tagaaatagc aagttaaaat aaggctagtc 60
cgttatcaac ttgaaaaagt ggcaccgagt cggtgcaacg aacaccccag gtaatgacta 120
agatg 125

<210> SEQ ID NO 61
<211> LENGTH: 125
<212> TYPE: DNA
<213> ORGANISM: Artificial
<220> FEATURE:
<223> OTHER INFORMATION: pegRNA

<400> SEQUENCE: 61
gtcatcttag tcattacctg gttttagagc tagaaatagc aagttaaaat aaggctagtc 60
cgttatcaac ttgaaaaagt ggcaccgagt cggtgcaacg aacacatcag gtaatgacta 120
agatg 125

<210> SEQ ID NO 62
<211> LENGTH: 125
<212> TYPE: DNA
<213> ORGANISM: Artificial
<220> FEATURE:
<223> OTHER INFORMATION: pegRNA

<400> SEQUENCE: 62
gtcatcttag tcattacctg gttttagagc tagaaatagc aagttaaaat aaggctagtc 60
cgttatcaac ttgaaaaagt ggcaccgagt cggtgcaacg aacatctcag gtaatgacta 120
agatg 125

<210> SEQ ID NO 63
<211> LENGTH: 126
<212> TYPE: DNA
<213> ORGANISM: Artificial
<220> FEATURE:
<223> OTHER INFORMATION: pegRNA

<400> SEQUENCE: 63
gcattttcag gaggaagcga gttttagagc tagaaatagc aagttaaaat aaggctagtc 60
cgttatcaac ttgaaaaagt ggcaccgagt cggtgctgtc tgaagcaatc gcttcctcct 120
gaaaat 126

<210> SEQ ID NO 64
<211> LENGTH: 126
<212> TYPE: DNA
<213> ORGANISM: Artificial
<220> FEATURE:
<223> OTHER INFORMATION: pegRNA

<400> SEQUENCE: 64
gcattttcag gaggaagcga gttttagagc tagaaatagc aagttaaaat aaggctagtc 60
cgttatcaac ttgaaaaagt ggcaccgagt cggtgctgtc tgaaggcatc gcttcctcct 120
gaaaat 126

<210> SEQ ID NO 65
<211> LENGTH: 129
<212> TYPE: DNA

<213> ORGANISM: Artificial
<220> FEATURE:
<223> OTHER INFORMATION: pegRNA

<400> SEQUENCE: 65
gcattttcag gaggaagcga gttttagagc tagaaatagc aagttaaaat aaggctagtc 60
cgttatcaac ttgaaaaagt ggcaccgagt cggtgctgtc tgaagccatc catgcttcct 120
cctgaaaat 129

<210> SEQ ID NO 66
<211> LENGTH: 125
<212> TYPE: DNA
<213> ORGANISM: Artificial
<220> FEATURE:
<223> OTHER INFORMATION: pegRNA

<400> SEQUENCE: 66
gcattttcag gaggaagcga gttttagagc tagaaatagc aagttaaaat aaggctagtc 60
cgttatcaac ttgaaaaagt ggcaccgagt cggtgctgtc tgaagccatg cttcctcctg 120
aaaat 125

<210> SEQ ID NO 67
<211> LENGTH: 120
<212> TYPE: DNA
<213> ORGANISM: Artificial
<220> FEATURE:
<223> OTHER INFORMATION: pegRNA

<400> SEQUENCE: 67
gattcctggt gccagaaaca gttttagagc tagaaatagc aagttaaaat aaggctagtc 60
cgttatcaac ttgaaaaagt ggcaccgagt cggtgcgtca ccactgtttc tggcaccagg 120

<210> SEQ ID NO 68
<211> LENGTH: 120
<212> TYPE: DNA
<213> ORGANISM: Artificial
<220> FEATURE:
<223> OTHER INFORMATION: pegRNA

<400> SEQUENCE: 68
gattcctggt gccagaaaca gttttagagc tagaaatagc aagttaaaat aaggctagtc 60
cgttatcaac ttgaaaaagt ggcaccgagt cggtgcgtca cgcctgtttc tggcaccagg 120

<210> SEQ ID NO 69
<211> LENGTH: 127
<212> TYPE: DNA
<213> ORGANISM: Artificial
<220> FEATURE:
<223> OTHER INFORMATION: pegRNA

<400> SEQUENCE: 69
gattcctggt gccagaaaca gttttagagc tagaaatagc aagttaaaat aaggctagtc 60
cgttatcaac ttgaaaaagt ggcaccgagt cggtgctccc gtcacccctg tgatttctgg 120
caccagg 127

<210> SEQ ID NO 70
<211> LENGTH: 121
<212> TYPE: DNA
<213> ORGANISM: Artificial
<220> FEATURE:
<223> OTHER INFORMATION: pegRNA

<400> SEQUENCE: 70
gattcctggt gccagaaaca gttttagagc tagaaatagc aagttaaaat aaggctagtc 60
cgttatcaac ttgaaaaagt ggcaccgagt cggtgctccc gtcaccgttt ctggcaccag 120
g 121

<210> SEQ ID NO 71
<211> LENGTH: 2631
<212> TYPE: DNA
<213> ORGANISM: Artificial
<220> FEATURE:
<223> OTHER INFORMATION: MCP::MuLV(5M)

<400> SEQUENCE: 71
atgaaacgga cagccgacgg aagcgagttc gagtcaccaa agaagaagcg gaaagtcgca 60
agcaacttca ctcagtttgt gctggtggac aacggaggaa ctggagatgt gacagtggct 120
ccatccaact tcgccaatgg ggtggcagag tggatttcta gcaactctag aagccaggcc 180
tataaggtga cctgcagcgt gagacagtcc tcagcacaga agaggaagta cactatcaag 240
gtggaggtgc ccaaggtggc cacccagact gtgggtgggg tggaactgcc tgtggctgcc 300
tggaggtcat atctgaacat ggagctgacc attcccatct ttgcaactaa ttctgactgt 360
gaactgattg tgaaggctat gcagggactg ctgaaggatg gcaaccctat tccatccgcc 420
atcgcagcta attctggaat ctactctgct ggaggcggag gatctggagg cggtgggagc 480
ggaggcggtg ggtctggacc taagaagaag agaaaggtgg ccgcagctgg ctccacactt 540
aatattgagg atgaacatag attgcacgag acctctaagg aacctgatgt ttctcttgga 600
tcaacttggt tgtcagattt cccacaagca tgggcagaga ccggaggtat gggtcttgct 660
gttaggcagg caccacttat tattcctttg aaggcaacct ctactcctgt gtcaattaag 720
caatatccaa tgtctcagga agctaggctt ggaattaagc ctcacattca aagacttttg 780
gatcagggta ttttggtgcc atgtcaatca ccttggaaca caccactttt gcctgttaag 840
aagcctggaa ctaatgatta cagaccagtg caagatttga gggaggttaa caagagagtg 900
gaagatattc acccaactgt tccaaaccct tataatcttt tgtctggatt gccaccttca 960
catcaatggt acactgtgct tgatttgaag gatgcatttt tctgccttag gttgcatcca 1020
acatctcagc ctctttttgc tttcgagtgg agagatcctg aaatgggaat ttctggtcaa 1080
cttacatgga ccaggttgcc tcagggtttc aagaactcac caaccttgtt taatgaggca 1140
cttcacaggg atttggctga ttttaggatt caacatcctg atcttatcct tttgcagtat 1200
gttgatgatc ttttgcttgc tgcaacttct gaattggatt gtcaacaggg aactagggca 1260
ttgcttcaaa cacttggaaa tttgggttac agagcttcag caaagaaggc tcagatttgc 1320
caaaagcagg ttaagtatct tggatacttg cttaaggaag gacaaaggtg gttgaccgag 1380
gctagaaagg aaactgtgat gggtcaacca acacctaaga cccctaggca gcttagagag 1440
ttcttgggaa aggcaggttt ttgtaggctt ttcattccag gatttgctga aatggctgca 1500
ccactttatc ctttgaccaa gcctggaact ttgtttaact ggggtccaga tcaacagaag 1560
gcataccaag aaattaagca ggctttgctt actgctccag cacttggttt gcctgatctt 1620
acaaagccat ttgagttgtt cgttgatgaa aagcaaggat atgcaaaggg tgtgcttacc 1680
cagaagttgg gaccttggag aaggcctgtt gcttaccttt ctaagaaact tgatccagtg 1740
gctgcaggtt ggccaccttg tcttagaatg gttgctgcaa ttgcagtgct tacaaaggat 1800
gctggaaagt tgactatggg acaacctctt gttattttgg caccacacgc tgttgaggca 1860
cttgtgaagc agccacctga taggtggttg tcaaacgcaa gaatgaccca ttatcaagct 1920
cttcttttgg atactgatag ggtgcagttc ggtcctgttg tggctttgaa tccagcaaca 1980
cttttgccac ttcctgagga aggattgcaa cacaactgcc ttgatatttt ggctgaggca 2040
catggtacaa gacctgatct taccgatcag ccattgcctg atgctgatca cacttggtac 2100
acagatggat cttcactttt gcaagaagga cagaggaagg ctggtgctgc agttactaca 2160
gagactgaag tgatttgggc taaggcactt ccagctggaa catctgctca aagagcagag 2220
cttattgctt tgacccaggc acttaagatg gctgaaggaa agaagttgaa cgtttacact 2280
gattctaggt atgctttcgc aacagctcat attcacggag aaatctatag aaggagagga 2340
tggttgacat cagagggaaa ggaaattaag aacaaggatg aaattcttgc acttttgaag 2400
gctctttttc ttcctaagag attgtctatt attcattgcc caggacacca aaagggtcat 2460
tcagcagaag ctaggggaaa tagaatggct gatcaggctg caagaaaggc tgcaattact 2520
gagacacctg atacctctac tcttttgatc gaaaactctt caccatctgg cggctcaaaa 2580
agaaccgccg acggcagcga attcgagccc aagaagaaga ggaaagtcta a 2631

<210> SEQ ID NO 72
<211> LENGTH: 156
<212> TYPE: DNA
<213> ORGANISM: Artificial
<220> FEATURE:
<223> OTHER INFORMATION: FANCF gRNA with MS2 scaffold (O2 target)

<400> SEQUENCE: 72
ggaatccctt ctgcagcacc gttttagagc taggccaaca tgaggatcac ccatgtctgc 60
agggcctagc aagttaaaat aaggctagtc cgttatcaac ttggccaaca tgaggatcac 120
ccatgtctgc agggccaagt ggcaccgagt cggtgc 156

<210> SEQ ID NO 73
<211> LENGTH: 156
<212> TYPE: DNA
<213> ORGANISM: Artificial
<220> FEATURE:
<223> OTHER INFORMATION: FANCF gRNA with MS2 scaffold (O3 target)

<400> SEQUENCE: 73
ccaaggtgaa agcggaagta gttttagagc taggccaaca tgaggatcac ccatgtctgc 60
agggcctagc aagttaaaat aaggctagtc cgttatcaac ttggccaaca tgaggatcac 120
ccatgtctgc agggccaagt ggcaccgagt cggtgc 156

<210> SEQ ID NO 74
<211> LENGTH: 5040
<212> TYPE: DNA
<213> ORGANISM: Artificial
<220> FEATURE:
<223> OTHER INFORMATION: nCas9(H840A)::P2A::EGFP

<400> SEQUENCE: 74
atgaaacgga cagccgacgg aagcgagttc gagtcaccaa agaagaagcg gaaagtcgac 60
aagaagtaca gcatcggcct ggacatcggc accaactctg tgggctgggc cgtgatcacc 120
gacgagtaca aggtgcccag caagaaattc aaggtgctgg gcaacaccga ccggcacagc 180
atcaagaaga acctgatcgg agccctgctg ttcgacagcg gcgaaacagc cgaggccacc 240
cggctgaaga gaaccgccag aagaagatac accagacgga agaaccggat ctgctatctg 300

```
caagagatct tcagcaacga gatggccaag gtggacgaca gcttcttcca cagactggaa    360
gagtccttcc tggtggaaga ggataagaag cacgagcggc accccatctt cggcaacatc    420
gtggacgagg tggcctacca cgagaagtac cccaccatct accacctgag aaagaaactg    480
gtggacagca ccgacaaggc cgacctgcgg ctgatctatc tggccctggc ccacatgatc    540
aagttccggg gccacttcct gatcgagggc gacctgaacc ccgacaacag cgacgtggac    600
aagctgttca tccagctggt gcagacctac aaccagctgt tcgaggaaaa ccccatcaac    660
gccagcggcg tggacgccaa ggccatcctg tctgccagac tgagcaagag cagacggctg    720
gaaaatctga tcgcccagct gcccggcgag aagaagaatg gcctgttcgg aaacctgatt    780
gccctgagcc tgggcctgac ccccaacttc aagagcaact tcgacctggc cgaggatgcc    840
aaactgcagc tgagcaagga cacctacgac gacgacctgg acaacctgct ggcccagatc    900
ggcgaccagt acgccgacct gtttctggcc gccaagaacc tgtccgacgc catcctgctg    960
agcgacatcc tgagagtgaa caccgagatc accaaggccc ccctgagcgc ctctatgatc   1020
aagagatacg acgagcacca ccaggacctg accctgctga aagctctcgt gcggcagcag   1080
ctgcctgaga agtacaaaga gattttcttc gaccagagca agaacggcta cgccggctac   1140
attgacggcg gagccagcca ggaagagttc tacaagttca tcaagcccat cctggaaaag   1200
atggacggca ccgaggaact gctcgtgaag ctgaacagag aggacctgct gcggaagcag   1260
cggaccttcg acaacggcag catcccccac cagatccacc tgggagagct gcacgccatt   1320
ctgcggcggc aggaagattt ttacccattc ctgaaggaca accgggaaaa gatcgagaag   1380
atcctgacct tccgcatccc ctactacgtg ggccctctgg ccaggggaaa cagcagattc   1440
gcctggatga ccagaaagag cgaggaaacc atcacccccct ggaacttcga ggaagtggtg   1500
gacaagggcg cttccgccca gagcttcatc gagcggatga ccaacttcga taagaacctg   1560
cccaacgaga aggtgctgcc caagcacagc ctgctgtacg agtacttcac cgtgtataac   1620
gagctgacca aagtgaaata cgtgaccgag ggaatgagaa agcccgcctt cctgagcggc   1680
gagcagaaaa aggccatcgt ggacctgctg ttcaagacca accggaaagt gaccgtgaag   1740
cagctgaaag aggactactt caagaaaatc gagtgcttcg actccgtgga aatctccggc   1800
gtggaagatc ggttcaacgc ctccctgggc acataccacg atctgctgaa aattatcaag   1860
gacaaggact tcctggacaa tgaggaaaac gaggacattc tggaagatat cgtgctgacc   1920
ctgacactgt ttgaggacag agagatgatc gaggaacggc tgaaaaccta tgcccacctg   1980
ttcgacgaca aagtgatgaa gcagctgaag cggcggagat acaccggctg gggcaggctg   2040
agccggaagc tgatcaacgg catccgggac aagcagtccg gcaagacaat cctggatttc   2100
ctgaagtccg acggcttcgc caacagaaac ttcatgcagc tgatccacga cgacagcctg   2160
acctttaaag aggacatcca gaaagcccag gtgtccggcc agggcgatag cctgcacgag   2220
cacattgcca atctggccgg cagccccgcc attaagaagg gcatcctgca gacagtgaag   2280
gtggtggacg agctcgtgaa agtgatgggc cggcacaagc ccgagaacat cgtgatcgaa   2340
atggccagag agaaccagac cacccagaag ggacagaaga acagccgcga gagaatgaag   2400
cggatcgaag agggcatcaa agagctgggc agccagatcc tgaaagaaca ccccgtggaa   2460
aacacccagc tgcagaacga gaagctgtac ctgtactacc tgcagaatgg gcgggatatg   2520
tacgtggacc aggaactgga catcaaccgg ctgtccgact acgatgtgga cgccatcgtg   2580
cctcagagct ttctgaagga cgactccatc gacaacaagg tgctgaccag aagcgacaag   2640
```

-continued aaccggggca agagcgacaa cgtgccctcc gaagaggtcg tgaagaagat gaagaactac 2700
tggcggcagc tgctgaacgc caagctgatt acccagagaa agttcgacaa tctgaccaag 2760
gccgagagag gcggcctgag cgaactggat aaggccggct tcatcaagag acagctggtg 2820
gaaacccggc agatcacaaa gcacgtggca cagatcctgg actcccggat gaacactaag 2880
tacgacgaga atgacaagct gatccgggaa gtgaaagtga tcaccctgaa gtccaagctg 2940
gtgtccgatt tccggaagga tttccagttt tacaaagtgc gcgagatcaa caactaccac 3000
cacgcccacg acgcctacct gaacgccgtc gtgggaaccg ccctgatcaa aaagtaccct 3060
aagctggaaa gcgagttcgt gtacggcgac tacaaggtgt acgacgtgcg gaagatgatc 3120
gccaagagcg agcaggaaat cggcaaggct accgccaagt acttcttcta cagcaacatc 3180
atgaactttt tcaagaccga gattaccctg gccaacggcg agatccggaa gcggcctctg 3240
atcgagacaa acggcgaaac cggggagatc gtgtgggata agggccggga ttttgccacc 3300
gtgcggaaag tgctgagcat gccccaagtg aatatcgtga aaaagaccga ggtgcagaca 3360
ggcggcttca gcaaagagtc tatcctgccc aagaggaaca gcgataagct gatcgccaga 3420
aagaaggact gggaccctaa gaagtacggc ggcttcgaca gccccaccgt ggcctattct 3480
gtgctggtgg tggccaaagt ggaaaagggc aagtccaaga aactgaagag tgtgaaagag 3540
ctgctgggga tcaccatcat ggaaagaagc agcttcgaga agaatcccat cgactttctg 3600
gaagccaagg gctacaaaga agtgaaaaag gacctgatca tcaagctgcc taagtactcc 3660
ctgttcgagc tggaaaacgg ccggaagaga atgctggcct ctgccggcga actgcagaag 3720
ggaaacgaac tggccctgcc ctccaaatat gtgaacttcc tgtacctggc cagccactat 3780
gagaagctga agggctcccc cgaggataat gagcagaaac agctgtttgt ggaacagcac 3840
aagcactacc tggacgagat catcgagcag atcagcgagt tctccaagag agtgatcctg 3900
gccgacgcta atctggacaa agtgctgtcc gcctacaaca agcaccggga taagcccatc 3960
agagagcagg ccgagaatat catccacctg tttaccctga ccaatctggg agcccctgcc 4020
gccttcaagt actttgacac caccatcgac cggaagaggt acaccagcac caaagaggtg 4080
ctggacgcca ccctgatcca ccagagcatc accggcctgt acgagacacg gatcgacctg 4140
tctcagctgg gaggtgactc tggcggctca aaaagaaccg ccgacggcag cgaattcgag 4200
cccaagaaga agaggaaagt cggaagcgga gctactaact tcagcctgct gaagcaggct 4260
ggagacgtgg aggagaaccc tggacctatg gtgagcaagg gcgaggagct gttcaccggg 4320
gtggtgccca tcctggtcga gctggacggc gacgtaaacg gccacaagtt cagcgtgtcc 4380
ggcgagggcg agggcgatgc cacctacggc aagctgaccc tgaagttcat ctgcaccacc 4440
ggcaagctgc ccgtgccctg gcccaccctc gtgaccaccc tgacctatgg agtgcagtgc 4500
ttcagccgct accccgacca catgaagcag cacgacttct tcaagtccgc catgcccgaa 4560
ggctacgtcc aggagcgcac catcttcttc aaggacgacg gcaactacaa gacccgcgcc 4620
gaggtgaagt tcgagggcga caccctggtg aaccgcatcg agctgaaggg catcgacttc 4680
aaggaggacg gcaacatcct ggggcacaag ctggagtaca actacaacag ccacaacgtc 4740
tatatcatgg ccgacaagca gaagaacggc atcaaggtga acttcaagat ccgccacaac 4800
atcgaggacg gcagcgtgca gctcgccgac cactaccagc agaacacccc catcggcgac 4860
ggccccgtgc tgctgcccga caaccactac ctgagcaccc agtccgccct gagcaaagac 4920
cccaacgaga agcgcgatca catggtcctg ctggagttcg tgaccgccgc cgggatcact 4980
ctcggcatgg acgagctgta caagtctggt ggttctccca agaagaagag gaaagtctaa 5040

<210> SEQ ID NO 75
<211> LENGTH: 155
<212> TYPE: DNA
<213> ORGANISM: Artificial
<220> FEATURE:
<223> OTHER INFORMATION: FANCF pegRNA (O2 Target)

<400> SEQUENCE: 75
ggggtcccag gtgctgacgt gttttagagc tagaaatagc aagttaaaat aaggctagtc 60
cgttatcaac ttgaaaaagt ggcaccgagt cggtgcaggt agtgtccgag accgccgtga 120
gctcggaaaa gcgattgcgg tgctgcagaa gggat 155

<210> SEQ ID NO 76
<211> LENGTH: 193
<212> TYPE: DNA
<213> ORGANISM: Artificial
<220> FEATURE:
<223> OTHER INFORMATION: FANCF pegRNA (O3 Target)

<400> SEQUENCE: 76
ggggtcccag gtgctgacgt gttttagagc tagaaatagc aagttaaaat aaggctagtc 60
cgttatcaac ttgaaaaagt ggcaccgagt cggtgcaggt agtgcttgag accgccgtga 120
gctcggaaaa gcgattgcgg tgctgcagaa gggattccat gaggtgcgcg aaggaattac 180
ttccgctttc acc 193

<210> SEQ ID NO 77
<211> LENGTH: 82
<212> TYPE: DNA
<213> ORGANISM: Homo sapiens

<400> SEQUENCE: 77
ggaatccctt ctgcagcacc tggatcgctt ttccgagctt ctggcggtct caagcactac 60
ctacgtcagc acctgggacc cc 82

<210> SEQ ID NO 78
<211> LENGTH: 82
<212> TYPE: DNA
<213> ORGANISM: Artificial
<220> FEATURE:
<223> OTHER INFORMATION: Edit sequence for site O2

<400> SEQUENCE: 78
ggaatccctt ctgcagcacc gcaatcgctt ttccgagctc acggcggtct cggacactac 60
ctacgtcagc acctgggacc cc 82

<210> SEQ ID NO 79
<211> LENGTH: 120
<212> TYPE: DNA
<213> ORGANISM: Homo sapiens

<400> SEQUENCE: 79
ccaaggtgaa agcggaagta gggccttcgc gcacctcatg gaatcccttc tgcagcacct 60
ggatcgcttt tccgagcttc tggcggtctc aagcactacc tacgtcagca cctgggaccc 120

<210> SEQ ID NO 80
<211> LENGTH: 120
<212> TYPE: DNA
<213> ORGANISM: Artificial
<220> FEATURE:

<223> OTHER INFORMATION: Edit sequence for site O3

<400> SEQUENCE: 80
ccaaggtgaa agcggaagta attccttcgc gcacctcatg gaatcccttc tgcagcaccg 60
caatcgcttt tccgagctca cggcggtctc aagcactacc tacgtcagca cctgggaccc 120

<210> SEQ ID NO 81
<211> LENGTH: 53
<212> TYPE: DNA
<213> ORGANISM: Homo sapiens

<400> SEQUENCE: 81
cagcacctgg atcgcttttc cgagcttctg gcggtctcaa gcactaccta cgt 53

<210> SEQ ID NO 82
<211> LENGTH: 53
<212> TYPE: DNA
<213> ORGANISM: Artificial
<220> FEATURE:
<223> OTHER INFORMATION: Bottom line of Fig. 14

<400> SEQUENCE: 82
cagcaccgca atcgcttttc cgagctcacg gcggtctcgg acactaccta cgt 53

<210> SEQ ID NO 83
<211> LENGTH: 61
<212> TYPE: DNA
<213> ORGANISM: Homo sapiens

<400> SEQUENCE: 83
gggccttcgc gcacctcatg gaatcccttc tgcagcacct ggatcgcttt tccgagcttc 60
t 61

<210> SEQ ID NO 84
<211> LENGTH: 61
<212> TYPE: DNA
<213> ORGANISM: Homo sapiens

<400> SEQUENCE: 84
gggccttcgc gcacctcatg gaatcccttc tgcagcacct ggatcgcttt tccgagcttc 60
t 61

<210> SEQ ID NO 85
<211> LENGTH: 61
<212> TYPE: DNA
<213> ORGANISM: Artificial
<220> FEATURE:
<223> OTHER INFORMATION: Bottom line of Fig. 15

<400> SEQUENCE: 85
attccttcgc gcacctcatg gaatcccttc tgcagcaccg caatcgcttt tccgagctca 60
c 61

<210> SEQ ID NO 86
<211> LENGTH: 2031
<212> TYPE: DNA
<213> ORGANISM: Artificial
<220> FEATURE:
<223> OTHER INFORMATION: MMLV_MO1

<400> SEQUENCE: 86
accctgaaca tcgaggacga gtatcggctt catgagacca gcaaagagcc ggacgtctcc 60

```
ctgggaagca cctggctgag cgacttcccg caagcctggg cggagaccgg tggtatgggg    120
ctcgcagtgc ggcaagcgcc gttgataatc ccgctaaagg ccacgagcac gcccgtgtct    180
atcaagcagt acccgatgag tcaagaggca cgcctcggta tcaagccgca tatccagcgc    240
ctcctggacc agggcatcct cgtgccctgc cagtctccct ggaatacgcc tctgctaccc    300
gtcaagaagc ctggcaccaa cgattacagg ccggtgcaag acctgcgtga ggtcaacaag    360
cgcgtggagg acatccaccc aacggtgccc aacccgtaca atctcctatc tggccttccg    420
ccctcgcacc agtggtacac ggtcttggac ctaaaggacg cattcttctg tctgaggctg    480
caccctacgt cccagccgct gttcgccttc gagtggcgcg acccggagat gggcatctct    540
ggccagctaa cttggacgcg attgccccag gggtttaaga actcgcccac actcttcaac    600
gaggcactcc accgtgacct ggccgacttt cgcatacagc accccgacct tatcctgttg    660
cagtacgtcg atgacctgct cctggcggcc acgtccgagc tggactgcca gcaaggcacc    720
cgcgccctac ttcaaaccct gggcaacctg ggttaccgtg cgtccgccaa gaaggcccaa    780
atctgccaaa agcaagtcaa gtacctcggc tacctcttga aggagggaca gcgctggctg    840
acggaggcga ggaaggagac ggtgatgggt cagcccacac ccaagacccc gaggcagcta    900
agggagttcc tggggaaggc gggcttctgc cgtctattca tccctggctt cgcggagatg    960
gcggcccccgc tgtacccgct aacgaagccg ggcacgctgt tcaactgggg ccctgaccag   1020
cagaaggcgt accaggagat caagcaagcg ttgcttactg ccccagcact cggcctcccc   1080
gacctcacaa agccgttcga gctattcgtt gacgagaaac agggctacgc gaagggtgtg   1140
ctgactcaaa agctagggcc gtggcgacgc ccagtagcct acctgagcaa gaagctcgac   1200
cccgtggcgg cgggctggcc accatgcctc cggatggtcg cggctatcgc ggtgctcaca   1260
aaggatgcgg ggaagctcac gatggggcag cccctggtga tcctggcccc acacgcggtg   1320
gaggcgttag tgaagcaacc tcccgaccga tggctgagca acgcccgcat gacccactac   1380
caggcgctcc tcctcgacac cgaccgcgtg caattcggcc ctgtcgtggc actgaacccg   1440
gccacgctgc tcccactgcc cgaggagggg ctacagcaca actgcctcga tatactggcg   1500
gaagcccacg gcacccgccc cgacttgacg gaccagccgc ttcccgacgc ggaccatacg   1560
tggtacaccg acgggagttc cttactccaa gagggccagc gaaaggcggg cgctgcggtg   1620
accactgaga cggaagtaat ctgggcaaag gcgctgcctg cgggcacgtc tgcccagcgg   1680
gcggagctga tcgccctgac ccaggccctc aagatggccg agggcaagaa gctgaacgtt   1740
tacaccgaca gtcggtatgc cttcgcaact gcccacatcc acggcgaaat ctaccgtcgg   1800
cgcggctggc tgacgagcga gggcaaggag atcaagaaca aggacgagat cctcgccctg   1860
ctaaaggcac tcttcctgcc caagcgactg tccatcattc actgtccggg gcaccagaag   1920
ggccattccg ccgaggcgcg gggcaaccgc atggcggatc aggccgctcg gaaggcggcg   1980
atcaccgaga cgcccgatac gagcacgctc ctgattgaaa actcgtcgcc g             2031
```

<210> SEQ ID NO 87
<211> LENGTH: 2031
<212> TYPE: DNA
<213> ORGANISM: Artificial
<220> FEATURE:
<223> OTHER INFORMATION: MMLV_MO2

<400> SEQUENCE: 87

```
accctgaaca ttgaggacga gtatcgcctg cacgagacca gcaaggagcc cgacgtgagc     60
```

ctcggctcaa cgtggctcag tgacttccca caagcctggg ccgagactgg tggaatgggg 120
ctggccgtgc gccaagctcc cctcatcatt cctctcaagg ccacttcgac gcctgtctcc 180
atcaagcagt accccatgtc ccaggaggct aggctgggca tcaagccgca catccaacgc 240
ctgttagatc aaggaatact ggtcccctgc cagtcgccgt ggaatactcc gctactgcct 300
gtcaagaagc cgggcacgaa cgactaccgg cctgtccaag acctgcgcga ggtgaacaag 360
cgggtcgagg acattcaccc caccgttccc aacccttaca acctattgtc tggcctccca 420
ccgagccatc agtggtacac cgtcctggac ctcaaggatg cgttcttctg tctgcggcta 480
caccctacgt cgcaaccact cttcgccttc gagtggcggg atccggagat ggggatctcg 540
gggcagctca cgtggactcg gctgcctcag gggttcaaga actccccaac actctttaac 600
gaggcactgc atcgggatct ggccgacttc cgtatccagc acccagacct catcctccta 660
cagtacgtgg acgacttgct gctggccgcg accagcgagc tggactgcca gcaagggaca 720
cgcgcgctgc tccagacgct cgggaacctg ggataccgcg ccagcgctaa gaaggctcaa 780
atctgtcaga aacaagtgaa gtacctgggt tacctgctca aggagggtca gcgttggctt 840
accgaggccc gcaaggagac cgtgatgggg caacccacgc caaagacgcc ccgacagcta 900
cgcgagttcc tgggcaaggc tgggttctgt cggttgttca tccccggttt cgctgagatg 960
gccgcccctc tctacccgct gacgaaacct gggactctgt tcaactgggg ccctgaccag 1020
cagaaggcgt accaggagat caagcaagcg ctgcttaccg ccccggcgct cggattgccg 1080
gaccttacca agcccttcga gctgttcgtg gacgagaagc aaggttacgc gaagggcgtc 1140
ctgacacaaa agttggggcc ctggcgtagg ccggtcgcct acctcagcaa gaagttggac 1200
cccgtggcgg cgggctggcc gccgtgcctc cgtatggtgg cagccatcgc cgttctcacc 1260
aaagacgctg gcaagctcac gatggggcag cctctggtga tcctggcacc ccatgccgtc 1320
gaggcgctcg tgaagcagcc gcctgaccgc tggctgagta acgcacggat gacccattac 1380
caagccctat tgctagacac ggatcgcgtc caatttgggc ccgtggtggc tctgaaccct 1440
gccactctcc ttcccctccc tgaggagggc ttgcagcata actgcctgga catactggct 1500
gaggcccacg ggacaaggcc ggacctaacg gaccagcctc taccggacgc ggatcacaca 1560
tggtacaccg acggctcctc tctcctacaa gaggggcagc ggaaggcggg tgccgccgtc 1620
accacggaga cggaggtgat ctgggctaag gcactgcccg ccgggacttc ggcacagcga 1680
gccgagctaa tagccctcac acaagcgctg aaaatggccg agggcaagaa gctaaacgtc 1740
tatacggact cccgatacgc tttcgccacc gcccacattc atggcgaaat ctaccgccgc 1800
cgtggctggc tgacgtccga gggcaaggag atcaagaaca aggacgagat cctcgccctc 1860
ctgaaagccc tgttcctgcc gaaaaggctt tcgataatcc actgccccgg ccaccagaag 1920
gggcactccg ccgaggcacg cggcaaccgt atggccgacc aggccgcccg gaaggcggcg 1980
atcacggaaa ccccggacac atccacgctc ctcatcgaga acagcagccc c 2031

<210> SEQ ID NO 88
<211> LENGTH: 2031
<212> TYPE: DNA
<213> ORGANISM: Artificial
<220> FEATURE:
<223> OTHER INFORMATION: MMLV_MO3

<400> SEQUENCE: 88
accctcaaca tcgaggacga gtaccgtctg cacgagacgt cgaaggagcc ggatgtctca 60
ctcggctcca cgtggctcag cgacttccca caggcgtggg cggagaccgg tggcatggga 120

-continued

```
ctggcggtgc gacaagcgcc ccttatcatt cccctaaagg cgacgtcaac tcctgtttcc    180

attaagcagt accctatgtc ccaggaggcc cggctcggca tcaagccaca catccaacgg    240

ctattggacc agggtatctt ggtgccgtgc caatccccgt ggaacactcc ccttctaccc    300

gtcaagaagc caggcaccaa cgactaccgc cccgtgcaag acctgcgcga ggtcaacaag    360

cgagtggagg acatccatcc taccgtcccg aacccgtaca acctgctttc cggcctcccg    420

ccctcgcacc agtggtacac cgttctcgac ttgaaggacg cattcttctg tctgcgcctc    480

cacccaacga gccagcccct cttcgctttc gagtggcgcg acccggagat gggaatttcg    540

ggccagctta catggacccg cctcccacag gggttcaaga acagcccgac gctgttcaac    600

gaggccctgc accgcgactt ggcagacttc cgaatccagc atcccgacct aatcctcctg    660

caatacgttg acgacttatt gctggccgcg accagcgagc ttgactgcca gcaagggact    720

cgcgcgcttc tacagacgct cgggaacctg ggctaccgtg cctcagctaa gaaggcccag    780

atttgccaga agcaagttaa gtatctcggc tacctcctca aggagggaca gcggtggctg    840

acggaggccc gcaaggagac ggtcatgggc cagccaacac cgaaaacgcc cagacaactc    900

cgcgagttcc tcggcaaagc gggcttctgt cggctgttta tccccggctt cgccgagatg    960

gccgcgcccc tctacccact gacgaaaccc ggcaccctgt tcaactgggg cccggatcag   1020

cagaaggcgt atcaggagat caagcaagca ctcctgacag ccccggccct gggattgccc   1080

gaccttacga agcccttcga gttattcgtg gacgagaagc aaggctatgc gaagggtgtc   1140

ctcacgcaga agctggggcc ctggaggcgg cccgtcgcgt acctaagcaa gaagctcgac   1200

ccagtggcgg cgggttggcc gccctgcctc cgcatggtgg ccgcgattgc ggttctcaca   1260

aaggacgccg ggaagctcac gatggggcag ccacttgtca tcctcgctcc gcacgccgtg   1320

gaggcactgg tgaagcagcc gccggatcgc tggctgtcta atgctcgcat gacccactat   1380

caggcgctgc tcctagacac tgacagggtt cagttcggcc ccgttgtcgc gcttaacccc   1440

gctacactac tcccgctgcc ggaggagggt ttgcagcata actgcctcga catcctcgcc   1500

gaggcccacg gcacgcgacc cgacctaacg gaccagccgc tgccggacgc tgaccacact   1560

tggtacaccg acggcagctc cctcctgcaa gagggacagc ggaaggccgg tgccgccgtg   1620

acgacggaga cggaggtgat atgggctaag gccctgcccg ctggtacgtc cgcccagcga   1680

gccgagctga tcgccctgac gcaagccctc aagatggccg agggcaagaa gctaaacgtc   1740

tatacggaca gccgctacgc attcgccaca gcccacattc acggagagat ataccggagg   1800

cgcggctggc ttacgtccga aggcaaggag attaagaaca aagatgagat tctggcgctg   1860

ttgaaggccc tcttcctccc caagcggctt tccatcatac actgtccagg ccaccagaag   1920

ggccactcgg cggaggcgcg gggcaaccgg atggccgacc aggcggcgcg caaagccgcg   1980

atcacggaga ccccagacac ttccacgctc ctgatcgaga acagtagccc c            2031
```

<210> SEQ ID NO 89
<211> LENGTH: 2031
<212> TYPE: DNA
<213> ORGANISM: Artificial
<220> FEATURE:
<223> OTHER INFORMATION: MMLV_DO1

<400> SEQUENCE: 89

```
actttgaata tcgaagatga gtaccggcta catgagacgt ctaaggagcc tgatgtttca     60

ctcgggagca cttggctaag cgatttccca caagcgtggg ctgaaacggg cgggatgggc    120
```

-continued

```
ctcgctgtaa gacaagcgcc acttatcatc ccgcttaaag ctacttctac tcccgtctct    180

attaagcaat acccaatgtc ccaggaagct cgtttgggca ttaagcctca tatacaaagg    240

ctactcgatc agggcatact tgttccctgc caatcaccgt ggaatacgcc cctattacca    300

gttaagaagc ctgggactaa cgactatcgc cccgtacagg atctacgtga ggtgaacaag    360

cgtgtagagg acatccatcc gaccgttccg aatccataca atttgctttc tggattacct    420

ccaagtcatc aatggtacac cgtgctggat ctcaaggacg cattcttctg tctaagatta    480

catcctacta gccagccact tttcgcattc gagtggcgag atcccgagat gggaatttcg    540

ggccagctta catggacgag gcttcctcaa ggcttcaaga actctcctac cttgttcaat    600

gaggctctac accgcgacct cgcagacttc cggatacaac atccggacct catactccta    660

caatatgtgg acgatctatt gctggccgcg acgagcgaat tggattgtca gcaaggaacc    720

cgcgccttgt tacaaacgtt ggggaacttg ggtatcgag catcagccaa gaaggcacaa    780

atctgccaga aacaagtgaa gtatttgggg tacttactga aagaggggca acgatggttg    840

accgaagctc gcaaggaaac tgttatgggc cagccgacac ctaagactcc aagacagctc    900

cgagagttcc tcggcaaggc tgggttctgt cgcctattca ttcctgggtt tgccgaaatg    960

gctgctcctc tgtacccgtt gaccaaaccg ggaaccttgt tcaattgggg accagatcaa   1020

cagaaggcgt atcaggagat caagcaagcg ctgttgactg cgcctgcgtt gggcttgccg   1080

gatttgacaa aaccctttga acttttcgtt gacgagaaac aaggttacgc gaagggagtt   1140

cttacacaaa agctgggccc ctggagacga cctgttgctt atcttagcaa gaagttagat   1200

cccgttgctg cggggtggcc gccctgcttg aggatggttg ccgccattgc ggttctgact   1260

aaagatgcgg gcaaattgac gatgggccag ccgctcgtaa ttctcgcccc gcacgcagtc   1320

gaagccctag tgaagcagcc tcctgaccgt tggctctcca acgctcggat gacccactat   1380

caagcgctgc tgttggatac cgatagagtt caattcgggc cggtcgtagc gctcaatccc   1440

gcaacgctat taccccctgcc tgaggaggga ctacaacata actgcttgga tattctagcg   1500

gaggctcatg ggacaagacc tgacttgaca gatcagccct tgccagatgc cgaccacaca   1560

tggtacactg acggctcatc acttctacaa gagggccaaa ggaaggccgg agctgcggtg   1620

acgactgaaa ccgaggtgat ctgggcaaag gctttacccg ctggaacttc tgctcagcgc   1680

gcagagctta tcgccctaac tcaagccctg aaaatggctg agggcaagaa gttgaatgtc   1740

tataccgatt cacggtatgc tttcgctacc gcccacattc atggagaaat ctatcggcga   1800

cgaggttggc tcacgtctga ggggaaggag attaagaaca aggacgaaat cttagctctg   1860

ctgaaagctc tattcttacc caaacgcttg tcgattatcc actgcccagg acaccaaaag   1920

ggccattccg ccgaagccag gggaaaccgt atggccgatc aagctgcccg gaaggctgca   1980

ataaccgaaa cccctgacac ttccacgcta ctcatcgaaa actctagccc a            2031


<210> SEQ ID NO 90
<211> LENGTH: 2031
<212> TYPE: DNA
<213> ORGANISM: Artificial
<220> FEATURE:
<223> OTHER INFORMATION: MMLV_DO2

<400> SEQUENCE: 90

accttgaata tcgaagatga gtacagactc catgagacca gcaaggagcc tgatgtgagc     60

ctgggaagta catggctatc tgactttcct caggcttggg cggagaccgg tggcatgggc    120

ctggctgtcc ggcaagcacc cctaatcatc ccgttgaaag caacgtccac acccgtatct    180
```

atcaagcagt acccgatgag ccaagaggca cggctaggga ttaagccgca catccaaaga 240
ttgttagacc aggggatact cgttccctgt caatctccgt ggaacacacc gttactgcct 300
gttaagaagc ccggcacaaa tgattatcgg cctgtacaag acctgcgcga agtgaacaaa 360
cgagtggaag atattcaccc caccgtgccg aatccttaca acttgctaag cggtttacca 420
cccagtcacc agtggtacac cgtcttggac ctcaaagacg cattcttctg cttgcggttg 480
catcctacga gtcagccgct ctttgccttt gaatggagag atcccgagat gggcataagt 540
ggtcagctta catggacgag gctacctcag ggattcaaga actcgcctac cttattcaat 600
gaggctctac acagggatct tgctgacttt cggatacaac accctgactt aattctgcta 660
caatatgttg acgatctgct gcttgcggcg accagtgaac tcgactgcca acaagggaca 720
agagccttgt tacagacact tggcaatctc ggctaccgcg cgtctgctaa gaaggcacag 780
atttgccaaa agcaagtgaa gtatctcggt tacctgctga aagagggaca aagatggttg 840
accgaagcca ggaaggaaac tgtcatgggg caacccaccc ctaaaacccc aagacagctt 900
agagagttcc tcgggaaagc tgggttctgc cgcctgttca ttcccggttt cgctgaaatg 960
gctgcacctc tatacccact gaccaaaccg ggcacgctat tcaattgggg accggatcaa 1020
caaaaggctt accaggagat caagcaagct ctattgacag ctccggctct gggtttaccc 1080
gacttgacta aacccttcga gttgttcgtt gacgagaaac agggctacgc gaaaggcgta 1140
ctgacgcaga aactgggccc gtggcggcga cccgttgctt acctttccaa gaagctggac 1200
cctgttgccg ctggctggcc gccctgcctt cgcatggttg cggccattgc tgtccttacg 1260
aaagatgctg ggaaactaac tatgggtcag ccgctcgtaa ttctcgcgcc acacgctgtc 1320
gaggctctag tcaaacaacc tcctgaccgc tggctgtcga atgcacggat gacacattac 1380
caggcgttgc tattggacac tgaccgagta caatttggac cagtagtggc tttaaatccc 1440
gcgacactcc ttccccttcc tgaggagggt ttgcaacaca actgtcttga tatacttgct 1500
gaggcccacg gaacaagacc cgatctcaca gatcaacccc tccccgacgc agatcacacc 1560
tggtacaccg acggttcaag cctgttacag gaaggccagc gaaaggccgg agcagccgtg 1620
acaaccgaaa ccgaagttat ctgggcaaag gccctaccag ccgggacaag cgcgcagagg 1680
gccgagctga tcgcgctcac acaagcactc aaaatggccg aaggcaagaa gctcaatgtt 1740
tacactgatt cccgctacgc attcgctacc gctcatattc acggagaaat ctacaggagg 1800
cgagggtggc ttactagcga aggaaaggag attaagaaca aagacgagat cctggcacta 1860
ttgaaagcct tgttcctgcc aaagcgctta tctatcattc actgtccggg ccaccagaag 1920
ggccacagtg ctgaggctcg gggcaatcgg atggcagatc aggccgcacg aaaagccgca 1980
attactgaga cacctgacac atctaccttg ctgattgaga actcgtctcc g 2031

<210> SEQ ID NO 91
<211> LENGTH: 2073
<212> TYPE: DNA
<213> ORGANISM: Soybean chlorotic mottle virus

<400> SEQUENCE: 91
aatactgaaa ttgtccaaaa acaccgagtt ttaaccaaag gtaaccctaa tgttactttc 60
ataaaagtta gtataggcaa aagaaatttc ttggcttata ttgatactgg agcaactctg 120
tgctttggaa aaagaaaaat ttcaaataat tgggaaattt taaaacaacc aaaagaaatt 180
atcattgcag ataaatcaaa acactatatt agagaagcta tttctaatgt gtttttaaaa 240

```
atcgaaaata aagaattctt aatccctatc atatatttac atgattcagg attagattta    300

attataggaa acaatttcct aaaattatac caacctttta ttcagagatt ggaaacaatt    360

gaattaagat ggaaaaatct taataaccca aaagaatctc aaatgatttc aaccaagatt    420

cttacaaaaa atgaagtatt aaaactttca tttgaaaaaa ttcatatttg tttagaaaaa    480

tatttatttt tcaaaacaat tgaagaacaa ctcgaagaag tatgttcaga acatccactg    540

gatgaaacaa aaaataaaaa tggtctttta atagaaataa gacttaaaga cccattacaa    600

gaaataaatg tcacaaatag aattccatat acaataagag atgtacaaga attcaaggag    660

gaatgtgaag acctcttaaa aaagggctta attcgagaat ctcaaagtcc acacagtgca    720

ccggcattct atgtcgaaaa tcacaatgaa atcaagcgtg gaaaaagacg catggtaatt    780

aattacaaaa aaatgaatga agccacaatt ggcgattcat ataagttacc aagaaaagat    840

tttattctgg aaaaaataaa aggatcttta tggttttcaa gcttggatgc taaatctgga    900

tactaccagc taaggctcca tgaaaataca aagcctctaa cagcttttc atgtccacct     960

cagaaacatt acgaatggaa tgttttaagt tttggactta aacaagcacc atctatatat   1020

caaagattta tggatcaatc cctcaaggga cttgaacata tatgtttggc atatattgat   1080

gacatcctga tctttacaaa aggatctaaa gaacaacatg taaatgatgt tcggattgtt   1140

ttgcaaagaa tcaaagaaaa aggaattatt atttctaaga aaaaatcaaa actgattcaa   1200

caggaaatcg aatatctcgg tttaaaaata caagggaatg gagaaattga tttatcacct   1260

catacccaag aaaaaattct tcaatttcct gatgaattag aagatagaaa acaaatacag   1320

cgttttcttg gctgtattaa ttacattgca aatgaaggat tttcaaaaa tcttgctcta    1380

gaaagaaagc accttcaaaa gaaaatttct gttaaaaacc cctggaaatg ggatacaata   1440

gatacaaaaa tggttcagtc cataaaaggc aaaattcaaa gcctaccaaa attatataat   1500

gcatcgattc aagacttttt aatagtcgag acagatgcat cgcaacactc ctggagtgga   1560

tgtttgcgag ctttacccaa gggaaagcaa aaaatcggac tcgatgaatt cgggataccg   1620

acagctgacc tctgcacagg tagcagttca gcttcaagcg ataattcgcc agctgagatt   1680

gacaaatgtc attcagccag taaacaggac actcatgtgg ccagtaaaat aaagaaactc   1740

gaaaacgagc ttctactttg caaatatgtt tcaggtacct tcacagatac ggaaacaaga   1800

taccctatag cagaactgga ggttcttgct ggagtaaaag tcctagaaaa atggagaatc   1860

gacctcctac aaacgaggtt cctcctccgc actgacagca agtactttgc aggtttttgt   1920

aggtacaaca tcaagacaga ctaccggaac ggacgtctaa tcaggtggca actacggtta   1980

caagcctatc aaccgtacgt ggaattaatc aaatcagaaa ataacccatt cgcagatacg   2040

cttacgcgag aatggagcaa gccatcaagc agt                                2073
```

<210> SEQ ID NO 92
<211> LENGTH: 2073
<212> TYPE: DNA
<213> ORGANISM: Artificial
<220> FEATURE:
<223> OTHER INFORMATION: SbCMV_DO1

<400> SEQUENCE: 92

```
aacactgaga ttgttcaaaa acatagagtg cttaccaaag gaaatccaaa tgttacattt     60

ataaaagtgt ccatagggaa gagaaatttt ttagcttata ttgacactgg agccacactc    120

tgttttggaa aaaggaaaat atcaaataac tgggaaatcc ttaagcaacc caaagaaatc    180

attatcgctg ataagtcaaa acactacatc agagaagcta taagtaacgt attcctgaaa    240
```

attgaaaaca aggagttctt gatacccatt atatatcttc atgattcagg gttggatttg 300
attattggga ataacttcct gaagctttat caaccattta ttcaaagact tgaaactatc 360
gaactcaggt ggaaaaactt gaacaatccc aaagagtctc aaatgattag cactaaaatt 420
cttacgaaaa atgaagttct taagctgagt tttgagaaga ttcatatttg tctcgaaaaa 480 tacctttct ttaaaaccat cgaggaacaa cttgaggagg tttgttctga acatccactt 540
gatgagacaa agaacaagaa tggtcttttg attgagatac gtctgaaaga tcctctgcag 600
gagattaacg tcacaaatag gattccatat accattagag atgtacagga attcaaggaa 660
gaatgtgaag atttacttaa gaagggtctc attcgtgaat cacaatctcc ccacagtgca 720
cccgcatttt acgttgaaaa tcataatgaa attaagagag gcaagcgtag aatggttatc 780
aactacaaga agatgaatga agcaaccata ggagatagct acaaactccc gcgaaaggat 840
tttatcttag agaagataaa gggcagtttg tggttttcaa gtttagatgc aaaatcaggt 900
tattatcagc ttcgcttaca tgagaacaca aagcctctca ctgctttctc ttgccctcct 960
caaaaacatt atgaatggaa tgtgttgagt ttcggtctaa aacaggcacc ttcgatttac 1020
cagcgcttca tggaccagtc cttaaaggga ttagagcaca tttgcttggc atatatagat 1080
gatatcttaa tctttactaa aggctcaaag gaacagcatg tcaatgatgt tcggattgtc 1140
ctgcaaagaa taaaagagaa aggaatcata atatctaaaa aaaaatcaaa attgattcag 1200
caagagattg aatatctagg attgaaaatt caaggtaatg gtgaaattga cctctcacca 1260
catactcaag aaaagatcct acagttccct gatgaactgg aggatagaaa acaaatacag 1320
aggtttctag gttgcattaa ttacattgcg aacgaaggat tttcaaaaa tcttgcccta 1380 gagagaaagc acttgcagaa gaagatttcc gtgaagaatc catggaagtg ggatacaata 1440
gacacaaaaa tggtgcaatc aatcaagggc aaaattcaat ccctgccgaa gctctacaat 1500
gcaagtattc aggatttcct aattgtagag actgacgcct cgcaacattc ttggtctggg 1560
tgtttgcggg ctcttccaaa gggcaagcag aaaatcggtc tggacgaatt tgggattcca 1620
acggcagatt tatgtactgg tagctccagt gcttcctctg ataattctcc tgctgagatc 1680
gacaagtgcc actcagcctc gaagcaggat acacacgtcg cctctaaaat aaagaaactt 1740
gagaatgagt tacttttgtg caagtatgtt tcagggactt tcacggacac cgagactagg 1800
tatcctatag ctgaactcga ggtgttggcg ggtgttaaag ttttggaaaa atggaggata 1860
gacttgttgc aaacacgatt tctacttagg acagattcca aatattttgc tggattttgt 1920
agatacaaca ttaagactga ttatcggaac gggaggctca taagatggca attgcgcctt 1980
caagcttacc agccttatgt ggaactgatc aagagtgaaa ataatccttt tgcagacacc 2040
ctaacacgag agtggagcaa accatcttct agc 2073

<210> SEQ ID NO 93
<211> LENGTH: 2034
<212> TYPE: DNA
<213> ORGANISM: Cauliflower mosaic virus

<400> SEQUENCE: 93
gatcatctac ttctgaagac tcagactcag actgagcagg tgatgaacgt caccaatccc 60
aattcgatct acatcaaggg aagactctac ttcaagggat acaagaagat agaacttcac 120
tgtttcgtag acacgggagc aagcctatgc atagcatcca agttcgtcat accagaagaa 180
cattgggtca atgcagaaag accaattatg gtcaaaatag cagatggaag ctcaatcacc 240
atcagcaaag tctgcaaaga catagacttg atcatagccg gcgagatatt cagaattccc 300
accgtctatc agcaagaaag tggcatcgat ttcattatcg gcaacaactt ctgtcagctg 360
tatgaaccat tcatacagtt tacggataga gttatcttca caaagaacaa gtcttatcct 420
gttcatattg cgaagctaac cagagcagtg cgagtaggca ccgaaggatt tcttgaatca 480
atgaagaaac gttcaaaaac tcaacaacca gagccagtga acatttctac aaacaagata 540
gaaaatccac tagaagaaat tgctattctt tcagagggga ggaggttatc agaagaaaaa 600
ctctttatca ctcaacaaag aatgcaaaaa atcgaagaac tacttgagaa agtatgttca 660
gaaaatccat tagatcctaa caagactaag caatggatga aagcttctat caagctcagc 720
gacccaagca aagctatcaa ggttaaaccc atgaagtata gcccaatgga tcgcgaagaa 780
tttgacaagc aaatcaaaga attactggac ctaaaagtca tcaagcccag taaaagccct 840
cacatggcac cagccttctt ggtcaacaat gaagccgaga agcgaagagg aaagaaacgt 900
atggtagtca actacaaagc tatgaacaaa gctactgtag gagatgccta caatcttccc 960
aacaaagacg agttacttac actcattcga ggaaagaaga tcttctcttc cttcgactgt 1020
aagtcaggat tctggcaagt tctgctagat caagaatcaa gacctctaac ggcattcaca 1080
tgtccacaag gtcactacga atggaatgtg gtccctttcg gcttaaagca agctccatcc 1140
atattccaaa gacacatgga cgaagcattt cgtgtgttca gaaagttctg ttgcgtttat 1200
gtcgacgaca ttctcgtatt cagtaacaac gaagaagatc atctacttca cgtagcaatg 1260
atcttacaaa agtgtaatca acatggaatt atcctttcca agaagaaagc acaactcttc 1320
aagaagaaga taaacttcct tggtctagaa atagatgaag gaacacataa gcctcaagga 1380
catatcttgg aacacatcaa caagttcccc gatacccttg aagacaagaa gcaacttcag 1440
agattcttag gcatactaac atatgcctcg gattacatcc cgaagctagc tcaaatcaga 1500
aagcctctgc aagccaagct taaagaaaac gttccatgga gatggacaaa agaggatacc 1560
ctctacatgc aaaaggtgaa gaaaaatctg caaggatttc ctccactaca tcatccctta 1620
ccagaggaga agctgatcat cgagaccgat gcatcagacg actactgggg aggtatgtta 1680
aaagctatca aaattaacga aggtactaat actgagttaa tttgcagata cgcatctgga 1740
agctttaaag ctgcagaaaa gaattaccac agcaatgaca aagagacatt ggcggtaata 1800
aatactataa agaaatttag tatttatcta actcctgttc attttctgat taggacagat 1860
aatactcatt tcaagagttt cgttaatctc aattacaaag gagattcgaa acttggaaga 1920
aacatcagat ggcaagcatg gcttagccac tattcatttg atgttgaaca cattaaagga 1980
accgacaacc actttgcgga cttcctttca agagaattca ataaggttaa ttcc 2034

<210> SEQ ID NO 94
<211> LENGTH: 2034
<212> TYPE: DNA
<213> ORGANISM: Artificial
<220> FEATURE:
<223> OTHER INFORMATION: CaMV_DO1

<400> SEQUENCE: 94
gatcaccttc tgcttaagac acagacacaa actgaacaag ttatgaatgt gaccaacccg 60
aattccattt acattaaggg acgactctac tttaaggggt ataagaaaat agaattacat 120
tgtttcgtcg acactggagc atctctctgc atagcgtcca agtttgttat tcctgaggaa 180
cattgggtaa atgcagaaag gccgattatg gttaaaattg cagatggtag cagcatcaca 240
atctcaaaag tttgcaagga cattgacttg atcattgctg gtgagatttt cagaattcct 300
acagtgtatc aacaagaatc cggcattgat tttataattg gtaataactt ttgtcaactt 360
tatgagccct tcatacaatt tacagatcga gtcattttta ctaaaaacaa gagttaccct 420
gttcacattg caaaactcac tcgtgccgtg agagttggaa cggaaggatt tctagaatct 480
atgaagaaga gatcgaaaac tcagcaacca gaacccgtta atatttctac aaataagatt 540
gaaaatccat tagaggaaat agccatcttg tccgaaggcc ggcggttgag tgaagaaaag 600
ttgtttatca cgcagcagag aatgcaaaaa atagaggagc ttctcgaaaa ggtttgttct 660
gagaatcctt tggatccaaa taaaacaaaa caatggatga aagctagtat aaagctttca 720
gacccatcaa aggcaattaa ggtgaagcca atgaaatata gccccatgga tagggaggag 780
tttgacaagc aaattaagga gctactcgat ctgaaagtaa taaaaccttc taaatcgcct 840
cacatggctc cagcattcct ggttaacaac gaggctgaaa agcgcagagg aaaaaaaaga 900
atggtggtga actacaaagc aatgaataag gctactgttg gagatgctta taatcttcct 960
aataaagatg agctcttgac cttaattaga gggaagaaaa ttttctcctc atttgattgt 1020
aaatcaggat tttggcaagt gttgctggat caagagtctc gtccactgac cgcctttacg 1080
tgccctcaag gacattatga atggaatgtc gtaccatttg gtctcaagca agcaccttct 1140
attttccaga ggcatatgga tgaagcattt agagtgttta ggaaattctg ctgtgtttat 1200
gtggatgata tattggtatt ctcaaataat gaggaagacc atttgctgca tgttgccatg 1260
attcttcaga agtgcaatca acatggaatc atcttatcca agaagaaggc tcagttgttc 1320
aagaagaaga taaatttttt gggtctcgag attgatgagg ggacacataa gcctcagggt 1380
catatactag aacatatcaa caagtttcca gacactttgg aagacaaaaa gcagttgcaa 1440
aggttccttg ggattctgac ttatgcttca gattatatac caaagcttgc tcaaataaga 1500
aaaccccttc aggcgaagct caaagaaaac gttccttgga ggtggactaa ggaggatacc 1560
ttatacatgc agaaagtcaa gaaaaacctc cagggtttcc caccgctcca ccatccttta 1620
cctgaagaaa aactaattat cgagacagat gcttctgatg actactgggg cggcatgttg 1680
aaggccatca aaatcaatga agggaccaat actgagctca tttgtcgata tgcaagcgga 1740
agttttaaag cagctgagaa aaattatcat agtaatgata aagagactct agccgttatt 1800
aacaccataa agaaattctc tatatatctt acccccgtcc actttttaat caggacagac 1860
aacactcact tcaaatcatt tgtgaacctg aattacaagg gtgatagtaa acttggccgt 1920
aacatacgct ggcaggcttg gttgagccac tactcttttg atgtagaaca cattaaagga 1980
acagataatc attttgctga tttcctttct cgcgagttca acaaagtaaa ttca 2034

<210> SEQ ID NO 95
<211> LENGTH: 117
<212> TYPE: DNA
<213> ORGANISM: Artificial
<220> FEATURE:
<223> OTHER INFORMATION: pegRNA

<400> SEQUENCE: 95
agatgaaacc aaaagaagag gttttagagc tagaaatagc aagttaaaat aaggctagtc 60
cgttatcaac ttgaaaaagt ggcaccgagt cggtgcatgg caatggttct tttggtt 117

<210> SEQ ID NO 96
<211> LENGTH: 117
<212> TYPE: DNA
<213> ORGANISM: Artificial
<220> FEATURE:

-continued

<223> OTHER INFORMATION: pegRNA

<400> SEQUENCE: 96
cacttcctat gcacaatgga gttttagagc tagaaatagc aagttaaaat aaggctagtc 60
cgttatcaac ttgaaaaagt ggcaccgagt cggtgctgag tctggcattg tgcatag 117

<210> SEQ ID NO 97
<211> LENGTH: 117
<212> TYPE: DNA
<213> ORGANISM: Artificial
<220> FEATURE:
<223> OTHER INFORMATION: pegRNA

<400> SEQUENCE: 97
ttggtagtag cgactccatg gttttagagc tagaaatagc aagttaaaat aaggctagtc 60
cgttatcaac ttgaaaaagt ggcaccgagt cggtgcttaa cttatgggag tcgctac 117

<210> SEQ ID NO 98
<211> LENGTH: 117
<212> TYPE: DNA
<213> ORGANISM: Artificial
<220> FEATURE:
<223> OTHER INFORMATION: pegRNA

<400> SEQUENCE: 98
gctcttcctg cgccattaaa gttttagagc tagaaatagc aagttaaaat aaggctagtc 60
cgttatcaac ttgaaaaagt ggcaccgagt cggtgctaag tacttaaatg gcgcagg 117

<210> SEQ ID NO 99
<211> LENGTH: 117
<212> TYPE: DNA
<213> ORGANISM: Artificial
<220> FEATURE:
<223> OTHER INFORMATION: pegRNA

<400> SEQUENCE: 99
gccgttaatt tgagagtcca gttttagagc tagaaatagc aagttaaaat aaggctagtc 60
cgttatcaac ttgaaaaagt ggcaccgagt cggtgcagct gaattaactc tcaaatt 117

<210> SEQ ID NO 100
<211> LENGTH: 117
<212> TYPE: DNA
<213> ORGANISM: Artificial
<220> FEATURE:
<223> OTHER INFORMATION: pegRNA

<400> SEQUENCE: 100
gagattgtta ttgctggtgc gttttagagc tagaaatagc aagttaaaat aaggctagtc 60
cgttatcaac ttgaaaaagt ggcaccgagt cggtgcgaaa aaatcacagc aataaca 117

<210> SEQ ID NO 101
<211> LENGTH: 117
<212> TYPE: DNA
<213> ORGANISM: Artificial
<220> FEATURE:
<223> OTHER INFORMATION: pegRNA

<400> SEQUENCE: 101
gaggcaagag atgtcctagg gttttagagc tagaaatagc aagttaaaat aaggctagtc 60
cgttatcaac ttgaaaaagt ggcaccgagt cggtgccttc acctttagga catctct 117

-continued

<210> SEQ ID NO 102
<211> LENGTH: 20
<212> TYPE: DNA
<213> ORGANISM: Artificial
<220> FEATURE:
<223> OTHER INFORMATION: spacer

<400> SEQUENCE: 102
agatgaaacc aaaagaagag 20

<210> SEQ ID NO 103
<211> LENGTH: 20
<212> TYPE: DNA
<213> ORGANISM: Artificial
<220> FEATURE:
<223> OTHER INFORMATION: spacer

<400> SEQUENCE: 103
cacttcctat gcacaatgga 20

<210> SEQ ID NO 104
<211> LENGTH: 20
<212> TYPE: DNA
<213> ORGANISM: Artificial
<220> FEATURE:
<223> OTHER INFORMATION: spacer

<400> SEQUENCE: 104
ttggtagtag cgactccatg 20

<210> SEQ ID NO 105
<211> LENGTH: 20
<212> TYPE: DNA
<213> ORGANISM: Artificial
<220> FEATURE:
<223> OTHER INFORMATION: spacer

<400> SEQUENCE: 105
gctcttcctg cgccattaaa 20

<210> SEQ ID NO 106
<211> LENGTH: 20
<212> TYPE: DNA
<213> ORGANISM: Artificial
<220> FEATURE:
<223> OTHER INFORMATION: spacer

<400> SEQUENCE: 106
gccgttaatt tgagagtcca 20

<210> SEQ ID NO 107
<211> LENGTH: 20
<212> TYPE: DNA
<213> ORGANISM: Artificial
<220> FEATURE:
<223> OTHER INFORMATION: spacer

<400> SEQUENCE: 107
gagattgtta ttgctggtgc 20

<210> SEQ ID NO 108
<211> LENGTH: 20
<212> TYPE: DNA
<213> ORGANISM: Artificial
<220> FEATURE:
<223> OTHER INFORMATION: spacer

<400> SEQUENCE: 108
gaggcaagag atgtcctagg 20

<210> SEQ ID NO 109
<211> LENGTH: 10
<212> TYPE: DNA
<213> ORGANISM: Artificial
<220> FEATURE:
<223> OTHER INFORMATION: reverse transcriptase target sequence

<400> SEQUENCE: 109
atggcaatgg 10

<210> SEQ ID NO 110
<211> LENGTH: 10
<212> TYPE: DNA
<213> ORGANISM: Artificial
<220> FEATURE:
<223> OTHER INFORMATION: reverse transcriptase target sequence

<400> SEQUENCE: 110
ttaacttatg 10

<210> SEQ ID NO 111
<211> LENGTH: 10
<212> TYPE: DNA
<213> ORGANISM: Artificial
<220> FEATURE:
<223> OTHER INFORMATION: reverse transcriptase target sequence

<400> SEQUENCE: 111
taagtactta 10

<210> SEQ ID NO 112
<211> LENGTH: 10
<212> TYPE: DNA
<213> ORGANISM: Artificial
<220> FEATURE:
<223> OTHER INFORMATION: reverse transcriptase target sequence

<400> SEQUENCE: 112
agctgaatta 10

<210> SEQ ID NO 113
<211> LENGTH: 10
<212> TYPE: DNA
<213> ORGANISM: Artificial
<220> FEATURE:
<223> OTHER INFORMATION: reverse transcriptase target sequence

<400> SEQUENCE: 113
gaaaaaatca 10

<210> SEQ ID NO 114
<211> LENGTH: 10
<212> TYPE: DNA
<213> ORGANISM: Artificial
<220> FEATURE:
<223> OTHER INFORMATION: reverse transcriptase target sequence

<400> SEQUENCE: 114
cttcaccttt 10

<210> SEQ ID NO 115
<211> LENGTH: 11

-continued

<212> TYPE: DNA
<213> ORGANISM: Artificial
<220> FEATURE:
<223> OTHER INFORMATION: primer binding site sequence

<400> SEQUENCE: 115
ttcttttggt t 11

<210> SEQ ID NO 116
<211> LENGTH: 11
<212> TYPE: DNA
<213> ORGANISM: Artificial
<220> FEATURE:
<223> OTHER INFORMATION: primer binding site sequence

<400> SEQUENCE: 116
attgtgcata g 11

<210> SEQ ID NO 117
<211> LENGTH: 11
<212> TYPE: DNA
<213> ORGANISM: Artificial
<220> FEATURE:
<223> OTHER INFORMATION: primer binding site sequence

<400> SEQUENCE: 117
ggagtcgcta c 11

<210> SEQ ID NO 118
<211> LENGTH: 11
<212> TYPE: DNA
<213> ORGANISM: Artificial
<220> FEATURE:
<223> OTHER INFORMATION: primer binding site sequence

<400> SEQUENCE: 118
aatggcgcag g 11

<210> SEQ ID NO 119
<211> LENGTH: 11
<212> TYPE: DNA
<213> ORGANISM: Artificial
<220> FEATURE:
<223> OTHER INFORMATION: primer binding site sequence

<400> SEQUENCE: 119
actctcaaat t 11

<210> SEQ ID NO 120
<211> LENGTH: 11
<212> TYPE: DNA
<213> ORGANISM: Artificial
<220> FEATURE:
<223> OTHER INFORMATION: primer binding site sequence

<400> SEQUENCE: 120
cagcaataac a 11

<210> SEQ ID NO 121
<211> LENGTH: 11
<212> TYPE: DNA
<213> ORGANISM: Artificial
<220> FEATURE:
<223> OTHER INFORMATION: primer binding site sequence

<400> SEQUENCE: 121
aggacatctc t 11

<210> SEQ ID NO 122
<211> LENGTH: 20
<212> TYPE: DNA
<213> ORGANISM: Artificial
<220> FEATURE:
<223> OTHER INFORMATION: nicking spacer sequence

<400> SEQUENCE: 122
ctggcccctc cattgtgcat 20

<210> SEQ ID NO 123
<211> LENGTH: 20
<212> TYPE: DNA
<213> ORGANISM: Artificial
<220> FEATURE:
<223> OTHER INFORMATION: nicking spacer sequence

<400> SEQUENCE: 123
taattatcat tataattctt 20

<210> SEQ ID NO 124
<211> LENGTH: 20
<212> TYPE: DNA
<213> ORGANISM: Artificial
<220> FEATURE:
<223> OTHER INFORMATION: nicking spacer sequence

<400> SEQUENCE: 124
cattcaaaac aaacctttaa 20

<210> SEQ ID NO 125
<211> LENGTH: 20
<212> TYPE: DNA
<213> ORGANISM: Artificial
<220> FEATURE:
<223> OTHER INFORMATION: nicking spacer sequence

<400> SEQUENCE: 125
tttgcataat caacgctgaa 20

<210> SEQ ID NO 126
<211> LENGTH: 20
<212> TYPE: DNA
<213> ORGANISM: Artificial
<220> FEATURE:
<223> OTHER INFORMATION: nicking spacer sequence

<400> SEQUENCE: 126
aatccttaac ttatgcccca 20

<210> SEQ ID NO 127
<211> LENGTH: 20
<212> TYPE: DNA
<213> ORGANISM: Artificial
<220> FEATURE:
<223> OTHER INFORMATION: nicking spacer sequence

<400> SEQUENCE: 127
atgaaaacta caaatataga 20

<210> SEQ ID NO 128
<211> LENGTH: 20
<212> TYPE: DNA
<213> ORGANISM: Artificial

<220> FEATURE:
<223> OTHER INFORMATION: nicking spacer sequence

<400> SEQUENCE: 128
gggaaggaca caaaagaaaa 20

<210> SEQ ID NO 129
<211> LENGTH: 76
<212> TYPE: DNA
<213> ORGANISM: Artificial
<220> FEATURE:
<223> OTHER INFORMATION: sgRNA scaffold

<400> SEQUENCE: 129
gttttagagc tagaaatagc aagttaaaat aaggctagtc cgttatcaac ttgaaaaagt 60
ggcaccgagt cggtgc 76

<210> SEQ ID NO 130
<211> LENGTH: 96
<212> TYPE: DNA
<213> ORGANISM: Artificial
<220> FEATURE:
<223> OTHER INFORMATION: sgRNA sequence

<400> SEQUENCE: 130
ctggcccctc cattgtgcat gttttagagc tagaaatagc aagttaaaat aaggctagtc 60
cgttatcaac ttgaaaaagt ggcaccgagt cggtgc 96

<210> SEQ ID NO 131
<211> LENGTH: 96
<212> TYPE: DNA
<213> ORGANISM: Artificial
<220> FEATURE:
<223> OTHER INFORMATION: sgRNA sequence

<400> SEQUENCE: 131
taattatcat tataattctt gttttagagc tagaaatagc aagttaaaat aaggctagtc 60
cgttatcaac ttgaaaaagt ggcaccgagt cggtgc 96

<210> SEQ ID NO 132
<211> LENGTH: 96
<212> TYPE: DNA
<213> ORGANISM: Artificial
<220> FEATURE:
<223> OTHER INFORMATION: sgRNA sequence

<400> SEQUENCE: 132
cattcaaaac aaacctttaa gttttagagc tagaaatagc aagttaaaat aaggctagtc 60
cgttatcaac ttgaaaaagt ggcaccgagt cggtgc 96

<210> SEQ ID NO 133
<211> LENGTH: 96
<212> TYPE: DNA
<213> ORGANISM: Artificial
<220> FEATURE:
<223> OTHER INFORMATION: sgRNA sequence

<400> SEQUENCE: 133
tttgcataat caacgctgaa gttttagagc tagaaatagc aagttaaaat aaggctagtc 60
cgttatcaac ttgaaaaagt ggcaccgagt cggtgc 96

<210> SEQ ID NO 134

-continued

<211> LENGTH: 96
<212> TYPE: DNA
<213> ORGANISM: Artificial
<220> FEATURE:
<223> OTHER INFORMATION: sgRNA sequence

<400> SEQUENCE: 134
aatccttaac ttatgcccca gttttagagc tagaaatagc aagttaaaat aaggctagtc 60
cgttatcaac ttgaaaaagt ggcaccgagt cggtgc 96

<210> SEQ ID NO 135
<211> LENGTH: 96
<212> TYPE: DNA
<213> ORGANISM: Artificial
<220> FEATURE:
<223> OTHER INFORMATION: sgRNA sequence

<400> SEQUENCE: 135
atgaaaacta caaatataga gttttagagc tagaaatagc aagttaaaat aaggctagtc 60
cgttatcaac ttgaaaaagt ggcaccgagt cggtgc 96

<210> SEQ ID NO 136
<211> LENGTH: 96
<212> TYPE: DNA
<213> ORGANISM: Artificial
<220> FEATURE:
<223> OTHER INFORMATION: sgRNA sequence

<400> SEQUENCE: 136
gggaaggaca caaaagaaaa gttttagagc tagaaatagc aagttaaaat aaggctagtc 60
cgttatcaac ttgaaaaagt ggcaccgagt cggtgc 96

<210> SEQ ID NO 137
<211> LENGTH: 20
<212> TYPE: DNA
<213> ORGANISM: Artificial
<220> FEATURE:
<223> OTHER INFORMATION: spacer

<400> SEQUENCE: 137
ctggcccctc cattgtgcat 20

<210> SEQ ID NO 138
<211> LENGTH: 20
<212> TYPE: DNA
<213> ORGANISM: Artificial
<220> FEATURE:
<223> OTHER INFORMATION: spacer

<400> SEQUENCE: 138
taattatcat tataattctt 20

<210> SEQ ID NO 139
<211> LENGTH: 20
<212> TYPE: DNA
<213> ORGANISM: Artificial
<220> FEATURE:
<223> OTHER INFORMATION: spacer

<400> SEQUENCE: 139
cattcaaaac aaacctttaa 20

<210> SEQ ID NO 140
<211> LENGTH: 20

<212> TYPE: DNA
<213> ORGANISM: Artificial
<220> FEATURE:
<223> OTHER INFORMATION: spacer

<400> SEQUENCE: 140
tttgcataat caacgctgaa 20

<210> SEQ ID NO 141
<211> LENGTH: 20
<212> TYPE: DNA
<213> ORGANISM: Artificial
<220> FEATURE:
<223> OTHER INFORMATION: spacer

<400> SEQUENCE: 141
aatccttaac ttatgcccca 20

<210> SEQ ID NO 142
<211> LENGTH: 20
<212> TYPE: DNA
<213> ORGANISM: Artificial
<220> FEATURE:
<223> OTHER INFORMATION: spacer

<400> SEQUENCE: 142
atgaaaacta caaatataga 20

<210> SEQ ID NO 143
<211> LENGTH: 20
<212> TYPE: DNA
<213> ORGANISM: Artificial
<220> FEATURE:
<223> OTHER INFORMATION: spacer

<400> SEQUENCE: 143
gggaaggaca caaaagaaaa 20

<210> SEQ ID NO 144
<211> LENGTH: 18668
<212> TYPE: DNA
<213> ORGANISM: Artificial
<220> FEATURE:
<223> OTHER INFORMATION: pWISE2780

<400> SEQUENCE: 144
aaggatccct gaaagcgacg ttggatgtta acatctacaa attgcctttt cttatcgacc 60
atgtacgtaa gcgcttacgt ttttggtgga cccttgagga aactggtagc tgttgtgggc 120
ctgtggtctc aagatggatc attaatttcc accttcacct acgatggggg gcatcgcacc 180
ggtgagtaat attgtacggc taagagcgaa tttggcctgt agacctcaat tgcgagcttt 240
ctaatttcaa actattcggg cctaactttt ggtgtgatga tgctgactgg caggatatat 300
accgttgtaa tttgagctcg tgtgaataag tcgctgtgta tgtttgtttg attgtttctg 360
ttggagtgca gcccatttca ccggacaagt cggctagatt gatttagccc tgatgaactg 420
ccgaggggaa gccatcttga gcgcggaatg ggaatggatt tcgttgtaca acgagacgac 480
agaacaccca cgggaccgag cttcgaagct ttaacgcttg agttaagccg cgccgcgaag 540
cggcgtcggc ttgaacgaat tgttagacat cagaagaact cgtcaagaag gcgatagaag 600
gcgatgcgct gcgaatcggg agcggcgata ccgtaaagca cgaggaagcg gtcagcccat 660
tcgccgccaa gctcttcagc aatatcacgg gtagccaacg ctatgtcctg atagcggtcc 720

-continued

```
gccacaccca gccggccaca gtcgatgaat ccagaaaagc ggccattttc caccatgata    780
ttcggcaagc aggcatcgcc atgggtcacg acgagatcct cgccgtcggg catgcgcgcc    840
ttgagcctgg cgaacagttc ggctggcgcg agcccctgat gctcttcgtc cagatcatcc    900
tgatcgacaa gaccggcttc catccgagta cgtgctcgct cgatgcgatg tttcgcttgg    960
tggtcgaatg ggcaggtagc cggatcaagc gtatgcagcc gccgcattgc atcagccatg   1020
atggatactt tctcggcagg agcaaggtga gatgacagga gatcctgccc cggcacttcg   1080
cccaatagca gccagtccct tcccgcttca gtgacaacgt cgagcacagc tgcgcaagga   1140
acgcccgtcg tggccagcca cgatagccgc gctgcctcgt cctgcagttc attcagggca   1200
ccggacaggt cggtcttgac aaaaagaacc gggcgcccct gcgctgacag ccggaacacg   1260
gcggcatcag agcagccgat tgtctgttgt gcccagtcat agccgaatag cctctccacc   1320
caagcggccg gagaacctgc gtgcaatcca tcttgttcaa tcatggcttt gtttctcctt   1380
caatcattga ctattgtcac gttattctga atcgacgaga actcacatca atctcaacaa   1440
gcatctctgc tcgcgaaatt ggtgttgtct cattaaaacg tgaccgtcaa agtctattca   1500
ctaggaccca aatctctcca ggtcccgcaa gctagcttcg ccgcccacgt ttctctttct   1560
tctcatattc aattgtcaaa aaacagacct catgaccaaa atcccttaac gtgagttttc   1620
gttccactga gcgtcagacc ccgtagaaaa gatcaaagga tcttcttgag atcctttttt   1680
tctgcgcgta atctgctgct tgcaaacaaa aaaaccaccg ctaccagcgg tggtttgttt   1740
gccggatcaa gagctaccaa ctctttttcc gaaggtaact ggcttcagca gagcgcagat   1800
accaaatact gtccttctag tgtagccgta gttaggccac cacttcaaga actctgtagc   1860
accgcctaca tacctcgctc tgctaatcct gttaccagtg gctgctgcca gtggcgataa   1920
gtcgtgtctt accgggttgg actcaagacg atagttaccg gataaggcgc agcggtcggg   1980
ctgaacgggg ggttcgtgca cacagcccag cttggagcga acgacctaca ccgaactgag   2040
atacctacag cgtgagctat gagaaagcgc cacgcttccc gaagggagaa aggcggacag   2100
gtatccggta agcggcaggg tcggaacagg agagcgcacg agggagcttc caggggggaaa  2160
cgcctggtat ctttatagtc ctgtcgggtt tcgccacctc tgacttgagc gtcgattttt   2220
gtgatgctcg tcaggggggc ggagcctatg gaaaaacgcc agcaacgcgg cctttttacg   2280
gttcctggcc ttttgctggc cttttgctca catgttcttt cctgcgttat cccctgattc   2340
tgtggataac cgtattaccg cctttgagtg agctgatacc gctcgccgca gccgaacgac   2400
cgagcgcagc gagtcagtga gcgaggaagc ggaagagcgc ctgatgcggt attttctcct   2460
tacgcatctg tgcggtattt cacaccgcat atggtgcact ctcagtacaa tctgctctga   2520
tgccgcatag ttaagccagt atacaggctc tccttcacga tcaacgatcg gcatggggcc   2580
ttcgtgcttg ttgagtaatg ttatcgctcc catcagagca cgcttggtac tccgggaatc   2640
ggatggtctg tcgatcatcc aaaaaacgct catgttttca acctattagg tctgtggtca   2700
gctgaccaca gaccatcctg ctccatactc gctaattcta gccaaaccgc aacgtcccct   2760
gcccgctagc cttcaagagc gccattatca tcgggccaag tgaaaacttc ccgagctcgc   2820
tccgccgtgt cagatctcgg agatagcccc cgggcgaatt gatgaagttc gctcgctcca   2880
aaatgcacgc catcgctgct gccgcattct ccggtcccat tgcctcacac gcgtcttggt   2940
aagccgacgg gctgaccccc agcatagacc gaaccaccac cgcagccgac atgaggtcac   3000
gccagctagc aaccgcaccg ctcggcccat aattgccaat ggtcgggcat gctttcagga   3060
tcatcccgag gggaacgct tttatcggct cgctccttgc ccggtctatt tcactcggct   3120
```

-continued

```
tagcgccctg ctccttttca gagcgaggtt caagttcatt aacggattcg ggttttgaat   3180
tctgtatgtg ctgctcgctc tgggcagcat tggtgctatt attttctgaa ttgtctctaa   3240
tttccaaccg gttgattatc tcttcctgga gcatccacat ctcttcgaga attgactcta   3300
catcagcaag cgtcggggcg cgtggaattc tacccacaag ttccacatag acttcctcga   3360
cagcttgcca gtcgccctcc gctccctctt ccatagctgc cgtaattagc ttccgaacgt   3420
cccgtcggca aatcgtcaga ctttctttgg ccatcctgaa tgctgctcga tcggccatca   3480
cctgctgtgc catcatcgct agctcttcgg accgcgcgag aagcggagac aaatcgaagc   3540
caaacgcgcg ctcgatctga ccagcgccat ccttacgagc gtaacgcttt ccgttggcgc   3600
tatccttccg gacgatcaag cctgactcca cgagcatggc gatgtgccta cgcaaagtcg   3660
cgccagccat cccatgcgcc cgaagggcaa gctgagcatt cgacgggaag acgatcagct   3720
gtgcctcctg acgcaactcc gtttccgggt gaaagctcaa tagcgcatca aggacggcaa   3780
gactgttgga ctggattcca agtagttcca tggccgcgga cgcgtctcta aagaccttcc   3840
acttgtccgc tgtcttgcct tgtttgatat cggccagcgc cgtctggcgc cgcacaagcg   3900
caagcgtcat tggccgccgc ccgaatggcg tcgttacact tcctgtctgc atcatctttc   3960
acctttcagc aggcaaagga aatcagctca ccaaaacggc gctaaaaact cttgacgagg   4020
attcgaggaa atgcgattct gttcgcgcta gagagacaga agggcttccg cgacggcgac   4080
gttgaggggg ctcttttctt ttgcggttta ctctccccgt ttccgttggt tctcagcgtg   4140
gtacgcttga tacagcgctg gcacatgatc gagcacgaag gtcgcaaaat cgggcgtcgc   4200
cttcctgtca atcgtgattt ccagtttggc cttgctctgc gtcacctgtg caattctggt   4260
gccgtctggg gtggccatga cctcgggaag tccacgcgca acccgactgg gcttcagact   4320
agcgatcacc gccttgaatc gttctgccga tggcagcgct tgaacttcct ccgacatagc   4380
atatttagcc acgtcggccg gtgaagaaac tttctcaatc agctcggcaa gttgttgcca   4440
actcggccgt ccaacaccag gagcggcacc aatagcatcg gtcagttcag aggggagggc   4500
gtcgacgagc agaagcatct tggacaaatt gctcttgtcg atcgacatcg cggcgatgac   4560
aatctctcga gaaaactgcc tgttcaggcg atgtgcgaag cgcgcctttt cgatgaaggt   4620
aagatcttcg cgctcattgt tttcctgacc ctgtgctacg accacttgct cgtccgtcag   4680
ttcgcgaacg accgctctga ccggaagtcc gagttctgaa acggcgcgta gccggcggtg   4740
gccgaaggca acctgatatc ggcccggctg gctcggatgc ggtcgcacaa ggattgggac   4800
ttgctgtcct tgttcccgga tcgaagtaag gagcccgtca atgtcccctc gcatacgatc   4860
ctgcacgaaa gacggttcta ttgacgaggc atccaactct atcactgcct gaccttcagc   4920
gagacgccgc tcgatctctt cggcacggct aagacgatcg ttttgctctc gcagtgcgtt   4980
accaatgttc gctgtgagct tcgttgccgg atcgcgctcc ttccttgtta cgccgaggag   5040
cggcatggag cggttctttg ccgtcctatt gtcggcgggc gacgtctcag gggcgtcagt   5100
tgagacgcca aggatgtgct tccggctcat gtgggcctac cccatgcttt tttgatcagt   5160
gtttcgatct cgtcgttgac ggcgttcatc gcctccaagg ctcgatcata ggtcgagcgc   5220
gtgaacaggc cacgctccac ttcgaataga gtctggtttg tcaggccagc gtccgaaacc   5280
gcggtggttt taagcatcgg aaaattgagg acattttcgc caaaaatcga ccgcagataa   5340
cctaccattt ggttctgtgg tccgtcgctc ggttcgaaac gggttatcag atagcgcatc   5400
caattaaact tgaacttggc gccagcattc tcgatttcac gcaaaaggtt cgatgtcatt   5460
```

-continued

```
gccagaaact ggttcatcga catcacatcc agcatctgcg gatggaccgt gacaagaatg   5520
gacgtcgccg cagtcaatgc ggatagcgtg agatacccaa gctggggagg gcagtcgatg   5580
accacgacgt catagttatc cgcgatatct tcaattactt ggctgatgcg accataaaag   5640
agcgtgtcgc cctctttgcg gttcatcagc gcgcgtggcg tatcgtgttc aaactccatc   5700
agctcaaggt taccaggaat caggtggagg tcgggaatgt aagtccctcg gacgactcgt   5760
tcgattgcca cctgctcatc atcatacctt atagcgccgt agagcgtttc gttcgggcca   5820
acgtccgtct ccggttggct cccaaagagt gcagaaaggc tcgcttgagg atcgagatca   5880
atggccaaga ctcgatatcc gcgcatagcg aggtactgcg ccagatgcgc ggcggtggtg   5940
gtcttacccg acccaccttt gaaattcatc acagagataa cctgaagctg ctcgccgcct   6000
cgacgatgtg gcaggtagcg ccggttcccg cggccgacct gatccatata cttccgaatc   6060
acatggatat cttcaattga gaacattcgc ctgccacccg ggctcatgct aacattcaac   6120
tctggcatct cagacgcggt ctgccgtaaa tatgactcgc caacgccgag cagcttggac   6180
gcctccgatg gcccgaatgt tcgaatgccc ttctcggaat gcggcgggaa aaccttaaga   6240
tgatgtgctt gaagttggct cgagagggca tcggcatgac gctccatcaa ggccgtcaac   6300
cctacaacta caggcgctgc ttttaggaca gacttcgcca tctcaaaccc attccttgcc   6360
agtggcgata tttttcgcga aactggaaaa gttccgccgc tggcaattag cgccgattct   6420
gctgtttggg caagagcttt taggttaaca gaaggttaac gccctcaggt cgaaaaactc   6480
cacccaactg ttatttgtat ttatttccaa tgccttagag agattgccat ttgaatatgt   6540
tcatgtattg ttttagtgat aatcctacaa tcgtaaccca aaaagaggtc gccctctgcg   6600
cgccgtcgtc caatataggc gaagtcaccc ttgcgactca ggcggattct accttgtaca   6660
cgtgtcgagt ggaaaagtcc catgtggatc actccgttgc cccgtcgctc accgtgttgg   6720
ggggaaggtg cacatggctc agttctcaat ggaaattatc tgcctaaccg gctcagttct   6780
gcgtagaaac caacatgcaa gctccaccgg gtgcaaagcg gcagcggcgg caggatatat   6840
tcaattgtaa atggcttcat gtccgggaaa tctacatgga tcagcaatga gtatgatggt   6900
caatatggag aaaaagaaag agtaattacc aatttttttt caattcaaaa atgtagatgt   6960
ccgcagcgtt attataaaat gaaagtacat tttgataaaa cgacaaatta cgatccgtcg   7020
tatttatagg cgaaagcaat aaacaaatta ttctaattcg gaaatcttta tttcgacgtg   7080
tctacattca cgtccaaatg gggggcttaga tgagaaactt cacgatcgat gcggccctag   7140
gcgtacgata acttcgtata atgtatgcta tacgaagtta tcactagtca acaattggcc   7200
aatctttgtt ctaaattgct aataaacgac catttccgtc aattctcctt ggttgcaaca   7260
gtctacccgt caaatgttta ctaatttata agtgtgaagt ttgaattatg aaagacgaaa   7320
tcgtattaaa aattcacaag aataaacaac tccatagatt ttcaaaaaaa cagtcacgag   7380
aaaaaaacca cagtccgttt gtctgctctt ctagttttta ttattttttct attaatagtt   7440
ttttgttatt tcgagaataa aatttgaacg atgtccgaac cacaaaagcc gagccgataa   7500
atcctaagcc gagcctaact ttagccgtaa ccatcagtca cggctcccgg gctaattcat   7560
ttgaaccgaa tcataatcaa cggtttagat caaactcaaa acaatctaac ggcaacatag   7620
acgcgtcggt gagctaaaaa gagtgtgaaa gccaggtcac catagcattg tctctcccag   7680
attttttatt tgggaaataa tagaagaaat agaaaaaaat aaaagagtga gaaaaatcgt   7740
agagctatat attcgcacat gtactcgttt cgctttcctt agtgttagct gctgccgctg   7800
ttgtttctcc tccatttctc tatctttctc tctcgctgct tctcgaatct tctgtatcat   7860
```

-continued

```
cttcttcttc ttcaaggtga gtctctagat ccgttcgctt gattttgctg ctcgttagtc   7920
gttattgttg attctctatg ccgatttcgc tagatctgtt tagcatgcgt tgtggtttta   7980
tgagaaaatc tttgttttgg gggttgcttg ttatgtgatt cgatccgtgc ttgttggatc   8040
gatctgagct aattcttaag gtttatgtgt tagatctatg gagtttgagg attcttctcg   8100
cttctgtcga tctctcgctg ttatttttgt ttttttcagt gaagtgaagt tgtttagttc   8160
gaaatgactt cgtgtatgct cgattgatct ggttttaatc ttcgatctgt taggtgttga   8220
tgtttacaag tgaattctag tgttttctcg ttgagatctg tgaagtttga acctagtttt   8280
ctcaataatc aacatatgaa gcgatgtttg agtttcaata aacgctgcta atcttcgaaa   8340
ctaagttgtg atctgattcg tgtttacttc atgagcttat ccaattcatt tcggtttcat   8400
tttacttttt ttttagtgaa ccatggcgca agttagcaga atctgcaatg gtgtgcagaa   8460
cccatctctt atctccaatc tctcgaaatc cagtcaacgc aaatctccct tatcggtttc   8520
tctgaagacg cagcagcatc cacgagctta tccgatttcg tcgtcgtggg gattgaagaa   8580
gagtgggatg acgttaattg gctctgagct tcgtcctctt aaggtcatgt cttctgtttc   8640
cacggcgtgc atgggggaag cggtgatcgc cgaagtatcg actcaactat cagaggtagt   8700
tggcgtcatc gagcgccatc tcgaaccgac gttgctggcc gtacatttgt acggctccgc   8760
agtggatggc ggcctgaagc cacacagtga tattgatttg ctggttacgg tgaccgtaag   8820
gcttgatgaa acaacgcggc gagctttgat caacgacctt ttggaaactt cggcttcccc   8880
tggagagagc gagattctcc gcgctgtaga agtcaccatt gttgtgcacg acgacatcat   8940
tccgtggcgt tatccagcta agcgcgaact gcaatttgga gaatggcagc gcaatgacat   9000
tcttgcaggt atcttcgagc cagccacgat cgacattgat ctggctatct tgctgacaaa   9060
agcaagagaa catagcgttg ccttggtagg tccagcggcg gaggaactct ttgatccggt   9120
tcctgaacag gatctatttg aggcgctaaa tgaaacctta acgctatgga actcgccgcc   9180
cgactgggct ggcgatgagc gaaatgtagt gcttacgttg tcccgcattt ggtacagcgc   9240
agtaaccggc aaaatcgcgc cgaaggatgt cgctgccgac tgggcaatgg agcgcctgcc   9300
ggcccagtat cagcccgtca tacttgaagc tagacaggct tatcttggac aagaagaaga   9360
tcgcttggcc tcgcgcgcag atcagttgga agaatttgtc cactacgtga aaggcgagat   9420
caccaaggta gtcggcaaat aaggatcaat tcccgatcgt tcaaacattt ggcaataaag   9480
tttcttaaga ttgaatcctg ttgccggtct tgcgatgatt atcatataat ttctgttgaa   9540
ttacgttaag catgtaataa ttaacatgta atgcatgacg ttatttatga gatgggtttt   9600
tatgattaga gtcccgcaat tatacattta atacgcgata gaaaacaaaa tatagcgcgc   9660
aaactaggat aaattatcgc gcgcggtgtc atctatgtta ctagatcggg gatccaacgt   9720
tataacttcg tataatgtat gctatacgaa gttattaact ataacggtcc taaggtagcg   9780
acttaggctg agcccgggca ggcctaccca taatacccat aatagctgtt tgccaatcgt   9840
tcttcttggc gcgccagaca tcctggacca atatgctgaa gattatgcta cctacaccag   9900
gataggactt gaagcactta accttgaaga ttggttcgaa gaaccagaac ccgatccacc   9960
taaccctgtg gaccgccaga ggatagagga catcctggac ctactgaacg tcagcaatga  10020
cgactgaaag attcccagga caccggcgga agtggtggac ccagtctagg tgcgatgctt  10080
agtcgcgcac gatgactatg tcggaaggca tctttgcttt cggcaaactt tagtaatact  10140
ttaaggaaag tattgtacaa gttaggtgca gagacaataa tgcacccagc tttagctttg  10200
```

-continued

```
tttatggaat tattgtgtcg gttgcattat tggatgcctg cgtgcaccct aagcaatcaa  10260
cggagaaaca aagataaaaa tcaattactc acatgaaaga gtattgatca cgagtcacta  10320
tggagcgaca atctccagac aggatgtcag catcttatct tcctttgaag aaagcatcat  10380
caataacgat gtaatggtgg ggacatccac taagttattg ctctgcaaac agctcaaaaa  10440
gctactggcc gacaatcata attgctcggc atgtgcaggt ggggcctcca ctagcaataa  10500
tacaagcttt acagcttgca gtgactcatc ctccaataat ggagaaaaag acgtcagcag  10560
tgacgaacaa gggtcgaaag acttgcctat ataagggcat tctcccctca gttgaagatc  10620
atcgaaagtt ggagcaataa actctctctt caacaaatct atcttttatc ttttatcggt  10680
accaaaaaat ggcgggatct aagaagagaa gaattaaaca agatgacaag aagtatagta  10740
ttggactcga tatcggaacc aactctgtgg ggtgggctgt tattacagat gaatataagg  10800
tgccatccaa aaagtttaaa gttctgggca atactgatag acactcaatc aagaagaatc  10860
tgataggtgc acttctgttt gatagtggag agactgccga ggcaaccaga cttaaaagga  10920
ctgcaagaag aagatatacc agaagaaaga ataggatttg ctatttgcag gaaatcttca  10980
gcaacgaaat ggccaaggtt gatgactcat ttttccatag gttggaggag agtttttcttg  11040
tggaggaaga taagaagcac gaaagacacc caattttcgg gaatatagtg gacgaggtgg  11100
cttatcatga gaagtatccc actatctacc acctgagaaa gaaacttgtg gactcaaccg  11160
ataaggctga tcttaggctt atatacttgg cccttgcaca tatgatcaaa ttcaggggcc  11220
attttcttat cgaaggcgat cttaatcccg ataactcaga tgtggacaag ctgtttatac  11280
aacttgtgca aacctacaat caactcttcg aggagaatcc cattaacgcc tccggcgtgg  11340
atgcaaaagc catactgtca gccagactga gcaaaagtag gagactggag aatcttatag  11400
cccaactgcc cggtgaaaag aagaatgggc tcttcggaaa tctgatcgct ctttcattgg  11460
ggttgacacc caactttaag agtaactttg acttggcaga agatgcaaag ttgcagctca  11520
gtaaagacac atatgacgat gaccttgaca atctcttggc acaaataggg gatcaatacg  11580
ctgacctttt cctcgctgcc aagaacctca gcgacgctat actgttgtcc gacattctta  11640
gggttaatac cgaaattaca aaggcccctc ttagtgcaag tatgatcaaa aggtatgatg  11700
agcatcacca agaccttaca ctgctgaagg ctctggttag acagcaactc cctgaaaagt  11760
ataaggaaat attcttcgac caaagtaaga acgggtacgc cggttatatt gatgggggcg  11820
caagtcaaga agaattttac aaattcatca agccaattct tgaaaagatg gacgggactg  11880
aggaattgct ggtgaaactg aatagagagg accttcttag aaaacagagg acatttgaca  11940
atgggtccat cccacaccag attcatctgg gggaactcca cgcaatattg aggagacaag  12000
aagactttta cccattcctt aaggataata gagagaaaat cgaaaaaatc ctgactttca  12060
ggattcctta ctatgttggg ccactggcca gggggaactc aagattcgct tggatgacaa  12120
ggaagtcaga agaaaccata accccttgga attttgaaga ggtggttgat aagggggcat  12180
cagcccagtc tttcatagag aggatgacca actttgataa aaatcttcca aatgagaagg  12240
ttttgccaaa acatagtctt ttgtacgagt actttactgt ttataacgaa ttgaccaagg  12300
tgaagtatgt gaccgaggga atgaggaagc cagcattttt gtccggggag caaaagaaag  12360
caatcgttga tcttctcttc aagaccaaca gaaaagtgac cgtgaaacaa ctgaaggaag  12420
actacttcaa aaagatagaa tgtttcgatt cagtggaaat tagcggtgtt gaagacaggt  12480
tcaatgcttc attgggtact taccacgacc tgttgaagat aatcaaagac aaggactttc  12540
tcgataatga ggagaacgaa gacatcttgg aagacattgt gcttacactc actttgtttg  12600
```

aggacaggga aatgattgag gaaagactca aaacttacgc tcatttgttt gatgataagg 12660
ttatgaaaca actaaaaaga agaaggtaca ccggctgggg aagattgagt aggaaactga 12720
tcaacggtat tagagataaa caatccggaa agactatcct cgatttcctt aagagtgatg 12780
gctttgcaaa taggaatttt atgcagctga ttcatgacga ctcacttacc ttcaaagaag 12840
acatccaaaa agctcaggtg tctgggcaag gcgacagtct gcatgaacat atagctaact 12900
tggctgggag tcccgccatc aagaagggga tacttcaaac agttaaagtt gtggacgaat 12960
tggtgaaggt aatgggaagg cacaagcctg aaaatatagt gatagaaatg gcaagggaaa 13020
atcaaacaac ccagaaggga cagaagaaca gtagggaaag gatgaaaagg atagaagagg 13080
ggatcaaaga gcttggtagc cagatcctca aggaacatcc agtggagaat acccaacttc 13140
aaaacgagaa actctatttg tactacttgc agaacggaag agatatgtat gtggaccaag 13200
agcttgatat taacaggctg agcgattatg acgttgacgc tatagtgccc caatcattcc 13260
tcaaggatga ctctattgat aataaggtgc tgacaaggag tgacaagaat agagggaaat 13320
ccgacaacgt tccatccgag gaagttgtga agaagatgaa gaactactgg aggcagttgc 13380
tgaacgctaa gctcattacc cagaggaaat tcgataacct gaccaaagca gagagaggcg 13440
ggctgagcga actcgataaa gcaggtttca tcaagagaca actcgtggag actaggcaaa 13500
ttactaagca cgtggctcaa atactcgaca gcaggatgaa cacaaagtac gacgagaacg 13560
acaagctcat tagagaggtt aaggttatta ctctgaaaag taaattggtt agcgatttca 13620
gaaaggattt ccaattctat aaggttagag agatcaacaa ttatcatcat gcacatgatg 13680
cctatctgaa tgctgtggtt ggtacagccc ttatcaagaa gtaccctaag ctagagagcg 13740
agtttgtgta cggagattat aaggtgtatg atgtgaggaa aatgatcgct aaaagtgagc 13800
aagagattgg aaaggctacc gccaaatact tcttttattc caatattatg aatttcttca 13860
agacagaaat caccctggct aacggcgaga taaggaagag gccgcttatc gaaactaatg 13920
gggagacagg cgaaatagtg tgggacaaag ggagggattt cgcaactgtg aggaaggttt 13980
tgagcatgcc tcaggtgaat atcgttaaga aaaccgaagt tcaaactgga gggttctcta 14040
aggaaagcat tctccccaag aggaactccg acaagctgat tgctagaaag aaagactggg 14100
accccaagaa gtatggcgga ttcgactcac ccactgtggc atatagcgtt ctcgtggtgg 14160
caaaggttga aaagggtaaa tccaaaaaac tcaaatccgt gaaggaactc cttggcataa 14220
ctattatgga aaggagtagc tttgaaaaga atcccatcga ctttctcgaa gctaagggct 14280
ataaggaagt taagaaggac cttataatca aacttccaaa atactccctt tttgagttgg 14340
aaaacggcag aaagagaatg ttggccagtg ccggggagct tcaaaagggc aacgaactgg 14400
ctctgcctag caaatatgtg aactttttgt atctggcatc acactacgag aaacttaaag 14460
gctctcctga ggacaacgag caaaaacagc tctttgttga acagcataag cactacctcg 14520
acgagattat tgagcagatc agcgagttct caaagagagt tattctggct gacgctaatc 14580
ttgacaaggt tttgtccgct tacaacaaac acagggataa gccaatcagg gagcaggcag 14640
aaaacataat ccatctcttt accctgacaa acctcggtgc ccccgctgct ttcaagtatt 14700
ttgatactac cattgacagg aagagatata cttccactaa ggaagtgctc gacgcaaccc 14760
tcatacacca aagtatcaca ggcctctatg aaactaggat agatttgtct caacttgggg 14820
gcgatagcgg cggcagctcg ggcggcagct cgggctccga aacgccgggg accagcgaga 14880
gcgccacgcc tgagagttcc ggcggaagca gcggcgggag ttccaccctg aacatcgagg 14940

-continued

```
acgagtatcg gcttcatgag accagcaaag agccggacgt ctccctggga agcacctggc  15000
tgagcgactt cccgcaagcc tgggcggaga ccggtggtat ggggctcgca gtgcggcaag  15060
cgccgttgat aatcccgcta aaggccacga gcacgcccgt gtctatcaag cagtacccga  15120
tgagtcaaga ggcacgcctc ggtatcaagc cgcatatcca gcgcctcctg gaccagggca  15180
tcctcgtgcc ctgccagtct ccctggaata cgcctctgct acccgtcaag aagcctggca  15240
ccaacgatta caggccggtg caagacctgc gtgaggtcaa caagcgcgtg gaggacatcc  15300
acccaacggt gcccaacccg tacaatctcc tatctggcct tccgccctcg caccagtggt  15360
acacggtctt ggacctaaag gacgcattct tctgtctgag gctgcaccct acgtcccagc  15420
cgctgttcgc cttcgagtgg cgcgacccgg agatgggcat ctctggccag ctaacttgga  15480
cgcgattgcc ccaggggttt aagaactcgc ccacactctt caacgaggca ctccaccgtg  15540
acctggccga ctttcgcata cagcaccccg accttatcct gttgcagtac gtcgatgacc  15600
tgctcctggc ggccacgtcc gagctggact gccagcaagg cacccgcgcc ctacttcaaa  15660
ccctgggcaa cctgggttac cgtgcgtccg ccaagaaggc ccaaatctgc caaaagcaag  15720
tcaagtacct cggctacctc ttgaaggagg gacagcgctg gctgacggag gcgaggaagg  15780
agacggtgat gggtcagccc acacccaaga ccccgaggca gctaagggag ttcctgggga  15840
aggcgggctt ctgccgtcta ttcatccctg gcttcgcgga gatggcggcc ccgctgtacc  15900
cgctaacgaa gccgggcacg ctgttcaact ggggccctga ccagcagaag gcgtaccagg  15960
agatcaagca agcgttgctt actgccccag cactcggcct ccccgacctc acaaagccgt  16020
tcgagctatt cgttgacgag aaacagggct acgcgaaggg tgtgctgact caaaagctag  16080
ggccgtggcg acgcccagta gcctacctga gcaagaagct cgacccggtg gcggcgggct  16140
ggccaccatg cctccggatg gtcgcggcta tcgcggtgct cacaaaggat gcggggaagc  16200
tcacgatggg gcagcccctg gtgatcctgg ccccacacgc ggtggaggcg ttagtgaagc  16260
aacctcccga ccgatggctg agcaacgccc gcatgaccca ctaccaggcg ctcctcctcg  16320
acaccgaccg cgtgcaattc ggccctgtcg tggcactgaa cccggccacg ctgctcccac  16380
tgcccgagga ggggctacag cacaactgcc tcgatatact ggcggaagcc cacggcaccc  16440
gccccgactt gacggaccag ccgcttcccg acgcggacca tacgtggtac accgacggga  16500
gttccttact ccaagagggc cagcgaaagg cgggcgctgc ggtgaccact gagacggaag  16560
taatctgggc aaaggcgctg cctgcgggca cgtctgccca gcgggcggag ctgatcgccc  16620
tgacccaggc cctcaagatg gccgagggca agaagctgaa cgtttacacc gacagtcggt  16680
atgccttcgc aactgcccac atccacggcg aaatctaccg tcggcgcggc tggctgacga  16740
gcgagggcaa ggagatcaag aacaaggacg agatcctcgc cctgctaaag gcactcttcc  16800
tgcccaagcg actgtccatc attcactgtc cggggcacca gaagggccat tccgccgagg  16860
cgcggggcaa ccgcatggcg gatcaggccg ctcggaaggc ggcgatcacc gagacgcccg  16920
atacgagcac gctcctgatt gaaaactcgt cgccggggag caagaaaagg cggatcaagc  16980
aagactagtt aattaaaggg ctctctgtca tgatttcata ctttcattat tgagctctgt  17040
aattacaatt atgaccatga gaacatctct tattgtgtgg ccttttaatt gctgatgtta  17100
gtactgaacc aaagcttatc gtgatgatgt aaaagcaata agtacttgtt tgtagcttct  17160
ttgtgtctcc ctttgggctt aatacatctg tttagtgttg tggctttggc atagacttct  17220
cttggtaata atgccttgca atgcaaaatt tcaattatca aattctatta tgttctcacc  17280
ttatggtaac agcttaccct gtggaagatg agattcttga gttgagtcat tgccaatttt  17340
```

tggcattagc ttttgaatta gtgaattttg acaaaaatta ccgtgacact gattttgttg 17400
aagctcttaa gtgtagtttt tacaaaattt cagtggctcg ttgtgattat gtcaaactca 17460
cggcgaatgt agttcttaca gaatttcagt ggctcgggcc cggccgtgac ggccacgagc 17520
gaactcctgc aggggcatgt gactttttat ttaaattatt ctcagaaata ttaaaatata 17580
atcaaatata ttttttata agatactgga aataacattt ttaggaatgt aacgaaagcc 17640
ccattacaaa cacttgaact cagggatcga tccaacttaa ttattatctg ctacttcaaa 17700
ttcaaattta taggccctac ctttatgttt tgctctgcac tttcttaaat ggaaacaagt 17760
aacacaatag agtaagatca tttacttgta agcggaaact gttgcatcaa ctgcaatatt 17820
ttcgggttag ttttataata taacaatgaa gagaattgcc gagaagatca tatcaagtcc 17880
catattccat ttattggcct ttacaagtcc cacatcggtc caaatattag acaaagaaac 17940
atttatatat cgtctgacaa acctgtaaga ttgccgttaa tttgagagtc cagttttaga 18000
gctagaaata gcaagttaaa ataaggctag tccgttatca acttgaaaaa gtggcaccga 18060
gtcggtgcag ctgaattaac tctcaaattt ttttttcgat aaaaatgttt taaacgatat 18120
atattataaa aaaaaacgtt tcaaaaataa atacaaaaat gtttttaaat atatataatt 18180
taactcatta aagaaaataa aaatgcaagt gcggtgacaa gacaagctaa aagttgcaaa 18240
agaaatggca gggctataag gctcacctac tcctggattt accaaatttt ggttcgtccc 18300
tatactcgaa aaataaaaca aaataaattt cagtatcttc gtttttgtat gctttgactg 18360
tgaggcgagg ccaactttct tcttctgtct gagatgaatt ttgtttgcct cctgtgaagg 18420
atgtatcatt caaagtgaat gttttgcaac tgccagtagt cccacatcga ccaaatattc 18480
ttattacagt gtgtttatat agcacctgga gaaggaatgg gttgaatcct taacttatgc 18540
cccagtttta gagctagaaa tagcaagtta aaataaggct agtccgttat caacttgaaa 18600
aagtggcacc gagtcggtgc tttttttgcg gccgcacaac aaacgcgccg gcgctctctt 18660
aaggtagc 18668

<210> SEQ ID NO 145
<211> LENGTH: 67
<212> TYPE: DNA
<213> ORGANISM: Nicotiana benthamiana

<400> SEQUENCE: 145
agtaaaatgc cccaaattgg acttgtttct gccgttaatt tgagagtcca aggtaattca 60
gcttatc 67

<210> SEQ ID NO 146
<211> LENGTH: 50
<212> TYPE: DNA
<213> ORGANISM: Artificial
<220> FEATURE:
<223> OTHER INFORMATION: second row of Fig. 17

<400> SEQUENCE: 146
ccaaattgga cttgtttctg ccgttaattt gagagttaat tcagctgctc 50

<210> SEQ ID NO 147
<211> LENGTH: 24
<212> TYPE: DNA
<213> ORGANISM: Artificial
<220> FEATURE:
<223> OTHER INFORMATION: bottom row of Fig. 17

<400> SEQUENCE: 147
aatttgagag ttaattcagc tgca 24

<210> SEQ ID NO 148
<211> LENGTH: 34
<212> TYPE: DNA
<213> ORGANISM: Bacteriophage P1

<400> SEQUENCE: 148
ataacttcgt ataatgtatg ctatacgaag ttat 34

<210> SEQ ID NO 149
<211> LENGTH: 34
<212> TYPE: DNA
<213> ORGANISM: Artificial
<220> FEATURE:
<223> OTHER INFORMATION: lox75

<400> SEQUENCE: 149
ataacttcgt ataatgtatg ctatacgccc ggta 34

<210> SEQ ID NO 150
<211> LENGTH: 34
<212> TYPE: DNA
<213> ORGANISM: Artificial
<220> FEATURE:
<223> OTHER INFORMATION: lox76

<400> SEQUENCE: 150
taccgggcgt ataatgtatg ctatacgaag ttat 34

<210> SEQ ID NO 151
<211> LENGTH: 34
<212> TYPE: DNA
<213> ORGANISM: Artificial
<220> FEATURE:
<223> OTHER INFORMATION: lox66

<400> SEQUENCE: 151
taccgttcgt ataatgtatg ctatacgaag ttat 34

<210> SEQ ID NO 152
<211> LENGTH: 34
<212> TYPE: DNA
<213> ORGANISM: Artificial
<220> FEATURE:
<223> OTHER INFORMATION: lox71

<400> SEQUENCE: 152
ataacttcgt ataatgtatg ctatacgaac ggta 34

<210> SEQ ID NO 153
<211> LENGTH: 34
<212> TYPE: DNA
<213> ORGANISM: Artificial
<220> FEATURE:
<223> OTHER INFORMATION: lox78

<400> SEQUENCE: 153
taccgggcgt ataatgtatg ctatacgccc ggta 34

<210> SEQ ID NO 154
<211> LENGTH: 34
<212> TYPE: DNA
<213> ORGANISM: Artificial

<220> FEATURE:
<223> OTHER INFORMATION: lox72

<400> SEQUENCE: 154
taccgttcgt ataatgtatg ctatacgaac ggta 34

<210> SEQ ID NO 155
<211> LENGTH: 34
<212> TYPE: DNA
<213> ORGANISM: Saccharomyces cerevisiae

<400> SEQUENCE: 155
gaagttccta ttctctagaa agtataggaa cttc 34

<210> SEQ ID NO 156
<211> LENGTH: 31
<212> TYPE: DNA
<213> ORGANISM: Zygosaccharomyces rouxii

<400> SEQUENCE: 156
ttgatgaaag aatacgttat tctttcatca a 31

<210> SEQ ID NO 157
<211> LENGTH: 39
<212> TYPE: DNA
<213> ORGANISM: Bacteriophage phi-C31

<400> SEQUENCE: 157
ccccaactgg ggtaaccttt gagttctctc agttggggg 39

<210> SEQ ID NO 158
<211> LENGTH: 34
<212> TYPE: DNA
<213> ORGANISM: Bacteriophage phi-C31

<400> SEQUENCE: 158
gtgccagggc gtgcccttgg gctccccggg cgcg 34

<210> SEQ ID NO 159
<211> LENGTH: 48
<212> TYPE: DNA
<213> ORGANISM: Unknown
<220> FEATURE:
<223> OTHER INFORMATION: bacteriophage Bxb1

<400> SEQUENCE: 159
ggtttgtctg gtcaaccacc gcggtctcag tggtgtacgg tacaaacc 48

<210> SEQ ID NO 160
<211> LENGTH: 42
<212> TYPE: DNA
<213> ORGANISM: Unknown
<220> FEATURE:
<223> OTHER INFORMATION: bacteriophage Bxb1

<400> SEQUENCE: 160
ccggcttgtc gacgacggcg gtctccgtcg tcaggatcat cc 42

-continued

```
<210> SEQ ID NO 161
<211> LENGTH: 10
<212> TYPE: DNA
<213> ORGANISM: Artificial
<220> FEATURE:
<223> OTHER INFORMATION: reverse transcriptase target sequence

<400> SEQUENCE: 161

tgagtctggc                                                          10
```